US009523127B2

(12) United States Patent
Singh et al.

(10) Patent No.: US 9,523,127 B2
(45) Date of Patent: Dec. 20, 2016

(54) KCNQ2 AND KCNQ3—POTASSIUM CHANNEL GENES WHICH ARE MUTATED IN BENIGN FAMILIAL NEONATAL CONVULSIONS (BFNC) AND OTHER EPILEPSIES

(75) Inventors: Nanda A. Singh, Heber City, UT (US); Mark F. Leppert, Salt Lake City, UT (US); Carole Charlier, Sprimont (BE)

(73) Assignee: THE UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 1240 days.

(21) Appl. No.: 11/702,218

(22) Filed: Feb. 5, 2007

(65) Prior Publication Data

US 2007/0254297 A1 Nov. 1, 2007

Related U.S. Application Data

(60) Continuation of application No. 10/096,578, filed on Mar. 14, 2002, now Pat. No. 7,214,483, which is a division of application No. 09/177,650, filed on Oct. 23, 1998, now Pat. No. 6,413,719.

(60) Provisional application No. 60/063,147, filed on Oct. 24, 1997.

(51) Int. Cl.
*C12Q 1/68* (2006.01)
*C07K 14/705* (2006.01)

(52) U.S. Cl.
CPC ............ *C12Q 1/6883* (2013.01); *C07K 14/705* (2013.01); *A01K 2217/05* (2013.01); *C12Q 2600/156* (2013.01)

(58) Field of Classification Search
None
See application file for complete search history.

(56) References Cited

U.S. PATENT DOCUMENTS

| 4,675,285 A | 6/1987 | Clark et al. |
| 6,403,360 B1 | 6/2002 | Blanar et al. |
| 7,041,496 B2 | 5/2006 | Blanar et al. |
| 7,262,289 B2 | 8/2007 | Blanar et al. |
| 7,482,431 B2 | 1/2009 | Blanar et al. |

FOREIGN PATENT DOCUMENTS

| CA | 2300985 A1 | 2/1999 |
| JP | 9-191882 A | 7/1997 |
| JP | 2001-521041 A | 11/2001 |
| WO | 9416716 A1 | 8/1994 |
| WO | 9507935 A1 | 3/1995 |
| WO | 9527057 A1 | 10/1995 |
| WO | WO 97/23598 A1 | 7/1997 |
| WO | 9907832 A1 | 2/1999 |
| WO | 99/21875 A1 | 5/1999 |
| WO | WO 99/31232 A1 | 6/1999 |

OTHER PUBLICATIONS http://www.bchu.org/pdf/Nutrition/Herbal_Teas_during_Pregnancy_-_with_changes2.pdf, "Herbal Teas During Pregnancy", Author unknown, no journal, volume, or issue, Published online by the Brant Count Health Unit, Brantford, Ontario, Canada, 2 pages long.*
Elmslie, F.V., "Genetic mapping of a major susceptibility locus for juvenile myoclonic epilepsy on chromosone 15q", Human Molecular Genetics, vol. 6, No. 8, 1997, pp. 1329-1334.
Leppert, M., "Searching for Human Epilepsy Genes: A Progress Report", Brain Pathoogy, vol. 3, 1993, pp. 357-369.
Yokoyama, M., "Identification and Cloning of Neuroblastoma-Specific and Nerve Tissue-Specific Genes through Compiled Expression Profiles," DNA Research, vol. 3, 1996, pp. 311-320.
Cooper et al, PNAS 96:4759-4766, 1999.
Berkovic, Samuel F., and Scheffer, Ingrid E., "Epilepsies with single gene inheritance", *Brain & Development*, 19 (1997) pp. 13-18.
Berkovic, MD, Samuel F., et al., "Phenotypic Expression of Benign Familial Neonatal Convulsions Linked to Chromosone 20", *Arch Neurol*, vol. 51, pp. 1125-1128, Nov. 1994.
Biervert, Christian, et al., "A Potassium Channel Mutation in Neonatal Human Epilepsy", *Science*, vol. 279, pp. 403-406, Jan. 16, 1998.
Charlier, Carole, et al., "A pore mutation in a novel KQT-like potassium channel gene in an idiopathic epilepsy family", *Nature Genetics*, vol. 18 pp. 53-55, Jan. 1998.
Lewis, T.B., et al., "Localization of a Gene for a Glutamate Binding Subunit of a NMDA Receptor (GRINA) to 8q24", *Genomics*, vol. 32, pp. 131-133, 1996.
Melis, Roberta, et al., "Physical and Genetic Localization of a *Shab* Subfamily Potassium Channel (KCNB1) Gene to Chromosomal Region 20q13.2", *Genomics*, vol. 25, pp. 285-287, 1995.
Phillips, H.A., et al., "Localization of a gene for autosomal dominant nocturnal frontal lobe epilepsy to chromosome 20q13.2", *Nature Genetics*, vol. 10, p. 117-118, May 1995.

(Continued)

Primary Examiner — Robert M Kelly
(74) Attorney, Agent, or Firm — Rothwell, Figg, Ernst & Manbeck, P.C.

(57) ABSTRACT

Generalized idiopathic epilepsies (IGE) cause 40% of all seizures and commonly have a genetic basis. One type of IGE is Benign Familial Neonatal Convulsions (BFNC), a dominantly inherited disorder of newborns. A submicroscopic deletion of chromosome 20q13.3 which co-segregates with seizures in a BFNC family has been identified. Characterization of cDNAs spanning the deleted region identified a novel voltage-gated potassium channel, KCNQ2, which belongs to a new KCNQ1-like class of potassium channels. Nine other BFNC probands were shown to have KCNQ2 mutations including three missense mutations, three frame-shifts, two nonsense mutations, and one splice site mutation. A second gene, KCNQ3, was found in a separate BFNC family in which the mutation had been localized to chromosome 8. A missense mutation was found in this gene in perfect cosegregation with the BFNC phenotype in this latter family. This demonstrates that defects in potassium channels can cause epilepsy. Furthermore, some members of one of the BFNC families with a mutation in KCNQ2 also exhibited rolandic epilepsy and one individual with juvenile myoclonic epilepsy has a mutation in an alternative exon of KCNQ3.

11 Claims, 16 Drawing Sheets

(56) References Cited

OTHER PUBLICATIONS

Sander, Thomas, et al., "Common Subtypes of Idiopathic Generalized Epilepsies: Lack of Linkage to D20S19 Close to Candidate Loci (EBN1, EEGV1) on Chromosome 20", *American Journal of Medical Genetics* ( *Neuropsychiatric Genetics*), 67:31-39 (1996).

Singh, Nanda A., et al., "A novel potassium channel gene, *KCNQ2*, is mutated in an inherited epilepsy of newborns," *Nature Genetics*, vol. 18, pp. 25-29, Jan. 1998.

Steinlein, Ortrud, et al., "Benign familial neonatal convulsions: confirmation of genetic heterogeneity and further evidence for a second locus on chromosome 8q", *Hum. Genet.*, (1995) 95:411-415.

Steinlein, Ortrud, "Detection of a *Cfo*I polymorphism within exon 5 of the human neuronal nicotinic acetylcholine receptor α4 subunit gene (CHRNA4)", *Hum. Genet.*, (1995) 96:130.

Steinlein, Ortrud, et al., "Exon-Intron Structure of the Human Neuronal Nicotinic Acetylcholine Receptor α4 Subunit (CHRNA4)", *Genomics*, vol. 32(1):289-294.

Steinlein, Ortrud K., "New insights into the molecular and genetic mechanisms underlying idiopathic epilepsies", *Clinical Genetics*, 1998: 54: 169-175.

Stoffel, Markus, and Jan, Lily Y., "Epilepsy genes: excitement traced to potassium channels", *Nature Genetics*, vol. 18, pp. 6-8, Jan. 1998.

Terwindt, G.M., et al., "Partial Cosegregation of Familial Hemiplegic Migraine and a Benign Familial Infantile Epileptic Syndrome", *Epilepsia*, 38(8):915-921, 1997.

Yang, Wen-Pin, et al., "Functional Expression of Two KvLQT1-related Potassium Channels Responsible for an Inherited Idiopathic Epilepsy", *The Journal of Biological Chemistry*, vol. 273, No. 31, pp. 19419-19423, Jul. 31, 1998.

Online Mendelian Inheritance in Man, OMIM (TM). John Hopkins University, Baltimore, MD. MIM No. 121200:Jan. 7, 1998. World Wide Web URL:http//www.ncbi.nlm.nih.gov/omim/.

Online Mendelian Inheritance in Man, OMIM (TM). John Hopkins University, Baltimore, MD. MIM No. 121201:Jan. 7, 1998. World Wide Web URL:http//www.ncbi.nlm.nih.gov/omim/.

Online Mendelian Inheritance in Man, OMIM (TM). Johns Hopkins University, Baltimore, MD. MIM No. 602232:Mar. 13, 1998. World Wide Web URL: http://www.ncbi.nlm.nih.gov/omim/.

Online Mendelian Inheritance in Man, OMIM (TM). Johns Hopkins University, Baltimore, MD. MIM No. 602235:Dec. 13, 1998. World Wide Web URL:http://www.ncbi.nlm.nih.gov/omim/.

GenBank Accession No. AF033347. World Wide Web URL: http://www.ncbi.nlm.nih.gov/.

GenBank Accession No. AF033348. World Wide Web URL: http://www.ncbi.nlm.nih.gov/.

Cendrin, F. et al, GenBank Acc. No. M97218, Jul. 26, 1993.

Hillier, L. et al., GenBank Acc. No. H23701, Jul. 6, 1995.

Mahairas, G. et al., GenBank Acc. No. U35017, Apr. 27, 1996.

Scheets, K. et al., GenBank Acc. No. M16060, Apr. 27, 1993.

Schwaiger, F. et al., GenBank Acc. No. U00185, Apr. 1, 1997.

Shinomiya, M. et al., GenBank Acc. No. AB000508, Oct. 21, 1997.

Yokoyama, M. et al., DNA Research, 1996, 3:311-320.

Office Action issued in Canadian Patent Application No. 2,712,809, 5 pages (Jan. 21, 2013).

Smart, S.L., et al "Deltion of the $K_v1.1$ Potassium Channel Causes Epilepsy in Mice," Cell Press, *Neuron*, vol. 20, pp. 809-819, (1998).

Fickett, J.W., "Recognition of Protein Coding Regions in DNA Sequences," Nucleic Acids Research, Jul. 1982, vol. 10, No. 17, pp. 5303-5318, © IRL Press Limited, Oxford, England.

Staden, R. et al, "Codon Preference and Its Use in Identifying Protein Coding Regions in Long DNA Sequences," Nucleic Acids Research, Sep. 1981, vol. 10, No. 1, pp. 141-156, © IRL Press Limited, 1 Falconberg Court, London W1V 5FG, U.K.

Hutchinson, G.B. et al, "The Prediction of Exons Through an Analysis of Spliceable Open Reading Frames," Nucleic Acids Research, May 1992, vol. 20, No. 13, pp. 3453-3462, © Oxford University Press.

Accession No. NM_004519, "*Homo sapiens* Potassium Voltage-Gated Channel, KQT-Like Subfamily, Member 3 (KCNQ3), Transcript Variant 1, mRNA," Feb. 2014, 8 pages.

Accession No. BF552857.1, "UI-R-C2-nn-a-12-0-Ul.r1 UI-R-C2 Rattus Norvegicus cDNA Clone UI-R-C2-nn-a-12-0-Ul 5-, mRNA Sequence," Dec. 2000, 2 pages.

Accession No. AI072578.1, "UI-R-C2-nn-a-12-0-Ul.s1 UI-R-C2 Rattus Norvegicus cDNA Clone UI-R-C2-nn-a-12-0-Ul 3-, mRNA Sequence," Aug. 1998, 2 pages.

Accession No. BM697310.1, "UI-E-DW0-agm-h-03-0-Ul.r1 UI-E-DW0 *Homo sapiens* cDNA Clone UI-E-DW0-agm-h-03-0-U1 5-, mRNA Sequence," Feb. 2002, 2 pages.

Accession No. AA019129.1, "ze58f12.s1 Soares Retina N2b4HR *Homo sapiens* cDNA Clone IMAGE:363215 3-, mRNA Sequence," Feb. 1996, 2 pages.

Accession No. NM_001204824.1, "*Homo Sapiens* Potassium Voltage-Gated Channel, KQT-Like Subfamily, Member 3 (KCNQ3), Transcript Variant 2, mRNA," Mar. 2014, 7 pages.

Accession No. NM_008008, "Mus Musculus Fibroblast Growth Factor 7 (Fgf7), mRNA," Feb. 2014, 4 pages.

Orita, M. et al., "Detection of Polymorphisms of Human DNA by Gel Electrophoresis as Single-Strand Conformation Polymorphisms," Proceedings of the National Academy of Sciences of USA, Apr. 1989, vol. 86, pp. 2766-2770.

Orita, M. et al., "Rapid and Sensitive Detection of Point Mutations and DNA Polymorphisms Using the Polymerase Chain Reaction," Genomics, 1989, vol. 5, No. 4, pp. 874-879, © 1989 Academic Press, Inc.

Office Action issued by Canadian Intellectual Property Office, Date: Nov. 27, 2013, CA Application No. 2,712,809, Owner: University of Utah Research Foundation, "KCNQ2 and KCNQ3—Potassium Channel Genes Which are Mutated in Benign Familial Neonatal Convulsions (BFNC) and Other Epilepsies," 5 pages.

Japanese Office Action (with English translation and Office Action Summary), dated Sep. 30, 2014, Application No. JP 2013-112986, 13 pages.

\* cited by examiner

D20S24

P1-K09-6b

P1-K09-7

```
KCNQ3  ................................................................................  1
KCNQ2  ................................................................................
KCNQ1  ................................................................................
nKQT1  ................................................................................

KCNQ3  ...................MGLKARRAAGAAGGGGDGGGGGAANPAGGDAAAGDEERKVGLAPGDVEQVT            54
KCNQ2  ..............................................MVQKSRNGGVYPGPSGEKKLKVGF            24
KCNQ1  ........MAAASSPPPRAERKRWGWGRLPGARRGSAGLAKKCPFSLELAEGGPAGGALYAP
nKQT1  MDEESGSSVSMLITMRKLSPVAMVSRSQKKTTDQAAPSDEQQEAGSSSAIGQESR
                                                                       S1

KCNQ3  LALGAGADKDGTLLEGGGRDEGQRRTPQGIGLLAKTPLSRPVKRNNAKYRRIQTLIYDALERPRGW.ALLYEALVFLIVLGCLILAVLT  143
KCNQ2  VGLDPGAPDSTRDGALLIAGSEAPKRGSILSKPRAGAGAGKPPKRNAFYRKLQNFLYNVLERPRGW.AFIYHAYVFLLVFSCLVLSVFS  113
KCNQ1  IAPGAPGPAPPASPAAPAAPPVASDLGPRPPVSDLPRVSIYSTRRPVLARTHVQGRVYNFLERPTGWKCFVYHFAVFLIVLCLIFSVLS
nKQT1  KTVVFQEPDIGFPSEHDQLTTLHDSEEGNRKMSLVGKPLTYKNYRTDQRFRMQNKMHNFLERPRGWKAATYELAVLFMVLMCLALSVFS
                                                                       S2

KCNQ3  TFFKEYETVSGDWLLLETFAIFIFGAEFALRIWAAGCCCRYKGWRGRLKFARKPLCMLDIFVLIASVPVVAVGNQGNVLATS.LRSLRFL  232
KCNQ2  TIKEYEKSSEGALYILEIVTIVVFGVEYFVRIWAAGCCCRYRGWRGRLKFARKPFCVIDIMVLIASIAVLAAGSQGNVFATSALRSLRFL  203
KCNQ1  TIEQYAALATGTLFWMEEVLVFFGTEVVRLWSAGCRSKYVGLWGRLRFARKPISIIDLIVVVASMVVLCVGSKGQVFATSAIRGIRFL
nKQT1  TMPDFEVNATIVLYLYFVIMLATEVICRWWSAGCRSRYRGISGRIRFATSAYCVIDIIVLASITVLCIGATGQVFAASAIRGLRFL
                                   S3                                          P   B

KCNQ3  QILRMLRMDRRGGTWKLLGSAICAHSKELITAWYIGFLTLILSSFLVYLVEKDVPEVDAQGEEMKEEFETYADALWWGLITLATIGYGDK  322
KCNQ2  QILRMIRMDRRGGTWKLLGGTWKLLVTAWYIGFLTLCLILASFLVYLAEK.......GENDHFDTYADALWWGLITLTTIGYGDK         283
KCNQ1  QILRMLHVDRQGGTWRLLGSVVFIHRQELITTLYIGFLGLIFSSYFVYLAEKDAVNES....GRVEFGSYADALWWGVTVTTIGYGDK
nKQT1  QILRMLRIDRRAGTWKLLGSVVWAHRQELLTTVIGFLGLIFSSFLVLCEK.........NTNDKYQTFADALWWGVITLSTVGYGDK
                                                                                             S4

KCNQ3  TPKTWEGRLIAATFSLIGVSFFALPAGILGSGLALKVQEEHRQKHFEKRRKPAAELIQAAWRYYATNPNRIDLVATWRFYESVVSFPFF   411
KCNQ2  YPQTWNGRLLAATFTLLGVSFFALPAGILGSGFALKVQEQHRQKHFEKRRNPAAGLIQSAWRFYATNLSRTDLHSTWQYYERTVTVPMY   372
KCNQ1  VPQTWVGKTIASCFSVFAISFFALPAGILGSGFALKVQQKQRQKHFNRQIPAAASLIQTAWRCYAA..ENPDS.STWKIYIRKAPRSHT
nKQT1  TPETWPGKIIAAFCALLGISFFALPAGILGSGFALKVQQHQRQKHLIRRRVPAAKLIQCLWRHYSAAPESTSL.ATWKIHLARELPPIV
                                                       S6

KCNQ3  ...................RKEQLEAASSQKLGLLDRVRLSNPRGSNTKGK                                         443
KCNQ2  SSQTQTYGASRLIPPLNQLELLRNL......KSKSGLAFRKDPPPEPSPSKGSPCRGPLCGCCPGRSSQKVSLKDRVF.SSPRGVAAKGK   457
KCNQ1  ..........LLSPSPKPKKSVVVK......KKKFKLDKDN...GVTPGEKMLTVPHI......TCDPPEERRLDH..FSVD....
nKQT1  ..........KLTPLGSNNATGLINRLRQSTKRTPNLNMQNLAVNSQATSKNLSVPRVRVHDTISLVSTSDISEIEQLGALGFSLGWKSK
```

FIG. 3A

```
KCNQ3  ..........LFTPLNVDAIEESPSKEPKPVGLNNKERF..............................................  472
KCNQ2  GSPQAQTVRRSPSADQSLEDSPSKVPKSWSFGDRSRA................................................  492
KCNQ1  .GYDSSVRKS......PTLLEVSMPHF............................MRTNSFAEDLDLEGETLL..TPI........
nKQT1  SKYGGSKKATDDSVLQSRMLAPSNAHLDDMRRRSRRSASLCRVVNTGQHLRPLQPRSTLSDSDVIGDYSLMMAPIYQWCEQMVQRNSTPG

KCNQ3  RTAFRMKAYAFWQSSE.DAGTGDPMAEDRGYGNDFPI....EDMIPTLKAAIRAVRILQFRLYKKKFKETLRPYDVKDVIEQYSAGHLDM  557
KCNQ2  RQAFRIKGAASRQNSEEASLPGEDIVDDKSCPCEFVT....EDLTPGLKVSIRAVCVMRFLVSKRKFKESLRPYDVMDVIEQYSAGHLDM  578
KCNQ1  .....THISQL......REHH..................RATIKVIRRMQYFVAKKFQQARKPYDVRDVIEQYSQGHLNL........
nKQT1  EDGVWSQLSQLSQLTTCATRRTEDISDGDEEEAVGYQPQTIEEFTPALKNCVRAIRRIQLLVARKKFKEALKPYDVKDVIEQYSAGHVDL

KCNQ3  LSRIKYLQTRIDMIFTPGPPSTPKHKKSQKGSAFTPSQQSPRNEPYVARPSTSEIEDQSMMGKFVKVERQVQDMGKKLDFLVDMHMQHM  647
KCNQ2  LSRIKSLQSRVDQIVRGPAITDK................DRTKGPAEAELPEDPSMMGRLGKVEKQVLSMEKKLDFLVNIYMQRM     648
KCNQ1  MVRIKELQRRLDQSIGKPSLFISVSEKS..............................KDRGSNTIGARLNRVEDKVTQLDQRLALITDMLHQLL
nKQT1  QSRVKTVQAKLDFICGKNIEKIEPKI..................................SMFTRIATLETTVGKMDKKLDLMVEMLMGRQ

KCNQ3  ERLQVQVTEYYPTKGTSSPAEAEKKEDNRYSDLKTIICNYSETGPPEPPYSFHQVTIDKVSPYGFFAHDPVNLPRGGPSSGKVQATPPSS  737
KCNQ2  GIPPTETEAYFGAKEPEPAPPYHSPEDSREHVDRHGCTVKIVRSSSSTGQKNFSAPPAAPPVQCPPSTSWQPQSHPRQGHGTSPVGDHGS  738
KCNQ1  SLHGGSTPGSGGPPREGGAHITQPCGSGGSVDPELFLPSNTLPTYEQLTVPRRGPDEGS.
nKQT1  ASQRVFSQNTSPRGEFSEPTSARQDLTRSRRSRSMVSTDMEMYTARSHSPGYHGDARPIIAQIDADDDDEDENVFDDSTPLNNGPGTSSC.

KCNQ3  ATTYVERPTVLPILTLLDSRVSCHSQADLQGPYSDRISPRQRRSITRDSDTPLSLMSVNHEELERSPSGFSISQ...DRDDYVFGPNGGS  824
KCNQ2  LVRIPPPAHERSLSAYGGNRASMEFLRQEDTPGCRPPEGNL...RDSDTSISIPSVDHEELERSFSGFSISQSKENLDALNSCYAAVA   825

KCNQ3  SWMREKRYLAEGETDTDTDPFTPSGSMPLSSTGDG.ISDSVWTPSNKPI.                                        872
KCNQ2  PCAKVRPYIAEGESDTDSDLCTPCGPPPRSATGEGPFGDVGWAGPRK.                                          872
```

FIG. 3B

*GTTCCTCCTGGTTTTCTCCTGCCTCGTGCTGTCTGTGTTTTCCACCATCAAGGAGTATGAGA
AGAGCTCGGAGGGGGCCCTCTACATCCTGG*GTGAGCCCCGAGGGAGGGCGGGGGCTGGAAGTG
CCCAGGAAGGAGCTGGAGCTGCCTGGGCGTCTGTCTT

FIG. 7A

*AGGCCTCAAGGTGGCCTCAGCTTT*CCTCCCCTGCAG**GAAATCGTGACTATCGTGGTGTTTGG
CGTGGAGTACTTCGTGCGGATCTGGGCCGCAGGCTGCTGCTGCCGGTACCGTGGCTGGAGGG
GGCGGCTCAAGTTTGCCCGGAAACCGTTCTGTGTGATT**GGTGAGGCCTGGTGGGGGTGG*TAT
TGCTAGAATCAGGGCCAG*

FIG. 7B

*ACATCATGGTGCTCATCGCCTCCATTGCGGTGCTGGCCGCCGGCTCCCAGGGCAACGTCTTT*
GCCACATCTGCGCTCCGGAGCCTGCGCTTCCTGCAGATTCTGCGGATGATCCGCATGGACCG
GCGGGGAGGCACCTGGAAGCTGCT*GGGCTCTGTGGTCTATGCCCACA*

FIG. 7C

*TGGTCACTGCCTGGTACATCGG*CTTCCTTTGTCTCATCCTGGCCTCGTTCCTGGTGTACTTG
GCAGAGAAGGGGGAGAACGACCACTTTGACACCTACGCGGATGCACTCTGGTGGGGCCTGGT
GAGTTGTGGTCATTGTGGTTTTCCCTTTCCCTGCTGATACACCCCTGTCCCTGTGCTGGGAC
CAGGC*TCTCACTGGCTGAGCCTGCTCCAT*

FIG. 7D

*GCAGGCCCTTCGTGTGACTAGAGCCTGCGGTCCCACAG***ATCACGCTGACCACCATTGGCTAC
GGGGACAAGTACCCCCAGACCTGGAACGGCAGGCTCCTTGCGGCAACCTTCACCCTCATCGG
TGTCTCCTTCTTCGCGCTGCCTGCA**GTAAGTCCAGCTGCCCCTGCCTGCCTTGGAGGGGGAC
GAGGTCTTGTAGGCTCCCGAGGTGACCACAGGCC*CCTGGGCACAGTTCCCTAGGT*

FIG. 7E

*ATGGTCTGACCCTGATGAATTGGGGTGTGGGGGGTCCCTGGGGTGTGACCTGACCCTGATGA
ATTGCAGG***GCATCTTGGGGTCTGGGTTTGCCCTGAAGGTTCAGGAGCAGCACAGGCAGAAGC
ACTTTGAGAAGAGGCGGAACCCGGCAGCAGGCCTGATCCAG**GTGAGTCCAGGTGTCCCCCGG
GGACCAGCACAGCCCTTGTCCTGGTCCCACC*TTGTTGAGGAGTGGAGGCCGC*

FIG. 7F

*AGCTGTGCAAGCAGAGGGAGGTGTCCCAGGACTCGGGAGGGTGAGACGCTCACTCCCCTCTC*
CTTCTCTTGCCC**CAGACTTATCCCCCCGCTGAACCAGCTGGAGCTGCTGAGGAACCTCAAGA
GTAAATCTGGACTCGCTTTCAGGT**CAGCTGGGGAGCTCCAGGTGGGGCGGGTGGGCGTCTCA
GTCCTCCTGGGGGCCCCAGCTGCC*CACAGAAGACACGCCAGGACAG*

FIG. 7G

*CCCAGGACTAACTGTGCTCTCCTCATTTCCAG***TAAAGGCAGCCCGTGCAGAGGGCCCCTGTG
TGGATGCTGCCCCGGACGCTCTAGG**TAC*NRCGGAACACRMSSCACGGACTGACGGCTGCTGC
ACGG*

FIG. 7H

*GCAGAGTGACTTCTCTCCCTGTTTTT*CTGTCTGTCTGTCTGTCTGTCGGTTCCCGTGGGAGC
AGCCAGAAGGTCAGTTTGAAAGATCGTGTCTTCTCCAGCCCCCGAGGCGTGGCTGCCAAGGG
GAAGGGGTCCCCGCAGGCCCAGACTGTGAGGCGGTCACCCAGCGCCGACCAGAGCCTCGAGG
ACAGCCCCAGCAAGGTGCCCAAGAGCTGGAGCTTCGGGGACCGCAGCCGGGCACGCCAGGCT
TTCCGCATCAAGGGTGCCGCGTCACGGCAGAACTCAGAAG*GGGTGTGGCCGCATCCTCTCCT
GGTCCATC*

FIG. 7I

*CCCTCACGGCATGTGTCCTTCCCCCCAGAA***GCAAGCCTCCCCGGAGAGGACATTGTGGATGA
CAAGAGCTGCCCCTGCGAGTTTGTGACCGAGGACCTGACCCCGGGCCTCAAAGTCAGCATCA
GAGCCGTGTG**G*TGAGGCCCCTGCCCAGCCGGGAGCCTGGGGGAGTGAGGAGGGGCCTCCCGC
T*

FIG. 7J

*GGTCTCTGGCCCAGGGCTCACAGCCCCACCCACCCCCCTGCAGT***GTCATGCGGTTCCTGGTG
TCCAAGCGGAAGTTCAAGGAGAGCCTGCGGCCCTACGACGTGATGGACGTCATCGAGCAGTA
CTCAGCCGGCCACCTGGACATGCTGTCCCGAATTAAGAGCCTGCAGTCCAGG**CAAGAGCCCC
GCCTGCCTGTCCAGCAGGGACAAG*

FIG. 7K

*CCCAGCCCAGCAGCCCCTTTTGCAG***GTCTTGTCCATGGAGAAGAAGCTGGACTTCCTGGTGA
ATATCTACATGCAGCGGATGGGCATCCCCCCGACAGAGACCGAGGCCTACTTTGGGGCCAAA
GAGCCGGAGCCGGCGCCGCCGTACCACAGCCCGGAAGACAGCCGGGAGCATGTCGACAGGCA
CGGCTGCATTGTCAAGATCGTGCGCTCCAGCAGCTCCACGGGCCAGAAGAACTTCTCGGCGC
CCCCGGCCGCGCCCCTGTCCAGT**GTCCGCCCTCCACCT*

FIG. 7L

*CTCCACGGGCCAGAAGAACTTCTCGGCGCCCCCGGCCGCGCCCCCTGTCCAGTGTCCGCCCT*
CCACCTCCTGGCAGCCACAGAGCCACCCGCGCCAGGGCCACGGCACCTCCCCCGTGGGGGAC
CACGGCTCCCTGGTGCGCATCCCGCCGCCGCCTGCCCACGAGCGGTCGCTGTCCGCCTACGG
CGGGGGCAACCGCGCCAGCATGGAGTTCCTGCGGCAGGAGGACACCCCGGGCTGCAGGCCCC
CCGAGGGGAACCTGCGGGA*CAGCGACACGTCCATCTCCATC*

FIG. 7M

*TGGAGTTCCTGCGGCAGGAGGACACCCCGAGCTGCAGGCCCCCCGAGGGGACCCTGCGGGAC*
AGCGACACGTCCATCTCCATCCCGTCCGTGGACCACGAGGAGCTGGAGCGTTCCTTCAGCGG
CTTCAGCATCTCCCAGTCCAAGGAGAACCTGGATGCTCTCAACAGCTGCTACGCGGCCGTGG
CGCCTTGTGCCAAAGTCAGGCCCTACA*TTGCGGAGGGAGAGTCAGACACC*

FIG. 7N

*GTGGCGCCTTGTGCCAAAGTCAGGCCCTACATTGCGGAGGGAGAGTCAGACACCGACTCCGA*
CCTCTGTACCCCGTGCGGGCCCCCGCCACGCTCGGCCACCGGCGAGGGTCCCTTTGGTGACG
TGGGCTGGGCCGGGCCCAGGAAGTGAGGCGGCGCTGGCCAGTGGACCCGCCCGCGGCCCTC
*CTCAGCACGGTGCCTCCGAGGTTTTGAGGCGGGAACCCTCTGGGGCCCTTTTCTTACAGTAA*
CTGAGTGTGGCGGGAAGGGTGGGCCCTGGAGGGGCCCATGTGGGCTGAAGGATGGGGGCTCC
TGGCAGTGACCTTTTACAAAAGTTATTTTCCAACAGGGGCTGGAGGGCTGGGCAGGGCCTGT
GGCTCCAGGAGCAGCGTGCAGGAGCAAGGCTGCCCTGTCCACTCTGCTCAAGGCCGCGGCCG
ACATCAGCCCGGTGTGAAGAGGGGCGGAGTGATGACGGGTGTTGCAACCTGGCAACAAGCNG
GGGGTTGNCCAGCCGANCCAAGGGAAGCACANAAGGAAGCTGTNCCCTAAGACCTNCCCNAA
AGGCGGCCTGTTTGGTAAGACTGCGCCTTGGTCCGGTGGGTTCCGGCAGCAAAAGCGGGTTT
TGCCGCCCCTGTCGTG

FIG. 7O

GGCGACGTGGAGCAAGTCACCTTGGCGCTCGGGGCCGGAGCCGACAAAGACGGGACCCTGCT
GCTGGAGGGCGGCGGCCGCGACGAGGGGCAGCGGAGGACCCCGCAGGGCATCGGGCTCCTGG
CCAAGACCCCGCTGAGCCGCCCAGTCAAGAGAAACAACGCCAAGTACCGGCGCATCCAAACT
TTGATCTACGACGCCCTGGAGAGACCGCGGGGCTGGGCGCTGCTTTACCACGCGTTGGT

FIG. 8A aacttctctcacattgttttatttaactgggatgattgtttccgcctgccttgcaggtttgt
cgtgaagattgaatgggatagcatataaagcacatgtcaatgtccagcagaagttgcagctt
catcctggaagacacctttccccatcttagcctcaaagcaagccatgactcaaaggttcctt
agtccatttctttcttccCctctagGTTCCTGATTGTCCTGGGGTGCTTGATTCTGGCTGTC
CTGACCACATTCAAGGAGTATGAGACTGTCTCGGGAGACTGGCTTCTGTTACTGgtaagatt
gcattctggggtaaatgcttctggttgggcttccagagtgatgaaaaggaggttgcccttgg
gtgcactcctccctgactggttgcagcttcttgtagtctccagtcaagtccaggcccaagga
aaagcaaagcctccattactyggtatggcccgccatgggcacatgtggggtgaagaatggca
ttcctggtaaagctttgctattccacattagagagaagggg aaataaagtcaaagcaaaaac
caatgcatgttattaaattataaaatacagcttcccaatcctctgaaaggtaacacaaaggc
atgtttcattctaaaacctgtctctgcttttcttcctgggatcctacaatctaaactccaa
ggatctctcattctctccaaggccaggtacagaattccatttatacacgaaacctctaaatc
tcccctcctggggcctgcatttgttttcactctctgtcctccatcaggtggtgtgatggaaa
cagagcaggattagaattcctgggcaagtcagcta

FIG. 8B agggctgcctggcccaggagccaggctttataaccattagccacaattagcaatgccagggt
acaggcactgggtggaatttacagattgtgtttcactcatatctctcttttcaacccaactg
cacttcttgggggcttttcattcattaaagggacttttaaagctgacctattggaacaaaaa
catagaaaaaagaacgagtaatcactgtgccaggtttaacagcattaaggacaattagcaca
tcagaatgaagatgggaggcctccaaactgaatggcggtgatggacctgttctcccggttcc
ccttccccaccccatccccagccatccctgccaaccagacaaccagcaacagcacaaaatg
gagttcttcagaacttccgaatagaaatcaccagctcccgacaagtggatctcggttaatca
gtgcctctccatatgctcttccatgcagGAGACATTTGCTATTTTCATCTTTGGAGCCGAGT
TTGCTTTGAGGATCTGGGCTGCTGGATGTTGCTGCCGATACAAAGGCTGGCGGGGCCGACTG
AAGTTTGCCAGGAAGCCCCTGTGCATGTTGGgtaagtcctgaccctgagcctcccagcctcc
tcagttcccttcttttggggcattgtttctctgagaaaagtttaagcagctattctgggaaa
tcacgcggcactgtggaggccagctcagcccctgacgctgcctcgatgagaagggacatgtc
aaccttctgggtcctcaaattcctccttctgtgactggtccttataaggactgcacaggaca
gggattcttatttggcagggtagggtgtcactcttggcaattgggttgtggag

FIG. 8C gggggccttggtaaattgctgctctggagccagcattaaagtgtggtaggcctatgctactt
ctggccaggtggccttggaaagtcactcaggctcagagcttcagtttcctcatcagtcatgg
gagaataatcccacttaccatgtgttgttggtggcaagattcaacagcagtgctcagattgt
cccactgcttggcacatgctgatctgccagcaaacagcacctatgatgacgccattgctttc
gcatgaccttcctttccctcttccctcccactctgtctgtcctctctcccagACATCTTTGT
GCTGATTGCCTCTGTGCCAGTGGTTGCTGTGGGAAACCAAGGCAATGTTCTGGCCACCTCCC
TGCGAAGCCTGCGCTTCCTGCAGATCCTGCGCATGCTGCGGATGGACCGGAGAGGTGGCACC
TGGAAGCTTCTGGGCTCAGCCATCTGTGCCCACAGCAAAgtaagtgtggtggagaaactgca
ggaccacatgggcttcccacccacctatgcccttccatgacatcccttcctttgcagtgtcc
ccagaaggcagtcattctgccaccttgatgataacgacaaagaggaagaggaggaggagaa
acaggaagtgcggggctggggtagggc

FIG. 8D acgcaagtcctggaatagacccaaagtttcctgagtcctgagccttgtattagaagaaggag
ccacttcctcctgccttcttgccttcctctgaagcctcttgagctgtgatattgaagtggcc
ctaagctagaaatcttcctctcctcctggagccatacactttttctggtaaattaatgaatg
aaataactaccatgttaatgatcccatttacagtgatggaagatgaagatcagagaaggtg
agtgatttgaccacagtcacagagctggtaaacttggactctaactctggtgtgtctggctc
cagcatccactcaacgactccccagtgaccacttttcatgtccactgttcattctttcagGA
ACTCATCACGGCCTGOTACATCGGTTTCCTGACACTCATCCTTTCTTCATTTCTTGTCTACC
TGGTTGAGAAAGACGTCCCAGAGGTGGATGCACAAGGAGAGGAGATGAAAGAGGAGTTTGAG
ACCTATGCAGATGCCCTGTGGTGGGGCCTGgtgagtcactaccttggaggccaattctgtga
gattgatggtcaagagtcagagagaggtggagggcatcacatgagcatgttcagccaggcag
ctgcattctgcagtcagaggtaagctctagaccaatttcagctcagaacctgctgacagaag
accctccttcaaggtgggcacttggaattgacttttctctagcgtttataagaagccagggc
ttggaacagcctggttgcatggtcgtttatggacttagccttattagtcataggctattttc
agccaagccatgcatgtgcaaacaaacccagtgacagatacatgtgtgctcacacagacc
tgtgtgtgcacaaccctacacccacaaggacacacagtactaaagctggcattcactgaagg
ctttctttgctccagagcatctctctgggtgctttactttcact

FIG. 8E gaacagatacatgcacagacattagacatacacacatatatacacaatacatacaaatatac
tcacaagcacacatatattcacaaacatggctataaataaaatcacaaattcacaaatatac
acacacatgaatgctcgtgtacatacacatttgcaattgctgaaatatttgttgactgacta
aggtaggaaacccttaacttatcaacaagtctcaaggcatccatataagttagtaggtactt
ggtgtcttttctcctaagggaaccttgttatgaatggggagcattgcccaagctgatggagag
gcttacaggtagagctcagttaacacgttcctgatattcctctccatgtggtactccatgtc
tgaactcttctctcttcagATCACACTGGCCACCATTGGCTATGGAGACAAGACACCCAAAA
CGTGGGAAGGCCGTCTGATTGCCGCCACCTTTTCCTTAATTGGCGTCTCCTTTTTTGCCCTT
CCAGCGgtaagtacctttgatatatgacatccccaatgtgacgtgcaggacccccttaccgcc
tggtgccagctcaactttccagtgtcatcttctatcctcttatacccctaccaactccctagc
cattcccttaagcatgatgatcctgccttttgccacaggccctgctgcttcctctgccaa
agatttcttcacacatcaactcctcttttcaatgctgccttctttaggctgagctagtcgctc
tgggcataactctgggaataattctgtaaaggagtttctggccctatgctaggattacacat
ttctagatctgccttccccagaggactgtgaattccttgggttctgggattatattttcat
tcatgcatttcccagtgccttgcacggagcaggtccttcatttatgtagttcccttctcttg
tcctgttacntactggcttatgtaaaaaatacatgtctctcaagaataagtctgacctatga
tagagtaactnccccaacgcccagtgtccaggtacgtaataataatgaaagcagattgcatt
tggttgaactcactgtggcctgaatcatgccaaaaggtttacccacatcatctcatttaatc
t

FIG. 8F gaaaatcaaaacagatcccaattctggggaagttccggctatagtcaaagtatcacgtgacag
ttcaagcagctaaaatatttttaaaactcagttaacattactgggcatctatttgtgcagt
accccttactggcagtttataaaggttatctcacttttttctaatcatgcattaggtattat
tatcccacatccctatagaaaaaaccaatatgcaacagggctaaggggcttgcccaggccct
cacacctggaaagtggcagtgtcagaattggaacccaggtcttcctgacttcaaggctcatt
tcacttaaccaagctccctactctcttcaagagaaggaagggctctttccccctttcccttct
tagtacagtgttgtcactgcaaggacttgaagtgcaattgagccctacagtccccattaccc
tggcaatggagcgggaatgctgggacagtctagctgggggctgactgcctgcctgcctctcc
ctcagGGCATCCTGGGGTCCGGGCTGGCCCTCAAGGTGCAGGAGCAACACCGTCAGAAGCAC
TTTGAGAAAAGGAGGAAGCCAGCTGCTGAGCTCATTCAGgtctgtctgcctgggaatgaact
ggaatgggattaagatccatgcatatgtacatacgtgtgtgtgtgtgtatgtgtgcatgtgt
gcacatgtggaggggacatactcatgaactgggacaggaccgattccatgtgtgtctgtgtg
tcttgtgtgtctgtgtgtgtgtgtgtgtatgtgtgtgtgtgtgtattaatgtgccc
aggcaggagcaggcctgcttgcacatgcttacttgtggatggctatggggagtttccatggg
tatctatttcacctgttcttctgtgtactgaaggtgacaatcctgtcactctctcattcagt
tcttaagccaagaaagaaatagacacagaactcaaggaccaacctatcatctttttttgat
acggtggttttttgaggttttttttgagactctcttgtccaggctggattgtagggtgcgat
catactcactgcagcctccatcnccagg  FIG. 8G aactcttggcctcaaagtgatcctcccaccttggtctcccaaagtgctgggattacaggcgt
gagccatagcaccggcctttagtacttgttcctttcagggattttatgcctactactctctt
ctctccctccactccagttcatctctccattcccccactcaccacaacaccaattatagctc
caagatggtcaaggaagttttcttcccaaagcagcttcaaaaagccaagaatctcggtttt
tctgaatgttggctcaatgcacattcaaattcttaggagtccagggcttaaacattgttttg
ttggtgtgggagtctgtgcgaaagtttcggtggtgcccactcattgttgcccctcttttctg
cccctcagGCTGCCTGGAGGTATTATGCTACCAACCCCAACAGGATTGACCTGGTGGCGACA
TGGGATTTTATGAATCAGTCGTCTCTTTTCCTTTCTTCAGgcaagtggggactcacctgaat
gctcagggcgtgaccagccatctctcctgcggtctgtattcgtgtctggcctcacgggtccc
tggagaacactcttcagggcaatgttccccaatttgggctgcaccctagaattatctggtag
cttaaacagttctggctgggcgcggtggctcacacccataatcccagcactttgggaggccg
aggcgggtggatcacctgaggtcaggagttccataccagcctggccaacatggtgaaatccc
gttcctactaaaaatgcaaaaattacccgggcgtggtggtgtgtgcctgtaatcccagctac
tcaggaggctgaa  FIG. 8H gactgaatggacttagtacaagttggtcataagggtcccgagggggtacaggaagatgctgg
ggtaggagtgatggcagattatacgttcttatatacaagcagggatgagggaagctgttaaa
aatcagacattgcttttataaacagagcatgtgcattgttttattcctggtagggagagtg
gaattatgtctggcttttcattttctatagctgcaccgttcaatatggtagccactagcctc
atgtggctagtgagaatttgactgttagcactgcaattgaggaacagatttttaattttaa
agtaaataaccttctatgactaatgactactctattggacagcacagctctggaattgttag
ctatgagaactgaaatggagataagaagacttcgcccacgatgtagaaaatacttgaccaag
aacaggtagttcattgtgtaaccaggacttgttccttttaacagGGTCAAGATTATTGGAGT
GCTTAGAAATGGAGAAAGGGGACTATATGCACTAGTCATTTCCTATGGCCAAATAACATTGG
ATCTGCTTTCATACATACTATCTTATTTAAGCTTTAGGATGTCCTGGAAGgtaagtagaagg
ggtaactccattttttcataaccccatttttataggtaaagaataagagagtcaatgagatta
attagcttgcttaatatcgctcagctgataagtgatggaacaaagattggaactcaggtctt
gtgccaaaacctatgtttttatttgcattgtatctctgggaagaaaacattatttagggag
aaaactggataaaagtaagatgacacaaggggttgtttggataataagacccatttttgaaga
ttgttgtttggatggtcaaactgagtaaaatgtgtgagagtggttg  FIG. 8I tacaatgtgatccacgtaataatgacagagtaccattccacttgtgaggggatttgctcagt
gtagaccttgggcaattgaataagaaccccctaggagggcccctggaggtgtacataaaggat
gagtaggcctgttccaagcagggaaaagaggaagggagttccaggcagaaggagagcctgag
aaaaggcttggagtcatgaatatgtgtaaagcacgggctggtgcacctcccagttaggagtg
agggctccagagccagatcacctgggtttggatcctgactttgctgcctcctaactgtgagc
ccttgagcaattcatttaatccctctgtgcctcaattttctcctcagggaaatggatgata
atagtacttcataggggttgttatgaggattaattgagttaagacaatgttcgctatgatgac
aatggtagtgacaaagttatgggggtgtgtgactgctacattatgacattcctggtttcctg
gtctgtctccaccaccaaataaatttcctgagctcaacatgagagctggggcagagtaagtg
ctcagcaaccattttctggatgaataaatgaatgaatgagtggctgaaaagagccctgaaaa
cctcagagccaacgggagtagcatgggctggggtctggatgggtaaacccgcctccttcatt
ggttccctccacactgaccatcctgtcctagagctcaactctgctccatcatcttcagagag
aagctttgcagcaatctttcgaggaaggatacagctgtttcacgtaatttatgctttattct
ttctccctcttctctttctag<u>GAAAGAACAGCTGGAGGCAGCATCCAG</u>gtaagtttctgatt
atgaattcccttcttcacatctctgtgtcaagacagagcatcctgctccatatggtgtaggg
ccccatgggaggtcatgctggtcccaagatagagtctttggggtcacactgttgctgaccac
catagtcctctgcctggtttccttctgg<u>ttgatctgagggaaact</u>taataggaatcatggca
gcagcctcttattgagggtctgggttctgtgtcaggagttctgcatatgttatctcatttgg
tcttcacaaccacaatgtaacgataggccctaatatcatcccttgtggatgaggagattgtg
gctcagagaggttgggttgagattgagtggcaacaaccaaaattcatagccagg

FIG. 8J aagaagtgttgctttacgtccatttgtgtggccagtttcttttcaaggaggaatcctttgat
aaggatttgtctgtctaaatcactatctgggtaccatgggatgatacacaggaaaggcagga
agttattgatgcaggaaatgggcatgggaaagatgaatctctgcagcatactaggatgagct
aggcaatttatagcgggcacctcatgtaagctacatttaatcgtatgggaaaattgacattc
agagaagtcttgcccagggtataagagctagcaggctgtggagctaggatttgaaccacgc
ctgtccgattccaagctgctgagtcagattcagcactgtgaaatgcacggtccccatttctc
cttggaggagaatgtgtgagtctttatggagggatgggaaatttt<u>aagagcctgcactgaag
gaggaaaattgttcacttttgcttatttgagCCAAAAGCTGGGTCTCTTGGATCGGGTTCG
CCTTAATCCTCGTGGTAGCAATACTAAAGGAAAGCTATTTACCCCTCTGAATGTAGATGCCA
TAGAAGAAAGTCCTTCTAAAGAACCAAAGCCTGTTGGCTTAAACAATAAAGAGCGTTTCCGC
ACGGCCTTCCGCATGAAAGCCTACGCTTTCTGGCAGAGTTCTGAAG</u>gtaatgccttttatc
tccctccctgtctcttccacttcttcctcccccaagtccacttccttcctcacctctcccttt
tgcccacttaagaacctttgactccacaagg<u>t</u>aactctctcccttccctcgacaagccaact
tcttgcttccctaactcctcctgtcccttgggctgaggcattgtgatgtattcccaggagtc
tagggctgcaggctcccaagttaggagcctggaaacctgtcaccttggtttctgagggtccg
ccccgacccccgccccatgattggattgttatggaggtcaacttgaaggatggggcggtgc
caggtgcaaagcaatttagagaccagggcacgggaagagtggcagaaaagcgccctctggag
gctgtaggagtcatggcctcatgtgcctcttttacttatgcaaagggaggacatgcagaaaa
gcctgtttcctcagtgtctgagcccacccaggccctcaatcctcattgtatcattca

FIG. 8K kttctctcmaaggcctctngatgtgtgsggctcagaaagtgacktctccaaggtcaccagga
tagagacttgasagagcaaawakcccagctgaggsctgcacagtgkgtgktgkttgctggst
tcwgtgtcstttgstggctkytggctctgggggccaytctggaactgsggagctcacttctc
ctccctgctagccttttccctcactaccagtcatgagtgcgcacacttttgacttggacttc
tgggtaatagaatgagggtgccaagaaaggctgaacagcatcacagcttgagaataccgtgg
agtcttgcaacgtggaaataaagactctggggattgacacatccagaggcgtggaaggcttt
gaccgaacagtggggtccccaagccttttccaggtctgtggcctgccgttcatatgtgtgtc
tccctcccagATGCCGGGACAGGTGACCCCATGGCGGAAGACAGGGGCTATGGGAATGACTT
CCCCATCGAAGACATGATCCCCACCCTGAAGGCCGCCATCCGAGCCgtcaggtaatgccccc
acggtcccacctgtgcctgtgtgcctccccgctccagctcaactcccacaggaaggggctt
ataaaattatcttgcactttgggaaggggaagagaagcccctccactaaccctgagttagg
tccctgaagtatgtaaatactgtatgctgccccagaaaaaatgatccagacgttagcaagtc
atgatgggtgactcgtaggtgcctgccttgttataaacacgccccacagccctcctgacagt
atttccacctgctatgttctgctctgtctgtaactaccatgtattttaaagggtgtcagagt
ggagggttttcttcctgtagaggcttcttgctcaaaatggttttcttctgcctaacttcat
ccatatagtttgttttaattagttcgcatttttaacaagataataaattatagtattttttt
gtctgtatcagcagagaccataatccattctaccta

FIG. 8L agcagtgtgacagtgattaagagcaccagccttgtcagcaccctgtctgggtttgaggacca
gctcagcccttattagctatatggccctgggatgatgctgaaggttcaaatccacaatcaca
tcatctataaatggatctgttatccaggattgttcataaagcattaattaagctcatggtct
ggcatacagtgaatgctcaataaatgttagctcttattaatactatgatttacttattattc
aaatgattgaagggagtaatcctgatggagatgtactaactctgtgtgttccaaggggtaga
accagaaccaaacgttggaagttcttccagcaagctcttttatctttggttctttttctcccc
ctgccctggagtttgctagccttctgttatagctccccgcactctccacatgggatgcacaa
atgcctctactttgccttgcagAATTCTACAATTCCGTCTCTATAAAAAAAAATTCAAGGAG
ACTTTGAGGCCTTACGATGTGAAGGATGTGATTGAGCAGTATTCTGCCGGGCATCTCGACAT
GCTTTCCAGGATAAAGTACCTTCAGACGAGgtgagacagtcacatctggagggactgcgctc
ccctcaaagccctatgaaccttagagtttaaggtgagaggtattcagaaataattcaaaatg
cagggagagattttaagaagacaaatatccacgaagccttgtggatgtctaggccaacaaag
caccagatcggacagactgtgaaatagctgtatgacattgccatggccaaggtcagcaccct
gatcaggcctgtcagagaggagaaagcacacatttaaatggcttctgactgtgatgctttcg
atgttgccaacaaaacaggatcatccgaattaaaccgaatccagctgcctaattaattctca
atacaattctttaccatatttaaaaatgttcatcaggtattacttataatagttgaaagata
tggaaatagcatcaatgcctaataa

FIG. 8M ccaagatgcagccgtcacctctctcagtggtttgtctgcctccctctctcctgggatagaaagatgctt
tcagtatcaccagatcaaaacaagcggaagaatataccgaggttataggttctctctggctctgtctt
ctctctgtagctagtatgcactctctctttcctctcctctcctccctctcctctcctcacttctcctc
tcctcccctctcctctcctcacttctcctctcctctcctctcttcttatatattccaaacccttatctc
attctagagagaatagaatgatttgttttcctgtcaaaacaaagctctgtgtaatttaatccctgctct
gtttgtttctttcagAATAGATATGATTTTCACCCCTGGACCTCCCTCCACGCCAAAACACAAGAAGTC
TCAGAAAGGGTCAGCATTCACCTTCCCATCCCAGCAATCTCCCAGGAATGAACCATATGTAGCCAGACC
ATCCACATCAGAAATCGAAGACCAAAGCATGATGGGGAAGTTTGTAAAAGTTGAAAGACAGgtaagtct
tttcttcctctcaccaaaaactggatctgtgacatttattttcaaatgccatttctttttttctttct
ttccttttttttttaagacgaaggttcNactctgttgcccaggctggagtgcaatggcgcgatcttga
ctcactgcaacctctgcctcccaggttcaagtgattctcctgcctcagcctcctnaggagctgagatta
caggcgcctgccatcatgcccagctaattttttgtatttntagtagagatggggtttcaccatgttggcc
aggctggtctcgaactcctgacctcaggtgatctgcccaactcggcctaccaaagtgctgggattacag
acatgagccactgtgcccagtcccaccattgttttcaaagggagataagatacttgagtactactac
ctaccattcaaaaaagatatggnaatcaaatcactgatttagcatttactgag cggggtgcctgtaatcccagctacttgggaggctgaggcatagcactgcntgaacccgggaggcggaagt
agcaatgagcccagatcgcgccactgcactccagcctgggtgacagaactgagcttcgtctcaaaaaaa
aaaaaaaaaaaaaaaaaagaatatttcctcccaaccaatagcaacgatccccaccctcagagaaagtg
gtaattcacagctcctttgattttccagGTTCAGGACATCCGGAAGAAGCTGGACTTCCTCGTGGATAT
GCACATGCAACACATGGAACGGTTGCAGGTGCAGGTCACGGAGTATTACCCAACCAAGGGCACCTCCTC
GCCAGCTGAAGCAGAGAAGAAGGAGGACAACAGGTATTCCGATTTGAAAACCATCATCTGCAACTATTC
TGAGACAGGCCCCCCGGAACCACCCTACAGCTTCCACCAGGTGACCATTGACAAAGTCAGCCCCTATGG
GTTTTTTGCACATGACCCTGTGAACCTGCCCCGAGGGGGACCCAGTTCTGGAAAGGTTCAGGCAACTCC
TCCTTCCTCAGCAACAACGTATGTGGAGAGGCCCACGGTCCTGCCTATCTTGACTCTTCTCGACTCCCG
AGTGAGCTGCCACTCCCAGGCTGACCTGCAGGGCCCCTACTCGGACCGAATCTCCCCCCGGCAGAGACG
TAGCATCACGCGAGACAGTGACACACCTCTGTCCCTGATGTCGGTCAACCACGAGGAGCTGGAGAGGTC
TCAAGTGGCTTCAGCATCTCCCAGGACAGAGATGATTATGTGTTCGGCCCCAATGGGGGGTCGAGCTGG
ATGAGGGAGAAGCGGTACCTCGCCGAGGGTGAGACGGACACAGACACGGACCCCTTCACGCCCAGCGGC
TCCATGCCTCTGTCGTCCACAGGGGATGGGATTTCTGATTCAGTATGGACCCCTTCCAATAAGCCCATT
TAAagaggtcactggctgacccctccttgtaatgtagacagactttgtatagttcacttactcttaca
cccgacgcttAccagcggggacaccaatggctgcatcaaatgcatgcgtgtgcgtggtggccccaccca
ggcaggggcttcccacaGcctcttcctccccatgtcaccacaacaaagtgcttccttttcagcatggnt
tgcatgactttacactatataaaatGgttccgctaatctcttctaggatacacatttatctgctgttctt
acttttattcacgattggaccagtacagggaGaaattactgatgagccatgctatttgtctgtttggtt
ggctggtatgggttttggtttggtaagcaa

KCNQ2 AND KCNQ3—POTASSIUM CHANNEL GENES WHICH ARE MUTATED IN BENIGN FAMILIAL NEONATAL CONVULSIONS (BFNC) AND OTHER EPILEPSIES

CROSS REFERENCE TO RELATED APPLICATIONS

This application is a continuation of U.S. patent application Ser. No. 10/096,578 filed 14 Mar. 2002 now U.S. Pat. No. 7,214,483 which in turn is a divisional of U.S. patent application Ser. No. 09/177,650 filed 23 Oct. 1998, now U.S. Pat. No. 6,413,719. Serial No. 09/177,650 is further related to and claims priority under 35 USC §119(e) to U.S. provisional patent application Ser. No. 60/063,147, filed 24 Oct. 1997. Each of these applications is incorporated herein by reference.

This application was made with Government support under Grant Nos. R01-NS32666 funded by the National Institutes of Health, Bethesda, Md.

BACKGROUND OF THE INVENTION

Epileptic disorders affect about 20 to 40 million people worldwide. Generalized idiopathic epilepsies (IGE) cause 40% of all epileptic disorders and commonly have a genetic basis (Plouin, 1994). Most of the IGEs that are inherited are complex, non-monogenic diseases. One type of IGE is Benign Familial Neonatal Convulsions (BFNC), a dominantly inherited disorder of newborns (Ronen et al., 1993; Hauser and Kurland, 1975). BFNC (OMIM 121200) is an autosomal dominantly inherited epilepsy of the newborn infant. This idiopathic, generalized epilepsy typically has an onset of seizures on day two to four of life. Spontaneous remission of the seizures occurs between two to fifteen, weeks (Ronen et al., 1993; Plouin, 1994; Hauser and Kurland, 1975). Seizures typically start with a tonic posture, ocular symptoms and other autonomic features which then often progress to clonic movements and motor automatisms. These neonates thrive normally between the seizures, and their neurologic examinations and later development indicate normal brain functioning (Ronen et al., 1993; Plouin, 1994; Hauser and Kurland, 1975). However, in spite of normal neurologic development, seizures recur later in life in approximately 16% of BFNC cases compared with a 2% cumulative lifetime risk of epilepsy in the general population (Ronen et al., 1993; Plouin, 1994; Hauser and Kurland, 1975).

Genetic heterogeneity of BFNC has been observed (Ryan et al., 1991). Two loci, EBN1 and EBN2, have been mapped by linkage analysis to chromosome 20q13 (Leppert et al., 1989; Malafosse et al., 1992) and chromosome 8q24 (Lewis et al., 1993; Steinlein et al., 1995), respectively.

The nomenclature of the genes of this invention as well as related genes has changed over time. Two of the genes of this invention from humans are now referred to as KCNQ2 and KCNQ3. These had originally been named KVEBN1 and KVEBN2, respectively. The two sets of names are equivalent and can be used interchangeably, but the accepted nomenclature is now KCNQ2 and KCNQ3 and these names will be used herein. Also, the related gene KCNQ1 had originally been called KVLQT1 in the literature, but again the accepted name now is KCNQ1 and this name will be used herein.

Linkage analysis in a large kindred demonstrated that a gene, herein called KCNQ2, responsible for BFNC maps to chromosome 20q13.3 close to the markers D20S20 and D20S19 (Leppert et al., 1989). Following the initial report, two centers confirmed linkage of BFNC to the same two genetic markers on chromosome 20, termed the EBN1 (epilepsy benign neonatal type 1) locus (Ryan et al., 1991; Malafosse et al., 1992; Steinlein et al., 1992). A more distal marker, D20S24, shows complete co-segregation with the BFNC phenotype in chromosome 20 linked families. Finding a distal flanking marker for the BFNC locus has not been successful probably because of its proximity to the telomere. This telomeric region is characterized by a high recombination rate between markers when compared to the physical distance (Steinlein et al., 1992). In fact, Steinlein et al. have demonstrated that the three markers D20S19, D20S20 and D20S24 are contained on the same 450 Mb Mlu I restriction fragment (Steinlein et al., 1992). All of the families in the present study used to find and study KCNQ2 show linkage to chromosome 20q markers with LOD scores of greater than 3.0 or have probands with clinical manifestations consistent with BFNC (Leppert et al., 1993). Each subject and control signed a Consent for Participation in these studies approved by the Institutional Review Board for Human Subject Research at their home institution. To find a gene responsible for BFNC, we narrowed a BFNC region with a sub-microscopic deletion in a single family, identified candidate cDNAs in this deletion, and then searched for mutations in other BFNC families. The gene has been identified and sequenced. Several distinct mutations have been found in this gene. These include a large deletion, three missense mutations, three frameshift mutations, two nonsense mutations and one splice site mutation. One of these mutations is associated with rolandic epilepsy as described in the Examples below.

A second chromosomal locus, EBN2, has also been identified for BFNC. Lewis et al. (1993) demonstrated linkage to markers on chromosome 8q24 in a single Hispanic family affected with BFNC. Evidence for this second locus was also reported in a Caucasian pedigree (Steinlein et al., 1995). The gene, herein called KCNQ3, responsible for EBN2 was mapped to chromosome 8, between markers D8S256 and D8S284 on a radiation hybrid map (Lewis et al., 1995). KCNQ3 has been identified as set out in the examples of the instant disclosure. KCNQ3 was screened for mutations in the large BFNC family previously linked to chromosome 8q24 in the same marker interval (Ryan et al., 1991; Lewis et al., 1993). A missense mutation was found in the critical pore region in perfect cosegregation with the BFNC phenotype. The same conserved amino acid is also mutated in KCNQ1 in an LQT patient (Wang et al., 1996). Furthermore, the segment of mouse chromosome 15 that harbors the stargazer (stg) locus (Noebels et al., 1990; Letts et al., 1997) is homologous to the human 8q24 region and the stg phenotype is close to a common form of IGE, the absence epilepsy. KCNQ2, KCNQ3 and other undiscovered genes of the same family of $K^+$ channels are strong candidates for other, more common IGEs. One individual with juvenile myoclonic epilepsy has been found who has a mutation in an alternative exon of KCNQ3 as shown in the Examples below.

IGEs include many different types of seizures. Common IGEs include generalized tonic-clonic seizure (GTCS), absence epilepsy of childhood (AEC), juvenile absence epilepsy (JAE) and juvenile myoclonic epilepsy (JME). Reutens and Berkovic (1995) have shown that the boundaries between the different IGE syndromes are indistinct and suggest that neurobiological and possibly genetic relationships exist between these syndromes. Interestingly, using non-parametric linkage methods, Zara et al. (1995) obtained evidence for involvement of an epilepsy locus at chromosome 8q24 in a panel of families with multiple cases of IGEs. Furthermore, in a population study, Steinlein et al. (1997) recently described a weak allelic association at the CHRNA4 locus, on chromosome 20q13.3, physically close to KCNQ2, in a group of unrelated patients with multiple forms of IGEs. Finally, an epileptic mutant mouse stargazer (stg) (Noebels et al., 1990) is a genetic model of spike wave epilepsy. This is a recessive mutation and the phenotype is related to a common form of human IGE, the absence epilepsy. Stg has been mapped on mouse chromosome 15 in a region homologous to the human 8q24 region. Screening the mouse homolog of KCNQ3 for mutations in an affected mouse will assess the hypothesis that the same gene is responsible for both BFNC and Stargazer phenotypes.

The present invention is directed to both KCNQ2 and KCNQ3 and their gene products, mutations in the genes, the mutated genes, probes for the wild-type and mutated genes, and to a process for the diagnosis and prevention of BFNC. Each of the genes encodes a potassium channel protein. The instant work shows that some families with BFNC have mutations in either KCNQ2 or KCNQ3. BFNC is diagnosed in accordance with the present invention by analyzing the DNA sequence of the KCNQ2 and/or KCNQ3 gene of an individual to be tested and comparing the respective DNA sequence to the known DNA sequence of a normal KCNQ2 and/or KCNQ3 gene. Alternatively, the KCNQ2 gene and/or KCNQ3 gene of an individual to be tested can be screened for mutations which cause BFNC. Prediction of BFNC will enable practitioners to prevent this disorder using existing medical therapy. Furthermore, a mutation in KCNQ2 has been found which is associated with rolandic epilepsy and a mutation in KCNQ3 has been found which is associated with JME. These two forms of epilepsy may also be diagnosed in accord with the invention.

Mouse genes homologous to the human KCNQ2 and KCNQ3 have also been found and sequenced and the sequences are disclosed. The mouse KCNQ2 gene has been only partially isolated and sequenced (shown as SEQ ID NO:88), the 3' end not yet having been found. The complete mouse KCNQ3 gene has been isolated and sequenced (shown as SEQ ID NO:90).

The publications and other materials used herein to illuminate the background of the invention or provide additional details respecting the practice, are incorporated by reference, and for convenience are respectively grouped in the appended List of References.

SUMMARY OF THE INVENTION

The present invention demonstrates a molecular basis of Benign Familial Neonatal Convulsions (BFNC) as well as for rolandic epilepsy and juvenile myoclonic epilepsy. More specifically, the present invention has determined that molecular variants of either the KCNQ2 gene or KCNQ3 gene cause or are involved in the pathogenesis of these three forms of epilepsy. Genotypic analyses show that KCNQ2 is linked to BFNC in ten unrelated families and KCNQ3 is linked to BFNC in one other family. Furthermore, one mutation in the KCNQ2 gene in two individuals of one family has been associated with rolandic epilepsy and one individual with a mutation in KCNQ3 has been diagnosed with juvenile myoclonic epilepsy. Analysis of the KCNQ2 and KCNQ3 genes will provide an early diagnosis of subjects with BFNC, rolandic epilepsy or JME. The diagnostic method comprises analyzing the DNA sequence of the KCNQ2 and/or the KCNQ3 gene of an individual to be tested and comparing it with the DNA sequence of the native, non-variant gene. In a second embodiment, the KCNQ2 and/or KCNQ3 gene of an individual to be tested is screened for mutations which cause BFNC, rolandic epilepsy or JME. The ability to predict these epilepsies will enable physicians to prevent the disease with medical therapy such as drugs which directly or indirectly modulate $K^+$ ion channels.

The invention shows that various genetic defects of a potassium channel are responsible for the human idiopathic epilepsy of BFNC, rolandic epilepsy and/or JME. This finding adds to the growing list of channelopathies in humans (Ptacek, 1997). Importantly, this result suggests that drugs which directly or indirectly modulate $K^+$ ion channels will be helpful in the treatment of seizure disorders.

BRIEF DESCRIPTION OF THE FIGURES

The file of this patent contains at least one drawing executed in color. Copies of this patent with color drawing(s) will be provided by the Patent and Trademark Office upon request and payment of the necessary fee.

FIGS. 3A and 3B. Amino acid alignment between human members (KCNQ2, KCNQ3 and KCNQ1) and the *C. elegans* homologue (nKQT1) of the KQT-like family. The six transmembrane domains and the pore are indicated by a solid line located above the corresponding sequence. The conserved charged amino acids in the transmembrane domains are highlighted in gray. The sequence of KCNQ2 is SEQ ID NO:2, the sequence of KCNQ3 is SEQ ID NO:7, the sequence of nKQT1 is SEQ ID NO:3 and the sequence of KCNQ1 is SEQ ID NO:4.

FIGS. 7A-O. Intron/exon sequence is shown for KCNQ2. Exon sequence is shown in bold and primer sequence is in italics. The primer sequences are found in Table 4. The sequences are SEQ ID NOs:100-114.

FIGS. 8A-O. Intron/exon sequence is shown for KCNQ3. Exon sequence is shown uppercase and intron is shown lowercase and primer sequences are underlined. The primer sequences are found in Table 5. The sequences are SEQ ID NOs:115-129. FIG. 8I shows the alternatively spliced exon found in a JME patient. FIG. 8N shows an "N" in the 3' intron region. This "N" stands for Alu repeats which are found in this region.

BRIEF DESCRIPTION OF THE SEQUENCE LISTING

Figure 1:
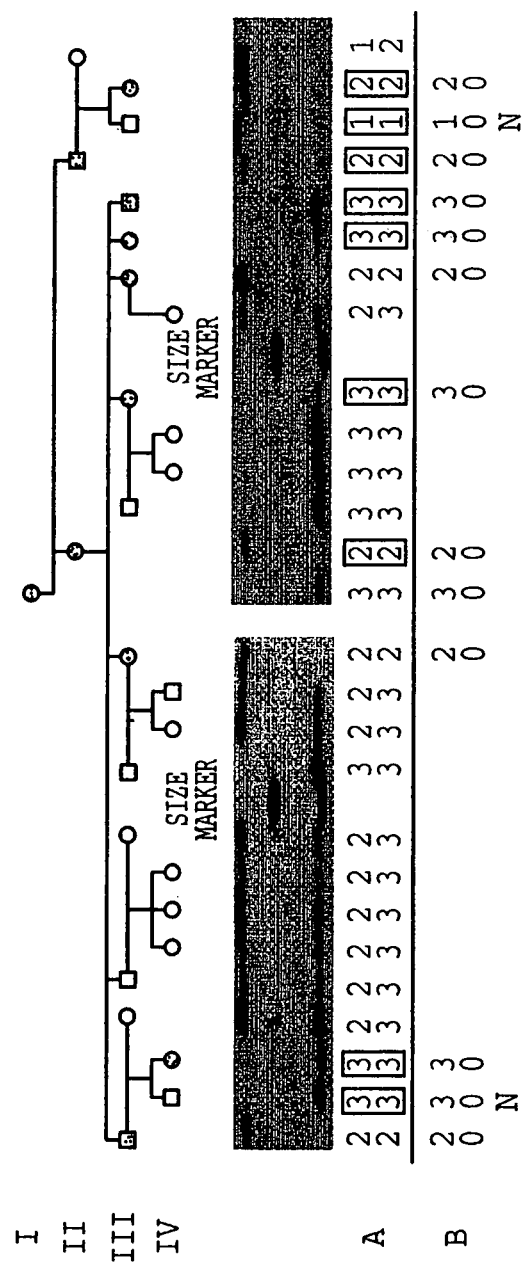
FIG. 1. Southern blot of kindred 1547 (showing 4 generations listed as I, II, I and IV) genomic DNA cut with TaqI and probed with the VNTR marker D20S24 showing a null allele in affected individuals. Line A shows genotype disinheritances shown in boxes; line B shows corrected genotypes. The "N" indicates non-penetrant individuals.

SEQ ID NO:1 is the cDNA sequence for KCNQ2.
SEQ ID NO:2 is the amino acid sequence for KCNQ2.
SEQ ID NO:3 is the amino acid sequence for nKQT1.
SEQ ID NO:4 is the amino acid sequence for KCNQ1.
SEQ ID NO:5 is nucleotide sequence at the intron/exon junction of the 3' end of the intron interrupting the two exons which encode amino acid 544 of KCNQ2.
SEQ ID NO:6 is the cDNA sequence for KCNQ3.
SEQ ID NO:7 is the amino acid sequence for KCNQ3.
SEQ ID NOs:8-9 are primers used for somatic cell hybrid panel genotyping (Example 7).
SEQ ID NOs:10-11 are primers used for genotyping a chromosome 8 radiation hybrid panel (Example 8).
SEQ ID NOs:12-17 are primers used to perform RACE to obtain full length cDNA (Example 9).
SEQ ID NOs:18-19 are primers used to prepare a PCR fragment which identified an SSCP variant for KCNQ3.
SEQ ID NOs:20-21 are hypothetical nucleic acid sequences to demonstrate calculation of percent homology between two nucleic acids.
SEQ ID NOs:22-53 are primers for amplifying portions of KCNQ2.
SEQ ID NOs:54-87 are primers for amplifying portions of KCNQ3.
SEQ ID NO:88 is a partial mouse KCNQ2.
SEQ ID NO:89 is a partial mouse KCNQ2 encoded by SEQ ID NO:88.
SEQ ID NO:90 is a mouse KCNQ3.
SEQ ID NO:91 is the mouse KCNQ3 encoded by SEQ ID NO:90.
SEQ ID NO:92 is an alternative exon found in KCNQ3.
SEQ ID NOs:93-94 are primers based on mouse sequence to amplify 5' end of human KCNQ3.
SEQ ID NO:95 is a mutated human KCNQ2 with a GGGCC insertion after nucleotide 2736.
SEQ ID NO:96 is a mutated human KCNQ2 encoded by SEQ ID NO:95.
SEQ ID NOs:97-99 are primers for amplifying portions of KCNQ2.
SEQ ID NOs:100-114 are intron/exon sequence for KCNQ2 (FIGS. 7A-O).
SEQ ID NOs:115-129 are intron/exon sequence for KCNQ3 (FIGS. 8A-O).

DETAILED DESCRIPTION OF THE INVENTION

The present invention is directed to the determination that BFNC maps to the KCNQ2 gene and to the KCNQ3 gene and that molecular variants of these genes cause or are involved in the pathogenesis of BFNC, rolandic epilepsy and/or JME. More specifically, the present invention relates to mutations in the KCNQ2 gene and in the KCNQ3 gene and their use in the diagnosis of BFNC, rolandic epilepsy and JME. The present invention is further directed to methods of screening humans for the presence of KCNQ2 and/or KCNQ3 gene variants which cause BFNC, rolandic epilepsy and/or JME. Since these forms of epilepsy can now be detected earlier (i.e., before symptoms appear) and more definitively, better treatment options will be available in those individuals identified as having BFNC, rolandic epilepsy or JME. The present invention is also directed to methods for screening for drugs useful in treating or preventing BFNC, rolandic epilepsy or JME.

The present invention provides methods of screening the KCNQ2 and/or KCNQ3 gene to identify mutations. Such methods may further comprise the step of amplifying a portion of the KCNQ2 or KCNQ3 gene, and may further include a step of providing a set of polynucleotides which are primers for amplification of said portion of the KCNQ2 or KCNQ3 gene. The method is useful for identifying mutations for use in either diagnosis of or prognosis of BFNC, rolandic epilepsy and JME.

Benign Familial Neonatal Convulsion is an autosomal dominantly inherited disorder that causes epilepsy of the newborn infant. This idiopathic, generalized epilepsy typically has an onset of seizures on day two to four of life. Spontaneous remission of the seizures occurs between two to fifteen weeks (Ronen et al., 1993; Plouin, 1994; Hauser and Kurland, 1975). Seizures typically start with a tonic posture, ocular symptoms and other autonomic features which then often progress to clonic movements and motor automatisms. These neonates thrive normally between the seizures, and their neurologic examinations and later development indicate normal brain functioning (Ronen et al., 1993; Plouin, 1994; Hauser and Kurland, 1975). However, in spite of normal neurologic development, seizures recur later in life in approximately 16% of BFNC cases compared with a 2% cumulative lifetime risk of epilepsy in the general population (Ronen et al., 1993; Plouin, 1994; Hauser and Kurland, 1975).

Linkage analysis in a large kindred demonstrated that a gene responsible for BFNC maps to chromosome 20q13.3 close to the markers D20S20 and D20S19 (Leppert et al, 1989). Following the initial report, two centers confirmed linkage of BFNC to the same two genetic markers on chromosome 20, termed the EBN1 (epilepsy benign neonatal type 1) locus (Ryan et al., 1991; Malafosse et al., 1992). A more distal marker, D20S24, shows complete co-segregation with the BFNC phenotype in chromosome 20 linked families. Finding a distal flanking marker for the BFNC locus has not been successful probably because of its proximity to the telomere. This telomeric region is characterized by a high recombination rate between markers when compared to the physical distance (Steinlein et al., 1992). In fact, Steinlein et al. have demonstrated that the three markers D20S19, D20S20 and D20S24 are contained on the same 450 Mb Mlu I restriction fragment (Steinlein et al., 1992). All of the families in the present study for KCNQ2 show linkage to chromosome 20q markers with LOD scores of greater than 3.0 or have probands with clinical manifestations consistent with BFNC (Leppert et al., 1993). To find this gene responsible for BFNC, we narrowed the BFNC region with a sub-microscopic deletion in a single family, identified candidate cDNAs in this deletion, and then searched for mutations in other BFNC families.

A second chromosomal locus, EBN2, has also been identified for BFNC. Lewis et al. (1993) demonstrated linkage to markers on chromosome 8q24 in a single Hispanic family affected with BFNC. Evidence for this second locus was also reported in a Caucasian pedigree (Steinlein et al., 1995). The gene for EBN2, KCNQ3, has now been found and characterized as detailed in this disclosure.

Finally, the present invention is directed to a method for screening drug candidates to identify drugs useful for treating or preventing BFNC, rolandic epilepsy or JME. Drug screening is performed by expressing mutant KCNQ2 or mutant KCNQ3 in cells, such as oocytes, mammalian cells or transgenic animals, and assaying the effect of a drug candidate on the KCNQ2 or KCNQ3 potassium channel. The effect is compared to the KCNQ2 or KCNQ3 potassium channel activity obtained using the wild-type KCNQ2 or KCNQ3 gene.

Proof that the KCNQ2 and KCNQ3 genes are involved in causing BFNC, rolandic epilepsy and JME is obtained by finding sequences in DNA extracted from affected kindred members which create abnormal KCNQ2 or abnormal KCNQ3 gene products or abnormal levels of the gene products. Such susceptibility alleles will co-segregate with the disease in large kindreds. They will also be present at a much higher frequency in non-kindred individuals with epilepsy than in individuals in the general population. The key is to find mutations which are serious enough to cause obvious disruption to the normal function of the gene product. These mutations can take a number of forms. The most severe forms would be frame shift mutations or large deletions which would cause the gene to code for an abnormal protein or one which would significantly alter protein expression. Less severe disruptive mutations would include small in-frame deletions and nonconservative base pair substitutions which would have a significant effect on the protein produced, such as changes to or from a cysteine residue, from a basic to an acidic amino acid or vice versa, from a hydrophobic to hydrophilic amino acid or vice versa, or other mutations which would affect secondary or tertiary protein structure. Silent mutations or those resulting in conservative amino acid substitutions would not generally be expected to disrupt protein function.

According to the diagnostic and prognostic method of the present invention, alteration of the wild-type KCNQ2 or KCNQ3 gene is detected. In addition, the method can be performed by detecting the wild-type KCNQ2 or KCNQ3 gene and confirming the lack of a cause of epilepsy as a result of this locus. "Alteration of a wild-type gene" encompasses all forms of mutations including deletions, insertions and point mutations in the coding and noncoding regions. Deletions may be of the entire gene or of only a portion of the gene. Point mutations may result in stop codons, frameshift mutations or amino acid substitutions. Somatic mutations are those which occur only in certain tissues and are not inherited in the germline. Germline mutations can be found in any of a body's tissues and are inherited. Point mutational events may occur in regulatory regions, such as in the promoter of the gene, leading to loss or diminution of expression of the mRNA. Point mutations may also abolish proper RNA processing, leading to loss of expression of the KCNQ2 or KCNQ3 gene product, or to a decrease in mRNA stability or translation efficiency.

Useful diagnostic techniques include, but are not limited to fluorescent in situ hybridization (FISH), direct DNA sequencing, PFGE analysis, Southern blot analysis, single stranded conformation analysis (SSCA), RNase protection assay, allele-specific oligonucleotide (ASO), dot blot analysis, hybridization using nucleic acid modified with gold nanoparticles and PCR-SSCP, as discussed in detail further below. Also useful is the recently developed technique of DNA microchip technology.

The presence of BFNC, rolandic epilepsy or JME may be ascertained by testing any tissue of a human for mutations of the KCNQ2 or KCNQ3 gene. For example, a person who has inherited a germline KCNQ2 mutation would be prone to develop BFNC. This can be determined by testing DNA from any tissue of the person's body. Most simply, blood can be drawn and DNA extracted from the cells of the blood. In addition, prenatal diagnosis can be accomplished by testing fetal cells, placental cells or amniotic cells for mutations of the KCNQ2 or KCNQ3 gene. Alteration of a wild-type KCNQ2 or KCNQ3 allele, whether, for example, by point mutation or deletion, can be detected by any of the means discussed herein.

There are several methods that can be used to detect DNA sequence variation. Direct DNA sequencing, either manual sequencing or automated fluorescent sequencing can detect sequence variation. Another approach is the single-stranded conformation polymorphism assay (SSCP) (Orita et al., 1989). This method does not detect all sequence changes, especially if the DNA fragment size is greater than 200 bp, but can be optimized to detect most DNA sequence variation. The reduced detection sensitivity is a disadvantage, but the increased throughput possible with SSCP makes it an attractive, viable alternative to direct sequencing for mutation detection on a research basis. The fragments which have shifted mobility on SSCP gels are then sequenced to determine the exact nature of the DNA sequence variation. Other approaches based on the detection of mismatches between the two complementary DNA strands include clamped denaturing gel electrophoresis (CDGE) (Sheffield et al., 1991), heteroduplex analysis (HA) (White et al., 1992) and chemical mismatch cleavage (CMC) (Grompe et al., 1989). None of the methods described above will detect large deletions, duplications or insertions, nor will they detect a regulatory mutation which affects transcription or translation of the protein. Other methods which might detect these classes of mutations such as a protein truncation assay or the asymmetric assay, detect only specific types of mutations and would not detect missense mutations. A review of currently available methods of detecting DNA sequence variation can be found in a recent review by Grompe (1993). Once a mutation is known, an allele specific detection approach such as allele specific oligonucleotide (ASO) hybridization can be utilized to rapidly screen large numbers of other samples for that same mutation. Such a technique can utilize probes which are labeled with gold nanoparticles to yield a visual color result (Elghanian et al., 1997).

A rapid preliminary analysis to detect polymorphisms in DNA sequences can be performed by looking at a series of Southern blots of DNA cut with one or more restriction enzymes, preferably with a large number of restriction enzymes. Each blot contains a series of normal individuals and a series of BFNC, rolandic epilepsy or JME cases. Southern blots displaying hybridizing fragments differing in length from control DNA when probed with sequences near or including the KCNQ2 locus indicate a possible mutation. If restriction enzymes which produce very large restriction fragments are used, then pulsed field gel electrophoresis (PFGE) is employed.

Detection of point mutations may be accomplished by molecular cloning of the KCNQ2 or KCNQ3 allele and sequencing the allele using techniques well known in the art. Also, the gene or portions of the gene may be amplified, e.g., by PCR or other amplification technique, and the amplified gene or amplified portions of the gene may be sequenced.

There are six well known methods for a more complete, yet still indirect, test for confirming the presence of a susceptibility allele: 1) single stranded conformation analysis (SSCP) (Orita et al., 1989); 2) denaturing gradient gel electrophoresis (DGGE) (Wartell et al., 1990; Sheffield et al., 1989); 3) RNase protection assays (Finkelstein et al., 1990; Kinszler et al., 1991); 4) allele-specific oligonucleotides (ASOs) (Conner et al., 1983); 5) the use of proteins which recognize nucleotide mismatches, such as the E. coli mutS protein (Modrich, 1991); and 6) allele-specific PCR (Ruano and Kidd, 1989). For allele-specific PCR, primers are used which hybridize at their 3 ends to a particular KCNQ2 or KCNQ3 mutation. If the particular mutation is not present, an amplification product is not observed. Amplification Refractory Mutation System (ARMS) can also be used, as disclosed in European Patent Application Publication No. 0332435 and in Newton et al., 1989. Insertions and deletions of genes can also be detected by cloning, sequencing and amplification. In addition, restriction fragment length polymorphism (RFLP) probes for the gene or surrounding marker genes can be used to score alteration of an allele or an insertion in a polymorphic fragment. Such a method is particularly useful for screening relatives of an affected individual for the presence of the mutation found in that individual. Other techniques for detecting insertions and deletions as known in the art can be used.

In the first three methods (SSCP, DGGE and RNase protection assay), a new electrophoretic band appears. SSCP detects a band which migrates differentially because the sequence change causes a difference in single-strand, intramolecular base pairing. RNase protection involves cleavage of the mutant polynucleotide into two or more smaller fragments. DGGE detects differences in migration rates of mutant sequences compared to wild-type sequences, using a denaturing gradient gel. In an allele-specific oligonucleotide assay, an oligonucleotide is designed which detects a specific sequence, and the assay is performed by detecting the presence or absence of a hybridization signal. In the mutS assay, the protein binds only to sequences that contain a nucleotide mismatch in a heteroduplex between mutant and wild-type sequences.

Mismatches, according to the present invention, are hybridized nucleic acid duplexes in which the two strands are not 100% complementary. Lack of total homology may be due to deletions, insertions, inversions or substitutions. Mismatch detection can be used to detect point mutations in the gene or in its mRNA product. While these techniques are less sensitive than sequencing, they are simpler to perform on a large number of samples. An example of a mismatch cleavage technique is the RNase protection method. In the practice of the present invention, the method involves the use of a labeled riboprobe which is complementary to the human wild-type KCNQ2 or KCNQ3 gene coding sequence. The riboprobe and either mRNA or DNA isolated from the person are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full length duplex RNA for the riboprobe and the mRNA or DNA. The riboprobe need not be the full length of the mRNA or gene but can be a segment of either. If the riboprobe comprises only a segment of the mRNA or gene, it will be desirable to use a number of these probes to screen the whole mRNA sequence for mismatches.

In similar fashion, DNA probes can be used to detect mismatches, through enzymatic or chemical cleavage. See, e.g., Cotton et al., 1988; Shenk et al., 1975; Novack et al., 1986. Alternatively, mismatches can be detected by shifts in the electrophoretic mobility of mismatched duplexes relative to matched duplexes. See, e.g., Cariello, 1988. With either riboprobes or DNA probes, the cellular mRNA or DNA which might contain a mutation can be amplified using PCR (see below) before hybridization. Changes in DNA of the KCNQ2 or KCNQ3 gene can also be detected using Southern hybridization, especially if the changes are gross rearrangements, such as deletions and insertions.

DNA sequences of the KCNQ2 or KCNQ3 gene which have been amplified by use of PCR may also be screened using allele-specific probes. These probes are nucleic acid oligomers, each of which contains a region of the gene sequence harboring a known mutation. For example, one oligomer may be about 30 nucleotides in length, corresponding to a portion of the gene sequence. By use of a battery of such allele-specific probes, PCR amplification products can be screened to identify the presence of a previously identified mutation in the gene. Hybridization of allele-specific probes with amplified KCNQ2 or KCNQ3 sequences can be performed, for example, on a nylon filter. Hybridization to a particular probe under high stringency hybridization conditions indicates the presence of the same mutation in the tissue as in the allele-specific probe. High stringency hybridization conditions are defined as those conditions which allow an 8 basepair stretch of a first nucleic acid (a probe) to bind to a 100% perfectly complementary 8 basepair stretch of nucleic acid while simultaneously preventing binding of said first nucleic acid to a nucleic acid which is not 100% complementary, i.e., binding will not occur if there is a mismatch.

The newly developed technique of nucleic acid analysis via microchip technology is also applicable to the present invention. In this technique, literally thousands of distinct oligonucleotide probes are built up in an array on a silicon chip. Nucleic acid to be analyzed is fluorescently labeled and hybridized to the probes on the chip. It is also possible to study nucleic acid-protein interactions using these nucleic acid microchips. Using this technique one can determine the presence of mutations or even sequence the nucleic acid being analyzed or one can measure expression levels of a gene of interest. The method is one of parallel processing of many, even thousands, of probes at once and can tremendously increase the rate of analysis. Several papers have been published which use this technique. Some of these are Hacia et al., 1996; Shoemaker et al., 1996; Chee et al., 1996; Lockhart et al., 1996; DeRisi et al., 1996; Lipshutz et al., 1995. This method has already been used to screen people for mutations in the breast cancer gene BRCA1 (Hacia et al., 1996). This new technology has been reviewed in a news article in Chemical and Engineering News (Borman, 1996) and been the subject of an editorial (Nature Genetics, 1996). Also see Fodor (1997).

The most definitive test for mutations in a candidate locus is to directly compare genomic KCNQ2 or KCNQ3 sequences from patients with those from a control population. Alternatively, one could sequence messenger RNA after amplification, e.g., by PCR, thereby eliminating the necessity of determining the exon structure of the candidate gene.

Mutations from patients falling outside the coding region of KCNQ2 or KCNQ3 can be detected by examining the non-coding regions, such as introns and regulatory sequences near or within the genes. An early indication that mutations in noncoding regions are important may come from Northern blot experiments that reveal messenger RNA molecules of abnormal size or abundance in patients as compared to control individuals.

Alteration of KCNQ2 or KCNQ3 mRNA expression can be detected by any techniques known in the art. These include Northern blot analysis, PCR amplification and RNase protection. Diminished mRNA expression indicates an alteration of the wild-type gene. Alteration of wild-type genes can also be detected by screening for alteration of wild-type KCNQ2 or KCNQ3 protein. For example, monoclonal antibodies immunoreactive with KCNQ2 or KCNQ3 can be used to screen a tissue. Lack of cognate antigen would indicate a mutation. Antibodies specific for products of mutant alleles could also be used to detect mutant gene product. Such immunological assays can be done in any convenient formats known in the art. These include Western blots, immunohistochemical assays and ELISA assays. Any means for detecting an altered KCNQ2 or KCNQ3 protein can be used to detect alteration of the wild-type KCNQ2 or KCNQ3 gene. Functional assays, such as protein binding determinations, can be used. In addition, assays can be used which detect KCNQ2 or KCNQ3 biochemical function. Finding a mutant KCNQ2 or KCNQ3 gene product indicates alteration of a wild-type KCNQ2 or KCNQ3 gene.

A mutant KCNQ2 or KCNQ3 gene or gene product can also be detected in other human body samples, such as serum, stool, urine and sputum. The same techniques discussed above for detection of mutant genes or gene products in tissues can be applied to other body samples. By screening such body samples, a simple early diagnosis can be achieved for BFNC, rolandic epilepsy or JME.

The primer pairs of the present invention are useful for determination of the nucleotide sequence of a particular KCNQ2 or KCNQ3 allele using PCR. The pairs of single-stranded DNA primers for KCNQ2 or KCNQ3 can be annealed to sequences within or surrounding the KCNQ2 gene on chromosome 20 or KCNQ3 gene on chromosome 8 in order to prime amplifying DNA synthesis of the gene itself. A complete set of these primers allows synthesis of all of the nucleotides of the gene coding sequences, i.e., the exons. The set of primers preferably allows synthesis of both intron and exon sequences. Allele-specific primers can also be used. Such primers anneal only to particular KCNQ2 or KCNQ3 mutant alleles, and thus will only amplify a product in the presence of the mutant allele as a template.

In order to facilitate subsequent cloning of amplified sequences, primers may have restriction enzyme site sequences appended to their 5' ends. Thus, all nucleotides of the primers are derived from KCNQ2 or KCNQ3 sequence or sequences adjacent to KCNQ2 or KCNQ3, except for the few nucleotides necessary to form a restriction enzyme site. Such enzymes and sites are well known in the art. The primers themselves can be synthesized using techniques which are well known in the art. Generally, the primers can be made using oligonucleotide synthesizing machines which are commercially available. Given the sequence of KCNQ2 and KCNQ3, design of particular primers is well within the skill of the art.

The nucleic acid probes provided by the present invention are useful for a number of purposes. They can be used in Southern hybridization to genomic DNA and in the RNase protection method for detecting point mutations already discussed above. The probes can be used to detect PCR amplification products. They may also be used to detect mismatches with the KCNQ2 or KCNQ3 gene or mRNA using other techniques.

It has been discovered that most individuals with the wild-type KCNQ2 and KCNQ3 genes do not have BFNC. However, mutations which interfere with the function of the KCNQ2 or KCNQ3 gene product are involved in the pathogenesis of BFNC. Thus, the presence of an altered (or a mutant) KCNQ2 or KCNQ3 gene which produces a protein having a loss of function, or altered function, directly causes BFNC which increases the risk of seizures. In order to detect a KCNQ2 or KCNQ3 gene mutation, a biological sample is prepared and analyzed for a difference between the sequence of the allele being analyzed and the sequence of the wild-type allele. Mutant KCNQ2 or KCNQ3 alleles can be initially identified by any of the techniques described above. The mutant alleles are then sequenced to identify the specific mutation of the particular mutant allele. Alternatively, mutant alleles can be initially identified by identifying mutant (altered) proteins, using conventional techniques. The mutant alleles are then sequenced to identify the specific mutation for each allele. The mutations, especially those which lead to an altered function of the protein, are then used for the diagnostic and prognostic methods of the present invention.

This is the first human idiopathic generalized epilepsy for which a $K^+$ channel has been implicated. BFNC is considered to be a true idiopathic epilepsy without the degenerative characteristics associated with other syndromes such as progressive myoclonus epilepsy of the Unverricht-Lundborg type. It is not surprising, therefore, that an alteration in a gene which directly regulates neuronal excitability causes this epileptic disorder. Voltage-gated potassium channels repolarize neuronal membranes that have been depolarized by $Na^+$ and $Ca^{++}$ voltage-gated ion channels. $K^+$ channels are also thought to repolarize neuronal membranes following activation of excitatory neurotransmitter ion channels, including glutamate and acetylcholine. In the presence of mutant KCNQ2 or KCNQ3 channels with reduced function, excitatory ligand and voltage-gated channels that are activated would remain open for a longer duration (Keating and Sanguinetti, 1996; Meldrum, 1995; McNamara, 1994). Such unchecked activity of excitatory systems could lead to an epileptic phenotype. Electrophysiologic analysis of the mutant KCNQ2 and KCNQ3 channels will shed light on how the mutations identified in the current study produce an epileptic phenotype. It is likely that KCNQ2 and KCNQ3 will have biophysical properties similar to the delayed rectifier KCNQ1 channel. KCNQ1 alpha subunits coassemble with minK beta subunits to form heteromultimeric $I_{Ks}$ channels in the heart (Sanguinetti et al., 1996). It is possible that KCNQ2 and KCNQ3 subunits coassemble with minK-like beta subunits in the brain. This interaction may also alter the gating properties of the resulting heteromultimeric channel as is the case for KCNQ1.

Mutations in $K^+$ channels have been associated with epilepsy in only one other case, the weaver mouse, where a single missense mutation in the GIRK2 gene produces spontaneous seizures (Patil et al., 1995; Signorini et al., 1997). Mutations in $K^+$ channels have been implicated in other human disorders such as the Long QT syndrome on chromosome 11 and ataxia/myokymia on chromosome 12 (Wang et al., 1996; Neyroud et al., 1997; Russell et al., 1996; Chandy and Gutman, 1995; Browne et al., 1994). Long QT is associated with four loci, two of which are the $K^+$ channel genes HERG and KCNQ1. In KCNQ1, mutational hot spots have been identified in the pore and S6 domains where missense mutations in these regions account for a majority of the disease causing mutations in LQT (Russell et al., 1996; Wang et al., 1996).

Since the first publications of the finding of the KCNQ2 and KCNQ3 genes, there have been several more publications. Iannotti et al. (1998) found that there are two splice variants of KCNQ2. These are a long and a short form which differ in their C-termini. The long form is expressed exclusively in human brain (adult and fetal), where it is restricted to neuronal rather than glial cells. The short form is expressed weakly in adult brain but is prominent in fetal brain and testes (Iannotti et al., 1998). Gribkoff et al. (1998) cloned and expressed a mouse homologue of KCNQ2 in *Xenopus* oocytes and performed two-electrode voltage clamp studies. Dworetzky et al. (1998) cloned a mouse homologue of KCNQ2 and also noted alternative splice variants in the 3' region of the gene. They also performed Northern blots and measured polarization in *Xenopus* oocytes expressing the mouse gene. Yang et al. (1998) have also cloned and expressed the human KCNQ2 and KCNQ3. They note that the encoded proteins act like KCNQ1 in eliciting voltage-gated, rapidly activating $K^+$-selective currents, but in contrast to KCNQ1, the KCNQ2 and KCNQ3 protein induced currents are not augmented by coexpression of KCNE1. However, coexpression of KCNQ2 and KCNQ3 results in a substantial synergistic increase in current amplitude (Yang et al., 1998). Finally, Biervert et al. (1998) cloned human KCNQ2 and expressed it in *Xenopus* oocytes.

DEFINITIONS

The present invention employs the following definitions.

"Amplification of Polynucleotides" utilizes methods such as the polymerase chain reaction (PCR), ligation amplification (or ligase chain reaction, LCR) and amplification methods based on the use of Q-beta replicase. Also useful are strand displacement amplification (SDA), thermophilic SDA, and nucleic acid sequence based amplification (3SR or NASBA). These methods are well known and widely practiced in the art. See, e.g., U.S. Pat. Nos. 4,683,195 and 4,683,202 and Innis et al., 1990 (for PCR); Wu and Wallace, 1989 (for LCR); U.S. Pat. Nos. 5,270,184 and 5,455,166 and Walker et al., 1992 (for SDA); Spargo et al., 1996 (for thermophilic SDA) and U.S. Pat. No. 5,409,818, Fahy et al., 1991 and Compton, 1991 for 3SR and NASBA. Reagents and hardware for conducting PCR are commercially available. Primers useful to amplify sequences from the KCNQ2 or KCNQ3 region are preferably complementary to, and hybridize specifically to sequences in the KCNQ2 or KCNQ3 region or in regions that flank a target region therein. KCNQ2 or KCNQ3 sequences generated by amplification may be sequenced directly. Alternatively, but less desirably, the amplified sequence(s) may be cloned prior to sequence analysis. A method for the direct cloning and sequence analysis of enzymatically amplified genomic segments has been described by Scharf et al., 1986.

"Analyte polynucleotide" and "analyte strand" refer to a single- or double-stranded polynucleotide which is suspected of containing a target sequence, and which may be present in a variety of types of samples, including biological samples.

"Antibodies." The present invention also provides polyclonal and/or monoclonal antibodies and fragments thereof, and immunologic binding equivalents thereof, which are capable of specifically binding to the KCNQ2 or KCNQ3 polypeptide and fragments thereof or to polynucleotide sequences from the KCNQ2 KCNQ3 region. The term "antibody" is used both to refer to a homogeneous molecular entity, or a mixture such as a serum product made up of a plurality of different molecular entities. Polypeptides may be prepared synthetically in a peptide synthesizer and coupled to a carrier molecule (e.g., keyhole limpet hemocyanin) and injected over several months into rabbits. Rabbit sera is tested for immunoreactivity to the KCNQ2 or KCNQ3 polypeptide or fragment. Monoclonal antibodies may be made by injecting mice with the protein polypeptides, fusion proteins or fragments thereof. Monoclonal antibodies will be screened by ELISA and tested for specific immunoreactivity with KCNQ2 or KCNQ3 polypeptide or fragments thereof. See, Harlow and Lane, 1988. These antibodies will be useful in assays as well as pharmaceuticals.

Once a sufficient quantity of desired polypeptide has been obtained, it may be used for various purposes. A typical use is the production of antibodies specific for binding. These antibodies may be either polyclonal or monoclonal, and may be produced by in vitro or in vivo techniques well known in the art. For production of polyclonal antibodies, an appropriate target immune system, typically mouse or rabbit, is selected. Substantially purified antigen is presented to the immune system in a fashion determined by methods appropriate for the animal and by other parameters well known to immunologists. Typical sites for injection are in footpads, intramuscularly, intraperitoneally, or intradermally. Of course, other species may be substituted for mouse or rabbit. Polyclonal antibodies are then purified using techniques known in the art, adjusted for the desired specificity.

An immunological response is usually assayed with an immunoassay. Normally, such immunoassays involve some purification of a source of antigen, for example, that produced by the same cells and in the same fashion as the antigen. A variety of immunoassay methods are well known in the art. See, e.g., Harlow and Lane, 1988, or Goding, 1986.

Monoclonal antibodies with affinities of $10^{-8}$ $M^{-1}$ or preferably $10^{-9}$ to $10^{-10}$ $M^{-1}$ or stronger will typically be made by standard procedures as described, e.g., in Harlow and Lane, 1988 or Goding, 1986. Briefly, appropriate animals will be selected and the desired immunization protocol followed. After the appropriate period of time, the spleens of such animals are excised and individual spleen cells fused, typically, to immortalized myeloma cells under appropriate selection conditions. Thereafter, the cells are clonally separated and the supernatants of each clone tested for their production of an appropriate antibody specific for the desired region of the antigen.

Other suitable techniques involve in vitro exposure of lymphocytes to the antigenic polypeptides, or alternatively, to selection of libraries of antibodies in phage or similar vectors. See Huse et al., 1989. The polypeptides and antibodies of the present invention may be used with or without modification. Frequently, polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent agents, chemiluminescent agents, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced (see U.S. Pat. No. 4,816,567).

"Binding partner" refers to a molecule capable of binding a ligand molecule with high specificity, as for example, an antigen and an antigen-specific antibody or an enzyme and its inhibitor. In general, the specific binding partners must bind with sufficient affinity to immobilize the analyte copy/complementary strand duplex (in the case of polynucleotide hybridization) under the isolation conditions. Specific binding partners are known in the art and include, for example, biotin and avidin or streptavidin, IgG and protein A, the numerous, known receptor-ligand couples, and complementary polynucleotide strands. In the case of complementary polynucleotide binding partners, the partners are normally at least about 15 bases in length, and may be at least 40 bases in length. It is well recognized by those of skill in the art that lengths shorter than 15 (e.g., 8 bases), between 15 and 40, and greater than 40 bases may also be used. The polynucleotides may be composed of DNA, RNA, or synthetic nucleotide analogs. Further binding partners can be identified using, e.g., the two-hybrid yeast screening assay as described herein.

A "biological sample" refers to a sample of tissue or fluid suspected of containing an analyte polynucleotide or polypeptide from an individual including, but not limited to, e.g., plasma, serum, spinal fluid, lymph fluid, the external sections of the skin, respiratory, intestinal, and genitourinary tracts, tears, saliva, blood cells, tumors, organs, tissue and samples of in vitro cell culture constituents.

"Encode". A polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

"Isolated" or "substantially pure". An "isolated" or "substantially pure" nucleic acid (e.g., an RNA, DNA or a mixed polymer) is one which is substantially separated from other cellular components which naturally accompany a native human sequence or protein, e.g., ribosomes, polymerases, many other human genome sequences and proteins. The term embraces a nucleic acid sequence or protein which has been removed from its naturally occurring environment, and includes recombinant or cloned DNA isolates and chemically synthesized analogs or analogs biologically synthesized by heterologous systems.

"KCNQ2 Allele" refers to normal alleles of the KCNQ2 locus as well as alleles of KCNQ2 carrying variations that cause BFNC and/or rolandic epilepsy.

"KCNQ3 Allele" refers to normal alleles of the KCNQ3 locus as well as alleles of KCNQ3 carrying variations that cause BFNC and/or JME.

"KCNQ2 Locus", "KCNQ2 Gene", "KCNQ2 Nucleic Acids" or "KCNQ2 Polynucleotide" each refer to polynucleotides, all of which are in the KCNQ2 region, that are likely to be expressed in normal tissue, certain alleles of which result in BFNC and/or rolandic epilepsy. The KCNQ2 locus is intended to include coding sequences, intervening sequences and regulatory elements controlling transcription and/or translation. The KCNQ2 locus is intended to include all allelic variations of the DNA sequence.

"KCNQ3 Locus", "KCNQ3 Gene", "KCNQ3 Nucleic Acids" or "KCNQ3 Polynucleotide" each refer to polynucleotides, all of which are in the KCNQ3 region, that are likely to be expressed in normal tissue, certain alleles of which result in BFNC and/or JME. The KCNQ3 locus is intended to include coding sequences, intervening sequences and regulatory elements controlling transcription and/or translation. The KCNQ3 locus is intended to include all allelic variations of the DNA sequence.

These terms, when applied to a nucleic acid, refer to a nucleic acid which encodes a human KCNQ2 or KCNQ3 polypeptide, fragment, homolog or variant, including, e.g., protein fusions or deletions. The nucleic acids of the present invention will possess a sequence which is either derived from, or substantially similar to a natural KCNQ2- or KCNQ3-encoding gene or one having substantial homology with a natural KCNQ2- or KCNQ3-encoding gene or a portion thereof.

The KCNQ2 or KCNQ3 gene or nucleic acid includes normal alleles of the KCNQ2 or KCNQ3 gene, respectively, including silent alleles having no effect on the amino acid sequence of the KCNQ2 or KCNQ3 polypeptide as well as alleles leading to amino acid sequence variants of the KCNQ2 or KCNQ3 polypeptide that do not substantially affect its function. These terms also include alleles having one or more mutations which adversely affect the function of the KCNQ2 or KCNQ3 polypeptide. A mutation may be a change in the KCNQ2 or KCNQ3 nucleic acid sequence which produces a deleterious change in the amino acid sequence of the KCNQ2 or KCNQ3 polypeptide, resulting in partial or complete loss of KCNQ2 or KCNQ3 function, respectively, or may be a change in the nucleic acid sequence which results in the loss of effective KCNQ2 or KCNQ3 expression or the production of aberrant forms of the KCNQ2 or KCNQ3 polypeptide.

The KCNQ2 or KCNQ3 nucleic acid may be that shown in SEQ ID NO:1 (KCNQ2) or SEQ ID NO:6 (KCNQ3) or it may be an allele as described above or a variant or derivative differing from that shown by a change which is one or more of addition, insertion, deletion and substitution of one or more nucleotides of the sequence shown. Changes to the nucleotide sequence may result in an amino acid change at the protein level, or not, as determined by the genetic code.

Thus, nucleic acid according to the present invention may include a sequence different from the sequence shown in SEQ ID NOs:1 and 6 yet encode a polypeptide with the same amino acid sequence as shown in SEQ ID NOs:2 (KCNQ2) and 7 (KCNQ3). That is, nucleic acids of the present invention include sequences which are degenerate as a result of the genetic code. On the other hand, the encoded polypeptide may comprise an amino acid sequence which differs by one or more amino acid residues from the amino acid sequence shown in SEQ ID NOs:2 and 7. Nucleic acid encoding a polypeptide which is an amino acid sequence variant, derivative or allele of the amino acid sequence shown in SEQ ID NOs:2 and 7 is also provided by the present invention.

The KCNQ2 or KCNQ3 gene, respectively, also refers to (a) any DNA sequence that (i) hybridizes to the complement of the DNA sequences that encode the amino acid sequence set forth in SEQ ID NO:1 or SEQ ID NO:6 under highly stringent conditions (Ausubel et al., 1992) and (ii) encodes a gene product functionally equivalent to KCNQ2 or KCNQ3, or (b) any DNA sequence that (i) hybridizes to the complement of the DNA sequences that encode the amino acid sequence set forth in SEQ ID NO:2 or SEQ ID NO:7 under less stringent conditions, such as moderately stringent conditions (Ausubel et al., 1992) and (ii) encodes a gene product functionally equivalent to KCNQ2 or KCNQ3. The invention also includes nucleic acid molecules that are the complements of the sequences described herein.

The polynucleotide compositions of this invention include RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

The present invention provides recombinant nucleic acids comprising all or part of the KCNQ2 or KCNQ3 region. The recombinant construct may be capable of replicating autonomously in a host cell. Alternatively, the recombinant construct may become integrated into the chromosomal DNA of the host cell. Such a recombinant polynucleotide comprises a polynucleotide of genomic, cDNA, semi-synthetic, or synthetic origin which, by virtue of its origin or manipulation, 1) is not associated with all or a portion of a polynucleotide with which it is associated in nature; 2) is linked to a polynucleotide other than that to which it is linked in nature; or 3) does not occur in nature. Where nucleic acid according to the invention includes RNA, reference to the sequence shown should be construed as reference to the RNA equivalent, with U substituted for T.

Therefore, recombinant nucleic acids comprising sequences otherwise not naturally occurring are provided by this invention. Although the wild-type sequence may be employed, it will often be altered, e.g., by deletion, substitution or insertion. cDNA or genomic libraries of various types may be screened as natural sources of the nucleic acids of the present invention, or such nucleic acids may be provided by amplification of sequences resident in genomic DNA or other natural sources, e.g., by PCR. The choice of cDNA libraries normally corresponds to a tissue source which is abundant in mRNA for the desired proteins. Phage libraries are normally preferred, but other types of libraries may be used. Clones of a library are spread onto plates, transferred to a substrate for screening, denatured and probed for the presence of desired sequences.

The DNA sequences used in this invention will usually comprise at least about five codons (15 nucleotides), more usually at least about 7-15 codons, and most preferably, at least about 35 codons. One or more introns may also be present. This number of nucleotides is usually about the minimal length required for a successful probe that would hybridize specifically with a KCNQ2- or KCNQ3-encoding sequence. In this context, oligomers of as low as 8 nucleotides, more generally 8-17 nucleotides, can be used for probes, especially in connection with chip technology.

Techniques for nucleic acid manipulation are described generally, for example, in Sambrook et al., 1989 or Ausubel et al., 1992. Reagents useful in applying such techniques, such as restriction enzymes and the like, are widely known in the art and commercially available from such vendors as New England BioLabs, Boehringer Mannheim, Amersham, Promega, U.S. Biochemicals, New England Nuclear, and a number of other sources. The recombinant nucleic acid sequences used to produce fusion proteins of the present invention may be derived from natural or synthetic sequences. Many natural gene sequences are obtainable from various cDNA or from genomic libraries using appropriate probes. See, GenBank, National Institutes of Health.

As used herein, a "portion" of the KCNQ2 or KCNQ3 locus or region or allele is defined as having a minimal size of at least about eight nucleotides, or preferably about 15 nucleotides, or more preferably at least about 25 nucleotides, and may have a minimal size of at least about 40 nucleotides. This definition includes all sizes in the range of 8-40 nucleotides as well as greater than 40 nucleotides. Thus, this definition includes nucleic acids of 8, 12, 15, 20, 25, 40, 60, 80, 100, 200, 300, 400, 500 nucleotides, or nucleic acids having any number of nucleotides within these ranges of values (e.g., 9, 10, 11, 16, 23, 30, 38, 50, 72, 121, etc., nucleotides), or nucleic acids having more than 500 nucleotides. The present invention includes all novel nucleic acids having at least 8 nucleotides derived from SEQ ID NO:1 or SEQ ID NO:6, its complement or functionally equivalent nucleic acid sequences. The present invention does not include nucleic acids which exist in the prior art. That is, the present invention includes all nucleic acids having at least 8 nucleotides derived from SEQ ID NO:1 or SEQ ID NO:6 with the proviso that it does not include nucleic acids existing in the prior art.

"KCNQ2 protein" or "KCNQ2 polypeptide" refers to a protein or polypeptide encoded by the KCNQ2 locus, variants or fragments thereof. The term "polypeptide" refers to a polymer of amino acids and its equivalent and does not refer to a specific length of the product; thus, peptides, oligopeptides and proteins are included within the definition of a polypeptide. This term also does not refer to, or exclude modifications of the polypeptide, for example, glycosylations, acetylations, phosphorylations, and the like. Included within the definition are, for example, polypeptides containing one or more analogs of an amino acid (including, for example, unnatural amino acids, etc.), polypeptides with substituted linkages as well as other modifications known in the art, both naturally and non-naturally occurring. Ordinarily, such polypeptides will be at least about 50% homologous to the native KCNQ2 sequence, preferably in excess of about 90%, and more preferably at least about 95% homologous. Also included are proteins encoded by DNA which hybridize under high or low stringency conditions, to KCNQ2-encoding nucleic acids and closely related polypeptides or proteins retrieved by antisera to the KCNQ2 protein(s).

"KCNQ3 protein" or "KCNQ3 polypeptide" refers to a protein or polypeptide encoded by the KCNQ3 locus, variants or fragments thereof. The term "polypeptide" refers to a polymer of amino acids and its equivalent and does not refer to a specific length of the product; thus, peptides, oligopeptides and proteins are included within the definition of a polypeptide. This term also does not refer to, or exclude modifications of the polypeptide, for example, glycosylations, acetylations, phosphorylations, and the like. Included within the definition are, for example, polypeptides containing one or more analogs of an amino acid (including, for example, unnatural amino acids, etc.), polypeptides with substituted linkages as well as other modifications known in the art, both naturally and non-naturally occurring. Ordinarily, such polypeptides will be at least about 50% homologous to the native KCNQ3 sequence, preferably in excess of about 90%, and more preferably at least about 95% homologous. Also included are proteins encoded by DNA which hybridize under high or low stringency conditions, to KCNQ3-encoding nucleic acids and closely related polypeptides or proteins retrieved by antisera to the KCNQ3 protein(s).

The KCNQ2 or KCNQ3 polypeptide may be that shown in SEQ ID NO:2 or SEQ ID NO:7 which may be in isolated and/or purified form, free or substantially free of material with which it is naturally associated. The polypeptide may, if produced by expression in a prokaryotic cell or produced synthetically, lack native post-translational processing, such as glycosylation. Alternatively, the present invention is also directed to polypeptides which are sequence variants, alleles or derivatives of the KCNQ2 or KCNQ3 polypeptide. Such polypeptides may have an amino acid sequence which differs from that set forth in SEQ ID NO:2 or SEQ ID NO:7 by one or more of addition, substitution, deletion or insertion of one or more amino acids. Preferred such polypeptides have KCNQ2 or KCNQ3 function.

Substitutional variants typically contain the exchange of one amino acid for another at one or more sites within the protein, and may be designed to modulate one or more properties of the polypeptide, such as stability against proteolytic cleavage, without the loss of other functions or properties. Amino acid substitutions may be made on the basis of similarity in polarity, charge, solubility, hydrophobicity, hydrophilicity, and/or the amphipathic nature of the residues involved. Preferred substitutions are ones which are conservative, that is, one amino acid is replaced with one of similar shape and charge. Conservative substitutions are well known in the art and typically include substitutions within the following groups: glycine, alanine; valine, isoleucine, leucine; aspartic acid, glutamic acid; asparagine, glutamine; serine, threonine; lysine, arginine; and tyrosine, phenylalanine.

Certain amino acids may be substituted for other amino acids in a protein structure without appreciable loss of interactive binding capacity with structures such as, for example, antigen-binding regions of antibodies or binding sites on substrate molecules or binding sites on proteins interacting with the KCNQ2 or KCNQ3 polypeptide. Since it is the interactive capacity and nature of a protein which defines that protein's biological functional activity, certain amino acid substitutions can be made in a protein sequence, and its underlying DNA coding sequence, and nevertheless obtain a protein with like properties. In making such changes, the hydropathic index of amino acids may be considered. The importance of the hydrophobic amino acid index in conferring interactive biological function on a protein is generally understood in the art (Kyte and Doolittle, 1982). Alternatively, the substitution of like amino acids can be made effectively on the basis of hydrophilicity. The importance of hydrophilicity in conferring interactive biological function of a protein is generally understood in the art (U.S. Pat. No. 4,554,101). The use of the hydrophobic index or hydrophilicity in designing polypeptides is further discussed in U.S. Pat. No. 5,691,198.

The length of polypeptide sequences compared for homology will generally be at least about 16 amino acids, usually at least about 20 residues, more usually at least about 24 residues, typically at least about 28 residues, and preferably more than about 35 residues.

"Operably linked" refers to a juxtaposition wherein the components so described are in a relationship permitting them to function in their intended manner. For instance, a promoter is operably linked to a coding sequence if the promoter affects its transcription or expression.

The term peptide mimetic or mimetic is intended to refer to a substance which has the essential biological activity of the KCNQ2 or KCNQ3 polypeptide. A peptide mimetic may be a peptide-containing molecule that mimics elements of protein secondary structure (Johnson et al., 1993). The underlying rationale behind the use of peptide mimetics is that the peptide backbone of proteins exists chiefly to orient amino acid side chains in such a way as to facilitate molecular interactions, such as those of antibody and antigen, enzyme and substrate or scaffolding proteins. A peptide mimetic is designed to permit molecular interactions similar to the natural molecule. A mimetic may not be a peptide at all, but it will retain the essential biological activity of natural KCNQ2 or KCNQ3 polypeptide.

"Probes". Polynucleotide polymorphisms associated with KCNQ2 or KCNQ3 alleles which predispose to BFNC, rolandic epilepsy or JME are detected by hybridization with a polynucleotide probe which forms a stable hybrid with that of the target sequence, under highly stringent to moderately stringent hybridization and wash conditions. If it is expected that the probes will be perfectly complementary to the target sequence, high stringency conditions will be used. Hybridization stringency may be lessened if some mismatching is expected, for example, if variants are expected with the result that the probe will not be completely complementary. Conditions are chosen which rule out nonspecific/adventitious bindings, that is, which minimize noise. (It should be noted that throughout this disclosure, if it is simply stated that "stringent" conditions are used that is meant to be read as "high stringency" conditions are used.) Since such indications identify neutral DNA polymorphisms as well as mutations, these indications need further analysis to demonstrate detection of a KCNQ2 or KCNQ3 susceptibility allele.

Probes for KCNQ2 alleles may be derived from the sequences of the KCNQ2 region, its cDNA, functionally equivalent sequences, or the complements thereof. Probes for KCNQ3 alleles may be derived from the sequences of the KCNQ3 region, its cDNA, functionally equivalent sequences, or the complements thereof. The probes may be of any suitable length, which span all or a portion of the KCNQ2 or KCNQ3 region, and which allow specific hybridization to the region. If the target sequence contains a sequence identical to that of the probe, the probes may be short, e.g., in the range of about 8-30 base pairs, since the hybrid will be relatively stable under even highly stringent conditions. If some degree of mismatch is expected with the probe, i.e., if it is suspected that the probe will hybridize to a variant region, a longer probe may be employed which hybridizes to the target sequence with the requisite specificity.

The probes will include an isolated polynucleotide attached to a label or reporter molecule and may be used to isolate other polynucleotide sequences, having sequence similarity by standard methods. For techniques for preparing and labeling probes see, e.g., Sambrook et al., 1989 or Ausubel et al., 1992. Other similar polynucleotides may be selected by using homologous polynucleotides. Alternatively, polynucleotides encoding these or similar polypeptides may be synthesized or selected by use of the redundancy in the genetic code. Various codon substitutions may be introduced, e.g., by silent changes (thereby producing various restriction sites) or to optimize expression for a particular system. Mutations may be introduced to modify the properties of the polypeptide, perhaps to change the polypeptide degradation or turnover rate.

Probes comprising synthetic oligonucleotides or other polynucleotides of the present invention may be derived from naturally occurring or recombinant single- or double-stranded polynucleotides, or be chemically synthesized. Probes may also be labeled by nick translation, Klenow fill-in reaction, or other methods known in the art.

Portions of the polynucleotide sequence having at least about eight nucleotides, usually at least about 15 nucleotides, and fewer than about 9 kb, usually fewer than about 1.0 kb, from a polynucleotide sequence encoding KCNQ2 or KCNQ3 are preferred as probes. This definition therefore includes probes of sizes 8 nucleotides through 9000 nucleotides. Thus, this definition includes probes of 8, 12, 15, 20, 25, 40, 60, 80, 100, 200, 300, 400 or 500 nucleotides or probes having any number of nucleotides within these ranges of values (e.g., 9, 10, 11, 16, 23, 30, 38, 50, 72, 121, etc., nucleotides), or probes having more than 500 nucleotides. The probes may also be used to determine whether mRNA encoding KCNQ2 or KCNQ3 is present in a cell or tissue. The present invention includes all novel probes having at least 8 nucleotides derived from SEQ ID NO:1 or SEQ ID NO:6, its complement or functionally equivalent nucleic acid sequences. The present invention does not include probes which exist in the prior art. That is, the present invention includes all probes having at least 8 nucleotides derived from SEQ ID NO:1 or SEQ ID NO:6 with the proviso that they do not include probes existing in the prior art.

Similar considerations and nucleotide lengths are also applicable to primers which may be used for the amplification of all or part of the KCNQ2 or KCNQ3 gene. Thus, a definition for primers includes primers of 8, 12, 15, 20, 25, 40, 60, 80, 100, 200, 300, 400, 500 nucleotides, or primers having any number of nucleotides within these ranges of values (e.g., 9, 10, 11, 16, 23, 30, 38, 50, 72, 121, etc. nucleotides), or primers having more than 500 nucleotides, or any number of nucleotides between 500 and 9000. The primers may also be used to determine whether mRNA encoding KCNQ2 or KCNQ3 is present in a cell or tissue. The present invention includes all novel primers having at least 8 nucleotides derived from the KCNQ2 or KCNQ3 locus for amplifying the KCNQ2 or KCNQ3 gene, its complement or functionally equivalent nucleic acid sequences. The present invention does not include primers which exist in the prior art. That is, the present invention includes all primers having at least 8 nucleotides with the proviso that it does not include primers existing in the prior art.

"Protein modifications or fragments" are provided by the present invention for KCNQ2 or KCNQ3 polypeptides or fragments thereof which are substantially homologous to primary structural sequence but which include, e.g., in vivo or in vitro chemical and biochemical modifications or which incorporate unusual amino acids. Such modifications include, for example, acetylation, carboxylation, phosphorylation, glycosylation, ubiquitination, labeling, e.g., with radionuclides, and various enzymatic modifications, as will be readily appreciated by those well skilled in the art. A variety of methods for labeling polypeptides and of substituents or labels useful for such purposes are well known in the art, and include radioactive isotopes such as $^{32}P$, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods of labeling polypeptides are well known in the art. See Sambrook et al., 1989 or Ausubel et al., 1992.

Besides substantially full-length polypeptides, the present invention provides for biologically active fragments of the polypeptides. Significant biological activities include ligand-binding, immunological activity and other biological activities characteristic of KCNQ2 or KCNQ3 polypeptides. Immunological activities include both immunogenic function in a target immune system, as well as sharing of immunological epitopes for binding, serving as either a competitor or substitute antigen for an epitope of the KCNQ2 or KCNQ3 protein. As used herein, "epitope" refers to an antigenic determinant of a polypeptide. An epitope could comprise three amino acids in a spatial conformation which is unique to the epitope. Generally, an epitope consists of at least five such amino acids, and more usually consists of at least 8-10 such amino acids. Methods of determining the spatial conformation of such amino acids are known in the art.

For immunological purposes, tandem-repeat polypeptide segments may be used as immunogens, thereby producing highly antigenic proteins. Alternatively, such polypeptides will serve as highly efficient competitors for specific binding. Production of antibodies specific for KCNQ2 or KCNQ3 polypeptides or fragments thereof is described below.

The present invention also provides for fusion polypeptides, comprising KCNQ2 or KCNQ3 polypeptides and fragments. Homologous polypeptides may be fusions between two or more KCNQ2 or KCNQ3 polypeptide sequences or between the sequences of KCNQ2 or KCNQ3 and a related protein. Likewise, heterologous fusions may be constructed which would exhibit a combination of properties or activities of the derivative proteins. For example, ligand-binding or other domains may be "swapped" between different new fusion polypeptides or fragments. Such homologous or heterologous fusion polypeptides may display, for example, altered strength or specificity of binding. Fusion partners include immunoglobulins, bacterial—galactosidase, trpE, protein A, -lactamase, alpha amylase, alcohol dehydrogenase and yeast alpha mating factor. See Godowski et al., 1988.

Fusion proteins will typically be made by either recombinant nucleic acid methods, as described below, or may be chemically synthesized. Techniques for the synthesis of polypeptides are described, for example, in Merrifield, 1963.

"Protein purification" refers to various methods for the isolation of the KCNQ2 or KCNQ3 polypeptides from other biological material, such as from cells transformed with recombinant nucleic acids encoding KCNQ2 or KCNQ3, and are well known in the art. For example, such polypeptides may be purified by immunoaffinity chromatography employing, e.g., the antibodies provided by the present invention. Various methods of protein purification are well known in the art, and include those described in Deutscher, 1990 and Scopes, 1982.

The terms "isolated", "substantially pure", and "substantially homogeneous" are used interchangeably to describe a protein or polypeptide which has been separated from components which accompany it in its natural state. A monomeric protein is substantially pure when at least about 60 to 75% of a sample exhibits a single polypeptide sequence. A substantially pure protein will typically comprise about 60 to 90% W/W of a protein sample, more usually about 95%, and preferably will be over about 99% pure. Protein purity or homogeneity may be indicated by a number of means well known in the art, such as polyacrylamide gel electrophoresis of a protein sample, followed by visualizing a single polypeptide band upon staining the gel. For certain purposes, higher resolution may be provided by using HPLC or other means well known in the art which are utilized for purification.

A KCNQ2 or KCNQ3 protein is substantially free of naturally associated components when it is separated from the native contaminants which accompany it in its natural state. Thus, a polypeptide which is chemically synthesized or synthesized in a cellular system different from the cell from which it naturally originates will be substantially free from its naturally associated components. A protein may also be rendered substantially free of naturally associated components by isolation, using protein purification techniques well known in the art.

A polypeptide produced as an expression product of an isolated and manipulated genetic sequence is an "isolated polypeptide," as used herein, even if expressed in a homologous cell type. Synthetically made forms or molecules expressed by heterologous cells are inherently isolated molecules.

"Recombinant nucleic acid" is a nucleic acid which is not naturally occurring, or which is made by the artificial combination of two otherwise separated segments of sequence. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions.

"Regulatory sequences" refers to those sequences normally within 100 kb of the coding region of a locus, but they may also be more distant from the coding region, which affect the expression of the gene (including transcription of the gene, and translation, splicing, stability or the like of the messenger RNA).

"Substantial homology or similarity". A nucleic acid or fragment thereof is "substantially homologous" ("or substantially similar") to another if, when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80%, preferably at least about 90%, and more preferably at least about 95-98% of the nucleotide bases.

To determine homology between two different nucleic acids, the percent homology is to be determined using the BLASTN program "BLAST 2 sequences". This program is available for public use from the National Center for Biotechnology Information (NCBI) over the Internet (http://www.ncbi.nlm.nih.gov/gorf/b12.html) (Altschul et al., 1997). The parameters to be used are whatever combination of the following yields the highest calculated percent homology (as calculated below) with the default parameters shown in parentheses:
 Program—blastn
 Matrix—0 BLOSUM62
 Reward for a match—0 or 1 (1)
 Penalty for a mismatch—0, −1, −2 or −3 (−2)
 Open gap penalty—0, 1, 2, 3, 4 or 5 (5)
 Extension gap penalty—0 or 1 (1)
 Gap x_dropoff—0 or 50 (50)
 Expect—10

Along with a variety of other results, this program shows a percent identity across the complete strands or across regions of the two nucleic acids being matched. The program shows as part of the results an alignment and identity of the two strands being compared. If the strands are of equal length then the identity will be calculated across the complete length of the nucleic acids. If the strands are of unequal lengths, then the length of the shorter nucleic acid is to be used. If the nucleic acids are quite similar across a portion of their sequences but different across the rest of their sequences, the blastn program "BLAST 2 Sequences" will show an identity across only the similar portions, and these portions are reported individually. For purposes of determining homology herein, the percent homology refers to the shorter of the two sequences being compared. If any one region is shown in different alignments with differing percent identities, the alignments which yield the greatest homology are to be used. The averaging is to be performed as in this example of SEQ ID NOs:20 and 21.

(SEQ ID NO: 20)
5'-ACCGTAGCTACGTACGTATATAGAAAGGGCGCGATCGTCGTCGCGTA
TGACGACTTAGCATGC-3'

(SEQ ID NO: 21)
5'-ACCGGTAGCTACGTACGTTATTTAGAAAGGGGTGTGTGTGTGTGTGT
AAACCGGGGTTTTCGGGATCGTCCGTCGCGTATGACGACTTAGCCATGCA
CGGTATATCGTATTAGGACTAGCGATTGACTAG-3'

The program "BLAST 2 Sequences" shows differing alignments of these two nucleic acids depending upon the parameters which are selected. As examples, four sets of parameters were selected for comparing SEQ ID NOs:20 and 21 (gap x_dropoff was 50 for all cases), with the results shown in Table 1. It is to be noted that none of the sets of parameters selected as shown in Table 1 is necessarily the best set of parameters for comparing these sequences. The percent homology is calculated by multiplying for each region showing identity the fraction of bases of the shorter strand within a region times the percent identity for that region and adding all of these together. For example, using the first set of parameters shown in Table 1, SEQ ID NO:20 is the short sequence (63 bases), and two regions of identity are shown, the first encompassing bases 4-29 (26 bases) of SEQ ID NO:20 with 92% identity to SEQ ID NO:21 and the second encompassing bases 39-59 (21 bases) of SEQ ID NO:20 with 100% identity to SEQ ID NO:21. Bases 1-3, 30-38 and 60-63 (16 bases) are not shown as having any identity with SEQ ID NO:21. Percent homology is calculated as: (26/63)(92)+(21/63)(100)+(16/63)(0)=71.3% homology. The percents of homology calculated using each of the four sets of parameters shown are listed in Table 1. Several other combinations of parameters are possible, but they are not listed for the sake of brevity. It is seen that each set of parameters resulted in a different calculated percent homology. Because the result yielding the highest percent homology is to be used, based solely on these four sets of parameters one would state that SEQ ID NOs:20 and 21 have 87.1% homology. Again it is to be noted that use of other parameters may show an even higher homology for SEQ ID NOs:20 and 21, but for brevity not all the possible results are shown.

TABLE 1

Parameter Values

| Match | Mis-match | Open Gap | Extension Gap | Regions of identity (%) | | Homology |
|---|---|---|---|---|---|---|
| 1 | −2 | 5 | 1 | 4-29 of 20 and 5-31 of 21 (92%) | 39-59 of 20 and 71-91 of 21 (100%) | 71.3 |
| 1 | −2 | 2 | 1 | 4-29 of 20 and 5-31 of 21 (92%) | 33-63 of 20 and 64-96 of 21 (93%) | 83.7 |
| 1 | −1 | 5 | 1 | — | 30-59 of 20 and 61-91 of 21 (93%) | 44.3 |

TABLE 1-continued

| | | | Parameter Values | | |
|---|---|---|---|---|---|
| Match | Mismatch | Open Gap | Extension Gap | Regions of identity (%) | Homology |
| 1 | −1 | 2 | 1 | 4-29 of 20 and 5-31 of 21 (92%) | 87.1 |
| | | | | 30-63 of 20 and 61-96 of 21 (91%) | |

Alternatively, substantial homology or (similarity) exists when a nucleic acid or fragment thereof will hybridize to another nucleic acid (or a complementary strand thereof) under selective hybridization conditions, to a strand, or to its complement. Selectivity of hybridization exists when hybridization which is substantially more selective than total lack of specificity occurs. Typically, selective hybridization will occur when there is at least about 55% homology over a stretch of at least about 14 nucleotides, preferably at least about 65%, more preferably at least about 75%, and most preferably at least about 90%. See, Kanehisa, 1984. The length of homology comparison, as described, may be over longer stretches, and in certain embodiments will often be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides.

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30 C, typically in excess of 37 C, and preferably in excess of 45 C. Stringent salt conditions will ordinarily be less than 1000 mM, typically less than 500 mM, and preferably less than 200 mM. However, the combination of parameters is much more important than the measure of any single parameter. The stringency conditions are dependent on the length of the nucleic acid and the base composition of the nucleic acid and can be determined by techniques well known in the art. See, e.g., Wetmur and Davidson, 1968.

Probe sequences may also hybridize specifically to duplex DNA under certain conditions to form triplex or other higher order DNA complexes. The preparation of such probes and suitable hybridization conditions are well known in the art.

The terms "substantial homology" or "substantial identity", when referring to polypeptides, indicate that the polypeptide or protein in question exhibits at least about 30% identity with an entire naturally-occurring protein or a portion thereof, usually at least about 70% identity, more usually at least about 80% identity, preferably at least about 90% identity, and more preferably at least about 95% identity.

Homology, for polypeptides, is typically measured using sequence analysis software. See, e.g., the Sequence Analysis Software Package of the Genetics Computer Group, University of Wisconsin Biotechnology Center, 910 University Avenue, Madison, Wis. 53705. Protein analysis software matches similar sequences using measures of homology assigned to various substitutions, deletions and other modifications. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine.

"Substantially similar function" refers to the function of a modified nucleic acid or a modified protein, with reference to the wild-type KCNQ2 or KCNQ3 nucleic acid or wild-type KCNQ2 or KCNQ3 polypeptide. The modified polypeptide will be substantially homologous to the wild-type KCNQ2 or KCNQ3 polypeptide and will have substantially the same function. The modified polypeptide may have an altered amino acid sequence and/or may contain modified amino acids. In addition to the similarity of function, the modified polypeptide may have other useful properties, such as a longer half-life. The similarity of function (activity) of the modified polypeptide may be substantially the same as the activity of the wild-type KCNQ2 or KCNQ3 polypeptide. Alternatively, the similarity of function (activity) of the modified polypeptide may be higher than the activity of the wild-type KCNQ2 or KCNQ3 polypeptide. The modified polypeptide is synthesized using conventional techniques, or is encoded by a modified nucleic acid and produced using conventional techniques. The modified nucleic acid is prepared by conventional techniques. A nucleic acid with a function substantially similar to the wild-type KCNQ2 or KCNQ3 gene function produces the modified protein described above.

A polypeptide "fragment," "portion" or "segment" is a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids.

The polypeptides of the present invention, if soluble, may be coupled to a solid-phase support, e.g., nitrocellulose, nylon, column packing materials (e.g., Sepharose beads), magnetic beads, glass wool, plastic, metal, polymer gels, cells, or other substrates. Such supports may take the form, for example, of beads, wells, dipsticks, or membranes.

"Target region" refers to a region of the nucleic acid which is amplified and/or detected. The term "target sequence" refers to a sequence with which a probe or primer will form a stable hybrid under desired conditions.

The practice of the present invention employs, unless otherwise indicated, conventional techniques of chemistry, molecular biology, microbiology, recombinant DNA, genetics, and immunology. See, e.g., Maniatis et al., 1982; Sambrook et al., 1989; Ausubel et al., 1992; Glover, 1985; Anand, 1992; Guthrie and Fink, 1991. A general discussion of techniques and materials for human gene mapping, including mapping of human chromosome 1, is provided, e.g., in White and Lalouel, 1988.

Preparation of Recombinant or Chemically Synthesized Nucleic Acids; Vectors, Transformation, Host Cells Large amounts of the polynucleotides of the present invention may be produced by replication in a suitable host cell. Natural or synthetic polynucleotide fragments coding for a desired fragment will be incorporated into recombinant polynucleotide constructs, usually DNA constructs, capable of introduction into and replication in a prokaryotic or eukaryotic cell. Usually the polynucleotide constructs will be suitable for replication in a unicellular host, such as yeast or bacteria, but may also be intended for introduction to (with and without integration within the genome) cultured mammalian or plant or other eukaryotic cell lines. The purification of nucleic acids produced by the methods of the present invention are described, e.g., in Sambrook et al., 1989 or Ausubel et al., 1992.

The polynucleotides of the present invention may also be produced by chemical synthesis, e.g., by the phosphoramidite method described by Beaucage and Carruthers (1981) or the triester method according to Matteucci and Caruthers (1981), and may be performed on commercial, automated oligonucleotide synthesizers. A double-stranded fragment may be obtained from the single-stranded product of chemical synthesis either by synthesizing the complementary strand and annealing the strands together under appropriate conditions or by adding the complementary strand using DNA polymerase with an appropriate primer sequence.

Polynucleotide constructs prepared for introduction into a prokaryotic or eukaryotic host may comprise a replication system recognized by the host, including the intended polynucleotide fragment encoding the desired polypeptide, and will preferably also include transcription and translational initiation regulatory sequences operably linked to the polypeptide encoding segment. Expression vectors may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Such vectors may be prepared by means of standard recombinant techniques well known in the art and discussed, for example, in Sambrook et al., 1989 or Ausubel et al., 1992.

An appropriate promoter and other necessary vector sequences will be selected so as to be functional in the host, and may include, when appropriate, those naturally associated with the KCNQ2 or KCNQ3 gene. Examples of workable combinations of cell lines and expression vectors are described in Sambrook et al., 1989 or Ausubel et al., 1992; see also, e.g., Metzger et al., 1988. Many useful vectors are known in the art and may be obtained from such vendors as Stratagene, New England Biolabs, Promega Biotech, and others. Promoters such as the trp, lac and phage promoters, tRNA promoters and glycolytic enzyme promoters may be used in prokaryotic hosts. Useful yeast promoters include promoter regions for metallothionein, 3-phosphoglycerate kinase or other glycolytic enzymes such as enolase or glyceraldehyde-3-phosphate dehydrogenase, enzymes responsible for maltose and galactose utilization, and others. Vectors and promoters suitable for use in yeast expression are further described in Hitzeman et al., EP 73,675A. Appropriate non-native mammalian promoters might include the early and late promoters from SV40 (Fiers et al., 1978) or promoters derived from murine Molony leukemia virus, mouse tumor virus, avian sarcoma viruses, adenovirus II, bovine papilloma virus or polyoma. Insect promoters may be derived from baculovirus. In addition, the construct may be joined to an amplifiable gene (e.g., DHFR) so that multiple copies of the gene may be made. For appropriate enhancer and other expression control sequences, see also *Enhancers and Eukaryotic Gene Expression*, Cold Spring Harbor Press, Cold Spring Harbor, N.Y. (1983). See also, e.g., U.S. Pat. Nos. 5,691,198; 5,735,500; 5,747,469 and 5,436,146.

While such expression vectors may replicate autonomously, they may also replicate by being inserted into the genome of the host cell, by methods well known in the art.

Expression and cloning vectors will likely contain a selectable marker, a gene encoding a protein necessary for survival or growth of a host cell transformed with the vector. The presence of this gene ensures growth of only those host cells which express the inserts. Typical selection genes encode proteins that a) confer resistance to antibiotics or other toxic substances, e.g. ampicillin, neomycin, methotrexate, etc., b) complement auxotrophic deficiencies, or c) supply critical nutrients not available from complex media, e.g., the gene encoding D-alanine racemase for *Bacilli*. The choice of the proper selectable marker will depend on the host cell, and appropriate markers for different hosts are well known in the art.

The vectors containing the nucleic acids of interest can be transcribed in vitro, and the resulting RNA introduced into the host cell by well-known methods, e.g., by injection (see, Kubo et al., 1988), or the vectors can be introduced directly into host cells by methods well known in the art, which vary depending on the type of cellular host, including electroporation; transfection employing calcium chloride, rubidium chloride, calcium phosphate, DEAE-dextran, or other substances; microprojectile bombardment; lipofection; infection (where the vector is an infectious agent, such as a retroviral genome); and other methods. See generally, Sambrook et al., 1989 and Ausubel et al., 1992. The introduction of the polynucleotides into the host cell by any method known in the art, including, inter alia, those described above, will be referred to herein as "transformation." The cells into which have been introduced nucleic acids described above are meant to also include the progeny of such cells.

Large quantities of the nucleic acids and polypeptides of the present invention may be prepared by expressing the KCNQ2 or KCNQ3 nucleic acid or portions thereof in vectors or other expression vehicles in compatible prokaryotic or eukaryotic host cells. The most commonly used prokaryotic hosts are strains of *Escherichia coli*, although other prokaryotes, such as *Bacillus subtilis* or *Pseudomonas* may also be used.

Mammalian or other eukaryotic host cells, such as those of yeast, filamentous fungi, plant, insect, or amphibian or avian species, may also be useful for production of the proteins of the present invention. Propagation of mammalian cells in culture is per se well known. See, Jakoby and Pastan (eds.) (1979). Examples of commonly used mammalian host cell lines are VERO and HeLa cells, Chinese hamster ovary (CHO) cells, and WI38, BHK, and COS cell lines, although it will be appreciated by the skilled practitioner that other cell lines may be appropriate, e.g., to provide higher expression, desirable glycosylation patterns, or other features. An example of a commonly used insect cell line is SF9.

Clones are selected by using markers depending on the mode of the vector construction. The marker may be on the same or a different DNA molecule, preferably the same DNA molecule. In prokaryotic hosts, the transformant may be selected, e.g., by resistance to ampicillin, tetracycline or other antibiotics. Production of a particular product based on temperature sensitivity may also serve as an appropriate marker.

Prokaryotic or eukaryotic cells transformed with the polynucleotides of the present invention will be useful not only for the production of the nucleic acids and polypeptides of the present invention, but also, for example, in studying the characteristics of KCNQ2 or KCNQ3 polypeptide.

The probes and primers based on the KCNQ2 or KCNQ3 gene sequence disclosed herein are used to identify homologous KCNQ2 or KCNQ3 gene sequences and proteins in other species. These gene sequences and proteins are used in the diagnostic/prognostic, therapeutic and drug screening methods described herein for the species from which they have been isolated.

Methods of Use: Drug Screening

This invention is particularly useful for screening compounds by using the KCNQ2 or KCNQ3 polypeptide or binding fragment thereof in any of a variety of drug screening techniques.

The KCNQ2 or KCNQ3 polypeptide or fragment employed in such a test may either be free in solution, affixed to a solid support, or borne on a cell surface. One method of drug screening utilizes eucaryotic or procaryotic host cells which are stably transformed with recombinant polynucleotides expressing the polypeptide or fragment, preferably in competitive binding assays. Such cells, either in viable or fixed form, can be used for standard binding assays. One may measure, for example, for the formation of complexes between a KCNQ2 or KCNQ3 polypeptide or fragment and the agent being tested, or examine the degree to which the formation of a complex between a KCNQ2 or KCNQ3 polypeptide or fragment and a known ligand is interfered with by the agent being tested.

Thus, the present invention provides methods of screening for drugs comprising contacting such an agent with a KCNQ2 or KCNQ3 polypeptide or fragment thereof and assaying (i) for the presence of a complex between the agent and the KCNQ2 or KCNQ3 polypeptide or fragment, or (ii) for the presence of a complex between the KCNQ2 or KCNQ3 polypeptide or fragment and a ligand, by methods well known in the art. In such competitive binding assays the KCNQ2 or KCNQ3 polypeptide or fragment is typically labeled. Free KCNQ2 or KCNQ3 polypeptide or fragment is separated from that present in a protein:protein complex, and the amount of free (i.e., uncomplexed) label is a measure of the binding of the agent being tested to KCNQ2 or KCNQ3 or its interference with KCNQ2 (or KCNQ3):ligand binding, respectively. One may also measure the amount of bound, rather than free, KCNQ2 or KCNQ3. It is also possible to label the ligand rather than the KCNQ2 or KCNQ3 and to measure the amount of ligand binding to KCNQ2 or KCNQ3 in the presence and in the absence of the drug being tested.

Another technique for drug screening provides high throughput screening for compounds having suitable binding affinity to the KCNQ2 or KCNQ3 polypeptides and is described in detail in Geysen (published PCT published application WO 84/03564). Briefly stated, large numbers of different small peptide test compounds are synthesized on a solid substrate, such as plastic pins or some other surface. The peptide test compounds are reacted with KCNQ2 or KCNQ3 polypeptide and washed. Bound KCNQ2 or KCNQ3 polypeptide is then detected by methods well known in the art.

Purified KCNQ2 or KCNQ3 can be coated directly onto plates for use in the aforementioned drug screening techniques. However, non-neutralizing antibodies to the polypeptide can be used to capture antibodies to immobilize the KCNQ2 or KCNQ3 polypeptide on the solid phase.

This invention also contemplates the use of competitive drug screening assays in which neutralizing antibodies capable of specifically binding the KCNQ2 or KCNQ3 polypeptide compete with a test compound for binding to the KCNQ2 or KCNQ3 polypeptide or fragments thereof. In this manner, the antibodies can be used to detect the presence of any peptide which shares one or more antigenic determinants of the KCNQ2 or KCNQ3 polypeptide.

The invention is particularly useful for screening compounds by using KCNQ2 or KCNQ3 protein in transformed cells, transfected oocytes or transgenic animals. The drug is added to the cells in culture or administered to a transgenic animal containing mutant KCNQ2 or KCNQ3 and the effect on the current of the potassium channel is compared to the current of a cell or animal containing the wild-type KCNQ2 or KCNQ3. Drug candidates which alter the current to a more normal level are useful for treating or preventing BFNC, rolandic epilepsy and JME.

The above screening methods are not limited to assays employing only KCNQ2 or KCNQ3 but are also applicable to studying KCNQ2- or KCNQ3-protein complexes. The effect of drugs on the activity of this complex is analyzed.

In accordance with these methods, the following assays are examples of assays which can be used for screening for drug candidates.

A mutant KCNQ2 or KCNQ3 (per se or as part of a fusion protein) is mixed with a wild-type protein (per se or as part of a fusion protein) to which wild-type KCNQ2 or KCNQ3 binds. This mixing is performed in both the presence of a drug and the absence of the drug, and the amount of binding of the mutant KCNQ2 or KCNQ3 with the wild-type protein is measured. If the amount of the binding is more in the presence of said drug than in the absence of said drug, the drug is a drug candidate for treating BFNC, rolandic epilepsy or JME resulting from a mutation in KCNQ2 or KCNQ3.

A wild-type KCNQ2 or KCNQ3 (per se or as part of a fusion protein) is mixed with a wild-type protein (per se or as part of a fusion protein) to which wild-type KCNQ2 or KCNQ3 binds. This mixing is performed in both the presence of a drug and the absence of the drug, and the amount of binding of the wild-type KCNQ2 or KCNQ3 with the wild-type protein is measured. If the amount of the binding is more in the presence of said drug than in the absence of said drug, the drug is a drug candidate for treating BFNC, rolandic epilepsy or JME resulting from a mutation in KCNQ2 or KCNQ3.

A mutant protein, which as a wild-type protein binds to KCNQ2 or KCNQ3 (per se or as part of a fusion protein) is mixed with a wild-type KCNQ2 or KCNQ3 (per se or as part of a fusion protein). This mixing is performed in both the presence of a drug and the absence of the drug, and the amount of binding of the mutant protein with the wild-type KCNQ2 or KCNQ3 is measured. If the amount of the binding is more in the presence of said drug than in the absence of said drug, the drug is a drug candidate for treating BFNC, rolandic epilepsy or JME resulting from a mutation in the gene encoding the protein.

The polypeptide of the invention may also be used for screening compounds developed as a result of combinatorial library technology. Combinatorial library technology provides an efficient way of testing a potential vast number of different substances for ability to modulate activity of a polypeptide. Such libraries and their use are known in the art. The use of peptide libraries is preferred. See, for example, WO 97/02048.

Briefly, a method of screening for a substance which modulates activity of a polypeptide may include contacting one or more test substances with the polypeptide in a suitable reaction medium, testing the activity of the treated polypeptide and comparing that activity with the activity of the polypeptide in comparable reaction medium untreated with the test substance or substances. A difference in activity between the treated and untreated polypeptides is indicative of a modulating effect of the relevant test substance or substances.

Prior to or as well as being screened for modulation of activity, test substances may be screened for ability to interact with the polypeptide, e.g., in a yeast two-hybrid system (e.g., Bartel et al., 1993; Fields and Song, 1989; Chevray and Nathans, 1992; Lee et al., 1995). This system may be used as a coarse screen prior to testing a substance for actual ability to modulate activity of the polypeptide. Alternatively, the screen could be used to screen test substances for binding to a KCNQ2 or KCNQ3 specific binding partner, or to find mimetics of the KCNQ2 or KCNQ3 polypeptide.

Following identification of a substance which modulates or affects polypeptide activity, the substance may be investigated further. Furthermore, it may be manufactured and/or used in preparation, i.e., manufacture or formulation, or a composition such as a medicament, pharmaceutical composition or drug. These may be administered to individuals.

Thus, the present invention extends in various aspects not only to a substance identified using a nucleic acid molecule as a modulator of polypeptide activity, in accordance with what is disclosed herein, but also a pharmaceutical composition, medicament, drug or other composition comprising such a substance, a method comprising administration of such a composition comprising such a substance, a method comprising administration of such a composition to a patient, e.g., for treatment (which may include preventative treatment) of BFNC, rolandic epilepsy or JME, use of such a substance in the manufacture of a composition for administration, e.g., for treatment of BFNC, rolandic epilepsy or JME, and a method of making a pharmaceutical composition comprising admixing such a substance with a pharmaceutically acceptable excipient, vehicle or carrier, and optionally other ingredients.

A substance identified as a modulator of polypeptide function may be peptide or non-peptide in nature. Non-peptide "small molecules" are often preferred for many in vivo pharmaceutical uses. Accordingly, a mimetic or mimic of the substance (particularly if a peptide) may be designed for pharmaceutical use.

The designing of mimetics to a known pharmaceutically active compound is a known approach to the development of pharmaceuticals based on a "lead" compound. This might be desirable where the active compound is difficult or expensive to synthesize or where it is unsuitable for a particular method of administration, e.g., pure peptides are unsuitable active agents for oral compositions as they tend to be quickly degraded by proteases in the alimentary canal. Mimetic design, synthesis and testing is generally used to avoid randomly screening large numbers of molecules for a target property.

There are several steps commonly taken in the design of a mimetic from a compound having a given target property. First, the particular parts of the compound that are critical and/or important in determining the target property are determined. In the case of a peptide, this can be done by systematically varying the amino acid residues in the peptide, e.g., by substituting each residue in turn. Alanine scans of peptide are commonly used to refine such peptide motifs. These parts or residues constituting the active region of the compound are known as its "pharmacophore".

Once the pharmacophore has been found, its structure is modeled according to its physical properties, e.g., stereochemistry, bonding, size and/or charge, using data from a range of sources, e.g., spectroscopic techniques, x-ray diffraction data and NMR. Computational analysis, similarity mapping (which models the charge and/or volume of a pharmacophore, rather than the bonding between atoms) and other techniques can be used in this modeling process.

In a variant of this approach, the three-dimensional structure of the ligand and its binding partner are modeled. This can be especially useful where the ligand and/or binding partner change conformation on binding, allowing the model to take account of this in the design of the mimetic.

A template molecule is then selected onto which chemical groups which mimic the pharmacophore can be grafted. The template molecule and the chemical groups grafted onto it can conveniently be selected so that the mimetic is easy to synthesize, is likely to be pharmacologically acceptable, and does not degrade in vivo, while retaining the biological activity of the lead compound. Alternatively, where the mimetic is peptide-based, further stability can be achieved by cyclizing the peptide, increasing its rigidity. The mimetic or mimetics found by this approach can then be screened to see whether they have the target property, or to what extent they exhibit it. Further optimization or modification can then be carried out to arrive at one or more final mimetics for in vivo or clinical testing.

Methods of Use: Nucleic Acid Diagnosis and Diagnostic Kits

In order to detect the presence of a KCNQ2 or KCNQ3 allele predisposing an individual to BFNC, rolandic epilepsy or JME, a biological sample such as blood is prepared and analyzed for the presence or absence of susceptibility alleles of KCNQ2 or KCNQ3. In order to detect the presence of BFNC, rolandic epilepsy or JME, or as a prognostic indicator, a biological sample is prepared and analyzed for the presence or absence of mutant alleles of KCNQ2 or KCNQ3. Results of these tests and interpretive information are returned to the health care provider for communication to the tested individual. Such diagnoses may be performed by diagnostic laboratories, or, alternatively, diagnostic kits are manufactured and sold to health care providers or to private individuals for self-diagnosis.

Initially, the screening method involves amplification of the relevant KCNQ2 or KCNQ3 sequences. In another preferred embodiment of the invention, the screening method involves a non-PCR based strategy. Such screening methods include two-step label amplification methodologies that are well known in the art. Both PCR and non-PCR based screening strategies can detect target sequences with a high level of sensitivity.

The most popular method used today is target amplification. Here, the target nucleic acid sequence is amplified with polymerases. One particularly preferred method using polymerase-driven amplification is the polymerase chain reaction (PCR). The polymerase chain reaction and other polymerase-driven amplification assays can achieve over a million-fold increase in copy number through the use of polymerase-driven amplification cycles. Once amplified, the resulting nucleic acid can be sequenced or used as a substrate for DNA probes.

When the probes are used to detect the presence of the target sequences the biological sample to be analyzed, such as blood or serum, may be treated, if desired, to extract the nucleic acids. The sample nucleic acid may be prepared in various ways to facilitate detection of the target sequence, e.g. denaturation, restriction digestion, electrophoresis or dot blotting. The targeted region of the analyte nucleic acid usually must be at least partially single-stranded to form hybrids with the targeting sequence of the probe. If the sequence is naturally single-stranded, denaturation will not be required. However, if the sequence is double-stranded, the sequence will probably need to be denatured. Denaturation can be carried out by various techniques known in the art.

Analyte nucleic acid and probe are incubated under conditions which promote stable hybrid formation of the target sequence in the probe with the putative targeted sequence in the analyte. The region of the probes which is used to bind to the analyte can be made completely complementary to the targeted region of human chromosome 20 for KCNQ2 or to the targeted region of human chromosome 8 for KCNQ3. Therefore, high stringency conditions are desirable in order to prevent false positives. However, conditions of high stringency are used only if the probes are complementary to regions of the chromosome which are unique in the genome. The stringency of hybridization is determined by a number of factors during hybridization and during the washing procedure, including temperature, ionic strength, base composition, probe length, and concentration of formamide. These factors are outlined in, for example, Maniatis et al., 1982 and Sambrook et al., 1989. Under certain circumstances, the formation of higher order hybrids, such as triplexes, quadraplexes, etc., may be desired to provide the means of detecting target sequences.

Detection, if any, of the resulting hybrid is usually accomplished by the use of labeled probes. Alternatively, the probe may be unlabeled, but may be detectable by specific binding with a ligand which is labeled, either directly or indirectly. Suitable labels, and methods for labeling probes and ligands are known in the art, and include, for example, radioactive labels which may be incorporated by known methods (e.g., nick translation, random priming or kinasing), biotin, fluorescent groups, chemiluminescent groups (e.g., dioxetanes, particularly triggered dioxetanes), enzymes, antibodies, gold nanoparticles and the like. Variations of this basic scheme are known in the art, and include those variations that facilitate separation of the hybrids to be detected from extraneous materials and/or that amplify the signal from the labeled moiety. A number of these variations are reviewed in, e.g., Matthews and Kricka, 1988; Landegren et al., 1988; Mifflin, 1989; U.S. Pat. No. 4,868,105; and in EPO Publication No. 225,807.

As noted above, non-PCR based screening assays are also contemplated in this invention. This procedure hybridizes a nucleic acid probe (or an analog such as a methyl phosphonate backbone replacing the normal phosphodiester), to the low level DNA target. This probe may have an enzyme covalently linked to the probe, such that the covalent linkage does not interfere with the specificity of the hybridization. This enzyme-probe-conjugate-target nucleic acid complex can then be isolated away from the free probe enzyme conjugate and a substrate is added for enzyme detection. Enzymatic activity is observed as a change in color development or luminescent output resulting in a $10^3$-$10^6$ increase in sensitivity. For an example relating to the preparation of oligodeoxynucleotide-alkaline phosphatase conjugates and their use as hybridization probes, see Jablonski et al., 1986.

Two-step label amplification methodologies are known in the art. These assays work on the principle that a small ligand (such as digoxigenin, biotin, or the like) is attached to a nucleic acid probe capable of specifically binding KCNQ2 or KCNQ3. Allele specific probes are also contemplated within the scope of this example and exemplary allele specific probes include probes encompassing the predisposing mutations of this disclosure.

In one example, the small ligand attached to the nucleic acid probe is specifically recognized by an antibody-enzyme conjugate. In one embodiment of this example, digoxigenin is attached to the nucleic acid probe. Hybridization is detected by an antibody-alkaline phosphatase conjugate which turns over a chemiluminescent substrate. For methods for labeling nucleic acid probes according to this embodiment see Martin et al., 1990. In a second example, the small ligand is recognized by a second ligand-enzyme conjugate that is capable of specifically complexing to the first ligand. A well known embodiment of this example is the biotin-avidin type of interactions. For methods for labeling nucleic acid probes and their use in biotin-avidin based assays see Rigby et al., 1977 and Nguyen et al., 1992.

It is also contemplated within the scope of this invention that the nucleic acid probe assays of this invention will employ a cocktail of nucleic acid probes capable of detecting KCNQ2 or KCNQ3. Thus, in one example to detect the presence of KCNQ2 or KCNQ3 in a cell sample, more than one probe complementary to the gene is employed and in particular the number of different probes is alternatively two, three, or five different nucleic acid probe sequences. In another example, to detect the presence of mutations in the KCNQ2 or KCNQ3 gene sequence in a patient, more than one probe complementary to these genes is employed where the cocktail includes probes capable of binding to the allele-specific mutations identified in populations of patients with alterations in KCNQ2 or KCNQ3. In this embodiment, any number of probes can be used, and will preferably include probes corresponding to the major gene mutations identified as predisposing an individual to BFNC, rolandic epilepsy or JME.

Methods of Use: Peptide Diagnosis and Diagnostic Kits

The presence of BFNC, rolandic epilepsy or JME can also be detected on the basis of the alteration of wild-type KCNQ2 or KCNQ3 polypeptide. Such alterations can be determined by sequence analysis in accordance with conventional techniques. More preferably, antibodies (polyclonal or monoclonal) are used to detect differences in, or the absence of KCNQ2 or KCNQ3 peptides. Techniques for raising and purifying antibodies are well known in the art and any such techniques may be chosen to achieve the preparations claimed in this invention. In a preferred embodiment of the invention, antibodies will immunoprecipitate KCNQ2 or KCNQ3 proteins from solution as well as react with these proteins on Western or immunoblots of polyacrylamide gels. In another preferred embodiment, antibodies will detect KCNQ2 or KCNQ3 proteins in paraffin or frozen tissue sections, using immunocytochemical techniques.

Preferred embodiments relating to methods for detecting KCNQ2 or KCNQ3 or their mutations include enzyme linked immunosorbent assays (ELISA), radioimmunoassays (RIA), immunoradiometric assays (IRMA) and immunoenzymatic assays (IEMA), including sandwich assays using monoclonal and/or polyclonal antibodies. Exemplary sandwich assays are described by David et al., in U.S. Pat. Nos. 4,376,110 and 4,486,530, hereby incorporated by reference.

Methods of Use: Rational Drug Design

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, 1991. In one approach, one first determines the three-dimensional structure of a protein of interest (e.g., KCNQ2 or KCNQ3 polypeptide) by x-ray crystallography, by computer modeling or most typically, by a combination of approaches. Less often, useful information regarding the structure of a polypeptide may be gained by modeling based on the structure of homologous proteins. An example of rational drug design is the development of HIV protease inhibitors (Erickson et al., 1990). In addition, peptides (e.g., KCNQ2 or KCNQ3 polypeptide) are analyzed by an alanine scan (Wells, 1991). In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced banks of peptides. Selected peptides would then act as the pharmacore.

Thus, one may design drugs which have, e.g., improved KCNQ2 or KCNQ3 polypeptide activity or stability or which act as inhibitors, agonists, antagonists, etc. of KCNQ2 or KCNQ3 polypeptide activity. By virtue of the availability of cloned KCNQ2 and KCNQ3 sequences, sufficient amounts of the KCNQ2 and KCNQ3 polypeptides may be made available to perform such analytical studies as x-ray crystallography. In addition, the knowledge of the KCNQ2 and KCNQ3 protein sequences provided herein will guide those employing computer modeling techniques in place of, or in addition to x-ray crystallography.

Methods of Use: Gene Therapy

According to the present invention, a method is also provided of supplying wild-type KCNQ2 or KCNQ3 function to a cell which carries a mutant KCNQ2 or KCNQ3 allele, respectively. Supplying such a function should allow normal functioning of the recipient cells. The wild-type gene or a part of the gene may be introduced into the cell in a vector such that the gene remains extrachromosomal. In such a situation, the gene will be expressed by the cell from the extrachromosomal location. More preferred is the situation where the wild-type gene or a part thereof is introduced into the mutant cell in such a way that it recombines with the endogenous mutant gene present in the cell. Such recombination requires a double recombination event which results in the correction of the gene mutation. Vectors for introduction of genes both for recombination and for extrachromosomal maintenance are known in the art, and any suitable vector may be used. Methods for introducing DNA into cells such as electroporation, calcium phosphate co-precipitation and viral transduction are known in the art, and the choice of method is within the competence of the practitioner.

As generally discussed above, the KCNQ2 or KCNQ3 gene or fragment, where applicable, may be employed in gene therapy methods in order to increase the amount of the expression products of such gene in cells. It may also be useful to increase the level of expression of the KCNQ2 or KCNQ3 gene even in those persons in which the mutant gene is expressed at a "normal" level, but the gene product is not fully functional.

Gene therapy would be carried out according to generally accepted methods, for example, as described by Friedman (1991) or Culver (1996). Cells from a patient would be first analyzed by the diagnostic methods described above, to ascertain the production of KCNQ2 and/or KCNQ3 polypeptide in the cells. A virus or plasmid vector (see further details below), containing a copy of the KCNQ2 or KCNQ3 gene linked to expression control elements and capable of replicating inside the cells, is prepared. The vector may be capable of replicating inside the cells. Alternatively, the vector may be replication deficient and is replicated in helper cells for use in gene therapy. Suitable vectors are known, such as disclosed in U.S. Pat. No. 5,252,479 and PCT published application WO 93/07282 and U.S. Pat. Nos. 5,691,198; 5,747,469; 5,436,146 and 5,753,500. The vector is then injected into the patient. If the transfected gene is not permanently incorporated into the genome of each of the targeted cells, the treatment may have to be repeated periodically.

Gene transfer systems known in the art may be useful in the practice of the gene therapy methods of the present invention. These include viral and nonviral transfer methods. A number of viruses have been used as gene transfer vectors or as the basis for repairing gene transfer vectors, including papovaviruses (e.g., SV40, Madzak et al., 1992), adenovirus (Berkner, 1992; Berkner et al., 1988; Gorziglia and Kapikian, 1992; Quantin et al., 1992; Rosenfeld et al., 1992; Wilkinson and Akrigg, 1992; Stratford-Perricaudet et al., 1990; Schneider et al., 1998), vaccinia virus (Moss, 1992; Moss, 1996), adeno-associated virus (Muzyczka, 1992; Ohi et al., 1990; Russell and Hirata, 1998), herpesviruses including HSV and EBV (Margolskee, 1992; Johnson et al., 1992; Fink et al., 1992; Breakefield and Geller, 1987; Freese et al., 1990; Fink et al., 1996), lentiviruses (Naldini et al., 1996), Sindbis and Semliki Forest virus (Berglund et al., 1993), and retroviruses of avian (Bandyopadhyay and Temin, 1984; Petropoulos et al., 1992), murine (Miller, 1992; Miller et al., 1985; Sorge et al., 1984; Mann and Baltimore, 1985; Miller et al., 1988), and human origin (Shimada et al., 1991; Helseth et al., 1990; Page et al., 1990; Buchschacher and Panganiban, 1992). Most human gene therapy protocols have been based on disabled murine retroviruses, although adenovirus and adeno-associated virus are also being used.

Nonviral gene transfer methods known in the art include chemical techniques such as calcium phosphate coprecipitation (Graham and van der Eb, 1973; Pellicer et al., 1980); mechanical techniques, for example microinjection (Anderson et al., 1980; Gordon et al., 1980; Brinster et al., 1981; Costantini and Lacy, 1981); membrane fusion-mediated transfer via liposomes (Felgner et al., 1987; Wang and Huang, 1989; Kaneda et al., 1989; Stewart et al., 1992; Nabel et al., 1990; Lim et al., 1991); and direct DNA uptake and receptor-mediated DNA transfer (Wolff et al., 1990; Wu et al., 1991; Zenke et al., 1990; Wu et al., 1989; Wolff et al., 1991; Wagner et al., 1990; Wagner et al., 1991; Cotten et al., 1990; Curiel et al., 1992; Curiel et al., 1991). Viral-mediated gene transfer can be combined with direct in vitro gene transfer using liposome delivery, allowing one to direct the viral vectors to the tumor cells and not into the surrounding nondividing cells. Alternatively, the retroviral vector producer cell line can be injected into tumors (Culver et al., 1992). Injection of producer cells would then provide a continuous source of vector particles. This technique has been approved for use in humans with inoperable brain tumors.

In an approach which combines biological and physical gene transfer methods, plasmid DNA of any size is combined with a polylysine-conjugated antibody specific to the adenovirus hexon protein, and the resulting complex is bound to an adenovirus vector. The trimolecular complex is then used to infect cells. The adenovirus vector permits efficient binding, internalization, and degradation of the endosome before the coupled DNA is damaged. For other techniques for the delivery of adenovirus based vectors see Schneider et al. (1998) and U.S. Pat. Nos. 5,691,198; 5,747,469; 5,436,146 and 5,753,500.

Liposome/DNA complexes have been shown to be capable of mediating direct in vivo gene transfer. While in standard liposome preparations the gene transfer process is nonspecific, localized in vivo uptake and expression have been reported in tumor deposits, for example, following direct in situ administration (Nabel, 1992).

Expression vectors in the context of gene therapy are meant to include those constructs containing sequences sufficient to express a polynucleotide that has been cloned therein. In viral expression vectors, the construct contains viral sequences sufficient to support packaging of the construct. If the polynucleotide encodes KCNQ2 or KCNQ3, expression will produce KCNQ2 or KCNQ3. If the polynucleotide encodes an antisense polynucleotide or a ribozyme, expression will produce the antisense polynucleotide or ribozyme. Thus in this context, expression does not require that a protein product be synthesized. In addition to the polynucleotide cloned into the expression vector, the vector also contains a promoter functional in eukaryotic cells. The cloned polynucleotide sequence is under control of this promoter. Suitable eukaryotic promoters include those described above. The expression vector may also include sequences, such as selectable markers and other sequences described herein.

Gene transfer techniques which target DNA directly to brain tissue is preferred. Receptor-mediated gene transfer, for example, is accomplished by the conjugation of DNA (usually in the form of covalently closed supercoiled plasmid) to a protein ligand via polylysine. Ligands are chosen on the basis of the presence of the corresponding ligand receptors on the cell surface of the target cell/tissue type. These ligand-DNA conjugates can be injected directly into the blood if desired and are directed to the target tissue where receptor binding and internalization of the DNA-protein complex occurs. To overcome the problem of intracellular destruction of DNA, coinfection with adenovirus can be included to disrupt endosome function.

The therapy is as follows: patients who carry a KCNQ2 or KCNQ3 susceptibility allele are treated with a gene delivery vehicle such that some or all of their brain precursor cells receive at least one additional copy of a functional normal KCNQ2 or KCNQ3 allele, respectively. In this step, the treated individuals have reduced risk of BFNC, rolandic epilepsy and/or JME to the extent that the effect of the susceptible allele has been countered by the presence of the normal allele.

Methods of Use: Peptide Therapy

Peptides which have KCNQ2 or KCNQ3 activity can be supplied to cells which carry mutant or missing KCNQ2 or KCNQ3 alleles, respectively. Protein can be produced by expression of the cDNA sequence in bacteria, for example, using known expression vectors. Alternatively, KCNQ2 or KCNQ3 polypeptide can be extracted from KCNQ2- or KCNQ3-producing mammalian cells. In addition, the techniques of synthetic chemistry can be employed to synthesize KCNQ2 or KCNQ3 protein. Any of such techniques can provide the preparation of the present invention which comprises the KCNQ2 or KCNQ3 protein. The preparation is substantially free of other human proteins. This is most readily accomplished by synthesis in a microorganism or in vitro.

Active KCNQ2 or KCNQ3 molecules can be introduced into cells by microinjection or by use of liposomes, for example. Alternatively, some active molecules may be taken up by cells, actively or by diffusion. Supply of molecules with KCNQ2 or KCNQ3 activity should lead to partial reversal of BFNC, rolandic epilepsy and/or JME. Other molecules with KCNQ2 or KCNQ3 activity (for example, peptides, drugs or organic compounds) may also be used to effect such a reversal. Modified polypeptides having substantially similar function are also used for peptide therapy.

Methods of Use: Transformed Hosts

Animals for testing therapeutic agents can be selected after mutagenesis of whole animals or after treatment of germline cells or zygotes. Such treatments include insertion of mutant KCNQ2 and/or KCNQ3 alleles, usually from a second animal species, as well as insertion of disrupted homologous genes. Alternatively, the endogenous KCNQ2 or KCNQ3 gene of the animals may be disrupted by insertion or deletion mutation or other genetic alterations using conventional techniques (Capecchi, 1989; Valancius and Smithies, 1991; Hasty et al., 1991; Shinkai et al., 1992; Mombaerts et al., 1992; Philpott et al., 1992; Snouwaert et al., 1992; Donehower et al., 1992). After test substances have been administered to the animals, the presence of BFNC, rolandic epilepsy or JME must be assessed. If the test substance prevents or suppresses the appearance of BFNC, rolandic epilepsy or JME, then the test substance is a candidate therapeutic agent for treatment of BFNC, rolandic epilepsy or JME. These animal models provide an extremely important testing vehicle for potential therapeutic products.

The identification of the association between the KCNQ2 and KCNQ3 gene mutations and BFNC, rolandic epilepsy and JME permits the early presymptomatic screening of individuals to identify those at risk for developing BFNC, rolandic epilepsy or JME. To identify such individuals, KCNQ2 and/or KCNQ3 alleles are screened for mutations either directly or after cloning the alleles. The alleles are tested for the presence of nucleic acid sequence differences from the normal allele using any suitable technique, including but not limited to, one of the following methods: fluorescent in situ hybridization (FISH), direct DNA sequencing, PFGE analysis, Southern blot analysis, single stranded conformation analysis (SSCP), linkage analysis, RNase protection assay, allele specific oligonucleotide (ASO), dot blot analysis and PCR-SSCP analysis. Also useful is the recently developed technique of DNA microchip technology. For example, either (1) the nucleotide sequence of both the cloned alleles and normal KCNQ2 or KCNQ3 gene or appropriate fragment (coding sequence or genomic sequence) are determined and then compared, or (2) the RNA transcripts of the KCNQ2 or KCNQ3 gene or gene fragment are hybridized to single stranded whole genomic DNA from an individual to be tested, and the resulting heteroduplex is treated with Ribonuclease A (RNase A) and run on a denaturing gel to detect the location of any mismatches. Two of these methods can be carried out according to the following procedures.

The alleles of the KCNQ2 or KCNQ3 gene in an individual to be tested are cloned using conventional techniques. For example, a blood sample is obtained from the individual. The genomic DNA isolated from the cells in this sample is partially digested to an average fragment size of approximately 20 kb. Fragments in the range from 18-21 kb are isolated. The resulting fragments are ligated into an appropriate vector. The sequences of the clones are then determined and compared to the normal KCNQ2 or KCNQ3 gene.

Alternatively, polymerase chain reactions (PCRs) are performed with primer pairs for the 5' region or the exons of the KCNQ2 or KCNQ3 gene. PCRs can also be performed with primer pairs based on any sequence of the normal KCNQ2 or KCNQ3 gene. For example, primer pairs for one of the introns can be prepared and utilized. Finally, RT-PCR can also be performed on the mRNA. The amplified products are then analyzed by single stranded conformation polymorphisms (SSCP) using conventional techniques to identify any differences and these are then sequenced and compared to the normal gene sequence.

Individuals can be quickly screened for common KCNQ2 or KCNQ3 gene variants by amplifying the individual s DNA using suitable primer pairs and analyzing the amplified product, e.g., by dot-blot hybridization using allele-specific oligonucleotide probes.

The second method employs RNase A to assist in the detection of differences between the normal KCNQ2 or KCNQ3 gene and defective genes. This comparison is performed in steps using small (~500 bp) restriction fragments of the KCNQ2 or KCNQ3 gene as the probe. First, the KCNQ2 or KCNQ3 gene is digested with a restriction enzyme(s) that cuts the gene sequence into fragments of approximately 500 bp. These fragments are separated on an electrophoresis gel, purified from the gel and cloned individually, in both orientations, into an SP6 vector (e.g., pSP64 or pSP65). The SP6-based plasmids containing inserts of the KCNQ2 or KCNQ3 gene fragments are transcribed in vitro using the SP6 transcription system, well known in the art, in the presence of $[-^{32}P]GTP$, generating radiolabeled RNA transcripts of both strands of the gene.

Individually, these RNA transcripts are used to form heteroduplexes with the allelic DNA using conventional techniques. Mismatches that occur in the RNA:DNA heteroduplex, owing to sequence differences between the KCNQ2 or KCNQ3 fragment and the KCNQ2 or KCNQ3 allele subclone from the individual, result in cleavage in the RNA strand when treated with RNase A. Such mismatches can be the result of point mutations or small deletions in the individual s allele. Cleavage of the RNA strand yields two or more small RNA fragments, which run faster on the denaturing gel than the RNA probe itself.

Any differences which are found, will identify an individual as having a molecular variant of the KCNQ2 or KCNQ3 gene and the consequent presence of BFNC, rolandic epilepsy or JME. These variants can take a number of forms. The most severe forms would be frame shift mutations or large deletions which would cause the gene to code for an abnormal protein or one which would significantly alter protein expression. Less severe disruptive mutations would include small in-frame deletions and nonconservative base pair substitutions which would have a significant effect on the protein produced, such as changes to or from a cysteine residue, from a basic to an acidic amino acid or vice versa, from a hydrophobic to hydrophilic amino acid or vice versa, or other mutations which would affect secondary or tertiary protein structure. Silent mutations or those resulting in conservative amino acid substitutions would not generally be expected to disrupt protein function.

Genetic testing will enable practitioners to identify individuals at risk for BFNC, rolandic epilepsy or JME, at, or even before, birth. Presymptomatic diagnosis of these epilepsies will enable prevention of these disorders. Finally, this invention changes our understanding of the cause and treatment of BFNC, rolandic epilepsy and JME. It is possible, for example, that potassium channel opening agents will reduce the risk of seizures in patients with KCNQ2 or KCNQ3 mutations.

Pharmaceutical Compositions and Routes of Administration

The KCNQ2 and KCNQ3 polypeptides, antibodies, peptides and nucleic acids of the present invention can be formulated in pharmaceutical compositions, which are prepared according to conventional pharmaceutical compounding techniques. See, for example, *Remington's Pharmaceutical Sciences,* 18th Ed. (1990, Mack Publishing Co., Easton, Pa.). The composition may contain the active agent or pharmaceutically acceptable salts of the active agent. These compositions may comprise, in addition to one of the active substances, a pharmaceutically acceptable excipient, carrier, buffer, stabilizer or other materials well known in the art. Such materials should be non-toxic and should not interfere with the efficacy of the active ingredient. The carrier may take a wide variety of forms depending on the form of preparation desired for administration, e.g., intravenous, oral, intrathecal, epineural or parenteral.

For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable to passage through the gastrointestinal tract while at the same time allowing for passage across the blood brain barrier. See for example, WO 96/11698.

For parenteral administration, the compound may be dissolved in a pharmaceutical carrier and administered as either a solution or a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. When the compounds are being administered intrathecally, they may also be dissolved in cerebrospinal fluid.

The active agent is preferably administered in a therapeutically effective amount. The actual amount administered, and the rate and time-course of administration, will depend on the nature and severity of the condition being treated. Prescription of treatment, e.g. decisions on dosage, timing, etc., is within the responsibility of general practitioners or specialists, and typically takes account of the disorder to be treated, the condition of the individual patient, the site of delivery, the method of administration and other factors known to practitioners. Examples of techniques and protocols can be found in *Remington's Pharmaceutical Sciences*.

Alternatively, targeting therapies may be used to deliver the active agent more specifically to certain types of cell, by the use of targeting systems such as antibodies or cell specific ligands. Targeting may be desirable for a variety of reasons, e.g. if the agent is unacceptably toxic, or if it would otherwise require too high a dosage, or if it would not otherwise be able to enter the target cells.

Instead of administering these agents directly, they could be produced in the target cell, e.g. in a viral vector such as described above or in a cell based delivery system such as described in U.S. Pat. No. 5,550,050 and published PCT application Nos. WO 92/19195, WO 94/25503, WO 95/01203, WO 95/05452, WO 96/02286, WO 96/02646, WO 96/40871, WO 96/40959 and WO 97/12635, designed for implantation in a patient. The vector could be targeted to the specific cells to be treated, or it could contain regulatory elements which are more tissue specific to the target cells. The cell based delivery system is designed to be implanted in a patient's body at the desired target site and contains a coding sequence for the active agent. Alternatively, the agent could be administered in a precursor form for conversion to the active form by an activating agent produced in, or targeted to, the cells to be treated. See for example, EP 425,731A and WO 90/07936.

The present invention is further detailed in the following Examples, which are offered by way of illustration and are not intended to limit the invention in any manner. Standard techniques well known in the art or the techniques specifically described below are utilized.

Example 1

Southern Blot Analysis

Five micrograms of genomic DNA were cut with Taq1 and transferred to a nylon membrane. Filters were hybridized overnight at 65° C. in PEG hyb (7% PEG, 10% SDA, 50 mM sodium phosphate and 200 µg/ml total human DNA) with the D20S24 plasmid probe labeled by random priming (Stratagene). Filters were washed at 2×SSC, 0.1% SDS twice at room temperature followed by one wash in 0.5× SSC, 0.1% SDS at 65° C.

Example 2

Fluorescence In Situ Hybridization

Chromosomes from transformed lymphocytes were prepared using a 30 minute ethidium bromide treatment followed by 3 hours in colcemid. Cells were then pelleted and resuspended in hypotonic solution (0.75 M KCl) for 20 minutes followed by the addition of four to five drops of fresh fixative (3:1 methanol:acetic acid). Cells were again pelleted, vortexed then carefully resuspended in fixative. After three washes in fixative, metaphases were stored at 4° C. Four hundred ng probe was labeled with biotin and hybridized to slides of metaphase spreads using standard hybridization procedures. Probes were then fluorescently tagged with avidin-FITC (Vector) and the signal intensified using biotin-labeled anti-avidin followed by avidin-FITC. The chromosomes were then counterstained using DAPI and visualized using a Zeiss Axioplan Fluorescent microscope equipped with FITC, DAPI and triple band pass filter sets. Images were captured by computer using Applied Imaging (Pittsburgh, Pa.) software Probevision and photographs printed on a Kodak XL 7700 color image printer.

Example 3

Localization of KCNQ2

Linkage analysis in a large kindred demonstrated that a gene responsible for BFNC maps to chromosome 20q13.3 close to the markers D20S20 and D20S19 (Leppert et al., 1989). Following the initial report, two centers confirmed linkage of BFNC to the same two genetic markers on chromosome 20, termed the EBN1 (epilepsy benign neonatal type 1) locus (Ryan et al., 1991; Malafosse et al., 1992). A more distal marker, D20S24, shows complete co-segregation with the BFNC phenotype in chromosome 20 linked families. Finding a distal flanking marker for the BFNC locus has not been successful probably because of its proximity to the telomere. This telomeric region is characterized by a high recombination rate between markers when compared to the physical distance (Steinlein et al., 1992). In fact, Steinlein et al. have demonstrated that the three markers D20S19, D20S20 and D20S24 are contained on the same 450 Mb Mlu I restriction fragment (Steinlein et al., 1992).

A second chromosomal locus, $EBN^2$, has also been identified for BFNC. Lewis et al. (1993) demonstrated linkage to markers on chromosome 8q24 in a single Hispanic family affected with BFNC. Evidence for this second locus was also reported in a Caucasian pedigree (Steinlein et al., 1995). All of the families in the present study show linkage to chromosome 20q markers with LOD scores of greater than 3.0 or have probands with clinical manifestations consistent with BFNC (Leppert et al., 1993). To find the gene responsible for BFNC, we narrowed the BFNC region with a sub-microscopic deletion in a single family, identified candidate cDNAs in this deletion, and then searched for mutations in other BFNC families.

Evidence for a small deletion came first from a genotypic observation with a three allele, RFLP marker, D20S24. Analysis of one family, kindred 1547, revealed that a null allele occurred exclusively in those individuals with BFNC and in two individuals previously shown to be non-penetrant with the VNTR markers D20S20 and D20S19 (FIG. 1). The existence of a deletion co-segregating with the BFNC phenotype in this family was confirmed by fluorescence in situ hybridization (FISH) in cell lines of kindred 1547 individuals using as probes, the D20S24 plasmid and two genomic P1 clones containing this marker.

Figure 2A:
FIGS. 2A-C. Metaphase spreads of cell lines from affected individuals of kindred 1547 probed with P1-KO9-7 (FIG. 2C) and P1-KO9-6b (FIG. 2B) genomic P1 clones and the 12 kb D20S24 RFLP marker (FIG. 2A) demonstrating a deletion of D20S24.
Figure 2B:
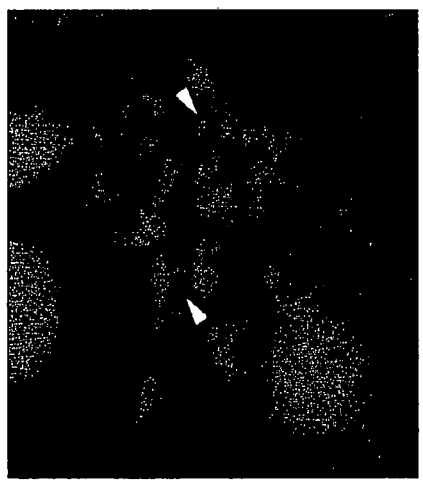
Figure 2C:

To confirm the presence of a deletion, two overlapping genomic P1 clones, P1-KO9-6b and P1-KO9-7, each of approximately 80 kb in size and each of which contains the D20S24 marker, were obtained and these were hybridized to cell lines of kindred 1547 BFNC affected individuals. When metaphase spread chromosomes are hybridized with P1-KO9-7 and P1-KO9-6b, both chromosome 20 homologs give signals on two sister chromatids. However when the 12 kb probe D20S24 is hybridized only signal from the one chromosome homolog is observed in 75% of metaphase spreads examined. The remaining minority of cells showed no hybridization for the 12 kb D20S24 probe (FIG. 2). The plasmid containing the D20S24 marker was a kind gift from J. Weissenbach.

While the 12 kb D20S24 probe was deleted on one chromosome in affected individuals, the overlapping P1 clones of 80 kb in size, and which together span approximately 130 kb, showed a positive FISH signal indicating that the deletion is smaller than 130 kb (FIG. 2).

Example 4

Isolation and Characterization of KCNQ2 Clones

Using the same probes as in Example 3, cDNAs in the region of the deletion were identified by screening a fetal brain cDNA library. Three of the cDNAs isolated showed significant homology to KCNQ1, the chromosome 11 potassium channel gene responsible for the Long QT syndrome and the Jervell and Lange-Nielsen cardioauditory syndrome (Wang et al., 1996; Altschul et al., 1990; Neyroud et al., 1997).

A fetal brain cDNA library (Stratagene) (10 clones) was probed with inserts from P1-KO9-6b and P1-KO9-7 and the plasmid D20S24. Hybridizations were performed in 5×SSC, 10×Denhardt's, 0.1 M sodium phosphate (pH 6.7), 100 µg/mL salmon sperm DNA, 0.1% SDS and 50% formamide. Blots were washed in 2×SSC, 0.1% SDS twice at room temperature followed by one wash in 0.5×SSC, 0.1% SDS at 42° C.

A single cDNA isolated with D20S24, cIPK, showed 75% homology to amino acids 511-562 of KCNQ1; a second probing of the fetal brain cDNA library using the probe P1-KO9-6b resulted in the isolation of two additional cDNAs, c6b-6 and c6b-12, which showed significant homology with KCNQ1 amino acids 398-406 and 354-378, respectively (Altschul et al., 1990; Wang et al., 1996; Neyroud et al., 1997). Additional sequence encoding this BFNC gene, named KVEBN1 (now KCNQ2) after the OMIM locus name, was obtained from RACE experiments using adaptor-ligated double-stranded cDNA from fetal and adult brain tissue and from other cDNA clones isolated from a temporal cortex cDNA library.

To identify the full length gene, 5' and 3' RACE were performed on adaptor-ligated fetal and adult brain cDNA (Clontech) using primers within c6b-6 and cIPK and screening a temporal cortex cDNA library (Stratagene) with sequence flanking cIPK. Unprocessed cDNAs were repeatedly isolated from cDNA libraries and RACE experiments. The longest transcript isolated from brain was 1455 nucleotides long and was obtained using 5' RACE and extended from the S1 domain (amino acid 100) to the 3' conserved C-terminal domain (amino acid 585).

Composite clones encoding 872 amino acids of the KCNQ2 gene have been isolated (FIG. 3). The cDNA sequence for KCNQ2 is shown as SEQ ID NO:1 and the amino acid sequence for KCNQ2 is shown as SEQ ID NO:2. The putative initiator methionine lies within a region similar to the Kozak consensus sequence (Kozak, 1987). KCNQ2 encodes a highly conserved six transmembrane motif as well as a pore region that are the hallmarks of a $K^+$ ion channel gene. The S2, S3 and S4 transmembrane regions also contain charged amino acids that are found in all members of the $K^+$ channel subfamilies, including Shaker, Shab, Shaw and Shal. A search of Genbank with KCNQ2 sequence shows identical nucleotide sequence to HNSPC (Accession # D82346), a 393 amino acid putative potassium channel cDNA isolated from a human neuroblastoma cell line (Yokoyama et al., 1996). However, the last 21 amino acids of HNSPC including a stop codon are encoded by a sequence that in KCNQ2 is intronic. A search of the human expressed sequence tag database (dbest) shows seven different clones encoding portions of KCNQ2. Wei et al. have identified a gene from *C. elegans*, nKQT1, that appears to be a homolog of KCNQ2 (Wei et al., 1996). This group also described the human EST homolog of nKQT1, hKQT2, which is a partial clone of KCNQ2 (Wei et al., 1996). In addition to the six transmembrane domains and the pore, a small region 5' of transmembrane domain S1 is also conserved between KCNQ2, KCNQ3, KCNQ1 and nKQT1. Unlike other $K^+$ channel subfamilies, the C-terminal domain appears to contain highly conserved residues as shown in FIG. 3 for KCNQ2, KCNQ3, nKQT1 and KCNQ1. The poly A tail for KCNQ2 has not been identified to date.

Example 5

Northern Blot Analysis

The KCNQ2 cDNA hybridizes to transcripts approximately 1.5, 3.8 and 9.5 kb in size on Northern blots made from brain. Multiple Tissue Northerns (Clontech) of fetal and adult brain were probed with a RACE product containing transmembrane domains S1 through S6 of KCNQ2. The 1.5 and 9.5 kb transcripts appear to be expressed in both adult and fetal brain. The 3.8 kb transcript is expressed in select areas from adult brain, particularly in the temporal lobe and the putamen.

Example 6

Mutational Analysis of KCNQ2

Mutational analysis of KCNQ2 was performed on one affected individual from each of our 12 BFNC families. Coding regions from S1 to S6 and conserved regions in the 3' end of KCNQ2 were amplified by PCR using primers within introns and analyzed by SSCP (Novex) using 20% TBE gels run at 4° C. The exon-intron boundaries were identified by sequencing products obtained by exon-exon PCR on genomic P1 clones or directly from RACE products which contained unprocessed transcripts. PCR products showing variants seen on SSCP were either cloned and sequenced or reamplified with M13 reverse and M13 universal-tailed primers and sequenced directly on an ABI 373 or 377 using dye-primer chemistry.

In addition to the substantial deletion in kindred 1547, mutations were identified in five other BFNC families. Mutational analysis was carried out by first screening probands for SSCP variants and then sequencing each individual's DNA to determine the basis for the molecular variation. Mutations identified include two missense mutations, two frameshift mutations and one splice site mutation (Table 2). Later analyses resulted in the finding of four more BFNC families with mutations in KCNQ2. These include two nonsense mutations (families K1525 and K4443), an insertion resulting in a frameshift which results in readthrough beyond the normal stop codon (K3963), and a missense mutation (K4516). These latter 4 mutations are listed in Table 2.

TABLE 2

Mutations in the KCNQ2 Gene in BFNC Families

| Mutation at Amino Acid | Region | Kindred | Controls | Nucleotide Change |
|---|---|---|---|---|
| large deletion | not available | K1547 | 70 | not available |
| frameshift at 283 | pore | K1504 | 70 | insert GT between nucleotides 975 and 976 of SEQ ID NO: 1 |
| Y284C | pore | K3904 | 70 | A G at base 978 of SEQ ID NO: 1 |
| A306T | S6 | K1705 | 70 | G A at base 1043 of SEQ ID NO: 1 |
| Q323Stop | C-terminal | K4443 | — | C T at base 1094 of SEQ ID NO: 1 |
| R333Q | C-terminal | K4516 | — | G A at base 1125 of SEQ ID NO: 1 |
| R448Stop | C-terminal | K1525 | — | C T at base 1469 of SEQ ID NO: 1 |

TABLE 2-continued

Mutations in the KCNQ2 Gene in BFNC Families

| Mutation at Amino Acid | Region | Kindred | Controls | Nucleotide Change |
|---|---|---|---|---|
| frameshift at 522 | C-terminal | K3369 | 70 | delete bases 1691 through 1703 of SEQ ID NO: 1 |
| splice site variant | C-terminal | K3933 | 70 | g a at 3' end of intron which occurs between bases 1758 and 1759 of SEQ ID NO: 1 |
| frameshift at 867 | C-terminal | K3963 | 70 | insert GGGCC after base 2736 of SEQ ID NO: 1 |

The splice site variant occurs in an intron which occurs between two exons encoding amino acid residue 544. The first exon includes the TG at the start of codon 544 and the following exon includes the final T of codon 544. The sequence at the 3' end of the intron (shown in lower case letters) and continuing into the exon region (shown in upper case letters) encoding the end of codon 544 and codons 545-546 is: 5'-tgcagTGTCATG-3' (SEQ ID NO:5). The "g" at position 5 of SEQ ID NO:5 is mutated to an "a" in kindred K3933.

Figure 4:
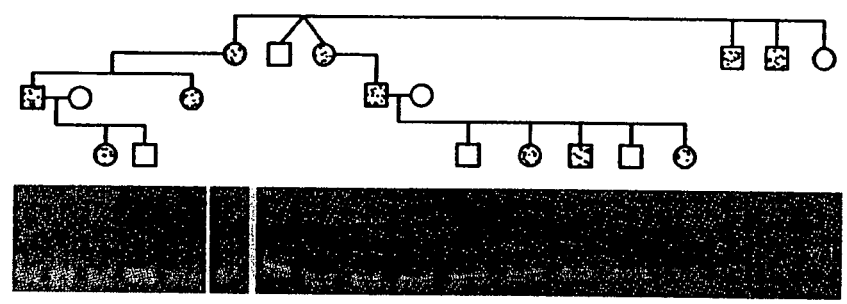
FIG. 4 shows a three generation pedigree with BFNC linked to chromosome 20. BFNC individuals are depicted by filled in black circles and squares. The data is from kindred 1504 which shows variants in the KCNQ2 pores. The lower portion of the figure shows the cosegregation of the variant form which is present only in affected individuals. Sequence analysis revealed the existence of a two base pair insertion in affected individuals showing the upper two (variant) bands.

None of the mutations seen in the first six families identified was seen in SSCP analysis of our panel of 70 unrelated, unaffected individuals. Furthermore, mutations were shown to segregate completely with affection status in all of the BFNC families where mutations were identified. In the case of the splice site mutation in kindred 3933 only the proband was sampled. An example of this segregation is shown in FIG. 4 for the two base-pair insertion identified in kindred 1504; all 11 affected members of the kindred have the SSCP variant and all seven unaffected individuals have wild type SSCP bands.

Of the four families (K1525, K3963, K4443 and K4516) which have been more recently found to have KCNQ2 mutations, three (K11525, K4443 and K4516) were found through direct sequencing and the mutation co-segregated in the family when other affected members were available for study. The mutation in K3963 was found via SSCP screening and this mutation was not detected in a panel of 70 normal, i.e., non BFNC, individuals. This mutation was found to co-segregate with affected individuals in family K3963. The wild-type gene includes two sets of GGGCC at bases 2727-2736 of SEQ ID NO:1. The sequence found in K3963 is three sets of GGGCC as a result of an insertion of GGGCC into this region. This results in the gene encoding the first 870 amino acids of the wild-type followed by an additional 60 amino acids of new sequence (amino acid residues 871 and 872 of the wild-type being replaced by the first 2 of the 60 additional amino acid residues). The gene including the 5 base insertion is shown as SEQ ID NO:95 and the protein encoded by this mutated gene is shown as SEQ ID NO:96.

Family K4443 has 6 BFNC affected individuals and two of these individuals have in addition seizures later in childhood that are classified as benign epilepsy with centrotemporal spikes (BERS), or rolandic epilepsy. The DNA of two affected individuals in this family was examined. The Q323Stop mutation is found in one of the affected individuals that expresses BFNC only and in one individual which has both BFNC and BERS or rolandic epilepsy, which developed later in childhood after the newborn seizures. This finding directly implicates the KCNQ2 gene on chromosome 20 in causing rolandic epilepsy. Rolandic epilepsy, or BERS, is a common childhood epilepsy and may account for 25% of all school age epilepsy. This is a genetic disorder that inherits as an autosomal dominant with reduced penetrance. It is possible that several genes may cause the rolandic phenotype, but this finding strongly suggests that at least some of the rolandic epilepsies will be caused by defects in KCNQ2, a potentially important finding.

Two neutral polymorphisms were identified in the KCNQ2 gene. One polymorphism is in codon 304 (TTC to TTT) in the S6 transmembrane domain and was seen in 10 of 71 controls who were each heterozygous (allelic frequency of 7.0%). The second polymorphism is in codon 573 (GCC to GCT) in the 3' region and was observed in 1 of 87 controls individuals as a heterozygote (allelic frequency of 0.57%).

It is predicted that the splice site mutation in the conserved 3' region of KCNQ2 and the two frameshift mutations, one in the pore region and one before the highly conserved 3' region, lead to altered protein products. In the case of the 283insGT pore mutation a predicted stop codon is found 36 amino acids downstream and in the case of the 522del13 3' mutation a predicted stop codon is found two amino acids downstream. Also, the two bp insertion mutation, 283insGT, would lead to a completely altered S6 transmembrane domain. While the breakpoints of the kindred 1547 deletion have not been determined, it is known that the 12 kb plasmid which includes the RFLP marker locus, D20S24, contains 80 codons (residues 509 to 588 of KCNQ2) of sequence from the highly conserved 3' region of the KCNQ2 gene, indicating that at least this portion of the gene is deleted in kindred 1547 affected individuals. The two missense mutations in families K3904 and K1705 change amino acid residues in key functional domains, the pore and S6 domain.

Ten unique mutations have been identified in KCNQ2 to date. The mutation defined by a 13 base pair deletion at amino acid 522 in kindred 3369 is of interest in that there is a greater variation in the reported clinical ages of onset within this family when compared to typical BFNC families. In kindred 3369, three individuals had onset of seizures within the first 2 weeks of life, while three individuals had initial onset of seizures at 3, 4, and 5 months of age.

The mutation in the BFNC kindred 1705 is an alanine to threonine substitution in the S6 transmembrane segment. This alanine residue is conserved in all members of the Shaker, Shab, Shaw and Shal subfamilies of potassium channels identified to date (Lopez et al., 1994; Nakamura et al., 1997; Tytgat, 1994). The KCNQ1 gene, which the KCNQ2 ion channel gene is most closely related to, also contains an alanine in this position. In six unrelated LQT1 families, the disease-causing mutation occurs at this same position where the alanine is changed to a valine (Wang et al., 1996; Russell et al., 1996). This S6 transmembrane domain has been shown to be involved in $K^+$ ion permeation in the Shaker subtype (Lopez et al., 1994) and may serve a similar function in KCNQ2. The C-terminal region appears to be important for gene function because a 13 bp deletion, a splice site mutation, a missense mutation, a nonsense mutation, and an insertion all produce an epileptic phenotype in separate BFNC families (see Table 2 and FIG. 3). Interestingly, this same region is known to have a deletion-insertion mutation in KCNQ1 in individuals with the Jervell and Lange-Nielsen recessive form of LQT and associated deafness (Neyroud et al., 1997). Disease-causing mutations in the C-terminal region further argue for a functional protein encoded by the KCNQ2 gene rather than the shorter HNSPC clone.

The pore region of K$^+$ ion channels belonging to the same structural class have been characterized extensively by mutational analysis. The two base-pair insertion observed in kindred 1504 occurs immediately after the universally conserved GYG motif. An insertion here not only alters the length of the pore that is believed to be crucial for function (Nakamura et al., 1997; Tytgat, 1994) but also modifies the signature sequence of the pore and produces a truncated protein.

In infants of families that have been linked to the chromosome 20 form of BFNC, EEG recordings show initial suppression of activity throughout the brain followed by generalized discharges of spikes and slow waves (Ronen et al., 1993; Plouin, 1994; Hauser and Kurland, 1975). It is therefore not surprising to find that the KCNQ2 gene is expressed in multiple brain areas in adults. Cortical regions as well as sub-cortical areas, such as the thalamus and caudate nucleus, contain multiple size transcripts of KCNQ2 (data not shown). It is possible that this expression pattern is also the same in the newborn infant.

The close homology (60% identity and 70% similarity of amino acids) of KCNQ2 to KCNQ1 and to the *C. elegans* nKQT1 gene and the reduced homology of these channels to the Shaker, Shab, Shaw and Shal subfamilies imply that they belong to a unique family of K$^+$ ion channels, called KQT-like (Wei et al., 1996). A new K$^+$ ion channel now known to be expressed in the brain raises the question of whether additional, undiscovered members of this gene family may be responsible for other forms of idiopathic, generalized epilepsies with tonic-clonic convulsions. A similar idiopathic seizure disorder seen early in development is Benign Familial Infantile Convulsions (BFIC). In BFIC the seizures begin at four to eight months of age and remit after several years. BFIC maps to chromosome 19q in five Italian families (Guipponi et al., 1997). It is reasonable to hypothesize that BFIC is also caused by mutations in as yet unidentified members of the KQT-like family of K$^+$ ion channels or by mink-like proteins.

Example 7

Somatic Cell Hybrid Panel Genotyping

Exploiting the putative conservation of intron-exon boundaries between KCNQ2 and KCNQ3 in the highly homologous transmembrane domains, a primer pair was designed from the available EST sequences (primer A: 5'-TTCCTGATTGTCCTGGGGTGCT-3' (SEQ ID NO:8), primer B: 5'-TTCATCTTTGGAGCCGAGTTTGC-3' (SEQ ID NO:9)) to cross an intron. The amplified fragment contains an intron in human (1.8 kb) as well as in rodent (800 bp) genomic DNA. This primer was used to amplify the Coriell panel. The reactions were performed in a 25 µL volume using 50 ng of template DNA and 1 unit of Taq DNA polymerase (Perkin Elmer), 10 pmol of each primer, 3 nmol of each deoxyribonucleotide in a 1.5 mM MgCl$_2$ buffer. Cycling conditions were 94° C. for 4 minutes, then 30 cycles of: denaturation at 94° C. for 30 seconds, annealing at 58° C. for 30 seconds and elongation at 72° C. for 1.5 minutes, followed by a final elongation at 72° C. for 10 minutes. The PCR products were electrophoresed in a 1.5% agarose gel.

Example 8

Chromosome 8 Radiation Hybrids Panel

An HSA8 radiation hybrid panel (Lewis et al., 1995) was genotyped with specific human intronic primers (primer D: 5'-TCCATGTGGTACTCCATGTCTGAA-3' (SEQ ID NO:10), primer E: 5'-GCACGTCACATTGGGGATGT-CAT-3' (SEQ ID NO:11)). The length of the PCR product is 190 bp. The reactions were performed in a 25 µL volume using 100 ng of template DNA and 1 unit of Taq polymerase (Perkin Elmer), 10 pmol of each primer, 3 nmol of each deoxyribonucleotide in a 1.5 mM MgCl$_2$ buffer. Cycling conditions were 94° C. for 4 minutes, then 30 cycles of: denaturation at 94° C. for 30 seconds, annealing at 62° C. for 30 seconds and elongation at 72° C. for 30 seconds, followed by a final elongation at 72° C. for 10 minutes. The PCR products were electrophoresed in a 2% agarose gel. The genotyping data was analyzed by the RHMAP V2.01 program (Boehnke et al., 1991).

Example 9

Full Length cDNA

To identify the full length KCNQ3 cDNA, 5' and 3' RACE were performed on adaptor-ligated fetal and adult brain cDNA (Clontech) using primers from the available EST sequences. The primers used for RACE experiments are given in Table 3. PCR products were subcloned (T/A Cloning® Kit, Invitrogen) and both strands were sequenced on an ABI 377 instrument.

Example 10

Genomic Organization/Intron-Exon Boundaries

A BAC genomic library was screened by PCR (as described for the Coriell panel) and three overlapping genomic clones were isolated. The intron/exon boundaries were identified by cloning (T/A Cloning® Kit, Invitrogen) and sequencing (ABI 377) products obtained by exon-exon PCR on genomic human DNA and/or on BAC genomic clones containing the KCNQ3 gene.

TABLE 3

RACE Primers

5' RACE

| | | |
|---|---|---|
| KV1b: | 5'-TGTGTTTTGGCGTGGAGGGAGGTC-3' | (SEQ ID NO: 12) |
| KV2b: | 5'-CAGTAACAGAAGCCAGTCTCC-3' | (SEQ ID NO: 13) |
| KV3b: | 5'-GCAAACTCGGCTCCAAAGATGAA-3' | (SEQ ID NO: 14) |
| KV4b: | 5'-CACCAACGCGTGGTAAAGCAGC-3' | (SEQ ID NO: 15) |

3' RACE

| | | |
|---|---|---|
| KV1a: | 5'-TTCCTGATTGTCCTGGGGTGCT-3' | (SEQ ID NO: 16) |
| KV2a: | 5'-AGTATCTGCCGGGCATCTCGACA-3' | (SEQ ID NO: 17) |

Example 11

SSCP Analysis and Characterization of Mutant and Polymorphic Alleles

Sixty percent of the coding region of KCNQ3 was amplified by PCR using primers within introns when available and analyzed by SSCP (Novex) using 20% TBE gels run at 4 C as described in Novex Thermoflow™ protocols (Novex, San Diego, Calif.). The PCR products presenting an SSCP polymorphism were cloned (T/A Cloning® Kit, Invitrogen), nine clones were sequenced on an ABI 373 or 377 using dye-primer chemistry and analyzed with the Sequencher™ 3.0 program.

Example 12

Characterization of the KCNQ3 Gene

The KQT-like family is a recently characterized family of voltage-gated potassium channels (Wei et al., 1996). Until now, only KCNQ2 (described in this disclosure) which is the gene mutated in the chromosome 20 BFNC disorder and KCNQ1, which is the chromosome 11 gene responsible for Long QT syndrome and the Jervell and Lange-Nielsen cardioauditory syndrome (Neyroud et al., 1997), were known to belong to this family. In order to identify new members of that family, possibly involved in other types of IGEs, a tBLASTx (Altschul et al., 1990) search was started with the KCNQ2 full length cDNA against the Expressed Sequence Tags (ESTs) database. Five human EST clones were identified that presented significant homologies with KCNQ2 (clone ID: 1-362079, 2-222324, 3-363215, 4-38822, 5-45636; Hillier et al., unpublished data). Interestingly, these clones come from two different cDNA libraries: retina (1-3) and infant brain (4-5) (Soares et al., 1994) and can be organized in two nonoverlapping contigs (1-3) and (4-5). It is demonstrated here that the two contigs belong to the same gene, KCNQ3.

Figure 5:
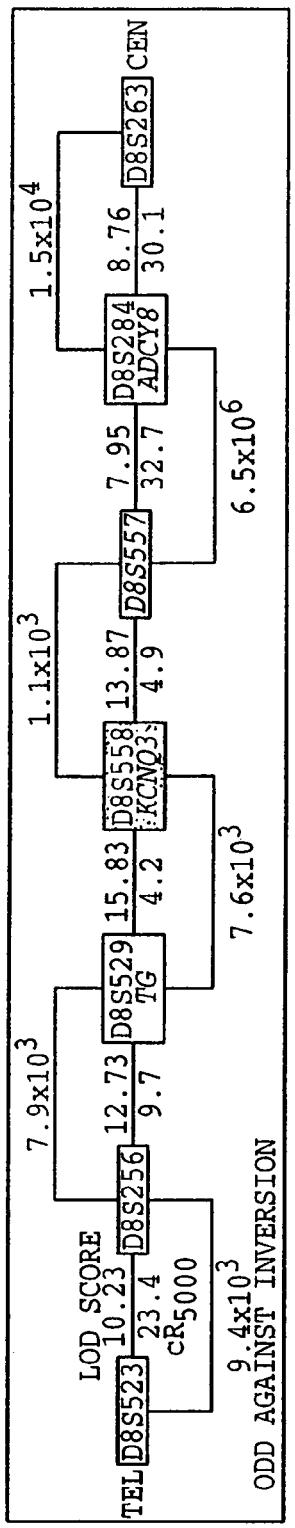
FIG. 5. Radiation Hybrid Mapping of the KCNQ3 locus. Interpair LOD scores are given above the center line and distance between marker pairs, in $cR_{5000}$, is shown below. The odds against inversion for adjacent loci is also given for each marker pair.

The first step in the characterization of the new gene was genomic localization of the ESTs. Using a commercial somatic cell hybrid panel (Coriell panel (Drwing a et al., 1993)), KCNQ3 was mapped on HSA8. In order to refine that assignment, a panel of 97 radiation hybrids previously constructed for determining the linear order and intermarker distance of chromosome 8 loci (Lewis et al., 1995) was genotyped. Specific human intronic primers were used and each RH was scored by PCR for the presence or absence of the locus. The data were analyzed using RHMAP V2.01 against results collected for other chromosome 8 markers. The retention frequency for KCNQ3 in the RH panel was 11.7%. Tight linkage of KCNQ3 locus was observed with markers previously mapped to chromosome band 8q24. The tightest linkage was seen with marker D8S558 (LOD 13.87, $\theta$ of 0.047 $R_{5000}$). The resulting RH map is shown in FIG. 5. The position of the KCNQ3 locus is localized to the interval defined by the markers previously linked to a chromosome 8 BFNC family (Lewis et al., 1993), making KCNQ3 a very strong positional candidate for the chromosome 8 BFNC locus. A second Caucasian family also demonstrates suggestive linkage to the same markers (Steinlein et al., 1995).

A partial cDNA sequence was obtained by a series of rapid amplification of cDNA ends (RACE) experiments. 5' and 3' RACE were performed by amplifying adult and fetal brain Marathon-Ready cDNAs (Clontech) using primers derived from the two EST contigs previously identified. The primer pairs are shown in Table 3. This was used to purify a mouse genomic homolog of KCNQ3. After determining the mouse sequence including intron/exon junctions, primers based upon the mouse sequence were used to clone the remainder of the human cDNA for KCNQ3. The primers used to amplify the 5' end of the human gene were CGCGGATCATGGCATTGGAGTTC (SEQ ID NO:93) and AAGCCCCAGAGACTTCTCAGCTC (SEQ ID NO:94). The complete KCNQ3 cDNA sequence (SEQ ID NO:6) encodes an 872 amino acid protein (SEQ ID NO:7) with six putative transmembrane domains, a pore region, a stop codon, and the 3' untranslated region containing the poly $A^+$ tail. This protein presents 58% similarity and 46% identity (calculated using BLAST) in the region from amino acid 101 to the stop codon with KCNQ2 and is also highly conserved with KCNQ1 (Yang et al., 1997) as well as with the *C. elegans* homologue nKQT1 (Wei et al., 1996). A comparison of sequences is shown in FIG. 3. The two EST contigs are identical to amino acids 86-265 and 477-575 of KCNQ3, respectively (see FIG. 3).

Figure 6:
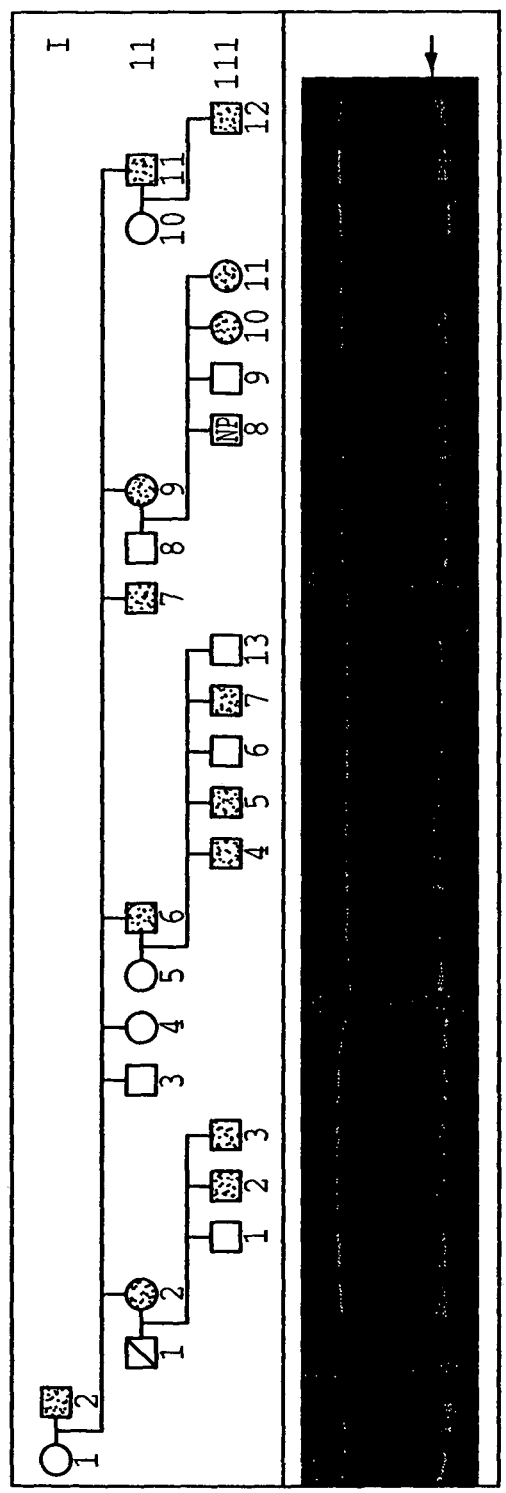
FIG. 6 shows a three generation pedigree with BFNC linked to chromosome 8. BFNC individuals are depicted by filled in black circles and squares. The non-penetrant individual 111-8 is indicated by the symbol NP. The lower portion of the figure shows the co-segregation of the 187 bp SSCP variant, present only in affected and non-penetrant individuals (arrow).

To test whether or not KCNQ3 is the gene responsible for the chromosome 8 BFNC phenotype, mutations were looked for in one affected individual of a phenotypically well characterized three-generation Mexican-American BFNC family (Ryan et al., 1991) (see FIG. 6). That family has been mapped by multipoint linkage analysis on chromosome 8q24 (Z=4.43) within the interval spanned by markers D8S198 (proximal to D8S284) and D8S274 (distal to D8S256) (see FIG. 5) (Lewis et al., 1993; Dib et al., 1996). It is here shown that this chromosomal region contains the KCNQ3 locus. So far, using intronic primers, 60% of the coding region of KCNQ3, containing the six transmembrane domains as well as the pore region, has been screened by a cold SSCP method. One SSCP variant was identified in a PCR fragment of 187 bp containing the transmembrane domain S5 and half of the pore. The primers used to prepare this fragment are: Ret.6a 5'-CATCACGGCCTGGTA-CATCGGTT-3' (SEQ ID NO:18) (corresponding to nucleotides 801-823 of SEQ ID NO:6) and Hebn2.3b 5'-AATCT-CACAGAATTGGCCTCCAAG-3' (SEQ ID NO:19). The Ret.6a primer is from coding region and the Hebn2.3b primer is from intronic region. This SSCP variant is in perfect cosegregation with the BFNC phenotype and it is also present in a single non-penetrant individual carrying the disease-marker haplotype (FIG. 6). Furthermore, this SSCP variant is absent from a panel of 72 Caucasian and 60 Mexican-American (264 chromosomes) unrelated individuals used as the control group. To characterize the nucleotide change of this variant, the PCR product of one affected individual was cloned and nine clones were sequenced on both strands. Four clones contained the wild-type allele and five the mutated allele. The mutation is a single missense mutation Gly (GGC) to Val (GTC) in position 310 of the highly conserved pore region (the mutation occurring at base 947 of SEQ ID NO:6). In addition, a silent polymorphism (frequency of 0.4%) was found in one Mexican-American control in the transmembrane region S5 at L278 (CTT CTC) (the polymorphism is at base 852 of SEQ ID NO:6). Four other polymorphisms in KCNQ3 have been seen. These are at N220 (AAC or AAT), Gly244 (GGT or GGC), L357 (CTG or CTC) and 1860 (ATT or ATC). These polymorphisms are at base numbers 678, 750, 1089 and 2598 of SEQ ID NO:6, respectively.

In addition, some individual probands with juvenile myoclonic epilepsy were screened with SSCP. JME is an inherited childhood seizure disorder. KCNQ3 was mutated in one individual who was tested. The mutation was found in an alternatively spliced exon that lies in an intron which splits codon 412. This alternatively spliced exon was found in adult brain after RACE experiments. This exon is SEQ ID NO:92. The exon was seen in an adult brain cDNA clone obtained from Clontech. This exon is 130 nucleotides long which is not a multiple of 3. Therefore the presence of this exon results not only in the addition of extra amino acid sequence but causes a frameshift (1 extra base) which results in a stop codon within the normal coding region of the gene. The mutation found in the JME proband is a 1 base pair deletion in the alternatively spliced exon (the loss of the G at base 118 of SEQ ID NO:92) that results in the frameshift from the alternative exon going back into frame resulting in a KCNQ3 with an additional 43 amino acid residues between amino acid residues 412 and 413 of the wild-type, and thus alters the protein in the brain cells of the JME proband. The patient with this deletion has a mother who has epilepsy, however this particular mutation is from the father, not from the mother. JME is a common, inherited childhood epilepsy and most likely is caused by defects not only in KCNQ3 but also in other genes.

This finding brings to three the number of human members of the KQT-like family, two of which are expressed in brain and one in heart. Defects in all three K$^+$ channel genes cause human diseases associated with altered regulation of excitability. Taking all these findings together, there is strong evidence that KCNQ2 and KCNQ3, as well as undiscovered genes of the same family or genes belonging to the same pathway, are involved in IGEs. Screening these KQT-like K$^+$ channel genes as well as other K$^+$ channel genes belonging to different families (Wei et al., 1996) for mutations in individuals with common types of IGEs will be a powerful alternative for identifying disease-causing genes. This is especially true given the difficult and controversial tentative linkages described in IGE disease pedigrees (Leppert et al., 1993).

Example 13

Generation of Polyclonal Antibody against KCNQ2 or KCNQ3

Segments of KCNQ2 or KCNQ3 coding sequence are expressed as fusion protein in *E. coli*. The overexpressed protein is purified by gel elution and used to immunize rabbits and mice using a procedure similar to the one described by Harlow and Lane, 1988. This procedure has been shown to generate Abs against various other proteins (for example, see Kraemer et al., 1993).

Briefly, a stretch of KCNQ2 or KCNQ3 coding sequence is cloned as a fusion protein in plasmid PET5A (Novagen, Inc., Madison, Wis.). After induction with IPTG, the overexpression of a fusion protein with the expected molecular weight is verified by SDS/PAGE. Fusion protein is purified from the gel by electroelution. Identification of the protein as the KCNQ2 or KCNQ3 fusion product is verified by protein sequencing at the N-terminus. Next, the purified protein is used as immunogen in rabbits. Rabbits are immunized with 100 µg of the protein in complete Freund's adjuvant and boosted twice in 3 week intervals, first with 100 µg of immunogen in incomplete Freund's adjuvant followed by 100 µg of immunogen in PBS. Antibody containing serum is collected two weeks thereafter.

This procedure is repeated to generate antibodies against the mutant forms of the KCNQ2 or KCNQ3 gene product. These antibodies, in conjunction with antibodies to wild type KCNQ2 or KCNQ3, are used to detect the presence and the relative level of the mutant forms in various tissues and biological fluids.

Example 14

Generation of Monoclonal Antibodies Specific for KCNQ2 or KCNQ3

Monoclonal antibodies are generated according to the following protocol. Mice are immunized with immunogen comprising intact KCNQ2, intact KCNQ3, KCNQ2 peptides or KCNQ3 peptides (wild type or mutant) conjugated to keyhole limpet hemocyanin using glutaraldehyde or EDC as is well known.

The immunogen is mixed with an adjuvant. Each mouse receives four injections of 10 to 100 µg of immunogen and after the fourth injection blood samples are taken from the mice to determine if the serum contains antibody to the immunogen. Serum titer is determined by ELISA or RIA. Mice with sera indicating the presence of antibody to the immunogen are selected for hybridoma production.

Spleens are removed from immune mice and a single cell suspension is prepared (see Harlow and Lane, 1988). Cell fusions are performed essentially as described by Kohler and Milstein, 1975. Briefly, P3.65.3 myeloma cells (American Type Culture Collection, Rockville, Md.) are fused with immune spleen cells using polyethylene glycol as described by Harlow and Lane, 1988. Cells are plated at a density of 2×10$^5$ cells/well in 96 well tissue culture plates. Individual wells are examined for growth and the supernatants of wells with growth are tested for the presence of KCNQ2 or KCNQ3 specific antibodies by ELISA or RIA using wild type or mutant KCNQ2 or KCNQ3 target protein. Cells in positive wells are expanded and subcloned to establish and confirm monoclonality.

Clones with the desired specificities are expanded and grown as ascites in mice or in a hollow fiber system to produce sufficient quantities of antibody for characterization and assay development.

Example 15

Sandwich Assay for KCNQ2 or KCNQ3

Monoclonal antibody is attached to a solid surface such as a plate, tube, bead or particle. Preferably, the antibody is attached to the well surface of a 96-well ELISA plate. 100 µL sample (e.g., serum, urine, tissue cytosol) containing the KCNQ2 or KCNQ3 peptide/protein (wild-type or mutants) is added to the solid phase antibody. The sample is incubated for 2 hrs at room temperature. Next the sample fluid is decanted, and the solid phase is washed with buffer to remove unbound material. 100 µL of a second monoclonal antibody (to a different determinant on the KCNQ2 or KCNQ3 peptide/protein) is added to the solid phase. This antibody is labeled with a detector molecule (e.g., $^{125}$I, enzyme, fluorophore, or a chromophore) and the solid phase with the second antibody is incubated for two hrs at room temperature. The second antibody is decanted and the solid phase is washed with buffer to remove unbound material.

The amount of bound label, which is proportional to the amount of KCNQ2 or KCNQ3 peptide/protein present in the sample, is quantified. Separate assays are performed using monoclonal antibodies which are specific for the wild-type KCNQ2 or KCNQ3 as well as monoclonal antibodies specific for each of the mutations identified in KCNQ2 or KCNQ3.

Example 16

Assay to Screen Drugs Affecting the KCNQ2 or KCNQ3 K$^+$ Channel

With the knowledge that KCNQ2 and KCNQ3 each forms a potassium channel, it is now possible to devise an assay to screen for drugs which will have an effect on one or both of these channels. The gene is transfected into oocytes or mammalian cells and expressed as described above. When the gene used for transfection contains a mutation which causes BFNC, rolandic epilepsy or JME, a change in the induced current is seen as compared to transfection with wild-type gene only. A drug candidate is added to the bathing solution of the transfected cells to test the effects of the drug candidates upon the induced current. A drug candidate which alters the induced current such that it is closer to the current seen with cells cotransfected with wild-type KCNQ2 or wild-type KCNQ3 is useful for treating BFNC, rolandic epilepsy or JME.

Example 17

Primer Pairs for Screening Each Exon of Kcnq2 for Mutation

The genomic KCNQ2 has been sequenced in the intron/exon borders and primer pairs useful for amplifying each exon have been developed. These primer pairs are shown in Table 4. For exons 13 and 17 primers within the exons are also utilized. Some exon/intron sequence is shown in FIGS. 7A-O.

TABLE 4

| Exon | Domain | Primer Sequence | (SEQ ID NO:) |
|---|---|---|---|
| 1 | met + SI | | |
| 2 | SI + SII | TTCCTCCTGGTTTTCTCCTGCCT | (SEQ ID NO: 22) |
| | | AAGACAGACGCCCAGGCAGCT | (SEQ ID NO: 23) |
| 3 | SII + SIII | AGGCCTCAAGGTGGCCTCAGCTTT | (SEQ ID NO: 24) |
| | | CTGGCCCTGATTCTAGCAATAC | (SEQ ID NO: 25) |
| 4 | SIII + SIV | ACATCATGGTGCTCATCGCCTCC | (SEQ ID NO: 97) |
| | | TGTGGGCATAGACCACAGAGCC | (SEQ ID NO: 26) |
| 5 | SV + pore | TGGTCACTGCCTGGTACATCGG | (SEQ ID NO: 27) |
| | | ATGGAGCAGGCTCAGCCAGTGAGA | (SEQ ID NO: 28) |
| 6 | pore + SVI | GCAGGCCCTTCGTGTGACTAGA | (SEQ ID NO:: 29) |
| | | ACCTAGGGAACTGTGCCCAGG | (SEQ ID NO: 30) |
| 7 | SVI | ATGGTCTGACCCTGATGAATTGG | (SEQ ID NO: 31) |
| | | GCGGCCTCCACTCCTCAACAA | (SEQ ID NO: 32) |
| 8 | C-term | | |
| 9 | C-term | | |
| 10 | variable | CCGCCGGGCACCTGCCACCAA | (SEQ ID NO: 33) |
| | | GCTTGCACAGCTCCATGGGCAG | (SEQ ID NO: 34) |
| 11 | C-term | GCTGTGCAAGCAGAGGGAGGTG | (SEQ ID NO: 98) |
| | | CTGTCCTGGCGTGTCTTCTGTG | (SEQ ID NO: 99) |
| 12 | variable cysteine insertion | CCCAGGACTAACTGTGCTCTCC | (SEQ ID NO: 35) |
| | | CCGTGCAGCAGCCGTCAGTCC | (SEQ ID NO: 36) |
| 13 | C-term | GCAGAGTGACTTCTCTCCCTGTT | (SEQ ID NO: 37) |
| | | GTCCCCGAAGCTCCAGCTCTT | (SEQ ID NO: 38) |
| | | AAGATCGTGTCTTCTCCAGCCC | (SEQ ID NO: 39) |
| | | GATGGACCAGGAGAGGATGCGG | (SEQ ID NO: 40) |
| 14 | C-term | CCCTCACGGCATGTGTCCTTCC | (SEQ ID NO: 41) |
| | | AGCGGGAGGCCCCTCCTCACT | (SEQ ID NO: 42) |
| 15 | C-term | GGTCTCTGGCCCAGGGCTCACA | (SEQ ID NO: 43) |
| | | CTTGTCCCCTGCTGGACAGGCA | (SEQ ID NO: 44) |
| 16 | C-term | TTGACGGCAGGCACCACAGCC | (SEQ ID NO: 45) |
| 17 | C-term | CCCAGCCCAGCAGCCCCTTTT | (SEQ ID NO: 46) |
| | | AGGTGGAGGGCGGACACTGGA | (SEQ ID NO: 47) |
| | | CTCCACGGGCCAGAAGAACTTC | (SEQ ID NO: 48) |
| | | GATGGAGATGGACGTGTCGCTGT | (SEQ ID NO: 49) |
| | | TGGAGTTCCTGCGGCAGGAGGACAC | (SEQ ID NO: 50) |
| | | GGTGTCTGACTCTCCCTCCGCAA | (SEQ ID NO: 51) |
| | | GTGGCGCCTTGTGCCAAAGTCA | (SEQ ID NO: 52) |
| | | ACCTCGGAGGCACCGTGCTGA | (SEQ ID NO: 53) |

Example 18

Intron Sequence of KCNQ3 and Primer Pairs for Amplifying the Exons of KCNQ3

Although the complete cDNA for KCNQ3 has been obtained and sequenced, the complete genomic DNA has not yet been sequenced. However, much of the intron DNA has been sequenced and this sequence information has been utilized to develop primer pairs which are useful for amplifying each exon. The intron/exon sequence is shown in FIGS. 8A-O. Some useful primer pairs for amplifying each exon are shown in Table 5 although one of skill in the art can easily develop other primer pairs using the intron sequence shown in FIGS. 8A-O.

TABLE 5

| Pair | Sequence 5' 3' | (SEQ ID NO:) | Size | Temp | Part of the gene |
|---|---|---|---|---|---|
| 1 | GCGACGTGGAGCAAGTACCTTG<br>CACCAACGCGTGGTAAAGCAGC | (54)<br>(55) | 245 | 62 | before S1 |
| 2 | ATGACTCAAAGGTTCCTTAGTCCA<br>GAAGCCCAACCAGAAGCATTTAC | (56)<br>(57) | 174 | 62 | S1 to beginning of S2 |
| 3 | TCAGTGCCTCTCCATATGCTCTT<br>ACTGAGGAGGCTGGGAGGCTC | (58)<br>(59) | 194 | 62 | end of S2 to beginning of S3 |
| 4 | GATGACGCCATTGCTTTCGCATGA<br>GTGGGAAGCCCATGTGGTCCTG | (60)<br>(61) | 298 | 65 | end of S3 to S4 |
| 5 | CATCCACTCAACGACTCCCAG<br>AATCTCACAGAATTGGCCTCCAAG | (62)<br>(63) | 249 | 65 | S5 to beginning of the pore |
| 6 | TCCATGTGGTACTCCATGTCTGAA<br>GCACGTCACATTGGGGATGTCAT | (64)<br>(65) | 190 | 58 | end of the pore to beginning of S6 |
| 7 | GGAATGCTGGGACAGTCTAGCTG<br>TACATATGCATGGATCTTAATCCCAT | (66)<br>(67) | 203 | 58 | end of S6 to start of C-terminal part |
| 8 | AAAGTTTCAGGTGGTGCCCACTCA<br>GAGGCCACAGACACGAATACAGAC | (68)<br>(69) | 230 | 65 | C-terminal |
| 9 | TGGGTAAACCCGCCTCCTTCATTG<br>ACTCTATCTTGGGACCAGCATGAC | (70)<br>(71) | 306 | 65 | C-terminal |
| 10 | TAAGAGCCTGCACTGAAGGAGGA<br>GGGGAGGAAGAAGTGGAAGAGAC | (72)<br>(73) | 302 | 65 | C-terminal |
| 11 | CAGGTCTGTGGCCTGCCGTTCAT<br>CCTTCCTGTGGGAGTTGAGCTGG | (74)<br>(75) | 233 | 65 | C-terminal |
| 12 | GTTTGCTAGCCTTCTGTTATAGCT<br>GGGAGCGCAGTCCCTCCAGAT | (76)<br>(77) | 239 | 62 | C-terminal |
| 13 | CTTATATATTCCAAACCCTTATCTCA<br>GGTGGGGATCGTTGCTATTGGTT | (78)<br>(79) | 277 | 62 | C-terminal |
| 14 | AACCAATAGCAACGATCCCCACC<br>CTGACTTTGTCAATGGTCACCTGG | (80)<br>(81) | 303 | 65 | C-terminal after last intron |
| 15 | CGGAACCACCCTACAGCTTCCA<br>GGGAGTGGCAGCTCACTCGGGA | (82)<br>(83) | 210 | 65 | C-terminal after last intron |
| 16 | AGGCCCACGGTCCTGCCTATCT<br>CCATTGGGGCCGAACACATAATC | (84)<br>(85) | 236 | 65 | C-terminal after last intron |
| 17 | CTTCAGCATCTCCCAGGACAGAG<br>AAGGAGGGGTCAGCCAGTGACCT | (86)<br>(87) | 228 | 65 | C-terminal after the STOP codon |

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

Altschul S F, et al. (1990). *J. Mol. Biol.* 251:403-410.

Altschul S F, et al. (1997). *Nucl. Acids Res.* 25:3389-3402.

Anand, R (1992). *Techniques for the Analysis of Complex Genomes*, (Academic Press).

Anderson W F, et al. (1980). *Proc. Natl. Acad. Sci. USA* 77:5399-5403.

Ausubel F M, et al. (1992). *Current Protocols in Molecular Biology*, (John Wiley and Sons, New York, N.Y.).

Bandyopadhyay P K and Temin H M (1984). *Mol. Cell. Biol.* 4:749-754.

Bartel P L, et al. (1993). "Using the 2-hybrid system to detect protein-protein interactions." In *Cellular Interactions in Development: A Practical Approach*, Oxford University Press, pp. 153-179.

Beaucage S L and Caruthers M H (1981). *Tetra. Letts.* 22:1859-1862.
Berglund P, et al. (1993). *Biotechnology* 11:916-920.
Berkner K L, et al. (1988). *BioTechniques* 6:616-629.
Berkner K L (1992). *Curr. Top. Microbiol. Immunol.* 158: 39-66.
Biervert C, et al. (1998). *Science* 279:403-406.
Boehnke M, et al. (1991). *Am. J. Hum. Genet.* 49:1174-1188.
Borman S (1996). *Chemical & Engineering News*, December 9 issue, pp. 42-43.
Breakefield X O and Geller A I (1987). *Mol. Neurobiol.* 1:337-371.
Brinster R L, et al. (1981). *Cell* 27:223-231.
Browne D L, et al. (1994). *Nature Genetics* 8:136-140.
Buchschacher G L and Panganiban A T (1992). *J. Virol.* 66:2731-2739.
Capecchi M R (1989). *Science* 244:1288-1292.
Cariello N F (1988). *Am. J. Human Genetics* 42:726-734.
Chandy K G and Gutman G A (1995). *Handbook of Receptors and Channels: Ligand and Voltage-Gated Ion Channels* (CRC Press, Ann Arbor, Mich.), pp. 1-71.
Chee M, et al. (1996). *Science* 274:610-614.
Chevray P M and Nathans D N (1992). *Proc. Natl. Acad. Sci. USA* 89:5789-5793.
Compton J (1991). *Nature* 350:91-92.
Conner B J, et al. (1983). *Proc. Natl. Acad. Sci. USA* 80:278-282.
Costantini F and Lacy E (1981). *Nature* 294:92-94.
Cotten M, et al. (1990). *Proc. Natl. Acad. Sci. USA* 87:4033-4037.
Cotton R G, et al. (1988). *Proc. Natl. Acad. Sci. USA* 85:4397-4401.
Culver K W, et al. (1992). *Science* 256:1550-1552.
Culver K (1996). *Gene Therapy: A Primer for Physicians*, 2nd Ed., Mary Ann Liebert.
Curiel D T, et al. (1991). *Proc. Natl. Acad. Sci. USA* 88:8850-8854.
Curiel D T, et al. (1992). *Hum. Gene Ther.* 3:147-154.
DeRisi J, et al. (1996). *Nat. Genet.* 14:457-460.
Deutscher M (1990). *Meth. Enzymology* 182:83-89 (Academic Press, San Diego, Cal.).
Dib C, et al. (1996). *Nature* 380:152-154.
Donehower L A, et al. (1992). *Nature* 356:215-221.
Drwing a H L et al. (1993). *Genomics* 16:311-314.
Dworetzky S I, et al. (1998). *Society for Neuroscience Abstracts* 24(part 2):813.1 (28th Annual Meeting, Los Angeles, Calif., Nov. 7-12, 1998).
Editorial (1996). *Nature Genetics* 14:367-370.
Elghanian R, et al. (1997). *Science* 277:1078-1081.
*Enhancers and Eukaryotic Gene Expression*, Cold Spring Harbor Press, Cold Spring Harbor, N.Y. (1983).
Erickson J, et al. (1990). *Science* 249:527-533.
Fahy E, et al. (1991). *PCR Methods Appl.* 1:25-33.
Felgner P L, et al. (1987). *Proc. Natl. Acad. Sci. USA* 84:7413-7417.
Fields S and Song O-K (1989). *Nature* 340:245-246.
Fiers W, et al. (1978). *Nature* 273:113-120.
Fink D J, et al. (1992). *Hum. Gene Ther.* 3:11-19.
Fink D J, et al. (1996). *Ann. Rev. Neurosci.* 19:265-287.
Finkelstein J, et al. (1990). *Genomics* 7:167-172.
Fodor S P A (1997). *Science* 277:393-395.
Freese A, et al. (1990). *Biochem. Pharmacol.* 40:2189-2199.
Friedman T (1991). In *Therapy for Genetic Diseases*, T. Friedman, ed., Oxford University Press, pp. 105-121.
Glover D (1985). *DNA Cloning*, I and II (Oxford Press).
Goding (1986). *Monoclonal Antibodies: Principles and Practice*, 2d ed. (Academic Press, N.Y.).
Godowski P J, et al. (1988). *Science* 241:812-816.
Gordon J W, et al. (1980). *Proc. Natl. Acad. Sci. USA* 77:7380-7384.
Gorziglia M and Kapikian A Z (1992). *J. Virol.* 66:4407-4412.
Graham F L and van der Eb A J (1973). *Virology* 52:456-467.
Gribkoff V K, et al. (1998). *Society for Neuroscience Abstracts* 24(part 2):813.10 (28th Annual Meeting, Los Angeles, Calif., Nov. 7-12, 1998).
Grompe M (1993). *Nature Genetics* 5:111-117.
Grompe M, et al. (1989). *Proc. Natl. Acad. Sci. USA* 86:5855-5892.
Guipponi M, et al. (1997). *Hum. Molec. Genet.* 6:473-477.
Guthrie G and Fink G R (1991). *Guide to Yeast Genetics and Molecular Biology* (Academic Press).
Hacia J G, et al. (1996). *Nature Genetics* 14:441-447.
Harlow E and Lane D (1988). *Antibodies: A Laboratory Manual* (Cold Spring Harbor Laboratory, Cold Spring Harbor, N.Y.).
Hasty P, et al. (1991). *Nature* 350:243-246.
Hauser W A and Kurland L T (1975). *Epilepsia* 16:1-66.
Helseth E, et al. (1990). *J. Virol.* 64:2416-2420.
Hodgson J (1991). *Bio/Technology* 9:19-21.
Huse W D, et al. (1989). *Science* 246:1275-1281.
Iannotti C, et al. (1998). *Society for Neuroscience Abstracts* 24(part 1):330.14 (28th Annual Meeting, Los Angeles, Calif., Nov. 7-12, 1998).
Innis M A, et al. (1990). *PCR Protocols: A Guide to Methods and Applications* (Academic Press, San Diego).
Jablonski E, et al. (1986). *Nuc. Acids Res.* 14:6115-6128.
Jakoby W B and Pastan I H (eds.) (1979). *Cell Culture Methods in Enzymology* volume 58 (Academic Press, Inc., Harcourt Brace Jovanovich (New York)).
Johnson P A, et al. (1992). *J. Virol.* 66:2952-2965.
Johnson, et al. (1993). "Peptide Turn Mimetics" in *Biotechnology and Pharmacy*, Pezzuto et al., eds., Chapman and Hall, New York.
Kaneda Y, et al. (1989). *J. Biol. Chem.* 264:12126-12129.
Kanehisa M (1984). *Nucl. Acids Res.* 12:203-213.
Keating M T and Sanguinetti M C (1996). *Curr. Opinion Genet. Dev.* 6:326-333.
Kinszler K W, et al. (1991). *Science* 251:1366-1370.
Kohler G and Milstein C (1975). *Nature* 256:495-497.
Kozak M (1987). *J. Mol. Biol.* 196:947-950.
Kraemer F B, et al. (1993). *J Lipid Res.* 34:663-672.
Kubo T, et al. (1988). *FEBS Lett.* 241:119-125.
Kyte J and Doolittle R F (1982). *J. Mol. Biol.* 157:105-132.
Landegren U, et al. (1988). *Science* 242:229-237.
Lee J E, et al. (1995). *Science* 268:836-844.
Leppert M, et al. (1989). *Nature* 337:647-648.
Leppert M, et al. (1993). *Brain Pathology* 3:357-369.
Letts V A, et al. (1997). *Genomics* 43:62-68.
Lewis T B, et al. (1993). *Am. J. Hum. Genet.* 53:670-675.
Lewis T B, et al. (1995). *Genome Res.* 5:334-341.
Lim C S, et al. (1991). *Circulation* 83:2007-2011.
Lipshutz R J, et al. (1995). *BioTechniques* 19:442-447.
Lockhart D J, et al. (1996). *Nature Biotechnology* 14:1675-1680.
Lopez G A, et al. (1994). *Nature* 367:179-182.
Madzak C, et al. (1992). *J. Gen. Virol.* 73:1533-1536.
Malafosse A, et al. (1992). *Hum. Genet.* 89:54-58.
Maniatis T, et al. (1982). *Molecular Cloning: A Laboratory Manual* (Cold Spring Harbor Laboratory, Cold Spring Harbor, N.Y.).
Mann R and Baltimore D (1985). *J. Virol.* 54:401-407.
Margolskee R F (1992). *Curr. Top. Microbiol. Immunol.* 158:67-95.

Martin R, et al. (1990). *BioTechniques* 9:762-768.
Matteucci M D and Caruthers M H (1981). *J. Am. Chem. Soc.* 103:3185.
Matthews J A and Kricka L J (1988). *Anal. Biochem.* 169:1.
McNamara J O (1994). *J. Neurosci.* 14:3413-3425.
Meldrum B S (1995). *Epilepsia* 36:S30-S35.
Merrifield B (1963). *J. Am. Chem. Soc.* 85:2149-2156.
Metzger D, et al. (1988). *Nature* 334:31-36.
Mifflin T E (1989). *Clinical Chem.* 35:1819-1825.
Miller A D (1992). *Curr. Top. Microbiol. Immunol.* 158:1-24.
Miller A D, et al. (1985). *Mol. Cell. Biol.* 5:431-437.
Miller A D, et al. (1988). *J. Virol.* 62:4337-4345.
Modrich P (1991). *Ann. Rev. Genet.* 25:229-253.
Mombaerts P, et al. (1992). *Cell* 68:869-877.
Moss B (1992). *Curr. Top. Microbiol. Immunol.* 158:25-38.
Moss B (1996). *Proc. Natl. Acad. Sci. USA* 93:11341-11348.
Muzyczka N (1992). *Curr. Top. Microbiol. Immunol.* 158:97-129.
Nabel E G, et al. (1990). *Science* 249:1285-1288.
Nabel (1992). *Hum. Gene Ther.* 3:399-410.
Nakamura R L, et al. (1997). *J. Biol. Chem.* 272:1011-1018.
Naldini L, et al. (1996). *Science* 272:263-267.
Newton C R, et al. (1989). *Nucl. Acids Res.* 17:2503-2516.
Neyroud N, et al. (1997). *Nat. Genet.* 15:186-189.
Nguyen Q, et al. (1992). *BioTechniques* 13:116-123.
Noebels J L, et al. (1990). *Epilepsy Res.* 7:129-135.
Novack D F, et al. (1986). *Proc. Natl. Acad. Sci. USA* 83:586-590.
Ohi S, et al. (1990). *Gene* 89:279-282.
Orita M, et al. (1989). *Proc. Natl. Acad. Sci. USA* 86:2766-2770.
Page K A, et al. (1990). *J. Virol.* 64:5270-5276.
Patil N, et al. (1995). *Nature Genetics* 11:126-129.
Pellicer A, et al. (1980). *Science* 209:1414-1422.
Petropoulos C J, et al. (1992). *J. Virol.* 66:3391-3397.
Philpott K L, et al. (1992). *Science* 256:1448-1452.
Plouin P (1994). *Idiopathic Generalized Epilepsies: Clinical, Experimental and Genetic Aspects* (John Libbey and Company Ltd., London), pp. 39-44.
Ptacek L J (1997). *Neuromuscular Disorders* 7: 250-255.
Quantin B, et al. (1992). *Proc. Natl. Acad. Sci. USA* 89:2581-2584. Remington's Pharmaceutical Sciences, 18th Ed. (1990, Mack Publishing Co., Easton, Pa.).
Reutens D C and Berkovic S F (1995). *Neurology* 45:1469-1476.
Rigby P W J, et al. (1977). *J. Mol. Biol.* 113:237-251.
Ronen G M, et al. (1993). *Neurology* 43:1355-1360.
Rosenfeld M A, et al. (1992). *Cell* 68:143-155.
Ruano G and Kidd K K (1989). *Nuc. Acids Res.* 17:8392.
Russell D and Hirata R (1998). *Nature Genetics* 18:323-328.
Russell M W, et al. (1996). *Hum. Molec. Genet.* 5:1319-1324.
Ryan S G, et al. (1991). *Ann. Neurol.* 29:469-473.
Sambrook J, et al. (1989). *Molecular Cloning: A Laboratory Manual*, 2nd Ed. (Cold Spring Harbor Laboratory, Cold Spring Harbor, N.Y.).
Sanguinetti M C, et al. (1996). *Nature* 384:80-83.
Scharf S J, et al. (1986). *Science* 233:1076-1078.
Schneider G, et al. (1998). *Nature Genetics* 18:180-183.
Scopes R (1982). *Protein Purification: Principles and Practice*, (Springer-Verlag, N.Y.).
Sheffield V C, et al. (1989). *Proc. Natl. Acad. Sci. USA* 86:232-236.
Sheffield V C, et al. (1991). *Am. J. Hum. Genet.* 49:699-706.
Shenk T E, et al. (1975). *Proc. Natl. Acad. Sci. USA* 72:989-993.
Shimada T, et al. (1991). *J. Clin. Invest.* 88:1043-1047.
Shinkai Y, et al. (1992). *Cell* 68:855-867.
Shoemaker D D, et al. (1996). *Nature Genetics* 14:450-456.
Signorini S, et al. (1997). *Proc. Natl. Acad. Sci. U.S.A.* 94:923-927.
Snouwaert J N, et al. (1992). *Science* 257:1083-1088.
Soares M B, et al. (1994). *Proc. Natl. Acad. Sci. U.S.A.* 91, 9228-9232.
Sorge J, et al. (1984). *Mol. Cell. Biol.* 4:1730-1737.
Spargo C A, et al. (1996). *Mol. Cell. Probes* 10:247-256.
Steinlein O, et al. (1992). *Hum. Molec. Genet.* 1:325-329.
Steinlein O, et al. (1995). *Hum. Genet.* 95:411-415.
Steinlein O, et al. (1997). *Am. J. Med. Genet.* 74:445-449.
Sternberg N (1990). *Proc. Natl. Acad. Sci. USA* 87:103-107.
Stewart M J, et al. (1992). *Hum. Gene Ther.* 3:267-275.
Stratford-Perricaudet L D, et al. (1990). *Hum. Gene Ther.* 1:241-256.
Tytgat J (1994). *Biochem. Biophys. Res. Commun.* 203:513-518.
Valancius V and Smithies O (1991). *Mol. Cell. Biol.* 11:1402-1408.
Wagner E, et al. (1991). *Proc. Natl. Acad. Sci. USA* 88:4255-4259.
Wagner E, et al. (1990). *Proc. Natl. Acad. Sci. USA* 87:3410-3414.
Walker G T, et al., (1992). *Nucl. Acids Res.* 20:1691-1696.
Wang C Y and Huang L (1989). *Biochemistry* 28:9508-9514.
Wang Q, et al. (1996). *Nat. Genet.* 12:17-23.
Wartell R M, et al. (1990). *Nucl. Acids Res.* 18:2699-2705.
Wei A, et al. (1996). *Neuropharmacology* 35:805-829.
Wells J A (1991). *Methods Enzymol.* 202:390-411.
Wetmur J G and Davidson N (1968). *J. Mol. Biol.* 31:349-370.
White M B, et al. (1992). *Genomics* 12:301-306.
White R and Lalouel J M (1988). *Annu. Rev. Genet.* 22:259-279.
Wilkinson G W and Akrigg A (1992). *Nucleic Acids Res.* 20:2233-2239.
Wolff J A, et al. (1990). *Science* 247:1465-1468.
Wolff J A, et al. (1991). *BioTechniques* 11:474-485.
Wu D Y and Wallace R B (1989). *Genomics* 4:560-569.
Wu C H, et al. (1989). *J. Biol. Chem.* 264:16985-16987.
Wu G Y, et al. (1991). *J. Biol. Chem.* 266:14338-14342.
Yang W P, et al. (1997). *Proc. Natl. Acad. Sci. USA* 94:4017-4021.
Yang W P, et al. (1998). *J. Biol. Chem.* 273:19419-19423.
Yokoyama M, et al. (1996). *DNA Res.* 3:311-320.
Zara F, et al. (1995). *Hum. Mol. Genet.* 4:1201-1207.
Zenke M, et al. (1990). *Proc. Natl. Acad. Sci. USA* 87:3655-3659.

Patents and Patent Applications:
European Patent Application Publication No. 0332435.
EPO Publication No. 225,807.
Hitzeman et al., EP 73,675A.
EP 425,731A.
WO 84/03564.
WO 90/07936.
WO 92/19195.
WO 93/07282.
WO 94/25503.
WO 95/01203.
WO 95/05452.
WO 96/02286.
WO 96/02646.
WO 96/11698.
WO 96/40871.
WO 96/40959.

WO 97/02048.
WO 97/12635.
U.S. Pat. No. 3,817,837.
U.S. Pat. No. 3,850,752.
U.S. Pat. No. 3,939,350.
U.S. Pat. No. 3,996,345.
U.S. Pat. No. 4,275,149.
U.S. Pat. No. 4,277,437.
U.S. Pat. No. 4,366,241.
U.S. Pat. No. 4,376,110.
U.S. Pat. No. 4,486,530.
U.S. Pat. No. 4,554,101.
U.S. Pat. No. 4,683,195.
U.S. Pat. No. 4,683,202.
U.S. Pat. No. 4,816,567.
U.S. Pat. No. 4,868,105.
U.S. Pat. No. 5,252,479.
U.S. Pat. No. 5,270,184.
U.S. Pat. No. 5,409,818.
U.S. Pat. No. 5,436,146.
U.S. Pat. No. 5,455,166.
U.S. Pat. No. 5,550,050.
U.S. Pat. No. 5,691,198.
U.S. Pat. No. 5,735,500.
U.S. Pat. No. 5,747,469.

What is claimed is:

1. A method of detecting a mutation in a KCNQ3 coding sequence in a human subject, comprising:
   (a) contacting a biological sample containing a KCNQ3 nucleic acid from the human subject with an allele-specific oligonucleotide under high stringency conditions, wherein the allele-specific oligonucleotide specifically binds to a mutation selected from the group consisting of: (i) a T at a position corresponding to nucleotide position 947 of SEQ ID NO:6 and (ii) an alternative exon of SEQ ID NO:92 in mRNA of KCNQ3, wherein the oligonucleotide is detectably labeled; and
   (b) detecting hybridization of the allele-specific oligonucleotide with the KCNQ3 nucleic acid, wherein detecting hybridization is indicative of the presence of a mutation in the KCNQ3 coding sequence.

2. A method according to claim 1 wherein the hybridization is performed in situ.

3. The method of claim 1 wherein said mutation is a T at a position corresponding to nucleotide position 947 of SEQ ID NO: 6.

4. The method of claim 1, wherein the method further comprises DNA sequencing.

5. The method of claim 1, wherein the KCNQ3 nucleic acid comprises amplified DNA or RNA.

6. The method of claim 1, wherein the allele specific oligonucleotide is detectably labeled with a fluorescent label, radionuclide, enzyme, chemluminescent agent or a magnetic particle.

7. The method of claim 1, wherein the allele specific oligonucleotide is between 15 and 40 nucleotides in length.

8. A method of detecting a mutation in a KCNQ3 coding sequence in a human subject, comprising:
   (a) contacting a biological sample containing a KCNQ3 nucleic acid from the human subject contacting with an allele-specific oligonucleotide under high stringency conditions, wherein the allele-specific oligonucleotide specifically binds to a portion of a KCNQ3 nucleic acid containing a deletion of a G at a position corresponding to nucleotide position 118 of SEQ ID NO:92, wherein the oligonucleotide is detectably labeled; and
   (b) detecting hybridization of the allele-specific oligonucleotide with the KCNQ3 nucleic acid, wherein detecting hybridization is indicative of the presence of a mutation in the KCNQ3 coding sequence.

9. The method of claim 6, wherein the method further comprises DNA sequencing.

10. The method of claim 8, wherein the allele specific oligonucleotide is detectably labeled with a fluorescent label, radionuclide, enzyme, chemluminescent agent or a magnetic particle.

11. The method of claim 8, wherein the allele specific oligonucleotide is between 15 and 40 nucleotides in length.

* * * * *

SEQUENCE LISTING

<160> NUMBER OF SEQ ID NOS: 129

<210> SEQ ID NO 1
<211> LENGTH: 3232
<212> TYPE: DNA
<213> ORGANISM: Homo sapiens
<220> FEATURE:
<221> NAME/KEY: CDS
<222> LOCATION: (128)..(2743)
<220> FEATURE:
<221> NAME/KEY: mutation
<222> LOCATION: (975)..(976)
<223> OTHER INFORMATION: There is an insertion of a GT between
    nucleotides 975 and 976 in kindred K1504.
<220> FEATURE:
<221> NAME/KEY: mutation
<222> LOCATION: (978)
<223> OTHER INFORMATION: The mutation A to G occurs at this base in
    kindred K3904.
<220> FEATURE:
<221> NAME/KEY: mutation
<222> LOCATION: (1043)
<223> OTHER INFORMATION: The mutation G to A occurs at this base in
    kindred K1705.
<220> FEATURE:
<221> NAME/KEY: mutation
<222> LOCATION: (1691)..(1703)
<223> OTHER INFORMATION: The thirteen nucleotides from 1691-1703 are
    deleted in kindred K3369.
<220> FEATURE:
<221> NAME/KEY: allele
<222> LOCATION: (1039)
<223> OTHER INFORMATION: This polymorphism of C to T was seen in 7.0% of
    the control population.
<220> FEATURE:
<221> NAME/KEY: allele
<222> LOCATION: (1846)
<223> OTHER INFORMATION: This polymorphism of C to T was seen in 0.57%
    of the control population.
<220> FEATURE:
<221> NAME/KEY: mutation
<222> LOCATION: (1469)
<223> OTHER INFORMATION: The mutation C to T occurs at this base in
    kindred K1525.
<220> FEATURE:
<221> NAME/KEY: mutation
<222> LOCATION: (1094)
<223> OTHER INFORMATION: The mutation C to T occurs at this base in
    kindred K4443.
<220> FEATURE:
<221> NAME/KEY: mutation
<222> LOCATION: (1125)
<223> OTHER INFORMATION: The mutation G to A occurs at this base in
    kindred K4516.
<220> FEATURE:
<221> NAME/KEY: mutation
<222> LOCATION: (2736)..(2737)
<223> OTHER INFORMATION: There is an insertion of GGGCC between these
    two nucleotides in K3963.
<220> FEATURE:
<221> NAME/KEY: misc_feature

```
<222> LOCATION: (3091)..(3152)
<223> OTHER INFORMATION: each n may be any nucleotide.

<400> SEQUENCE: 1
gagtgcggaa ccgccgcctc ggccatgcgg ctcccggccg ggggcctgg gctggggccc      60 gcgccgcccc ccgcgctccg cccccgctga gcctgagccc gacccggggc gcctcccgcc     120 aggcacc atg gtg cag aag tcg cgc aac ggc ggc gta tac ccc ggc ccg     169
        Met Val Gln Lys Ser Arg Asn Gly Gly Val Tyr Pro Gly Pro
        1               5                   10 agc ggg gag aag aag ctg aag gtg ggc ttc gtg ggg ctg gac ccc ggc     217
Ser Gly Glu Lys Lys Leu Lys Val Gly Phe Val Gly Leu Asp Pro Gly
15                  20                  25                  30 gcg ccc gac tcc acc cgg gac ggg gcg ctg ctg atc gcc ggc tcc gag     265
Ala Pro Asp Ser Thr Arg Asp Gly Ala Leu Leu Ile Ala Gly Ser Glu
                35                  40                  45 gcc ccc aag cgc ggc agc atc ctc agc aaa cct cgc gcg ggc ggc gcg     313
Ala Pro Lys Arg Gly Ser Ile Leu Ser Lys Pro Arg Ala Gly Gly Ala
            50                  55                  60 ggc gcc ggg aag ccc ccc aag cgc aac gcc ttc tac cgc aag ctg cag     361
Gly Ala Gly Lys Pro Pro Lys Arg Asn Ala Phe Tyr Arg Lys Leu Gln
65                  70                  75 aat ttc ctc tac aac gtg ctg gag cgg ccg cgc ggc tgg gcg ttc atc     409
Asn Phe Leu Tyr Asn Val Leu Glu Arg Pro Arg Gly Trp Ala Phe Ile
        80                  85                  90 tac cac gcc tac gtg ttc ctc ctg gtt ttc tcc tgc ctc gtg ctg tct     457
Tyr His Ala Tyr Val Phe Leu Leu Val Phe Ser Cys Leu Val Leu Ser
    95                  100                 105                 110 gtg ttt tcc acc atc aag gag tat gag aag agc tcg gag ggg gcc ctc     505
Val Phe Ser Thr Ile Lys Glu Tyr Glu Lys Ser Ser Glu Gly Ala Leu
                115                 120                 125 tac atc ctg gaa atc gtg act atc gtg gtg ttt ggc gtg gag tac ttc     553
Tyr Ile Leu Glu Ile Val Thr Ile Val Val Phe Gly Val Glu Tyr Phe
            130                 135                 140 gtg cgg atc tgg gcc gca ggc tgc tgc tgc cgg tac cgt ggc tgg agg     601
Val Arg Ile Trp Ala Ala Gly Cys Cys Cys Arg Tyr Arg Gly Trp Arg
        145                 150                 155 ggg cgg ctc aag ttt gcc cgg aaa ccg ttc tgt gtg att gac atc atg     649
Gly Arg Leu Lys Phe Ala Arg Lys Pro Phe Cys Val Ile Asp Ile Met
    160                 165                 170 gtg ctc atc gcc tcc att gcg gtg ctg gcc gcc ggc tcc cag ggc aac     697
Val Leu Ile Ala Ser Ile Ala Val Leu Ala Ala Gly Ser Gln Gly Asn
175                 180                 185                 190 gtc ttt gcc aca tct gcg ctc cgg agc ctg cgc ttc ctg cag att ctg     745
Val Phe Ala Thr Ser Ala Leu Arg Ser Leu Arg Phe Leu Gln Ile Leu
                195                 200                 205 cgg atg atc cgc atg gac cgg cgg gga ggc acc tgg aag ctg ctg ggc     793
Arg Met Ile Arg Met Asp Arg Arg Gly Gly Thr Trp Lys Leu Leu Gly
            210                 215                 220 tct gtg gtc tat gcc cac agc aag gag ctg gtc act gcc tgg tac atc     841
Ser Val Val Tyr Ala His Ser Lys Glu Leu Val Thr Ala Trp Tyr Ile
        225                 230                 235 ggc ttc ctt tgt ctc atc ctg gcc tcg ttc ctg gtg tac ttg gca gag     889
Gly Phe Leu Cys Leu Ile Leu Ala Ser Phe Leu Val Tyr Leu Ala Glu
    240                 245                 250 aag ggg gag aac gac cac ttt gac acc tac gcg gat gca ctc tgg tgg     937
Lys Gly Glu Asn Asp His Phe Asp Thr Tyr Ala Asp Ala Leu Trp Trp
255                 260                 265                 270 ggc ctg atc acg ctg acc acc att ggc tac ggg gac aag tac ccc cag     985
Gly Leu Ile Thr Leu Thr Thr Ile Gly Tyr Gly Asp Lys Tyr Pro Gln
```

```
                          275                 280                 285
acc tgg aac ggc agg ctc ctt gcg gca acc ttc acc ctc atc ggt gtc     1033
Thr Trp Asn Gly Arg Leu Leu Ala Ala Thr Phe Thr Leu Ile Gly Val
        290                 295                 300 tcc ttc ttc gcg ctg cct gca ggc atc ttg ggg tct ggg ttt gcc ctg     1081
Ser Phe Phe Ala Leu Pro Ala Gly Ile Leu Gly Ser Gly Phe Ala Leu
            305                 310                 315 aag gtt cag gag cag cac agg cag aag cac ttt gag aag agg cgg aac     1129
Lys Val Gln Glu Gln His Arg Gln Lys His Phe Glu Lys Arg Arg Asn
320                 325                 330 ccg gca gca ggc ctg atc cag tcg gcc tgg aga ttc tac gcc acc aac     1177
Pro Ala Ala Gly Leu Ile Gln Ser Ala Trp Arg Phe Tyr Ala Thr Asn
335                 340                 345                 350 ctc tcg cgc aca gac ctg cac tcc acg tgg cag tac tac gag cga acg     1225
Leu Ser Arg Thr Asp Leu His Ser Thr Trp Gln Tyr Tyr Glu Arg Thr
                355                 360                 365 gtc acc gtg ccc atg tac agt tcg caa act caa acc tac ggg gcc tcc     1273
Val Thr Val Pro Met Tyr Ser Ser Gln Thr Gln Thr Tyr Gly Ala Ser
            370                 375                 380 aga ctt atc ccc ccg ctg aac cag ctg gag ctg ctg agg aac ctc aag     1321
Arg Leu Ile Pro Pro Leu Asn Gln Leu Glu Leu Leu Arg Asn Leu Lys
                385                 390                 395 agt aaa tct gga ctc gct ttc agg aag gac ccc ccg gag ccg tct         1369
Ser Lys Ser Gly Leu Ala Phe Arg Lys Asp Pro Pro Glu Pro Ser
    400                 405                 410 cca agt aaa ggc agc ccg tgc aga ggg ccc ctg tgt gga tgc tgc ccc     1417
Pro Ser Lys Gly Ser Pro Cys Arg Gly Pro Leu Cys Gly Cys Cys Pro
415                 420                 425                 430 gga cgc tct agc cag aag gtc agt ttg aaa gat cgt gtc ttc tcc agc     1465
Gly Arg Ser Ser Gln Lys Val Ser Leu Lys Asp Arg Val Phe Ser Ser
                435                 440                 445 ccc cga ggc gtg gct gcc aag ggg aag ggg tcc ccg cag gcc cag act     1513
Pro Arg Gly Val Ala Ala Lys Gly Lys Gly Ser Pro Gln Ala Gln Thr
            450                 455                 460 gtg agg cgg tca ccc agc gcc gac cag agc ctc gag gac agc ccc agc     1561
Val Arg Arg Ser Pro Ser Ala Asp Gln Ser Leu Glu Asp Ser Pro Ser
                465                 470                 475 aag gtg ccc aag agc tgg agc ttc ggg gac cgc agc cgg gca cgc cag     1609
Lys Val Pro Lys Ser Trp Ser Phe Gly Asp Arg Ser Arg Ala Arg Gln
            480                 485                 490 gct ttc cgc atc aag ggt gcc gcg tca cgg cag aac tca gaa gaa gca     1657
Ala Phe Arg Ile Lys Gly Ala Ala Ser Arg Gln Asn Ser Glu Glu Ala
495                 500                 505                 510 agc ctc ccc gga gag gac att gtg gat gac aag agc tgc ccc tgc gag     1705
Ser Leu Pro Gly Glu Asp Ile Val Asp Asp Lys Ser Cys Pro Cys Glu
                515                 520                 525 ttt gtg acc gag gac ctg acc ccg ggc ctc aaa gtc agc atc aga gcc     1753
Phe Val Thr Glu Asp Leu Thr Pro Gly Leu Lys Val Ser Ile Arg Ala
            530                 535                 540 gtg tgt gtc atg cgg ttc ctg gtg tcc aag cgg aag ttc aag gag agc     1801
Val Cys Val Met Arg Phe Leu Val Ser Lys Arg Lys Phe Lys Glu Ser
                545                 550                 555 ctg cgg ccc tac gac gtg atg gac gtc atc gag cag tac tca gcc ggc     1849
Leu Arg Pro Tyr Asp Val Met Asp Val Ile Glu Gln Tyr Ser Ala Gly
            560                 565                 570 cac ctg gac atg ctg tcc cga att aag agc ctg cag tcc aga gtg gac     1897
His Leu Asp Met Leu Ser Arg Ile Lys Ser Leu Gln Ser Arg Val Asp
575                 580                 585                 590 cag atc gtg ggg cgg ggc cca gcg atc acg gac aag gac cgc acc aag     1945
```

-continued

```
Gln Ile Val Gly Arg Gly Pro Ala Ile Thr Asp Lys Asp Arg Thr Lys
                595                 600                 605 ggc ccg gcc gag gcg gag ctg ccc gag gac ccc agc atg atg gga cgg      1993
Gly Pro Ala Glu Ala Glu Leu Pro Glu Asp Pro Ser Met Met Gly Arg
610                 615                 620 ctc ggg aag gtg gag aag cag gtc ttg tcc atg gag aag aag ctg gac      2041
Leu Gly Lys Val Glu Lys Gln Val Leu Ser Met Glu Lys Lys Leu Asp
            625                 630                 635 ttc ctg gtg aat atc tac atg cag cgg atg ggc atc ccc ccg aca gag      2089
Phe Leu Val Asn Ile Tyr Met Gln Arg Met Gly Ile Pro Pro Thr Glu
        640                 645                 650 acc gag gcc tac ttt ggg gcc aaa gag ccg gag ccg gcg ccg ccg tac      2137
Thr Glu Ala Tyr Phe Gly Ala Lys Glu Pro Glu Pro Ala Pro Pro Tyr
655                 660                 665                 670 cac agc ccg gaa gac agc cgg gag cat gtc gac agg cac ggc tgc att      2185
His Ser Pro Glu Asp Ser Arg Glu His Val Asp Arg His Gly Cys Ile
            675                 680                 685 gtc aag atc gtg cgc tcc agc agc tcc acg ggc cag aag aac ttc tcg      2233
Val Lys Ile Val Arg Ser Ser Ser Ser Thr Gly Gln Lys Asn Phe Ser
        690                 695                 700 gcg ccc ccg gcc gcg ccc cct gtc cag tgt ccg ccc tcc acc tcc tgg      2281
Ala Pro Pro Ala Ala Pro Pro Val Gln Cys Pro Pro Ser Thr Ser Trp
    705                 710                 715 cag cca cag agc cac ccg cgc cag ggc cac ggc acc tcc ccc gtg ggg      2329
Gln Pro Gln Ser His Pro Arg Gln Gly His Gly Thr Ser Pro Val Gly
720                 725                 730 gac cac ggc tcc ctg gtg cgc atc ccg ccg ccg cct gcc cac gag cgg      2377
Asp His Gly Ser Leu Val Arg Ile Pro Pro Pro Pro Ala His Glu Arg
735                 740                 745                 750 tcg ctg tcc gcc tac ggc ggg ggc aac cgc gcc agc atg gag ttc ctg      2425
Ser Leu Ser Ala Tyr Gly Gly Gly Asn Arg Ala Ser Met Glu Phe Leu
            755                 760                 765 cgg cag gag gac acc ccg ggc tgc agg ccc ccc gag ggg aac ctg cgg      2473
Arg Gln Glu Asp Thr Pro Gly Cys Arg Pro Pro Glu Gly Asn Leu Arg
        770                 775                 780 gac agc gac acg tcc atc tcc atc ccg tcc gtg gac cac gag gag ctg      2521
Asp Ser Asp Thr Ser Ile Ser Ile Pro Ser Val Asp His Glu Glu Leu
    785                 790                 795 gag cgt tcc ttc agc ggc ttc agc atc tcc cag tcc aag gag aac ctg      2569
Glu Arg Ser Phe Ser Gly Phe Ser Ile Ser Gln Ser Lys Glu Asn Leu
800                 805                 810 gat gct ctc aac agc tgc tac gcg gcc gtg gcg cct tgt gcc aaa gtc      2617
Asp Ala Leu Asn Ser Cys Tyr Ala Ala Val Ala Pro Cys Ala Lys Val
815                 820                 825                 830 agg ccc tac att gcg gag gga gag tca gac acc gac tcc gac ctc tgt      2665
Arg Pro Tyr Ile Ala Glu Gly Glu Ser Asp Thr Asp Ser Asp Leu Cys
            835                 840                 845 acc ccg tgc ggg ccc ccg cca cgc tcg gcc acc ggc gag ggt ccc ttt      2713
Thr Pro Cys Gly Pro Pro Pro Arg Ser Ala Thr Gly Glu Gly Pro Phe
        850                 855                 860 ggt gac gtg ggc tgg gcc ggg ccc agg aag tgaggcggcg ctgggccagt        2763
Gly Asp Val Gly Trp Ala Gly Pro Arg Lys
    865                 870 ggacccgccc gcggccctcc tcagcacggt gcctccgagg ttttgaggcg ggaaccctct    2823
ggggcccttt tcttacagta actgagtgtg gcgggaaggg tgggccctgg aggggcccat    2883
gtgggctgaa ggatggggc tcctggcagt gacctttac aaaagttatt ttccaacagg      2943
ggctggaggg ctgggcaggg cctgtggctc caggagcagc gtgcaggagc aaggctgccc    3003
```

```
tgtccactct gctcaaggcc gcggccgaca tcagcccggt gtgaagaggg gcggagtgat    3063
gacgggtgtt gcaacctggc aacaagcngg gggttgncca gccganccaa gggaagcaca    3123
naaggaagct gtnccctaag acctncccna aaggcggcct gtttggtaag actgcgcctt    3183
ggtccggtgg gttccggcag caaaagcggg ttttgccgcc cctgtcgtg                3232
```

<210> SEQ ID NO 2
<211> LENGTH: 872
<212> TYPE: PRT
<213> ORGANISM: Homo sapiens

<400> SEQUENCE: 2

```
Met Val Gln Lys Ser Arg Asn Gly Gly Val Tyr Pro Gly Pro Ser Gly
 1               5                  10                  15

Glu Lys Lys Leu Lys Val Gly Phe Val Gly Leu Asp Pro Gly Ala Pro
            20                  25                  30

Asp Ser Thr Arg Asp Gly Ala Leu Leu Ile Ala Gly Ser Glu Ala Pro
        35                  40                  45

Lys Arg Gly Ser Ile Leu Ser Lys Pro Arg Ala Gly Gly Ala Gly Ala
    50                  55                  60

Gly Lys Pro Pro Lys Arg Asn Ala Phe Tyr Arg Lys Leu Gln Asn Phe
65                  70                  75                  80

Leu Tyr Asn Val Leu Glu Arg Pro Arg Gly Trp Ala Phe Ile Tyr His
                85                  90                  95

Ala Tyr Val Phe Leu Leu Val Phe Ser Cys Leu Val Leu Ser Val Phe
            100                 105                 110

Ser Thr Ile Lys Glu Tyr Glu Lys Ser Ser Glu Gly Ala Leu Tyr Ile
        115                 120                 125

Leu Glu Ile Val Thr Ile Val Val Phe Gly Val Glu Tyr Phe Val Arg
    130                 135                 140

Ile Trp Ala Ala Gly Cys Cys Cys Arg Tyr Arg Gly Trp Arg Gly Arg
145                 150                 155                 160

Leu Lys Phe Ala Arg Lys Pro Phe Cys Val Ile Asp Ile Met Val Leu
                165                 170                 175

Ile Ala Ser Ile Ala Val Leu Ala Ala Gly Ser Gln Gly Asn Val Phe
            180                 185                 190

Ala Thr Ser Ala Leu Arg Ser Leu Arg Phe Leu Gln Ile Leu Arg Met
        195                 200                 205

Ile Arg Met Asp Arg Arg Gly Gly Thr Trp Lys Leu Leu Gly Ser Val
    210                 215                 220

Val Tyr Ala His Ser Lys Glu Leu Val Thr Ala Trp Tyr Ile Gly Phe
225                 230                 235                 240

Leu Cys Leu Ile Leu Ala Ser Phe Leu Val Tyr Leu Ala Glu Lys Gly
                245                 250                 255

Glu Asn Asp His Phe Asp Thr Tyr Ala Asp Ala Leu Trp Trp Gly Leu
            260                 265                 270

Ile Thr Leu Thr Thr Ile Gly Tyr Gly Asp Lys Tyr Pro Gln Thr Trp
        275                 280                 285

Asn Gly Arg Leu Leu Ala Ala Thr Phe Thr Leu Ile Gly Val Ser Phe
    290                 295                 300

Phe Ala Leu Pro Ala Gly Ile Leu Gly Ser Gly Phe Ala Leu Lys Val
305                 310                 315                 320

Gln Glu Gln His Arg Gln Lys His Phe Glu Lys Arg Arg Asn Pro Ala
                325                 330                 335
```

-continued

```
Ala Gly Leu Ile Gln Ser Ala Trp Arg Phe Tyr Ala Thr Asn Leu Ser
            340                 345                 350

Arg Thr Asp Leu His Ser Thr Trp Gln Tyr Tyr Glu Arg Thr Val Thr
        355                 360                 365

Val Pro Met Tyr Ser Ser Gln Thr Gln Thr Tyr Gly Ala Ser Arg Leu
    370                 375                 380

Ile Pro Pro Leu Asn Gln Leu Glu Leu Leu Arg Asn Leu Lys Ser Lys
385                 390                 395                 400

Ser Gly Leu Ala Phe Arg Lys Asp Pro Pro Glu Pro Ser Pro Ser
                405                 410                 415

Lys Gly Ser Pro Cys Arg Gly Pro Leu Cys Gly Cys Cys Pro Gly Arg
                420                 425                 430

Ser Ser Gln Lys Val Ser Leu Lys Asp Arg Val Phe Ser Ser Pro Arg
            435                 440                 445

Gly Val Ala Ala Lys Gly Lys Gly Ser Pro Gln Ala Gln Thr Val Arg
        450                 455                 460

Arg Ser Pro Ser Ala Asp Gln Ser Leu Glu Asp Ser Pro Ser Lys Val
465                 470                 475                 480

Pro Lys Ser Trp Ser Phe Gly Asp Arg Ser Arg Ala Arg Gln Ala Phe
                485                 490                 495

Arg Ile Lys Gly Ala Ala Ser Arg Gln Asn Ser Glu Glu Ala Ser Leu
            500                 505                 510

Pro Gly Glu Asp Ile Val Asp Asp Lys Ser Cys Pro Cys Glu Phe Val
        515                 520                 525

Thr Glu Asp Leu Thr Pro Gly Leu Lys Val Ser Ile Arg Ala Val Cys
    530                 535                 540

Val Met Arg Phe Leu Val Ser Lys Arg Lys Phe Lys Glu Ser Leu Arg
545                 550                 555                 560

Pro Tyr Asp Val Met Asp Val Ile Glu Gln Tyr Ser Ala Gly His Leu
                565                 570                 575

Asp Met Leu Ser Arg Ile Lys Ser Leu Gln Ser Arg Val Asp Gln Ile
            580                 585                 590

Val Gly Arg Gly Pro Ala Ile Thr Asp Lys Asp Arg Thr Lys Gly Pro
        595                 600                 605

Ala Glu Ala Glu Leu Pro Glu Asp Pro Ser Met Met Gly Arg Leu Gly
    610                 615                 620

Lys Val Glu Lys Gln Val Leu Ser Met Glu Lys Lys Leu Asp Phe Leu
625                 630                 635                 640

Val Asn Ile Tyr Met Gln Arg Met Gly Ile Pro Pro Thr Glu Thr Glu
                645                 650                 655

Ala Tyr Phe Gly Ala Lys Glu Pro Glu Pro Ala Pro Pro Tyr His Ser
            660                 665                 670

Pro Glu Asp Ser Arg Glu His Val Asp Arg His Gly Cys Ile Val Lys
        675                 680                 685

Ile Val Arg Ser Ser Ser Ser Thr Gly Gln Lys Asn Phe Ser Ala Pro
    690                 695                 700

Pro Ala Ala Pro Pro Val Gln Cys Pro Pro Ser Thr Ser Trp Gln Pro
705                 710                 715                 720

Gln Ser His Pro Arg Gln Gly His Gly Thr Ser Pro Val Gly Asp His
                725                 730                 735

Gly Ser Leu Val Arg Ile Pro Pro Pro Ala His Glu Arg Ser Leu
            740                 745                 750

Ser Ala Tyr Gly Gly Gly Asn Arg Ala Ser Met Glu Phe Leu Arg Gln
```

```
                    755                 760                 765
Glu Asp Thr Pro Gly Cys Arg Pro Pro Glu Gly Asn Leu Arg Asp Ser
770                 775                 780

Asp Thr Ser Ile Ser Ile Pro Ser Val Asp His Glu Glu Leu Glu Arg
785                 790                 795                 800

Ser Phe Ser Gly Phe Ser Ile Ser Gln Ser Lys Glu Asn Leu Asp Ala
                805                 810                 815

Leu Asn Ser Cys Tyr Ala Ala Val Ala Pro Cys Ala Lys Val Arg Pro
                820                 825                 830

Tyr Ile Ala Glu Gly Glu Ser Asp Thr Asp Ser Asp Leu Cys Thr Pro
                835                 840                 845

Cys Gly Pro Pro Arg Ser Ala Thr Gly Glu Gly Pro Phe Gly Asp
850                 855                 860

Val Gly Trp Ala Gly Pro Arg Lys
865                 870

<210> SEQ ID NO 3
<211> LENGTH: 807
<212> TYPE: PRT
<213> ORGANISM: Homo sapiens

<400> SEQUENCE: 3

Met Asp Glu Glu Ser Gly Ser Ser Val Ser Met Trp Leu Thr Met Arg
1               5                   10                  15

Lys Leu Ser Pro Val Ala Met Val Ser Arg Ser Gln Lys Lys Thr Thr
                20                  25                  30

Asp Gln Ala Ala Pro Ser Asp Glu Gln Gln Glu Ala Gly Ser Ser Ser
            35                  40                  45

Ala Ile Gly Gln Glu Ser Arg Lys Thr Val Val Phe Gln Glu Pro Asp
        50                  55                  60

Ile Gly Phe Pro Ser Glu His Asp Gln Leu Thr Thr Leu His Asp Ser
65              70                  75                  80

Glu Glu Gly Asn Arg Lys Met Ser Leu Val Gly Lys Pro Leu Thr Tyr
                85                  90                  95

Lys Asn Tyr Arg Thr Asp Gln Arg Phe Arg Met Gln Asn Lys Met
                100                 105                 110

His Asn Phe Leu Glu Arg Pro Arg Gly Trp Lys Ala Ala Thr Tyr His
            115                 120                 125

Leu Ala Val Leu Phe Met Val Leu Met Cys Leu Ala Leu Ser Val Phe
        130                 135                 140

Ser Thr Met Pro Asp Phe Glu Val Asn Ala Thr Ile Val Leu Tyr Tyr
145                 150                 155                 160

Leu Glu Ile Val Phe Val Ile Trp Leu Ala Thr Glu Tyr Ile Cys Arg
                165                 170                 175

Val Trp Ser Ala Gly Cys Arg Ser Arg Tyr Arg Gly Ile Ser Gly Arg
                180                 185                 190

Ile Arg Phe Ala Thr Ser Ala Tyr Cys Val Ile Asp Ile Val Ile
            195                 200                 205

Leu Ala Ser Ile Thr Val Leu Cys Ile Gly Ala Thr Gly Gln Val Phe
        210                 215                 220

Ala Ala Ser Ala Ile Arg Gly Leu Arg Phe Phe Gln Leu Arg Met Leu
225                 230                 235                 240

Arg Ile Asp Arg Arg Ala Gly Thr Trp Lys Leu Leu Gly Ser Val Val
                245                 250                 255
```

Trp Ala His Arg Gln Glu Leu Leu Thr Thr Val Tyr Ile Gly Phe Leu
            260                 265                 270

Gly Leu Ile Phe Ser Ser Phe Leu Val Tyr Leu Cys Glu Lys Asn Thr
        275                 280                 285

Asn Asp Lys Tyr Gln Thr Phe Ala Asp Ala Leu Trp Trp Gly Val Ile
    290                 295                 300

Thr Leu Ser Thr Val Gly Tyr Gly Asp Lys Thr Pro Glu Thr Trp Pro
305                 310                 315                 320

Gly Lys Ile Ile Ala Ala Phe Cys Ala Leu Leu Gly Ile Ser Phe Phe
                325                 330                 335

Ala Leu Pro Ala Gly Ile Leu Gly Ser Gly Phe Ala Leu Lys Val Gln
            340                 345                 350

Gln His Gln Arg Gln Lys His Leu Ile Arg Arg Val Pro Ala Ala
        355                 360                 365

Lys Leu Ile Gln Cys Leu Trp Arg His Tyr Ser Ala Ala Pro Glu Ser
    370                 375                 380

Thr Ser Leu Ala Thr Trp Lys Ile His Leu Ala Arg Glu Leu Pro Pro
385                 390                 395                 400

Ile Val Lys Leu Thr Pro Leu Gly Ser Asn Asn Ala Thr Gly Leu Ile
                405                 410                 415

Asn Arg Leu Arg Gln Ser Thr Lys Arg Thr Pro Asn Leu Asn Asn Gln
            420                 425                 430

Asn Leu Ala Val Asn Ser Gln Ala Thr Ser Lys Asn Leu Ser Val Pro
        435                 440                 445

Arg Val Arg Val His Asp Thr Ile Ser Leu Val Ser Thr Ser Asp Ile
    450                 455                 460

Ser Glu Ile Glu Gln Leu Gly Ala Leu Gly Phe Ser Leu Gly Trp Lys
465                 470                 475                 480

Ser Lys Ser Lys Tyr Gly Gly Ser Lys Lys Ala Thr Asp Asp Ser Val
                485                 490                 495

Leu Gln Ser Arg Met Leu Ala Pro Ser Asn Ala His Leu Asp Asp Met
            500                 505                 510

Arg Arg Arg Ser Arg Arg Ser Ala Ser Leu Cys Arg Val Val Asn Thr
        515                 520                 525

Gly Gln His Leu Arg Pro Leu Gln Pro Arg Ser Thr Leu Ser Asp Ser
    530                 535                 540

Asp Val Ile Gly Asp Tyr Ser Leu Met Met Ala Pro Ile Tyr Gln Trp
545                 550                 555                 560

Cys Glu Gln Met Val Gln Arg Asn Ser Thr Pro Gly Glu Asp Gly Val
                565                 570                 575

Trp Ser Gln Leu Ser Gln Leu Ser Gln Leu Thr Thr Cys Ala Thr Arg
            580                 585                 590

Arg Thr Glu Asp Ile Ser Asp Gly Asp Glu Glu Ala Val Gly Tyr
        595                 600                 605

Gln Pro Gln Thr Ile Glu Glu Phe Thr Pro Ala Leu Lys Asn Cys Val
    610                 615                 620

Arg Ala Ile Arg Arg Ile Gln Leu Leu Val Ala Arg Lys Lys Phe Lys
625                 630                 635                 640

Glu Ala Leu Lys Pro Tyr Asp Val Lys Asp Val Ile Glu Gln Tyr Ser
                645                 650                 655

Ala Gly His Val Asp Leu Gln Ser Arg Val Lys Thr Val Gln Ala Lys
            660                 665                 670

Leu Asp Phe Ile Cys Gly Lys Asn Ile Glu Lys Ile Glu Pro Lys Ile

```
            675                 680                 685
Ser Met Phe Thr Arg Ile Ala Thr Leu Glu Thr Thr Val Gly Lys Met
    690                 695                 700

Asp Lys Lys Leu Asp Leu Met Val Glu Met Leu Met Gly Arg Gln Ala
705                 710                 715                 720

Ser Gln Arg Val Phe Ser Gln Asn Thr Ser Pro Arg Gly Glu Phe Ser
                725                 730                 735

Glu Pro Thr Ser Ala Arg Gln Asp Leu Thr Arg Ser Arg Ser Met
                740                 745                 750

Val Ser Thr Asp Met Glu Met Tyr Thr Ala Arg Ser His Ser Pro Gly
            755                 760                 765

Tyr His Gly Asp Ala Arg Pro Ile Ile Ala Gln Ile Asp Ala Asp Asp
    770                 775                 780

Asp Asp Glu Asp Glu Asn Val Phe Asp Asp Ser Thr Pro Leu Asn Asn
785                 790                 795                 800

Gly Pro Gly Thr Ser Ser Cys
                805

<210> SEQ ID NO 4
<211> LENGTH: 677
<212> TYPE: PRT
<213> ORGANISM: Homo sapiens

<400> SEQUENCE: 4

Met Ala Ala Ser Ser Pro Pro Arg Ala Glu Arg Lys Arg Trp Gly
1               5                   10                  15

Trp Gly Arg Leu Pro Gly Ala Arg Gly Ser Ala Gly Leu Ala Lys
            20                  25                  30

Lys Cys Pro Phe Ser Leu Glu Leu Ala Glu Gly Gly Pro Ala Gly Gly
            35                  40                  45

Ala Leu Tyr Ala Pro Ile Ala Pro Gly Ala Pro Gly Pro Ala Pro Pro
        50                  55                  60

Ala Ser Pro Ala Ala Pro Ala Ala Pro Pro Val Ala Ser Asp Leu Gly
65                  70                  75                  80

Pro Arg Pro Pro Val Ser Asp Leu Pro Arg Val Ser Ile Tyr Ser Thr
                85                  90                  95

Arg Arg Pro Val Leu Ala Arg Thr His Val Gln Gly Arg Val Tyr Asn
            100                 105                 110

Phe Leu Glu Arg Pro Thr Gly Trp Lys Cys Phe Val Tyr His Phe Ala
        115                 120                 125

Val Phe Leu Ile Val Leu Val Cys Leu Ile Phe Ser Val Leu Ser Thr
    130                 135                 140

Ile Glu Gln Tyr Ala Ala Leu Ala Thr Gly Thr Leu Phe Trp Met Glu
145                 150                 155                 160

Ile Val Leu Val Val Phe Phe Gly Thr Glu Tyr Val Val Arg Leu Trp
                165                 170                 175

Ser Ala Gly Cys Arg Ser Lys Tyr Val Gly Leu Trp Gly Arg Leu Arg
            180                 185                 190

Phe Phe Ala Arg Lys Pro Ile Ser Ile Asp Leu Ile Val Val Val
        195                 200                 205

Ala Ser Met Val Val Leu Cys Val Gly Ser Lys Gly Gln Val Phe Ala
    210                 215                 220

Thr Ser Ala Ile Arg Gly Ile Arg Phe Leu Gln Ile Leu Arg Met Leu
225                 230                 235                 240
```

-continued

His Val Asp Arg Gln Gly Gly Thr Trp Arg Leu Leu Gly Ser Val Val
            245                 250                 255

Phe Ile His Arg Gln Glu Leu Ile Thr Thr Leu Tyr Ile Gly Phe Leu
            260                 265                 270

Gly Leu Ile Phe Ser Ser Tyr Phe Val Tyr Leu Ala Glu Lys Asp Ala
            275                 280                 285

Val Asn Glu Ser Gly Arg Val Glu Phe Gly Ser Tyr Ala Asp Ala Leu
            290                 295                 300

Trp Trp Gly Val Val Thr Val Thr Thr Ile Gly Tyr Gly Asp Lys Val
305                 310                 315                 320

Pro Gln Thr Trp Val Gly Lys Thr Ile Ala Ser Cys Phe Ser Val Phe
            325                 330                 335

Ala Ile Ser Phe Phe Ala Leu Pro Ala Gly Ile Leu Gly Ser Gly Phe
            340                 345                 350

Ala Leu Lys Val Gln Gln Lys Gln Arg Gln Lys His Phe Asn Arg Gln
            355                 360                 365

Ile Pro Ala Ala Ala Ser Leu Ile Gln Thr Ala Trp Arg Cys Tyr Ala
            370                 375                 380

Ala Glu Asn Pro Asp Ser Ser Thr Trp Lys Ile Tyr Ile Arg Lys Ala
385                 390                 395                 400

Pro Arg Ser His Thr Leu Leu Ser Pro Ser Pro Lys Pro Lys Lys Ser
            405                 410                 415

Val Val Val Lys Lys Lys Phe Lys Leu Asp Lys Asp Asn Gly Val
            420                 425                 430

Thr Pro Gly Glu Lys Met Leu Thr Val Pro His Ile Thr Cys Asp Pro
            435                 440                 445

Pro Glu Glu Arg Arg Leu Asp His Phe Ser Val Asp Gly Tyr Asp Ser
            450                 455                 460

Ser Val Arg Lys Ser Pro Thr Leu Leu Glu Val Ser Met Pro His Phe
465                 470                 475                 480

Met Arg Thr Asn Ser Phe Ala Glu Asp Leu Asp Leu Glu Gly Glu Thr
            485                 490                 495

Leu Leu Thr Pro Ile Thr His Ile Ser Gln Leu Arg Glu His His Arg
            500                 505                 510

Ala Thr Ile Lys Val Ile Arg Arg Met Gln Tyr Phe Val Ala Lys Lys
            515                 520                 525

Lys Phe Gln Gln Ala Arg Lys Pro Tyr Asp Val Arg Asp Val Ile Glu
            530                 535                 540

Gln Tyr Ser Gln Gly His Leu Asn Leu Met Val Arg Ile Lys Glu Leu
545                 550                 555                 560

Gln Arg Arg Leu Asp Gln Ser Ile Gly Lys Pro Ser Leu Phe Ile Ser
            565                 570                 575

Val Ser Glu Lys Ser Lys Asp Arg Gly Ser Asn Thr Ile Gly Ala Arg
            580                 585                 590

Leu Asn Arg Val Glu Asp Lys Val Thr Gln Leu Asp Gln Arg Leu Ala
            595                 600                 605

Leu Ile Thr Asp Met Leu His Gln Leu Leu Ser Leu His Gly Gly Ser
            610                 615                 620

Thr Pro Gly Ser Gly Gly Pro Pro Arg Glu Gly Gly Ala His Ile Thr
625                 630                 635                 640

Gln Pro Cys Gly Ser Gly Gly Ser Val Asp Pro Glu Leu Phe Leu Pro
            645                 650                 655

Ser Asn Thr Leu Pro Thr Tyr Glu Gln Leu Thr Val Pro Arg Arg Gly

-continued

```
                    660             665             670

Pro Asp Glu Gly Ser
        675

<210> SEQ ID NO 5
<211> LENGTH: 12
<212> TYPE: DNA
<213> ORGANISM: Homo sapiens
<220> FEATURE:
<221> NAME/KEY: mutation
<222> LOCATION: (5)
<223> OTHER INFORMATION: The mutation from G to A occurs at this site in
      kindred K3933.
<220> FEATURE:
<221> NAME/KEY: intron
<222> LOCATION: (1)..(5)
<220> FEATURE:
<221> NAME/KEY: exon
<222> LOCATION: (6)..(11)

<400> SEQUENCE: 5 tgcag tgt cat g                                                      12

<210> SEQ ID NO 6
<211> LENGTH: 2914
<212> TYPE: DNA
<213> ORGANISM: Homo sapiens
<220> FEATURE:
<221> NAME/KEY: CDS
<222> LOCATION: (19)..(2634)
<220> FEATURE:
<221> NAME/KEY: allele
<222> LOCATION: (840)
<223> OTHER INFORMATION: The polymorphism of a T to a C at this position
      has appeared in one individual.
<220> FEATURE:
<221> NAME/KEY: mutation
<222> LOCATION: (947)
<223> OTHER INFORMATION: The missense mutation from a G to a T occurs at
      this position in a BFNC family.
<220> FEATURE:
<221> NAME/KEY: allele
<222> LOCATION: (678)
<223> OTHER INFORMATION: This position is polymorphic for C or T.
<220> FEATURE:
<221> NAME/KEY: allele
<222> LOCATION: (750)
<223> OTHER INFORMATION: This position is polymorphic for T or C.
<220> FEATURE:
<221> NAME/KEY: allele
<222> LOCATION: (1089)
<223> OTHER INFORMATION: This position is polymorphic for G or C.
<220> FEATURE:
<221> NAME/KEY: allele
<222> LOCATION: (2598)
<223> OTHER INFORMATION: This position is polymorphic for T or C.

<400> SEQUENCE: 6
ccggcggggg cgaggcag atg ggg ctc aag gcg cgc agg gcg gcg ggg gcg      51
                    Met Gly Leu Lys Ala Arg Arg Ala Ala Gly Ala
                     1               5                  10 gct ggc ggc ggc ggc gac ggg ggc ggc gga ggc ggc ggg gcg gct aac      99
Ala Gly Gly Gly Gly Asp Gly Gly Gly Gly Gly Gly Gly Ala Ala Asn
             15                  20                  25 cca gcc gga ggg gac gcg gcg gcg gcc ggc gac gag gag cgg aaa gtg     147
Pro Ala Gly Gly Asp Ala Ala Ala Ala Gly Asp Glu Glu Arg Lys Val
         30                  35                  40 ggg ctg gcg ccc ggc gac gtg gag caa gtc acc ttg gcg ctc ggg gcc     195
Gly Leu Ala Pro Gly Asp Val Glu Gln Val Thr Leu Ala Leu Gly Ala
     45                  50                  55
```

```
gga gcc gac aaa gac ggg acc ctg ctg ctg gag ggc ggc ggc cgc gac      243
Gly Ala Asp Lys Asp Gly Thr Leu Leu Leu Glu Gly Gly Gly Arg Asp
 60              65                  70                  75 gag ggg cag cgg agg acc ccg cag ggc atc ggg ctc ctg gcc aag acc      291
Glu Gly Gln Arg Arg Thr Pro Gln Gly Ile Gly Leu Leu Ala Lys Thr
             80                  85                  90 ccg ctg agc cgc cca gtc aag aga aac aac gcc aag tac cgg cgc atc      339
Pro Leu Ser Arg Pro Val Lys Arg Asn Asn Ala Lys Tyr Arg Arg Ile
                 95                 100                 105 caa act ttg atc tac gac gcc ctg gag aga ccg cgg ggc tgg gcg ctg      387
Gln Thr Leu Ile Tyr Asp Ala Leu Glu Arg Pro Arg Gly Trp Ala Leu
             110                 115                 120 ctt tac cac gcg ttg gtg ttc ctg att gtc ctg ggg tgc ttg att ctg      435
Leu Tyr His Ala Leu Val Phe Leu Ile Val Leu Gly Cys Leu Ile Leu
         125                 130                 135 gct gtc ctg acc aca ttc aag gag tat gag act gtc tcg gga gac tgg      483
Ala Val Leu Thr Thr Phe Lys Glu Tyr Glu Thr Val Ser Gly Asp Trp
140             145                 150                 155 ctt ctg tta ctg gag aca ttt gct att ttc atc ttt gga gcc gag ttt      531
Leu Leu Leu Leu Glu Thr Phe Ala Ile Phe Ile Phe Gly Ala Glu Phe
                 160                 165                 170 gct ttg agg atc tgg gct gct gga tgt tgc tgc cga tac aaa ggc tgg      579
Ala Leu Arg Ile Trp Ala Ala Gly Cys Cys Cys Arg Tyr Lys Gly Trp
             175                 180                 185 cgg ggc cga ctg aag ttt gcc agg aag ccc ctg tgc atg ttg gac atc      627
Arg Gly Arg Leu Lys Phe Ala Arg Lys Pro Leu Cys Met Leu Asp Ile
         190                 195                 200 ttt gtg ctg att gcc tct gtg cca gtg gtt gct gtg gga aac caa ggc      675
Phe Val Leu Ile Ala Ser Val Pro Val Val Ala Val Gly Asn Gln Gly
205             210                 215 aat gtt ctg gcc acc tcc ctg cga agc ctg cgc ttc ctg cag atc ctg      723
Asn Val Leu Ala Thr Ser Leu Arg Ser Leu Arg Phe Leu Gln Ile Leu
220                 225                 230                 235 cgc atg ctg cgg atg gac cgg aga ggt ggc acc tgg aag ctt ctg ggc      771
Arg Met Leu Arg Met Asp Arg Arg Gly Gly Thr Trp Lys Leu Leu Gly
             240                 245                 250 tca gcc atc tgt gcc cac agc aaa gaa ctc atc acg gcc tgg tac atc      819
Ser Ala Ile Cys Ala His Ser Lys Glu Leu Ile Thr Ala Trp Tyr Ile
         255                 260                 265 ggt ttc ctg aca ctc atc ctt tct tca ttt ctt gtc tac ctg gtt gag      867
Gly Phe Leu Thr Leu Ile Leu Ser Ser Phe Leu Val Tyr Leu Val Glu
         270                 275                 280 aaa gac gtc cca gag gtg gat gca caa gga gag gag atg aaa gag gag      915
Lys Asp Val Pro Glu Val Asp Ala Gln Gly Glu Glu Met Lys Glu Glu
285                 290                 295 ttt gag acc tat gca gat gcc ctg tgg tgg ggc ctg atc aca ctg gcc      963
Phe Glu Thr Tyr Ala Asp Ala Leu Trp Trp Gly Leu Ile Thr Leu Ala
300                 305                 310                 315 acc att ggc tat gga gac aag aca ccc aaa acg tgg gaa ggc cgt ctg     1011
Thr Ile Gly Tyr Gly Asp Lys Thr Pro Lys Thr Trp Glu Gly Arg Leu
             320                 325                 330 att gcc gcc acc ttt tcc tta att ggc gtc tcc ttt ttt gcc ctt cca     1059
Ile Ala Ala Thr Phe Ser Leu Ile Gly Val Ser Phe Phe Ala Leu Pro
         335                 340                 345 gcg ggc atc ctg ggg tcc ggg ctg gcc ctc aag gtg cag gag caa cac     1107
Ala Gly Ile Leu Gly Ser Gly Leu Ala Leu Lys Val Gln Glu Gln His
         350                 355                 360 cgt cag aag cac ttt gag aaa agg agg aag cca gct gct gag ctc att     1155
Arg Gln Lys His Phe Glu Lys Arg Arg Lys Pro Ala Ala Glu Leu Ile
365                 370                 375
```

```
cag gct gcc tgg agg tat tat gct acc aac ccc aac agg att gac ctg    1203
Gln Ala Ala Trp Arg Tyr Tyr Ala Thr Asn Pro Asn Arg Ile Asp Leu
380             385                 390                 395 gtg gcg aca tgg aga ttt tat gaa tca gtc gtc tct ttt cct ttc ttc    1251
Val Ala Thr Trp Arg Phe Tyr Glu Ser Val Val Ser Phe Pro Phe Phe
                400                 405                 410 agg aaa gaa cag ctg gag gca gca tcc agc caa aag ctg ggt ctc ttg    1299
Arg Lys Glu Gln Leu Glu Ala Ala Ser Ser Gln Lys Leu Gly Leu Leu
            415                 420                 425 gat cgg gtt cgc ctt tct aat cct cgt ggt agc aat act aaa gga aag    1347
Asp Arg Val Arg Leu Ser Asn Pro Arg Gly Ser Asn Thr Lys Gly Lys
        430                 435                 440 cta ttt acc cct ctg aat gta gat gcc ata gaa gaa agt cct tct aaa    1395
Leu Phe Thr Pro Leu Asn Val Asp Ala Ile Glu Glu Ser Pro Ser Lys
    445                 450                 455 gaa cca aag cct gtt ggc tta aac aat aaa gag cgt ttc cgc acg gcc    1443
Glu Pro Lys Pro Val Gly Leu Asn Asn Lys Glu Arg Phe Arg Thr Ala
460                 465                 470                 475 ttc cgc atg aaa gcc tac gct ttc tgg cag agt tct gaa gat gcc ggg    1491
Phe Arg Met Lys Ala Tyr Ala Phe Trp Gln Ser Ser Glu Asp Ala Gly
                480                 485                 490 aca ggt gac ccc atg gcg gaa gac agg ggc tat ggg aat gac ttc ccc    1539
Thr Gly Asp Pro Met Ala Glu Asp Arg Gly Tyr Gly Asn Asp Phe Pro
            495                 500                 505 atc gaa gac atg atc ccc acc ctg aag gcc gcc atc cga gcc gtc aga    1587
Ile Glu Asp Met Ile Pro Thr Leu Lys Ala Ala Ile Arg Ala Val Arg
        510                 515                 520 att cta caa ttc cgt ctc tat aaa aaa aaa ttc aag gag act ttg agg    1635
Ile Leu Gln Phe Arg Leu Tyr Lys Lys Lys Phe Lys Glu Thr Leu Arg
    525                 530                 535 cct tac gat gtg aag gat gtg att gag cag tat tct gcc ggg cat ctc    1683
Pro Tyr Asp Val Lys Asp Val Ile Glu Gln Tyr Ser Ala Gly His Leu
540                 545                 550                 555 gac atg ctt tcc agg ata aag tac ctt cag acg aga ata gat atg att    1731
Asp Met Leu Ser Arg Ile Lys Tyr Leu Gln Thr Arg Ile Asp Met Ile
                560                 565                 570 ttc acc cct gga cct ccc tcc acg cca aaa cac aag aag tct cag aaa    1779
Phe Thr Pro Gly Pro Pro Ser Thr Pro Lys His Lys Lys Ser Gln Lys
            575                 580                 585 ggg tca gca ttc acc ttc cca tcc cag caa tct ccc agg aat gaa cca    1827
Gly Ser Ala Phe Thr Phe Pro Ser Gln Gln Ser Pro Arg Asn Glu Pro
        590                 595                 600 tat gta gcc aga cca tcc aca tca gaa atc gaa gac caa agc atg atg    1875
Tyr Val Ala Arg Pro Ser Thr Ser Glu Ile Glu Asp Gln Ser Met Met
    605                 610                 615 ggg aag ttt gta aaa gtt gaa aga cag gtt cag gac atg ggg aag aag    1923
Gly Lys Phe Val Lys Val Glu Arg Gln Val Gln Asp Met Gly Lys Lys
620                 625                 630                 635 ctg gac ttc ctc gtg gat atg cac atg caa cac atg gaa cgg ttg cag    1971
Leu Asp Phe Leu Val Asp Met His Met Gln His Met Glu Arg Leu Gln
                640                 645                 650 gtg cag gtc acg gag tat tac cca acc aag ggc acc tcc tcg cca gct    2019
Val Gln Val Thr Glu Tyr Tyr Pro Thr Lys Gly Thr Ser Ser Pro Ala
            655                 660                 665 gaa gca gag aag aag gag gac aac agg tat tcc gat ttg aaa acc atc    2067
Glu Ala Glu Lys Lys Glu Asp Asn Arg Tyr Ser Asp Leu Lys Thr Ile
        670                 675                 680 atc tgc aac tat tct gag aca ggc ccc ccg gaa cca ccc tac agc ttc    2115
Ile Cys Asn Tyr Ser Glu Thr Gly Pro Pro Glu Pro Pro Tyr Ser Phe
```

```
                    685                 690                 695
cac cag gtg acc att gac aaa gtc agc ccc tat ggg ttt ttt gca cat    2163
His Gln Val Thr Ile Asp Lys Val Ser Pro Tyr Gly Phe Phe Ala His
700                 705                 710                 715 gac cct gtg aac ctg ccc cga ggg gga ccc agt tct gga aag gtt cag    2211
Asp Pro Val Asn Leu Pro Arg Gly Gly Pro Ser Ser Gly Lys Val Gln
                720                 725                 730 gca act cct cct tcc tca gca aca acg tat gtg gag agg ccc acg gtc    2259
Ala Thr Pro Pro Ser Ser Ala Thr Thr Tyr Val Glu Arg Pro Thr Val
            735                 740                 745 ctg cct atc ttg act ctt ctc gac tcc cga gtg agc tgc cac tcc cag    2307
Leu Pro Ile Leu Thr Leu Leu Asp Ser Arg Val Ser Cys His Ser Gln
        750                 755                 760 gct gac ctg cag ggc ccc tac tcg gac cga atc tcc ccc cgg cag aga    2355
Ala Asp Leu Gln Gly Pro Tyr Ser Asp Arg Ile Ser Pro Arg Gln Arg
765                 770                 775 cgt agc atc acg cga gac agt gac aca cct ctg tcc ctg atg tcg gtc    2403
Arg Ser Ile Thr Arg Asp Ser Asp Thr Pro Leu Ser Leu Met Ser Val
780                 785                 790                 795 aac cac gag gag ctg gag agg tct cca agt ggc ttc agc atc tcc cag    2451
Asn His Glu Glu Leu Glu Arg Ser Pro Ser Gly Phe Ser Ile Ser Gln
                800                 805                 810 gac aga gat gat tat gtg ttc ggc ccc aat ggg ggg tcg agc tgg atg    2499
Asp Arg Asp Asp Tyr Val Phe Gly Pro Asn Gly Gly Ser Ser Trp Met
            815                 820                 825 agg gag aag cgg tac ctc gcc gag ggt gag acg gac aca gac acg gac    2547
Arg Glu Lys Arg Tyr Leu Ala Glu Gly Glu Thr Asp Thr Asp Thr Asp
        830                 835                 840 ccc ttc acg ccc agc ggc tcc atg cct ctg tcg tcc aca ggg gat ggg    2595
Pro Phe Thr Pro Ser Gly Ser Met Pro Leu Ser Ser Thr Gly Asp Gly
845                 850                 855 att tct gat tca gta tgg acc cct tcc aat aag ccc att taaaagaggt    2644
Ile Ser Asp Ser Val Trp Thr Pro Ser Asn Lys Pro Ile
860                 865                 870 cactggctga cccctccttg taatgtagac agactttgta tagttcactt actcttacac  2704
ccgacgctta ccagcgggga caccaatggc tgcatcaaat gcatgcgtgt gcgtggtggc  2764
cccacccagg caggggcttc ccacagcctc ttcctcccca tgtcaccaca acaaagtgct  2824
tccttttcag catggtttgc atgacttttac actatataaa tggttccgct aatctcttct  2884
aggataaaaa aaaaaaaaaa aaaaaaaaa                                    2914

<210> SEQ ID NO 7
<211> LENGTH: 872
<212> TYPE: PRT
<213> ORGANISM: Homo sapiens

<400> SEQUENCE: 7

Met Gly Leu Lys Ala Arg Arg Ala Ala Gly Ala Ala Gly Gly Gly Gly
1               5                   10                  15

Asp Gly Gly Gly Gly Gly Gly Ala Ala Asn Pro Ala Gly Gly Asp
                20                  25                  30

Ala Ala Ala Ala Gly Asp Glu Glu Arg Lys Val Gly Leu Ala Pro Gly
            35                  40                  45

Asp Val Glu Gln Val Thr Leu Ala Leu Gly Gly Ala Asp Lys Asp
        50                  55                  60

Gly Thr Leu Leu Leu Glu Gly Gly Gly Arg Asp Glu Gly Gln Arg Arg
65                  70                  75                  80
```

-continued

```
Thr Pro Gln Gly Ile Gly Leu Leu Ala Lys Thr Pro Leu Ser Arg Pro
                 85                  90                  95

Val Lys Arg Asn Asn Ala Lys Tyr Arg Arg Ile Gln Thr Leu Ile Tyr
            100                 105                 110

Asp Ala Leu Glu Arg Pro Arg Gly Trp Ala Leu Leu Tyr His Ala Leu
            115                 120                 125

Val Phe Leu Ile Val Leu Gly Cys Leu Ile Leu Ala Val Leu Thr Thr
            130                 135                 140

Phe Lys Glu Tyr Glu Thr Val Ser Gly Asp Trp Leu Leu Leu Leu Glu
145                 150                 155                 160

Thr Phe Ala Ile Phe Ile Phe Gly Ala Glu Phe Ala Leu Arg Ile Trp
                165                 170                 175

Ala Ala Gly Cys Cys Cys Arg Tyr Lys Gly Trp Arg Gly Arg Leu Lys
            180                 185                 190

Phe Ala Arg Lys Pro Leu Cys Met Leu Asp Ile Phe Val Leu Ile Ala
            195                 200                 205

Ser Val Pro Val Val Ala Val Gly Asn Gln Gly Asn Val Leu Ala Thr
            210                 215                 220

Ser Leu Arg Ser Leu Arg Phe Leu Gln Ile Leu Arg Met Leu Arg Met
225                 230                 235                 240

Asp Arg Arg Gly Gly Thr Trp Lys Leu Leu Gly Ser Ala Ile Cys Ala
                245                 250                 255

His Ser Lys Glu Leu Ile Thr Ala Trp Tyr Ile Gly Phe Leu Thr Leu
            260                 265                 270

Ile Leu Ser Ser Phe Leu Val Tyr Leu Val Glu Lys Asp Val Pro Glu
            275                 280                 285

Val Asp Ala Gln Gly Glu Glu Met Lys Glu Glu Phe Glu Thr Tyr Ala
            290                 295                 300

Asp Ala Leu Trp Trp Gly Leu Ile Thr Leu Ala Thr Ile Gly Tyr Gly
305                 310                 315                 320

Asp Lys Thr Pro Lys Thr Trp Glu Gly Arg Leu Ile Ala Ala Thr Phe
                325                 330                 335

Ser Leu Ile Gly Val Ser Phe Phe Ala Leu Pro Ala Gly Ile Leu Gly
            340                 345                 350

Ser Gly Leu Ala Leu Lys Val Gln Glu Gln His Arg Gln Lys His Phe
            355                 360                 365

Glu Lys Arg Arg Lys Pro Ala Ala Glu Leu Ile Gln Ala Ala Trp Arg
            370                 375                 380

Tyr Tyr Ala Thr Asn Pro Asn Arg Ile Asp Leu Val Ala Thr Trp Arg
385                 390                 395                 400

Phe Tyr Glu Ser Val Val Ser Phe Pro Phe Phe Arg Lys Glu Gln Leu
                405                 410                 415

Glu Ala Ala Ser Ser Gln Lys Leu Gly Leu Leu Asp Arg Val Arg Leu
            420                 425                 430

Ser Asn Pro Arg Gly Ser Asn Thr Lys Gly Lys Leu Phe Thr Pro Leu
            435                 440                 445

Asn Val Asp Ala Ile Glu Glu Ser Pro Ser Lys Glu Pro Lys Pro Val
            450                 455                 460

Gly Leu Asn Asn Lys Glu Arg Phe Arg Thr Ala Phe Arg Met Lys Ala
465                 470                 475                 480

Tyr Ala Phe Trp Gln Ser Ser Glu Asp Ala Gly Thr Gly Asp Pro Met
                485                 490                 495

Ala Glu Asp Arg Gly Tyr Gly Asn Asp Phe Pro Ile Glu Asp Met Ile
```

```
                500                 505                 510
Pro Thr Leu Lys Ala Ala Ile Arg Ala Val Arg Ile Leu Gln Phe Arg
            515                 520                 525
Leu Tyr Lys Lys Lys Phe Lys Glu Thr Leu Arg Pro Tyr Asp Val Lys
        530                 535                 540
Asp Val Ile Glu Gln Tyr Ser Ala Gly His Leu Asp Met Leu Ser Arg
545                 550                 555                 560
Ile Lys Tyr Leu Gln Thr Arg Ile Asp Met Ile Phe Thr Pro Gly Pro
                565                 570                 575
Pro Ser Thr Pro Lys His Lys Lys Ser Gln Lys Gly Ser Ala Phe Thr
            580                 585                 590
Phe Pro Ser Gln Gln Ser Pro Arg Asn Glu Pro Tyr Val Ala Arg Pro
        595                 600                 605
Ser Thr Ser Glu Ile Glu Asp Gln Ser Met Met Gly Lys Phe Val Lys
        610                 615                 620
Val Glu Arg Gln Val Gln Asp Met Gly Lys Lys Leu Asp Phe Leu Val
625                 630                 635                 640
Asp Met His Met Gln His Met Glu Arg Leu Gln Val Gln Val Thr Glu
                645                 650                 655
Tyr Tyr Pro Thr Lys Gly Thr Ser Ser Pro Ala Glu Ala Glu Lys Lys
            660                 665                 670
Glu Asp Asn Arg Tyr Ser Asp Leu Lys Thr Ile Cys Asn Tyr Ser
        675                 680                 685
Glu Thr Gly Pro Pro Glu Pro Pro Tyr Ser Phe His Gln Val Thr Ile
        690                 695                 700
Asp Lys Val Ser Pro Tyr Gly Phe Phe Ala His Asp Pro Val Asn Leu
705                 710                 715                 720
Pro Arg Gly Gly Pro Ser Ser Gly Lys Val Gln Ala Thr Pro Pro Ser
                725                 730                 735
Ser Ala Thr Thr Tyr Val Glu Arg Pro Thr Val Leu Pro Ile Leu Thr
            740                 745                 750
Leu Leu Asp Ser Arg Val Ser Cys His Ser Gln Ala Asp Leu Gln Gly
        755                 760                 765
Pro Tyr Ser Asp Arg Ile Ser Pro Arg Gln Arg Ser Ile Thr Arg
        770                 775                 780
Asp Ser Asp Thr Pro Leu Ser Leu Met Ser Val Asn His Glu Glu Leu
785                 790                 795                 800
Glu Arg Ser Pro Ser Gly Phe Ser Ile Ser Gln Asp Arg Asp Tyr
                805                 810                 815
Val Phe Gly Pro Asn Gly Gly Ser Ser Trp Met Arg Glu Lys Arg Tyr
            820                 825                 830
Leu Ala Glu Gly Glu Thr Asp Thr Asp Thr Asp Pro Phe Thr Pro Ser
        835                 840                 845
Gly Ser Met Pro Leu Ser Ser Thr Gly Asp Gly Ile Ser Asp Ser Val
        850                 855                 860
Trp Thr Pro Ser Asn Lys Pro Ile
865                 870

<210> SEQ ID NO 8
<211> LENGTH: 22
<212> TYPE: DNA
<213> ORGANISM: Homo sapiens

<400> SEQUENCE: 8
```

```
ttcctgattg tcctggggtg ct                                            22

<210> SEQ ID NO 9
<211> LENGTH: 23
<212> TYPE: DNA
<213> ORGANISM: Homo sapiens

<400> SEQUENCE: 9
ttcatctttg gagccgagtt tgc                                           23

<210> SEQ ID NO 10
<211> LENGTH: 24
<212> TYPE: DNA
<213> ORGANISM: Homo sapiens

<400> SEQUENCE: 10
tccatgtggt actccatgtc tgaa                                          24

<210> SEQ ID NO 11
<211> LENGTH: 23
<212> TYPE: DNA
<213> ORGANISM: Homo sapiens

<400> SEQUENCE: 11
gcacgtcaca ttggggatgt cat                                           23

<210> SEQ ID NO 12
<211> LENGTH: 24
<212> TYPE: DNA
<213> ORGANISM: Homo sapiens

<400> SEQUENCE: 12
tgtgttttgg cgtggaggga ggtc                                          24

<210> SEQ ID NO 13
<211> LENGTH: 21
<212> TYPE: DNA
<213> ORGANISM: Homo sapiens

<400> SEQUENCE: 13
cagtaacaga agccagtctc c                                             21

<210> SEQ ID NO 14
<211> LENGTH: 23
<212> TYPE: DNA
<213> ORGANISM: Homo sapiens

<400> SEQUENCE: 14
gcaaactcgg ctccaaagat gaa                                           23

<210> SEQ ID NO 15
<211> LENGTH: 22
<212> TYPE: DNA
<213> ORGANISM: Homo sapiens

<400> SEQUENCE: 15
caccaacgcg tggtaaagca gc                                            22

<210> SEQ ID NO 16
<211> LENGTH: 22
<212> TYPE: DNA
<213> ORGANISM: Homo sapiens

<400> SEQUENCE: 16
```

```
ttcctgattg tcctggggtg ct                                              22

<210> SEQ ID NO 17
<211> LENGTH: 23
<212> TYPE: DNA
<213> ORGANISM: Homo sapiens

<400> SEQUENCE: 17
agtatctgcc gggcatctcg aca                                             23

<210> SEQ ID NO 18
<211> LENGTH: 23
<212> TYPE: DNA
<213> ORGANISM: Homo sapiens

<400> SEQUENCE: 18
catcacggcc tggtacatcg gtt                                             23

<210> SEQ ID NO 19
<211> LENGTH: 24
<212> TYPE: DNA
<213> ORGANISM: Homo sapiens

<400> SEQUENCE: 19
aatctcacag aattggcctc caag                                            24

<210> SEQ ID NO 20
<211> LENGTH: 63
<212> TYPE: DNA
<213> ORGANISM: Artificial Sequence
<220> FEATURE:
<223> OTHER INFORMATION: Description of Artificial Sequence:Hypothetical
      sequence to demonstrate calculation of homology or
      identity - not derived from any genetic source.

<400> SEQUENCE: 20
accgtagcta cgtacgtata tagaaagggc gcgatcgtcg tcgcgtatga cgacttagca     60
tgc                                                                   63

<210> SEQ ID NO 21
<211> LENGTH: 130
<212> TYPE: DNA
<213> ORGANISM: Artificial Sequence
<220> FEATURE:
<223> OTHER INFORMATION: Description of Artificial Sequence:Hypothetical
      sequence to demonstrate calculation of homology or
      identity - not derived from any genetic source.

<400> SEQUENCE: 21
accggtagct acgtacgtta tttagaaagg ggtgtgtgtg tgtgtgtaaa ccggggtttt     60
cgggatcgtc cgtcgcgtat gacgacttag ccatgcacgg tatatcgtat taggactagc   120
gattgactag                                                           130

<210> SEQ ID NO 22
<211> LENGTH: 23
<212> TYPE: DNA
<213> ORGANISM: Homo sapiens

<400> SEQUENCE: 22
ttcctcctgg ttttctcctg cct                                             23

<210> SEQ ID NO 23
```

```
<211> LENGTH: 21
<212> TYPE: DNA
<213> ORGANISM: Homo sapiens

<400> SEQUENCE: 23
aagacagacg cccaggcagc t                                             21

<210> SEQ ID NO 24
<211> LENGTH: 24
<212> TYPE: DNA
<213> ORGANISM: Homo sapiens

<400> SEQUENCE: 24
aggcctcaag gtggcctcag cttt                                          24

<210> SEQ ID NO 25
<211> LENGTH: 22
<212> TYPE: DNA
<213> ORGANISM: Homo sapiens

<400> SEQUENCE: 25
ctggccctga ttctagcaat ac                                            22

<210> SEQ ID NO 26
<211> LENGTH: 22
<212> TYPE: DNA
<213> ORGANISM: Homo sapiens

<400> SEQUENCE: 26
tgtgggcata gaccacagag cc                                            22

<210> SEQ ID NO 27
<211> LENGTH: 22
<212> TYPE: DNA
<213> ORGANISM: Homo sapiens

<400> SEQUENCE: 27
tggtcactgc ctggtacatc gg                                            22

<210> SEQ ID NO 28
<211> LENGTH: 24
<212> TYPE: DNA
<213> ORGANISM: Homo sapiens

<400> SEQUENCE: 28
atggagcagg ctcagccagt gaga                                          24

<210> SEQ ID NO 29
<211> LENGTH: 22
<212> TYPE: DNA
<213> ORGANISM: Homo sapiens

<400> SEQUENCE: 29
gcaggccctt cgtgtgacta ga                                            22

<210> SEQ ID NO 30
<211> LENGTH: 21
<212> TYPE: DNA
<213> ORGANISM: Homo sapiens

<400> SEQUENCE: 30
acctagggaa ctgtgcccag g                                             21
```

```
<210> SEQ ID NO 31
<211> LENGTH: 23
<212> TYPE: DNA
<213> ORGANISM: Homo sapiens

<400> SEQUENCE: 31
atggtctgac cctgatgaat tgg                                              23

<210> SEQ ID NO 32
<211> LENGTH: 21
<212> TYPE: DNA
<213> ORGANISM: Homo sapiens

<400> SEQUENCE: 32
gcggcctcca ctcctcaaca a                                                21

<210> SEQ ID NO 33
<211> LENGTH: 21
<212> TYPE: DNA
<213> ORGANISM: Homo sapiens

<400> SEQUENCE: 33
ccgccgggca cctgccacca a                                                21

<210> SEQ ID NO 34
<211> LENGTH: 22
<212> TYPE: DNA
<213> ORGANISM: Homo sapiens

<400> SEQUENCE: 34
gcttgcacag ctccatgggc ag                                               22

<210> SEQ ID NO 35
<211> LENGTH: 22
<212> TYPE: DNA
<213> ORGANISM: Homo sapiens

<400> SEQUENCE: 35
cccaggacta actgtgctct cc                                               22

<210> SEQ ID NO 36
<211> LENGTH: 21
<212> TYPE: DNA
<213> ORGANISM: Homo sapiens

<400> SEQUENCE: 36
ccgtgcagca gccgtcagtc c                                                21

<210> SEQ ID NO 37
<211> LENGTH: 23
<212> TYPE: DNA
<213> ORGANISM: Homo sapiens

<400> SEQUENCE: 37
gcagagtgac ttctctccct gtt                                              23

<210> SEQ ID NO 38
<211> LENGTH: 21
<212> TYPE: DNA
<213> ORGANISM: Homo sapiens

<400> SEQUENCE: 38
gtccccgaag ctccagctct t                                                21
```

```
<210> SEQ ID NO 39
<211> LENGTH: 22
<212> TYPE: DNA
<213> ORGANISM: Homo sapiens

<400> SEQUENCE: 39
aagatcgtgt cttctccagc cc                                              22

<210> SEQ ID NO 40
<211> LENGTH: 22
<212> TYPE: DNA
<213> ORGANISM: Homo sapiens

<400> SEQUENCE: 40
gatggaccag gagaggatgc gg                                              22

<210> SEQ ID NO 41
<211> LENGTH: 22
<212> TYPE: DNA
<213> ORGANISM: Homo sapiens

<400> SEQUENCE: 41
ccctcacggc atgtgtcctt cc                                              22

<210> SEQ ID NO 42
<211> LENGTH: 21
<212> TYPE: DNA
<213> ORGANISM: Homo sapiens

<400> SEQUENCE: 42
agcgggaggc ccctcctcac t                                               21

<210> SEQ ID NO 43
<211> LENGTH: 22
<212> TYPE: DNA
<213> ORGANISM: Homo sapiens

<400> SEQUENCE: 43
ggtctctggc ccagggctca ca                                              22

<210> SEQ ID NO 44
<211> LENGTH: 22
<212> TYPE: DNA
<213> ORGANISM: Homo sapiens

<400> SEQUENCE: 44
cttgtcccct gctggacagg ca                                              22

<210> SEQ ID NO 45
<211> LENGTH: 21
<212> TYPE: DNA
<213> ORGANISM: Homo sapiens

<400> SEQUENCE: 45
ttgacggcag gcaccacagc c                                               21

<210> SEQ ID NO 46
<211> LENGTH: 21
<212> TYPE: DNA
<213> ORGANISM: Homo sapiens

<400> SEQUENCE: 46
cccagcccag cagccccttt t                                               21
```

<210> SEQ ID NO 47
<211> LENGTH: 21
<212> TYPE: DNA
<213> ORGANISM: Homo sapiens

<400> SEQUENCE: 47
aggtggaggg cggacactgg a                                          21

<210> SEQ ID NO 48
<211> LENGTH: 22
<212> TYPE: DNA
<213> ORGANISM: Homo sapiens

<400> SEQUENCE: 48
ctccacgggc cagaagaact tc                                         22

<210> SEQ ID NO 49
<211> LENGTH: 23
<212> TYPE: DNA
<213> ORGANISM: Homo sapiens

<400> SEQUENCE: 49
gatggagatg gacgtgtcgc tgt                                        23

<210> SEQ ID NO 50
<211> LENGTH: 25
<212> TYPE: DNA
<213> ORGANISM: Homo sapiens

<400> SEQUENCE: 50
tggagttcct gcggcaggag gacac                                      25

<210> SEQ ID NO 51
<211> LENGTH: 23
<212> TYPE: DNA
<213> ORGANISM: Homo sapiens

<400> SEQUENCE: 51
ggtgtctgac tctccctccg caa                                        23

<210> SEQ ID NO 52
<211> LENGTH: 22
<212> TYPE: DNA
<213> ORGANISM: Homo sapiens

<400> SEQUENCE: 52
gtggcgcctt gtgccaaagt ca                                         22

<210> SEQ ID NO 53
<211> LENGTH: 21
<212> TYPE: DNA
<213> ORGANISM: Homo sapiens

<400> SEQUENCE: 53
acctcggagg caccgtgctg a                                          21

<210> SEQ ID NO 54
<211> LENGTH: 22
<212> TYPE: DNA
<213> ORGANISM: Homo sapiens

<400> SEQUENCE: 54
gcgacgtgga gcaagtacct tg 22

<210> SEQ ID NO 55
<211> LENGTH: 22
<212> TYPE: DNA
<213> ORGANISM: Homo sapiens

<400> SEQUENCE: 55
caccaacgcg tggtaaagca gc 22

<210> SEQ ID NO 56
<211> LENGTH: 24
<212> TYPE: DNA
<213> ORGANISM: Homo sapiens

<400> SEQUENCE: 56
atgactcaaa ggttccttag tcca 24

<210> SEQ ID NO 57
<211> LENGTH: 23
<212> TYPE: DNA
<213> ORGANISM: Homo sapiens

<400> SEQUENCE: 57
gaagcccaac cagaagcatt tac 23

<210> SEQ ID NO 58
<211> LENGTH: 23
<212> TYPE: DNA
<213> ORGANISM: Homo sapiens

<400> SEQUENCE: 58
tcagtgcctc tccatatgct ctt 23

<210> SEQ ID NO 59
<211> LENGTH: 21
<212> TYPE: DNA
<213> ORGANISM: Homo sapiens

<400> SEQUENCE: 59
actgaggagg ctgggaggct c 21

<210> SEQ ID NO 60
<211> LENGTH: 24
<212> TYPE: DNA
<213> ORGANISM: Homo sapiens

<400> SEQUENCE: 60
gatgacgcca ttgctttcgc atga 24

<210> SEQ ID NO 61
<211> LENGTH: 22
<212> TYPE: DNA
<213> ORGANISM: Homo sapiens

<400> SEQUENCE: 61
gtgggaagcc catgtggtcc tg 22

<210> SEQ ID NO 62
<211> LENGTH: 22
<212> TYPE: DNA
<213> ORGANISM: Homo sapiens

<400> SEQUENCE: 62

```
catccactca acgactcccc ag                                                     22

<210> SEQ ID NO 63
<211> LENGTH: 24
<212> TYPE: DNA
<213> ORGANISM: Homo sapiens

<400> SEQUENCE: 63
aatctcacag aattggcctc caag                                                   24

<210> SEQ ID NO 64
<211> LENGTH: 24
<212> TYPE: DNA
<213> ORGANISM: Homo sapiens

<400> SEQUENCE: 64
tccatgtggt actccatgtc tgaa                                                   24

<210> SEQ ID NO 65
<211> LENGTH: 23
<212> TYPE: DNA
<213> ORGANISM: Homo sapiens

<400> SEQUENCE: 65
gcacgtcaca ttggggatgt cat                                                    23

<210> SEQ ID NO 66
<211> LENGTH: 23
<212> TYPE: DNA
<213> ORGANISM: Homo sapiens

<400> SEQUENCE: 66
ggaatgctgg gacagtctag ctg                                                    23

<210> SEQ ID NO 67
<211> LENGTH: 26
<212> TYPE: DNA
<213> ORGANISM: Homo sapiens

<400> SEQUENCE: 67
tacatatgca tggatcttaa tcccat                                                 26

<210> SEQ ID NO 68
<211> LENGTH: 24
<212> TYPE: DNA
<213> ORGANISM: Homo sapiens

<400> SEQUENCE: 68
aaagtttcag gtggtgccca ctca                                                   24

<210> SEQ ID NO 69
<211> LENGTH: 24
<212> TYPE: DNA
<213> ORGANISM: Homo sapiens

<400> SEQUENCE: 69
gaggccacag acacgaatac agac                                                   24

<210> SEQ ID NO 70
<211> LENGTH: 24
<212> TYPE: DNA
<213> ORGANISM: Homo sapiens
```

```
<400> SEQUENCE: 70
tgggtaaacc cgcctccttc attg                                          24

<210> SEQ ID NO 71
<211> LENGTH: 24
<212> TYPE: DNA
<213> ORGANISM: Homo sapiens

<400> SEQUENCE: 71
actctatctt gggaccagca tgac                                          24

<210> SEQ ID NO 72
<211> LENGTH: 23
<212> TYPE: DNA
<213> ORGANISM: Homo sapiens

<400> SEQUENCE: 72
taagagcctg cactgaagga gga                                           23

<210> SEQ ID NO 73
<211> LENGTH: 23
<212> TYPE: DNA
<213> ORGANISM: Homo sapiens

<400> SEQUENCE: 73
ggggaggaag aagtggaaga gac                                           23

<210> SEQ ID NO 74
<211> LENGTH: 23
<212> TYPE: DNA
<213> ORGANISM: Homo sapiens

<400> SEQUENCE: 74
caggtctgtg gcctgccgtt cat                                           23

<210> SEQ ID NO 75
<211> LENGTH: 23
<212> TYPE: DNA
<213> ORGANISM: Homo sapiens

<400> SEQUENCE: 75
ccttcctgtg ggagttgagc tgg                                           23

<210> SEQ ID NO 76
<211> LENGTH: 24
<212> TYPE: DNA
<213> ORGANISM: Homo sapiens

<400> SEQUENCE: 76
gtttgctagc cttctgttat agct                                          24

<210> SEQ ID NO 77
<211> LENGTH: 21
<212> TYPE: DNA
<213> ORGANISM: Homo sapiens

<400> SEQUENCE: 77
gggagcgcag tccctccaga t                                             21

<210> SEQ ID NO 78
<211> LENGTH: 26
<212> TYPE: DNA
<213> ORGANISM: Homo sapiens
```

```
<400> SEQUENCE: 78
cttatatatt ccaaacccitt atctca                                           26

<210> SEQ ID NO 79
<211> LENGTH: 1
<212> TYPE: DNA
<213> ORGANISM: Homo sapiens

<400> SEQUENCE: 79 a                                                                        1

<210> SEQ ID NO 80
<211> LENGTH: 23
<212> TYPE: DNA
<213> ORGANISM: Homo sapiens

<400> SEQUENCE: 80
aaccaatagc aacgatcccc acc                                               23

<210> SEQ ID NO 81
<211> LENGTH: 24
<212> TYPE: DNA
<213> ORGANISM: Homo sapiens

<400> SEQUENCE: 81
ctgactttgt caatggtcac ctgg                                              24

<210> SEQ ID NO 82
<211> LENGTH: 22
<212> TYPE: DNA
<213> ORGANISM: Homo sapiens

<400> SEQUENCE: 82
cggaaccacc ctacagcttc ca                                                22

<210> SEQ ID NO 83
<211> LENGTH: 22
<212> TYPE: DNA
<213> ORGANISM: Homo sapiens

<400> SEQUENCE: 83
gggagtggca gctcactcgg ga                                                22

<210> SEQ ID NO 84
<211> LENGTH: 22
<212> TYPE: DNA
<213> ORGANISM: Homo sapiens

<400> SEQUENCE: 84
aggcccacgg tcctgcctat ct                                                22

<210> SEQ ID NO 85
<211> LENGTH: 23
<212> TYPE: DNA
<213> ORGANISM: Homo sapiens

<400> SEQUENCE: 85
ccattggggc cgaacacata atc                                               23

<210> SEQ ID NO 86
<211> LENGTH: 23
<212> TYPE: DNA
```

<210> SEQ ID NO 87
<211> LENGTH: 23
<212> TYPE: DNA
<213> ORGANISM: Homo sapiens

<400> SEQUENCE: 86
cttcagcatc tcccaggaca gag                                                23

<210> SEQ ID NO 87
<211> LENGTH: 23
<212> TYPE: DNA
<213> ORGANISM: Homo sapiens

<400> SEQUENCE: 87 aaggagggt cagccagtga cct                                                 23

<210> SEQ ID NO 88
<211> LENGTH: 2273
<212> TYPE: DNA
<213> ORGANISM: Mus musculus
<220> FEATURE:
<221> NAME/KEY: CDS
<222> LOCATION: (1)..(2271)
<220> FEATURE:
<221> NAME/KEY: misc_feature
<222> LOCATION: (1)..(2273)
<223> OTHER INFORMATION: n may be any nucleotide except at position
      272 at which n may be t, c or g.
<220> FEATURE:
<221> NAME/KEY: PEPTIDE
<222> LOCATION: (1)..(757)
<223> OTHER INFORMATION: Xaa may be: S or R at 18, 19 and 69; V, A, E or
      G at 31; D or E at 33; S, P, T or A at 39; I, T, N or
      S at 52; F, L, I, M or V at 53; S, P, T or A at 64;
      P at 68; L, S or W at 91; R at 365; V at 509 and 516.

<400> SEQUENCE: 88

| atg gtg cag aag tcg cgc aac ggt ggc gtg tac ccc ggc acc agc ggg | 48 |
| Met Val Gln Lys Ser Arg Asn Gly Gly Val Tyr Pro Gly Thr Ser Gly | |
| 1               5                   10                  15      | |

| gaa aan aan ctc aag gtg ggc ttc gtg ggg ctg gac ccc ggc nng ccc | 96 |
| Glu Xaa Xaa Leu Lys Val Gly Phe Val Gly Leu Asp Pro Gly Xaa Pro | |
|         20                  25                  30              | |

| gan tcc aca cgc gac ggc ncn cta ctc atc gcg ggc tcc gag gcc ccc | 144 |
| Xaa Ser Thr Arg Asp Gly Xaa Leu Leu Ile Ala Gly Ser Glu Ala Pro | |
|     35                  40                  45                  | |

| aag cgc ggc anc ntn ttg agc aag ccg cgg acg ggc ggc gcg gga ncc | 192 |
| Lys Arg Gly Xaa Xaa Leu Ser Lys Pro Arg Thr Gly Gly Ala Gly Xaa | |
| 50                  55                  60                      | |

| ggg aag ccc ccn aan cgc aac gcc ttc tac cgc aag ctg cag aat ttc | 240 |
| Gly Lys Pro Xaa Xaa Arg Asn Ala Phe Tyr Arg Lys Leu Gln Asn Phe | |
| 65                  70                  75                  80  | |

| ctc tac aac gtg cta gag cgg ccc cgc ggc tng gcg ttc atc tac cac | 288 |
| Leu Tyr Asn Val Leu Glu Arg Pro Arg Gly Xaa Ala Phe Ile Tyr His | |
|                 85                  90                  95      | |

| gcc tac gtg ttc ctc ctg gtt ttc tcc tgc ctt gtg ctt tct gtg ttt | 336 |
| Ala Tyr Val Phe Leu Leu Val Phe Ser Cys Leu Val Leu Ser Val Phe | |
|                 100                 105                 110     | |

| tcc acc atc aag gag tac gag aag agc tct gag ggg gcc ctc tac atc | 384 |
| Ser Thr Ile Lys Glu Tyr Glu Lys Ser Ser Glu Gly Ala Leu Tyr Ile | |
|             115                 120                 125         | |

| ttg gaa atc gtg act atc gtg gta ttc ggt gtt gag tac ttt gtg agg | 432 |
| Leu Glu Ile Val Thr Ile Val Val Phe Gly Val Glu Tyr Phe Val Arg | |
|         130                 135                 140             | |

| atc tgg gct gca ggc tgc tgt tgc cgg tat cga ggc tgg agg ggc agg | 480 |
| Ile Trp Ala Ala Gly Cys Cys Cys Arg Tyr Arg Gly Trp Arg Gly Arg | |
| 145                 150                 155                 160 | |

-continued

| | |
|---|---|
| ctc aag ttt gcc agg aag ccg ttc tgt gtg att gat atc atg gtg ctg<br>Leu Lys Phe Ala Arg Lys Pro Phe Cys Val Ile Asp Ile Met Val Leu<br>                 165                       170                   175 | 528 |
| att gcc tcc att gct gtg ctg gct gct ggt tcc cag ggc aat gtc ttt<br>Ile Ala Ser Ile Ala Val Leu Ala Ala Gly Ser Gln Gly Asn Val Phe<br>180                       185                       190 | 576 |
| gcc aca tct gcg ctt cgg agc ttg cgg ttc ttg caa atc ttg cgg atg<br>Ala Thr Ser Ala Leu Arg Ser Leu Arg Phe Leu Gln Ile Leu Arg Met<br>         195                   200                   205 | 624 |
| atc cgt atg gac cgg agg ggt ggc acc tgg aag ctc ttg gga tcg gta<br>Ile Arg Met Asp Arg Arg Gly Gly Thr Trp Lys Leu Leu Gly Ser Val<br>210                       215                       220 | 672 |
| gtc tac gct cac agc aag gag ctg gtg act gcc tgg tac att ggc ttc<br>Val Tyr Ala His Ser Lys Glu Leu Val Thr Ala Trp Tyr Ile Gly Phe<br>225                       230                   235                   240 | 720 |
| ctc tgc ctc atc ctg gcc tca ttt ctg gtg tac ttg gca gaa aag ggt<br>Leu Cys Leu Ile Leu Ala Ser Phe Leu Val Tyr Leu Ala Glu Lys Gly<br>                 245                   250                   255 | 768 |
| gag aat gac cac ttt gac acc tac gca gat gca ctc tgg tgg ggt ctg<br>Glu Asn Asp His Phe Asp Thr Tyr Ala Asp Ala Leu Trp Trp Gly Leu<br>             260                       265                   270 | 816 |
| atc acc ctg acg acc att ggc tac ggg gac aag tac cct cag acc tgg<br>Ile Thr Leu Thr Thr Ile Gly Tyr Gly Asp Lys Tyr Pro Gln Thr Trp<br>         275                   280                   285 | 864 |
| aac ggg agg ctg ctg gca gcg acc ttt acc ctc att ggt gtc tcg ttc<br>Asn Gly Arg Leu Leu Ala Ala Thr Phe Thr Leu Ile Gly Val Ser Phe<br>290                       295                       300 | 912 |
| ttt gct ctt ccg gct ggc att ttg gga tcc ggc ttt gcc ctg aaa gtc<br>Phe Ala Leu Pro Ala Gly Ile Leu Gly Ser Gly Phe Ala Leu Lys Val<br>305                       310                   315                   320 | 960 |
| caa gag cag cat cgg caa aaa cac ttt gag aaa cgg cgg aac cct gcg<br>Gln Glu Gln His Arg Gln Lys His Phe Glu Lys Arg Arg Asn Pro Ala<br>                 325                   330                   335 | 1008 |
| gca ggt ctg atc cag tct gcc tgg aga ttc tat gct act aac ctc tca<br>Ala Gly Leu Ile Gln Ser Ala Trp Arg Phe Tyr Ala Thr Asn Leu Ser<br>             340                       345                   350 | 1056 |
| cgc acc gac ctg cac tcc acg tgg cag tac tac gag cgn aca gtc act<br>Arg Thr Asp Leu His Ser Thr Trp Gln Tyr Tyr Glu Xaa Thr Val Thr<br>         355                   360                   365 | 1104 |
| gtc ccc atg tac agc tca caa act caa acc tat ggg gcc tcc aga ctc<br>Val Pro Met Tyr Ser Ser Gln Thr Gln Thr Tyr Gly Ala Ser Arg Leu<br>370                       375                       380 | 1152 |
| atc cca cct ctg aac cag ctg gag ctg ctg agg aat ctc aag agc aaa<br>Ile Pro Pro Leu Asn Gln Leu Glu Leu Leu Arg Asn Leu Lys Ser Lys<br>385                       390                   395                   400 | 1200 |
| tct gga ctc acc ttc agg aag gag cca cag cca gag cca tca cca agc<br>Ser Gly Leu Thr Phe Arg Lys Glu Pro Gln Pro Glu Pro Ser Pro Ser<br>                 405                   410                   415 | 1248 |
| ccc cga ggc atg gct gcc aag gga aag ggg tct ccc cag gcc cag acg<br>Pro Arg Gly Met Ala Ala Lys Gly Lys Gly Ser Pro Gln Ala Gln Thr<br>             420                       425                   430 | 1296 |
| gtc cgg cgg tcc ccc agt gcg gat cag agt ctt gat gac agc ccg agc<br>Val Arg Arg Ser Pro Ser Ala Asp Gln Ser Leu Asp Asp Ser Pro Ser<br>         435                   440                   445 | 1344 |
| aag gtg ccc aag agc tgg agc ttt ggt gac cgc agc cgc aca cgc cag<br>Lys Val Pro Lys Ser Trp Ser Phe Gly Asp Arg Ser Arg Thr Arg Gln<br>450                       455                       460 | 1392 |
| gct ttc cgc atc aag ggt gct gca tcc cgg cag aat tca gaa gaa gca<br>Ala Phe Arg Ile Lys Gly Ala Ala Ser Arg Gln Asn Ser Glu Glu Ala<br>465                       470                   475                   480 | 1440 |

```
agc ctc cct ggg gag gac atc gta gag gac aac aag agc tgt aac tgc   1488
Ser Leu Pro Gly Glu Asp Ile Val Glu Asp Asn Lys Ser Cys Asn Cys
                485                 490                 495 gag ttt gtg act gaa gat ctt acc cct ggc ctc aaa gty agc atc aga   1536
Glu Phe Val Thr Glu Asp Leu Thr Pro Gly Leu Lys Xaa Ser Ile Arg
            500                 505                 510 gcc gtg tgt gty atg cgg ttc ttg gta tct aag cga aag ttc aaa gag   1584
Ala Val Cys Xaa Met Arg Phe Leu Val Ser Lys Arg Lys Phe Lys Glu
        515                 520                 525 agt ctg cgc cca tat gat gtg atg gac gtc atc gaa cag tac tcg gct   1632
Ser Leu Arg Pro Tyr Asp Val Met Asp Val Ile Glu Gln Tyr Ser Ala
    530                 535                 540 gga cac ttg gat atg ttg tcc cgc atc aag agc ctg cag acc aga gtg   1680
Gly His Leu Asp Met Leu Ser Arg Ile Lys Ser Leu Gln Thr Arg Val
545                 550                 555                 560 gac cag att gtg ggg cgg ggc cca aca ata acg gat aag gat cgc acc   1728
Asp Gln Ile Val Gly Arg Gly Pro Thr Ile Thr Asp Lys Asp Arg Thr
                565                 570                 575 aaa ggc cca gcg gaa acg gag ctg ccc gaa gac ccc agc atg atg gga   1776
Lys Gly Pro Ala Glu Thr Glu Leu Pro Glu Asp Pro Ser Met Met Gly
            580                 585                 590 cgg ctt ggg aag gtg gag aaa cag gtc ttg tcc atg gaa aag aag ctc   1824
Arg Leu Gly Lys Val Glu Lys Gln Val Leu Ser Met Glu Lys Lys Leu
        595                 600                 605 gac ttc ttg gtg agc atc tat aca cag aga atg ggc atc caa cca gca   1872
Asp Phe Leu Val Ser Ile Tyr Thr Gln Arg Met Gly Ile Gln Pro Ala
    610                 615                 620 gag aca gag gcc tat ttt ggg gcc aag gag cct gag ccg gca cca ccc   1920
Glu Thr Glu Ala Tyr Phe Gly Ala Lys Glu Pro Glu Pro Ala Pro Pro
625                 630                 635                 640 tac cac agc cca gag gac agc cgt gac cat gca gac aag cat ggc tgt   1968
Tyr His Ser Pro Glu Asp Ser Arg Asp His Ala Asp Lys His Gly Cys
                645                 650                 655 atc att aag atc gtc cgc tcc acc agc tct acg ggc cag agg aac tac   2016
Ile Ile Lys Ile Val Arg Ser Thr Ser Ser Thr Gly Gln Arg Asn Tyr
            660                 665                 670 gca gca ccc cca gcc atc ccc cct gcc cag tgt cct ccc tcc acc tcg   2064
Ala Ala Pro Pro Ala Ile Pro Pro Ala Gln Cys Pro Pro Ser Thr Ser
        675                 680                 685 tgg cgg cag agc cac cag cgc cat ggc acc tcc cct gtg gga gac cat   2112
Trp Arg Gln Ser His Gln Arg His Gly Thr Ser Pro Val Gly Asp His
    690                 695                 700 ggc tca ctg gta cgc atc cca cca ctc cct gca cac gag cgg tcg ctg   2160
Gly Ser Leu Val Arg Ile Pro Pro Leu Pro Ala His Glu Arg Ser Leu
705                 710                 715                 720 tct gcc tac ggt ggg ggc aac aga gcc agt acc gag ttc ttg agg ctg   2208
Ser Ala Tyr Gly Gly Gly Asn Arg Ala Ser Thr Glu Phe Leu Arg Leu
                725                 730                 735 gag ggc acc cca gcc tgc agg ccc tct gag gct gct gcg gga cag cga   2256
Glu Gly Thr Pro Ala Cys Arg Pro Ser Glu Ala Ala Ala Gly Gln Arg
            740                 745                 750 cac gtc cat ctc cat cg                                             2273
His Val His Leu His
        755

<210> SEQ ID NO 89
<211> LENGTH: 757
<212> TYPE: PRT
<213> ORGANISM: Mus musculus
<220> FEATURE:
```

<221> NAME/KEY: PEPTIDE
<222> LOCATION: (1)..(757)
<223> OTHER INFORMATION: Xaa may be: S or R at 18, 19 and 69; V, A, E or
      G at 31; D or E at 33; S, P, T or A at 39; I, T, N or
      S at 52; F, L, I, M or V at 53; S, P, T or A at 64;
      P at 68; L, S or W at 91; R at 365; V at 509 and 516.

<400> SEQUENCE: 89

```
Met Val Gln Lys Ser Arg Asn Gly Gly Val Tyr Pro Gly Thr Ser Gly
  1               5                  10                  15

Glu Xaa Xaa Leu Lys Val Gly Phe Val Gly Leu Asp Pro Gly Xaa Pro
             20                  25                  30

Xaa Ser Thr Arg Asp Gly Xaa Leu Leu Ile Ala Gly Ser Glu Ala Pro
         35                  40                  45

Lys Arg Gly Xaa Xaa Leu Ser Lys Pro Arg Thr Gly Gly Ala Gly Xaa
 50                  55                  60

Gly Lys Pro Xaa Xaa Arg Asn Ala Phe Tyr Arg Lys Leu Gln Asn Phe
 65                  70                  75                  80

Leu Tyr Asn Val Leu Glu Arg Pro Arg Gly Xaa Ala Phe Ile Tyr His
                 85                  90                  95

Ala Tyr Val Phe Leu Leu Val Phe Ser Cys Leu Val Leu Ser Val Phe
            100                 105                 110

Ser Thr Ile Lys Glu Tyr Glu Lys Ser Ser Glu Gly Ala Leu Tyr Ile
            115                 120                 125

Leu Glu Ile Val Thr Ile Val Val Phe Gly Val Glu Tyr Phe Val Arg
        130                 135                 140

Ile Trp Ala Ala Gly Cys Cys Cys Arg Tyr Arg Gly Trp Arg Gly Arg
145                 150                 155                 160

Leu Lys Phe Ala Arg Lys Pro Phe Cys Val Ile Asp Ile Met Val Leu
                165                 170                 175

Ile Ala Ser Ile Ala Val Leu Ala Ala Gly Ser Gln Gly Asn Val Phe
            180                 185                 190

Ala Thr Ser Ala Leu Arg Ser Leu Arg Phe Leu Gln Ile Leu Arg Met
        195                 200                 205

Ile Arg Met Asp Arg Arg Gly Gly Thr Trp Lys Leu Leu Gly Ser Val
210                 215                 220

Val Tyr Ala His Ser Lys Glu Leu Val Thr Ala Trp Tyr Ile Gly Phe
225                 230                 235                 240

Leu Cys Leu Ile Leu Ala Ser Phe Leu Val Tyr Leu Ala Glu Lys Gly
                245                 250                 255

Glu Asn Asp His Phe Asp Thr Tyr Ala Asp Ala Leu Trp Trp Gly Leu
            260                 265                 270

Ile Thr Leu Thr Thr Ile Gly Tyr Gly Asp Lys Tyr Pro Gln Thr Trp
        275                 280                 285

Asn Gly Arg Leu Leu Ala Ala Thr Phe Thr Leu Ile Gly Val Ser Phe
290                 295                 300

Phe Ala Leu Pro Ala Gly Ile Leu Gly Ser Gly Phe Ala Leu Lys Val
305                 310                 315                 320

Gln Glu Gln His Arg Gln Lys His Phe Glu Lys Arg Arg Asn Pro Ala
                325                 330                 335

Ala Gly Leu Ile Gln Ser Ala Trp Arg Phe Tyr Ala Thr Asn Leu Ser
            340                 345                 350

Arg Thr Asp Leu His Ser Thr Trp Gln Tyr Tyr Glu Xaa Thr Val Thr
        355                 360                 365

Val Pro Met Tyr Ser Ser Gln Thr Gln Thr Tyr Gly Ala Ser Arg Leu
```

```
                370                 375                 380
Ile Pro Pro Leu Asn Gln Leu Glu Leu Arg Asn Leu Lys Ser Lys
385                 390                 395                 400

Ser Gly Leu Thr Phe Arg Lys Glu Pro Gln Pro Glu Pro Ser Pro Ser
                405                 410                 415

Pro Arg Gly Met Ala Ala Lys Gly Lys Gly Ser Pro Gln Ala Gln Thr
                420                 425                 430

Val Arg Arg Ser Pro Ser Ala Asp Gln Ser Leu Asp Asp Ser Pro Ser
                435                 440                 445

Lys Val Pro Lys Ser Trp Ser Phe Gly Asp Arg Ser Arg Thr Arg Gln
450                 455                 460

Ala Phe Arg Ile Lys Gly Ala Ala Ser Arg Gln Asn Ser Glu Glu Ala
465                 470                 475                 480

Ser Leu Pro Gly Glu Asp Ile Val Glu Asp Asn Lys Ser Cys Asn Cys
                485                 490                 495

Glu Phe Val Thr Glu Asp Leu Thr Pro Gly Leu Lys Xaa Ser Ile Arg
                500                 505                 510

Ala Val Cys Xaa Met Arg Phe Leu Val Ser Lys Arg Lys Phe Lys Glu
                515                 520                 525

Ser Leu Arg Pro Tyr Asp Val Met Asp Val Ile Glu Gln Tyr Ser Ala
                530                 535                 540

Gly His Leu Asp Met Leu Ser Arg Ile Lys Ser Leu Gln Thr Arg Val
545                 550                 555                 560

Asp Gln Ile Val Gly Arg Gly Pro Thr Ile Thr Asp Lys Asp Arg Thr
                565                 570                 575

Lys Gly Pro Ala Glu Thr Glu Leu Pro Glu Asp Pro Ser Met Met Gly
                580                 585                 590

Arg Leu Gly Lys Val Glu Lys Gln Val Leu Ser Met Glu Lys Lys Leu
                595                 600                 605

Asp Phe Leu Val Ser Ile Tyr Thr Gln Arg Met Gly Ile Gln Pro Ala
                610                 615                 620

Glu Thr Glu Ala Tyr Phe Gly Ala Lys Glu Pro Glu Pro Ala Pro Pro
625                 630                 635                 640

Tyr His Ser Pro Glu Asp Ser Arg Asp His Ala Asp Lys His Gly Cys
                645                 650                 655

Ile Ile Lys Ile Val Arg Ser Thr Ser Ser Thr Gly Gln Arg Asn Tyr
                660                 665                 670

Ala Ala Pro Pro Ala Ile Pro Pro Ala Gln Cys Pro Pro Ser Thr Ser
                675                 680                 685

Trp Arg Gln Ser His Gln Arg His Gly Thr Ser Pro Val Gly Asp His
                690                 695                 700

Gly Ser Leu Val Arg Ile Pro Pro Leu Pro Ala His Glu Arg Ser Leu
705                 710                 715                 720

Ser Ala Tyr Gly Gly Gly Asn Arg Ala Ser Thr Glu Phe Leu Arg Leu
                725                 730                 735

Glu Gly Thr Pro Ala Cys Arg Pro Ser Glu Ala Ala Ala Gly Gln Arg
                740                 745                 750

His Val His Leu His
                755

<210> SEQ ID NO 90
<211> LENGTH: 2814
<212> TYPE: DNA
<213> ORGANISM: Mus musculus
```

-continued

```
<220> FEATURE:
<221> NAME/KEY: CDS
<222> LOCATION: (202)..(2811)
<220> FEATURE:
<221> NAME/KEY: misc_feature
<222> LOCATION: (1)..(2811)
<223> OTHER INFORMATION: n may be any nucleotide.
<220> FEATURE:
<221> NAME/KEY: PEPTIDE
<222> LOCATION: (1)..(870)
<223> OTHER INFORMATION: Xaa may be: K or E at 320; S or R at 484; I or
      V at 504; E or A at 507; T or A at 512; L at 513;
      S or F at 636; K at 659.

<400> SEQUENCE: 90
ctccccaccc gacctcctct ggcccccggg aggcccgcct ttgcctgctt ttggggggt          60 gggcggggag gggcgcgcgg atcatggcat tggagttccc gggcttgcag ccgccgccgc       120
cgcctcgtcc acgtaccccca gtgctcccta cttcccggag cagcagcgga gaaggcgaag      180
cgcccggtgg gggcgaggca g atg ggt ctc aag gct cgc agg gcg gct ggc         231
                        Met Gly Leu Lys Ala Arg Arg Ala Ala Gly
                         1               5                  10 ggg ggc ggc ggc gaa ggg ggc ggc gga ggc ggc ggg gcc gct aac cct         279
Gly Gly Gly Gly Glu Gly Gly Gly Gly Gly Gly Gly Ala Ala Asn Pro
             15                  20                  25 gct gga ggg gac tcg gcg gtg gcc ggc gac gag gag cgg aaa gtg ggg         327
Ala Gly Gly Asp Ser Ala Val Ala Gly Asp Glu Glu Arg Lys Val Gly
         30                  35                  40 ctg gcg cca gga gac gtg gag caa gtc acc ttg gcg cta ggg gcc gga         375
Leu Ala Pro Gly Asp Val Glu Gln Val Thr Leu Ala Leu Gly Ala Gly
     45                  50                  55 gcc gac aaa gac ggg acc ctg ctg ctg gag ggc ggt ggc cgc gaa gag         423
Ala Asp Lys Asp Gly Thr Leu Leu Leu Glu Gly Gly Gly Arg Glu Glu
 60                  65                  70 ggg cag agg agg acc ccg cag ggc atc ggg ctc ctg gca aag acc ccc         471
Gly Gln Arg Arg Thr Pro Gln Gly Ile Gly Leu Leu Ala Lys Thr Pro
 75                  80                  85                  90 ctg agc cgc cca gtc aag agg aac aac gcc aag tac agg cgc atc caa         519
Leu Ser Arg Pro Val Lys Arg Asn Asn Ala Lys Tyr Arg Arg Ile Gln
                 95                 100                 105 act ttg atc tat gac gcc ctg gag aga ccg cgg ggc tgg gcg ctg ctc         567
Thr Leu Ile Tyr Asp Ala Leu Glu Arg Pro Arg Gly Trp Ala Leu Leu
             110                 115                 120 tac cac gcg ctt gtg ttc ctg att gtc ctg gga tgc ttg att ctg gcc         615
Tyr His Ala Leu Val Phe Leu Ile Val Leu Gly Cys Leu Ile Leu Ala
         125                 130                 135 gtg ctc acc acc ttc aag gaa tat gag act gtg tct gga gac tgg ctt         663
Val Leu Thr Thr Phe Lys Glu Tyr Glu Thr Val Ser Gly Asp Trp Leu
     140                 145                 150 ttg ctg ctg gaa aca ttt gct att ttc atc ttt gga gct gag ttt gct         711
Leu Leu Leu Glu Thr Phe Ala Ile Phe Ile Phe Gly Ala Glu Phe Ala
155                 160                 165                 170 ttg agg atc tgg gct gca gga tgt tgc tgt cga tac aaa ggc tgg cgt         759
Leu Arg Ile Trp Ala Ala Gly Cys Cys Cys Arg Tyr Lys Gly Trp Arg
                 175                 180                 185 gga cgg cta aag ttt gcc agg aag ccc ctg tgc atg ttg gac atc ttc         807
Gly Arg Leu Lys Phe Ala Arg Lys Pro Leu Cys Met Leu Asp Ile Phe
             190                 195                 200 gta ctg att gcc tct gtg cca gtg gtt gcc gtg gga aac cag ggc aat         855
Val Leu Ile Ala Ser Val Pro Val Val Ala Val Gly Asn Gln Gly Asn
         205                 210                 215 gtc ttg gcc acc tcc ctg cga agc ctt cgc ttc ctg cag atc ctg cgc         903
```

```
            Val Leu Ala Thr Ser Leu Arg Ser Leu Arg Phe Leu Gln Ile Leu Arg
                220                 225                 230 atg ctt cga atg gat agg agg ggt ggc acc tgg aag ctc ctg ggc tcg            951
Met Leu Arg Met Asp Arg Arg Gly Gly Thr Trp Lys Leu Leu Gly Ser
235                 240                 245                 250 gct atc tgt gcc cac agc aaa gaa ctc atc act gcc tgg tac ata ggc            999
Ala Ile Cys Ala His Ser Lys Glu Leu Ile Thr Ala Trp Tyr Ile Gly
                    255                 260                 265 ttc ctg aca ctc atc ctt tct tca ttt ctt gtc tac ctg gtg gag aag           1047
Phe Leu Thr Leu Ile Leu Ser Ser Phe Leu Val Tyr Leu Val Glu Lys
                270                 275                 280 gat gtg cca gaa atg gat gcc caa gga gag gag atg aag gag gag ttt           1095
Asp Val Pro Glu Met Asp Ala Gln Gly Glu Glu Met Lys Glu Glu Phe
            285                 290                 295 gag acc tat gca gat gct ctg tgg tgg ggc ctg atc aca ctg gcc acc           1143
Glu Thr Tyr Ala Asp Ala Leu Trp Trp Gly Leu Ile Thr Leu Ala Thr
        300                 305                 310 att ggt tat gga gac rag aca cct aaa acc tgg gaa gga cgt ctg att           1191
Ile Gly Tyr Gly Asp Xaa Thr Pro Lys Thr Trp Glu Gly Arg Leu Ile
315                 320                 325                 330 gct gcc acc ttt tct tta atc ggc gtc tcc ttt ttt gcc ctt ccg gca           1239
Ala Ala Thr Phe Ser Leu Ile Gly Val Ser Phe Phe Ala Leu Pro Ala
                335                 340                 345 ggc atc ctt ggc tca gga ctg gca ctg aag gtt cag gag cag cac cgt           1287
Gly Ile Leu Gly Ser Gly Leu Ala Leu Lys Val Gln Glu Gln His Arg
                350                 355                 360 cag aag cac ttt gag aag aga agg aag cca gct gcg aac ctc atc cag           1335
Gln Lys His Phe Glu Lys Arg Arg Lys Pro Ala Ala Glu Leu Ile Gln
            365                 370                 375 gct gcc tgg aga tat tat gct acc aac ccc aac agg ttg gat ctg gtg           1383
Ala Ala Trp Arg Tyr Tyr Ala Thr Asn Pro Asn Arg Leu Asp Leu Val
        380                 385                 390 gca acc tgg aga tct tat gaa tca gtt gtc tct ttc cca ttc ttc agg           1431
Ala Thr Trp Arg Ser Tyr Glu Ser Val Val Ser Phe Pro Phe Phe Arg
395                 400                 405                 410 aaa gaa caa ctg gaa gca gca gcc agc caa aag ctg ggt ctc ttg gat           1479
Lys Glu Gln Leu Glu Ala Ala Ala Ser Gln Lys Leu Gly Leu Leu Asp
                415                 420                 425 cgg gtt cgc ctt tct aat cct cgt ggt agc aat act aaa gga aag cta           1527
Arg Val Arg Leu Ser Asn Pro Arg Gly Ser Asn Thr Lys Gly Lys Leu
                430                 435                 440 ttt acc cct ctg aat gta gat gcc ata gaa gaa agc cct tcc aaa gag           1575
Phe Thr Pro Leu Asn Val Asp Ala Ile Glu Glu Ser Pro Ser Lys Glu
            445                 450                 455 cca aag cct gtt ggc tta aac aat aaa gag cgt ttc cgc acc gcc ttc           1623
Pro Lys Pro Val Gly Leu Asn Asn Lys Glu Arg Phe Arg Thr Ala Phe
        460                 465                 470 cgc atg aaa gcc tac gct ttc tgg cag agw tct gaa gat gct ggg aca           1671
Arg Met Lys Ala Tyr Ala Phe Trp Gln Xaa Ser Glu Asp Ala Gly Thr
475                 480                 485                 490 ggc gac ccc atg gca gaa gac agg ggc tat ggg aat gac wtc ctc att           1719
Gly Asp Pro Met Ala Glu Asp Arg Gly Tyr Gly Asn Asp Xaa Leu Ile
                495                 500                 505 gma gac atg atc cct rcc ctw aag gct gcc atc cga gct gtc aga att           1767
Xaa Asp Met Ile Pro Xaa Xaa Lys Ala Ala Ile Arg Ala Val Arg Ile
                510                 515                 520 cta cag ttc cgt cta tat aaa aaa aag ttc aag gag acg ttg agg cct           1815
Leu Gln Phe Arg Leu Tyr Lys Lys Lys Phe Lys Glu Thr Leu Arg Pro
            525                 530                 535
```

| | | |
|---|---|---|
| tat gat gtg aaa gat gtg att gag cag tat tcg gcc gga cat ctt gac<br>Tyr Asp Val Lys Asp Val Ile Glu Gln Tyr Ser Ala Gly His Leu Asp<br>540 545 550 | 1863 | |
| atg ctt tcc agg ata aag tac cta cag aca aga ata gat atg att ttc<br>Met Leu Ser Arg Ile Lys Tyr Leu Gln Thr Arg Ile Asp Met Ile Phe<br>555 560 565 570 | 1911 | |
| acc cct gga cct cca tcc act cca aaa cat aag aag tct cag aaa ggg<br>Thr Pro Gly Pro Pro Ser Thr Pro Lys His Lys Lys Ser Gln Lys Gly<br>575 580 585 | 1959 | |
| aca gca ttt acc tac cca tcc cag cag tct cca agg aat gaa cca tat<br>Thr Ala Phe Thr Tyr Pro Ser Gln Gln Ser Pro Arg Asn Glu Pro Tyr<br>590 595 600 | 2007 | |
| gta gcc agg gca gcc aca tca gaa act gaa gac caa agc atg atg ggg<br>Val Ala Arg Ala Ala Thr Ser Glu Thr Glu Asp Gln Ser Met Met Gly<br>605 610 615 | 2055 | |
| aag ttt gta aaa gtt gaa aga cag gtt cat gac atg ggg aag aaa ctg<br>Lys Phe Val Lys Val Glu Arg Gln Val His Asp Met Gly Lys Lys Leu<br>620 625 630 | 2103 | |
| gac tyc ctc gtg gac atg cat atg cag cat atg gaa cgc tta cag gta<br>Asp Xaa Leu Val Asp Met His Met Gln His Met Glu Arg Leu Gln Val<br>635 640 645 650 | 2151 | |
| cat gtc act gag tac tac cca act aar ggg gcc tcc tcc cca gcc gaa<br>His Val Thr Glu Tyr Tyr Pro Thr Xaa Gly Ala Ser Ser Pro Ala Glu<br>655 660 665 | 2199 | |
| ggg gag aag aaa gaa gac aac agg tac tct gat ttg aaa acc atc atc<br>Gly Glu Lys Lys Glu Asp Asn Arg Tyr Ser Asp Leu Lys Thr Ile Ile<br>670 675 680 | 2247 | |
| tgc aac tac tca gag aca ggg ccc cct gac cct cct tac agc ttc cac<br>Cys Asn Tyr Ser Glu Thr Gly Pro Pro Asp Pro Pro Tyr Ser Phe His<br>685 690 695 | 2295 | |
| cag gtg ccc atc gac aga gtt ggc cct tac ggg ttt ttt gca cat gat<br>Gln Val Pro Ile Asp Arg Val Gly Pro Tyr Gly Phe Phe Ala His Asp<br>700 705 710 | 2343 | |
| cct gtg aaa ctg acc cga ggg gga ccc agt tct aca aag gct caa gct<br>Pro Val Lys Leu Thr Arg Gly Gly Pro Ser Ser Thr Lys Ala Gln Ala<br>715 720 725 730 | 2391 | |
| aac ctt ccc tcc tcg gga agt aca tat gca gag agg ccc aca gtc ctg<br>Asn Leu Pro Ser Ser Gly Ser Thr Tyr Ala Glu Arg Pro Thr Val Leu<br>735 740 745 | 2439 | |
| ccc atc ttg act ctt ctg gac tca tgt gtg agc tac cac tcc cag aca<br>Pro Ile Leu Thr Leu Leu Asp Ser Cys Val Ser Tyr His Ser Gln Thr<br>750 755 760 | 2487 | |
| gaa ctg caa ggt ccc tat tcg gac cac atc tcg ccc gcc cag aga cgc<br>Glu Leu Gln Gly Pro Tyr Ser Asp His Ile Ser Pro Arg Gln Arg Arg<br>765 770 775 | 2535 | |
| agc atc act agg gac agt gat aca cct ctg tcc ctc atg tcc gtc aat<br>Ser Ile Thr Arg Asp Ser Asp Thr Pro Leu Ser Leu Met Ser Val Asn<br>780 785 790 | 2583 | |
| cac gag gaa ctg gag cgg tct cca agt ggc ttc agc atc tca caa gac<br>His Glu Glu Leu Glu Arg Ser Pro Ser Gly Phe Ser Ile Ser Gln Asp<br>795 800 805 810 | 2631 | |
| aga gat gat tat gta ttt ggc ccc agt ggg gga tcg agc tgg atg ggg<br>Arg Asp Asp Tyr Val Phe Gly Pro Ser Gly Gly Ser Ser Trp Met Gly<br>815 820 825 | 2679 | |
| gaa aag cgg tac ctg gct gaa gga gaa acg gac acg gac aca gac ccc<br>Glu Lys Arg Tyr Leu Ala Glu Gly Glu Thr Asp Thr Asp Thr Asp Pro<br>830 835 840 | 2727 | |
| ttc aca ccc agt ggt tcc atg cct atg tca tcc act ggg gat ggt att<br>Phe Thr Pro Ser Gly Ser Met Pro Met Ser Ser Thr Gly Asp Gly Ile<br>845 850 855 | 2775 | |

-continued

```
tca gat tcc ata tgg acc cct tcc aat aag ccc att taa                2814
Ser Asp Ser Ile Trp Thr Pro Ser Asn Lys Pro Ile
    860                 865                 870
```

<210> SEQ ID NO 91
<211> LENGTH: 870
<212> TYPE: PRT
<213> ORGANISM: Mus musculus
<220> FEATURE:
<221> NAME/KEY: PEPTIDE
<222> LOCATION: (1)..(870)
<223> OTHER INFORMATION: Xaa may be: K or E at 320; S or R at 484; I or
      V at 504; E or A at 507; T or A at 512; L at 513;
      S or F at 636; K at 659.

<400> SEQUENCE: 91

```
Met Gly Leu Lys Ala Arg Arg Ala Ala Gly Gly Gly Gly Glu Gly
 1               5                  10                  15

Gly Gly Gly Gly Gly Ala Ala Asn Pro Ala Gly Gly Asp Ser Ala
            20                  25                  30

Val Ala Gly Asp Glu Glu Arg Lys Val Gly Leu Ala Pro Gly Asp Val
        35                  40                  45

Glu Gln Val Thr Leu Ala Leu Gly Ala Gly Ala Asp Lys Asp Gly Thr
    50                  55                  60

Leu Leu Leu Glu Gly Gly Gly Arg Glu Gly Gln Arg Arg Thr Pro
65                  70                  75                  80

Gln Gly Ile Gly Leu Leu Ala Lys Thr Pro Leu Ser Arg Pro Val Lys
                85                  90                  95

Arg Asn Asn Ala Lys Tyr Arg Arg Ile Gln Thr Leu Ile Tyr Asp Ala
            100                 105                 110

Leu Glu Arg Pro Arg Gly Trp Ala Leu Leu Tyr His Ala Leu Val Phe
        115                 120                 125

Leu Ile Val Leu Gly Cys Leu Ile Leu Ala Val Leu Thr Thr Phe Lys
    130                 135                 140

Glu Tyr Glu Thr Val Ser Gly Asp Trp Leu Leu Leu Glu Thr Phe
145                 150                 155                 160

Ala Ile Phe Ile Phe Gly Ala Glu Phe Ala Leu Arg Ile Trp Ala Ala
                165                 170                 175

Gly Cys Cys Cys Arg Tyr Lys Gly Trp Arg Gly Arg Leu Lys Phe Ala
            180                 185                 190

Arg Lys Pro Leu Cys Met Leu Asp Ile Phe Val Leu Ile Ala Ser Val
        195                 200                 205

Pro Val Val Ala Val Gly Asn Gln Gly Asn Val Leu Ala Thr Ser Leu
    210                 215                 220

Arg Ser Leu Arg Phe Leu Gln Ile Leu Arg Met Leu Arg Met Asp Arg
225                 230                 235                 240

Arg Gly Gly Thr Trp Lys Leu Leu Gly Ser Ala Ile Cys Ala His Ser
                245                 250                 255

Lys Glu Leu Ile Thr Ala Trp Tyr Ile Gly Phe Leu Thr Leu Ile Leu
            260                 265                 270

Ser Ser Phe Leu Val Tyr Leu Val Glu Lys Asp Val Pro Glu Met Asp
        275                 280                 285

Ala Gln Gly Glu Glu Met Lys Glu Glu Phe Glu Thr Tyr Ala Asp Ala
    290                 295                 300

Leu Trp Trp Gly Leu Ile Thr Leu Ala Thr Ile Gly Tyr Gly Asp Xaa
305                 310                 315                 320
```

-continued

Thr Pro Lys Thr Trp Glu Gly Arg Leu Ile Ala Ala Thr Phe Ser Leu
              325                 330                 335

Ile Gly Val Ser Phe Phe Ala Leu Pro Ala Gly Ile Leu Gly Ser Gly
            340                 345                 350

Leu Ala Leu Lys Val Gln Glu Gln His Arg Gln Lys His Phe Glu Lys
            355                 360                 365

Arg Arg Lys Pro Ala Ala Glu Leu Ile Gln Ala Ala Trp Arg Tyr Tyr
            370                 375                 380

Ala Thr Asn Pro Asn Arg Leu Asp Leu Val Ala Thr Trp Arg Ser Tyr
385                 390                 395                 400

Glu Ser Val Val Ser Phe Pro Phe Phe Arg Lys Glu Gln Leu Glu Ala
                405                 410                 415

Ala Ala Ser Gln Lys Leu Gly Leu Leu Asp Arg Val Arg Leu Ser Asn
            420                 425                 430

Pro Arg Gly Ser Asn Thr Lys Gly Lys Leu Phe Thr Pro Leu Asn Val
            435                 440                 445

Asp Ala Ile Glu Glu Ser Pro Ser Lys Glu Pro Lys Pro Val Gly Leu
450                 455                 460

Asn Asn Lys Glu Arg Phe Arg Thr Ala Phe Arg Met Lys Ala Tyr Ala
465                 470                 475                 480

Phe Trp Gln Xaa Ser Glu Asp Ala Gly Thr Gly Asp Pro Met Ala Glu
                485                 490                 495

Asp Arg Gly Tyr Gly Asn Asp Xaa Leu Ile Xaa Asp Met Ile Pro Xaa
            500                 505                 510

Xaa Lys Ala Ala Ile Arg Ala Val Arg Ile Leu Gln Phe Arg Leu Tyr
    515                 520                 525

Lys Lys Lys Phe Lys Glu Thr Leu Arg Pro Tyr Asp Val Lys Asp Val
530                 535                 540

Ile Glu Gln Tyr Ser Ala Gly His Leu Asp Met Leu Ser Arg Ile Lys
545                 550                 555                 560

Tyr Leu Gln Thr Arg Ile Asp Met Ile Phe Thr Pro Gly Pro Pro Ser
                565                 570                 575

Thr Pro Lys His Lys Lys Ser Gln Lys Gly Thr Ala Phe Thr Tyr Pro
            580                 585                 590

Ser Gln Gln Ser Pro Arg Asn Glu Pro Tyr Val Ala Arg Ala Ala Thr
            595                 600                 605

Ser Glu Thr Glu Asp Gln Ser Met Met Gly Lys Phe Val Lys Val Glu
            610                 615                 620

Arg Gln Val His Asp Met Gly Lys Lys Leu Asp Xaa Leu Val Asp Met
625                 630                 635                 640

His Met Gln His Met Glu Arg Leu Gln Val His Val Thr Glu Tyr Tyr
                645                 650                 655

Pro Thr Xaa Gly Ala Ser Ser Pro Ala Glu Gly Lys Lys Glu Asp
            660                 665                 670       Asp

Asn Arg Tyr Ser Asp Leu Lys Thr Ile Ile Cys Asn Tyr Ser Glu Thr
            675                 680                 685

Gly Pro Pro Asp Pro Tyr Ser Phe His Gln Val Pro Ile Asp Arg
    690                 695                 700

Val Gly Pro Tyr Gly Phe Ala His Asp Pro Val Lys Leu Thr Arg
705                 710                 715                 720

Gly Gly Pro Ser Ser Thr Lys Ala Gln Ala Asn Leu Pro Ser Ser Gly
            725                 730                 735

Ser Thr Tyr Ala Glu Arg Pro Thr Val Leu Pro Ile Leu Thr Leu Leu

```
                740                 745                 750
Asp Ser Cys Val Ser Tyr His Ser Gln Thr Glu Leu Gln Gly Pro Tyr
        755                 760                 765

Ser Asp His Ile Ser Pro Arg Gln Arg Arg Ser Ile Thr Arg Asp Ser
    770                 775                 780

Asp Thr Pro Leu Ser Leu Met Ser Val Asn His Glu Glu Leu Glu Arg
785                 790                 795                 800

Ser Pro Ser Gly Phe Ser Ile Ser Gln Asp Arg Asp Asp Tyr Val Phe
                805                 810                 815

Gly Pro Ser Gly Gly Ser Ser Trp Met Gly Glu Lys Arg Tyr Leu Ala
            820                 825                 830

Glu Gly Glu Thr Asp Thr Asp Thr Asp Pro Phe Thr Pro Ser Gly Ser
        835                 840                 845

Met Pro Met Ser Ser Thr Gly Asp Gly Ile Ser Asp Ser Ile Trp Thr
    850                 855                 860

Pro Ser Asn Lys Pro Ile
865                 870

<210> SEQ ID NO 92
<211> LENGTH: 130
<212> TYPE: DNA
<213> ORGANISM: Homo sapiens
<220> FEATURE:
<221> NAME/KEY: mutation
<222> LOCATION: (118)
<223> OTHER INFORMATION: This nucleotide is deleted in a person with
      JME.

<400> SEQUENCE: 92
ggtcaagatt attggagtgc ttagaaatgg agaaagggga ctatatgcac tagtcatttc      60
ctatggccaa ataacattgg atctgctttc atacatacta tcttatttaa gctttaggat    120
gtcctggaag                                                            130

<210> SEQ ID NO 93
<211> LENGTH: 23
<212> TYPE: DNA
<213> ORGANISM: Mus musculus

<400> SEQUENCE: 93
cgcggatcat ggcattggag ttc                                              23

<210> SEQ ID NO 94
<211> LENGTH: 23
<212> TYPE: DNA
<213> ORGANISM: Mus musculus

<400> SEQUENCE: 94
aagccccaga gacttctcag ctc                                              23

<210> SEQ ID NO 95
<211> LENGTH: 3237
<212> TYPE: DNA
<213> ORGANISM: Homo sapiens
<220> FEATURE:
<221> NAME/KEY: CDS
<222> LOCATION: (128)..(2917)
<220> FEATURE:
<221> NAME/KEY: misc_feature
<222> LOCATION: (1)..(3237)
<223> OTHER INFORMATION: each n may be any nucleotide

<400> SEQUENCE: 95
```

```
gagtgcggaa ccgccgcctc ggccatgcgg ctcccggccg ggggccctgg gctgggcc      60 gcgccgcccc ccgcgctccg cccccgctga gcctgagccc gacccggggc gcctcccgcc    120 aggcacc atg gtg cag aag tcg cgc aac ggc ggc gta tac ccc ggc ccg     169
        Met Val Gln Lys Ser Arg Asn Gly Gly Val Tyr Pro Gly Pro
          1               5                  10 agc ggg gag aag aag ctg aag gtg ggc ttc gtg ggg ctg gac ccc ggc     217
Ser Gly Glu Lys Lys Leu Lys Val Gly Phe Val Gly Leu Asp Pro Gly
 15              20                  25                  30 gcg ccc gac tcc acc cgg gac ggg gcg ctg ctg atc gcc ggc tcc gag     265
Ala Pro Asp Ser Thr Arg Asp Gly Ala Leu Leu Ile Ala Gly Ser Glu
                 35                  40                  45 gcc ccc aag cgc ggc agc atc ctc agc aaa cct cgc gcg ggc ggc gcg     313
Ala Pro Lys Arg Gly Ser Ile Leu Ser Lys Pro Arg Ala Gly Gly Ala
             50                  55                  60 ggc gcc ggg aag ccc ccc aag cgc aac gcc ttc tac cgc aag ctg cag     361
Gly Ala Gly Lys Pro Pro Lys Arg Asn Ala Phe Tyr Arg Lys Leu Gln
 65                  70                  75 aat ttc ctc tac aac gtg ctg gag cgg ccg cgc ggc tgg gcg ttc atc     409
Asn Phe Leu Tyr Asn Val Leu Glu Arg Pro Arg Gly Trp Ala Phe Ile
         80                  85                  90 tac cac gcc tac gtg ttc ctc ctg gtt ttc tcc tgc ctc gtg ctg tct     457
Tyr His Ala Tyr Val Phe Leu Leu Val Phe Ser Cys Leu Val Leu Ser
 95                 100                 105                 110 gtg ttt tcc acc atc aag gag tat gag aag agc tcg gag ggg gcc ctc     505
Val Phe Ser Thr Ile Lys Glu Tyr Glu Lys Ser Ser Glu Gly Ala Leu
                115                 120                 125 tac atc ctg gaa atc gtg act atc gtg gtg ttt ggc gtg gag tac ttc     553
Tyr Ile Leu Glu Ile Val Thr Ile Val Val Phe Gly Val Glu Tyr Phe
            130                 135                 140 gtg cgg atc tgg gcc gca ggc tgc tgc tgc cgg tac cgt ggc tgg agg     601
Val Arg Ile Trp Ala Ala Gly Cys Cys Cys Arg Tyr Arg Gly Trp Arg
        145                 150                 155 ggg cgg ctc aag ttt gcc cgg aaa ccg ttc tgt gtg att gac atc atg     649
Gly Arg Leu Lys Phe Ala Arg Lys Pro Phe Cys Val Ile Asp Ile Met
160                 165                 170 gtg ctc atc gcc tcc att gcg gtg ctg gcc gcc ggc tcc cag ggc aac     697
Val Leu Ile Ala Ser Ile Ala Val Leu Ala Ala Gly Ser Gln Gly Asn
175                 180                 185                 190 gtc ttt gcc aca tct gcg ctc cgg agc ctg cgc ttc ctg cag att ctg     745
Val Phe Ala Thr Ser Ala Leu Arg Ser Leu Arg Phe Leu Gln Ile Leu
                195                 200                 205 cgg atg atc cgc atg gac cgg cgg gga ggc acc tgg aag ctg ctg ggc     793
Arg Met Ile Arg Met Asp Arg Arg Gly Gly Thr Trp Lys Leu Leu Gly
            210                 215                 220 tct gtg gtc tat gcc cac agc aag gag ctg gtc act gcc tgg tac atc     841
Ser Val Val Tyr Ala His Ser Lys Glu Leu Val Thr Ala Trp Tyr Ile
        225                 230                 235 ggc ttc ctt tgt ctc atc ctg gcc tcg ttc ctg gtg tac ttg gca gag     889
Gly Phe Leu Cys Leu Ile Leu Ala Ser Phe Leu Val Tyr Leu Ala Glu
240                 245                 250 aag ggg gag aac gac cac ttt gac acc tac gcg gat gca ctc tgg tgg     937
Lys Gly Glu Asn Asp His Phe Asp Thr Tyr Ala Asp Ala Leu Trp Trp
255                 260                 265                 270 ggc ctg atc acg ctg acc acc att ggc tac ggg gac aag tac ccc cag     985
Gly Leu Ile Thr Leu Thr Thr Ile Gly Tyr Gly Asp Lys Tyr Pro Gln
                275                 280                 285 acc tgg aac ggc agg ctc ctt gcg gca acc ttc acc ctc atc ggt gtc    1033
Thr Trp Asn Gly Arg Leu Leu Ala Ala Thr Phe Thr Leu Ile Gly Val
```

```
              290             295             300
tcc ttc ttc gcg ctg cct gca ggc atc ttg ggg tct ggg ttt gcc ctg    1081
Ser Phe Phe Ala Leu Pro Ala Gly Ile Leu Gly Ser Gly Phe Ala Leu
        305             310             315 aag gtt cag gag cag cac agg cag aag cac ttt gag aag agg cgg aac    1129
Lys Val Gln Glu Gln His Arg Gln Lys His Phe Glu Lys Arg Arg Asn
320             325             330 ccg gca gca ggc ctg atc cag tcg gcc tgg aga ttc tac gcc acc aac    1177
Pro Ala Ala Gly Leu Ile Gln Ser Ala Trp Arg Phe Tyr Ala Thr Asn
335             340             345             350 ctc tcg cgc aca gac ctg cac tcc acg tgg cag tac tac gag cga acg    1225
Leu Ser Arg Thr Asp Leu His Ser Thr Trp Gln Tyr Tyr Glu Arg Thr
        355             360             365 gtc acc gtg ccc atg tac agt tcg caa act caa acc tac ggg gcc tcc    1273
Val Thr Val Pro Met Tyr Ser Ser Gln Thr Gln Thr Tyr Gly Ala Ser
        370             375             380 aga ctt atc ccc ccg ctg aac cag ctg gag ctg ctg agg aac ctc aag    1321
Arg Leu Ile Pro Pro Leu Asn Gln Leu Glu Leu Leu Arg Asn Leu Lys
            385             390             395 agt aaa tct gga ctc gct ttc agg aag gac ccc ccg gag ccg tct        1369
Ser Lys Ser Gly Leu Ala Phe Arg Lys Asp Pro Pro Glu Pro Ser
400             405             410 cca agt aaa ggc agc ccg tgc aga ggg ccc ctg tgt gga tgc tgc ccc    1417
Pro Ser Lys Gly Ser Pro Cys Arg Gly Pro Leu Cys Gly Cys Cys Pro
415             420             425             430 gga cgc tct agc cag aag gtc agt ttg aaa gat cgt gtc ttc tcc agc    1465
Gly Arg Ser Ser Gln Lys Val Ser Leu Lys Asp Arg Val Phe Ser Ser
            435             440             445 ccc cga ggc gtg gct gcc aag ggg aag ggg tcc ccg cag gcc cag act    1513
Pro Arg Gly Val Ala Ala Lys Gly Lys Gly Ser Pro Gln Ala Gln Thr
        450             455             460 gtg agg cgg tca ccc agc gcc gac cag agc ctc gag gac agc ccc agc    1561
Val Arg Arg Ser Pro Ser Ala Asp Gln Ser Leu Glu Asp Ser Pro Ser
        465             470             475 aag gtg ccc aag agc tgg agc ttc ggg gac cgc agc cgg gca cgc cag    1609
Lys Val Pro Lys Ser Trp Ser Phe Gly Asp Arg Ser Arg Ala Arg Gln
        480             485             490 gct ttc cgc atc aag ggt gcc gcg tca cgg cag aac tca gaa gaa gca    1657
Ala Phe Arg Ile Lys Gly Ala Ala Ser Arg Gln Asn Ser Glu Glu Ala
495             500             505             510 agc ctc ccc gga gag gac att gtg gat gac aag agc tgc ccc tgc gag    1705
Ser Leu Pro Gly Glu Asp Ile Val Asp Asp Lys Ser Cys Pro Cys Glu
            515             520             525 ttt gtg acc gag gac ctg acc ccg ggc ctc aaa gtc agc atc aga gcc    1753
Phe Val Thr Glu Asp Leu Thr Pro Gly Leu Lys Val Ser Ile Arg Ala
        530             535             540 gtg tgt gtc atg cgg ttc ctg gtg tcc aag cgg aag ttc aag gag agc    1801
Val Cys Val Met Arg Phe Leu Val Ser Lys Arg Lys Phe Lys Glu Ser
        545             550             555 ctg cgg ccc tac gac gtg atg gac gtc atc gag cag tac tca gcc ggc    1849
Leu Arg Pro Tyr Asp Val Met Asp Val Ile Glu Gln Tyr Ser Ala Gly
        560             565             570 cac ctg gac atg ctg tcc cga att aag agc ctg cag tcc aga gtg gac    1897
His Leu Asp Met Leu Ser Arg Ile Lys Ser Leu Gln Ser Arg Val Asp
575             580             585             590 cag atc gtg ggg cgg ggc cca gcg atc acg gac aag gac cgc acc aag    1945
Gln Ile Val Gly Arg Gly Pro Ala Ile Thr Asp Lys Asp Arg Thr Lys
            595             600             605 ggc ccg gcc gag gcg gag ctg ccc gag gac ccc agc atg atg gga cgg    1993
```

```
                                       -continued

Gly Pro Ala Glu Ala Glu Leu Pro Glu Asp Pro Ser Met Met Gly Arg
            610                 615                 620 ctc ggg aag gtg gag aag cag gtc ttg tcc atg gag aag aag ctg gac     2041
Leu Gly Lys Val Glu Lys Gln Val Leu Ser Met Glu Lys Lys Leu Asp
            625                 630                 635 ttc ctg gtg aat atc tac atg cag cgg atg ggc atc ccc ccg aca gag     2089
Phe Leu Val Asn Ile Tyr Met Gln Arg Met Gly Ile Pro Pro Thr Glu
640                 645                 650 acc gag gcc tac ttt ggg gcc aaa gag ccg gag ccg gcg ccg ccg tac     2137
Thr Glu Ala Tyr Phe Gly Ala Lys Glu Pro Glu Pro Ala Pro Pro Tyr
655                 660                 665                 670 cac agc ccg gaa gac agc cgg gag cat gtc gac agg cac ggc tgc att     2185
His Ser Pro Glu Asp Ser Arg Glu His Val Asp Arg His Gly Cys Ile
                675                 680                 685 gtc aag atc gtg cgc tcc agc agc tcc acg ggc cag aag aac ttc tcg     2233
Val Lys Ile Val Arg Ser Ser Ser Ser Thr Gly Gln Lys Asn Phe Ser
            690                 695                 700 gcg ccc ccg gcc gcg ccc cct gtc cag tgt ccg ccc tcc acc tcc tgg     2281
Ala Pro Pro Ala Ala Pro Pro Val Gln Cys Pro Pro Ser Thr Ser Trp
705                 710                 715 cag cca cag agc cac ccg cgc cag ggc cac ggc acc tcc ccc gtg ggg     2329
Gln Pro Gln Ser His Pro Arg Gln Gly His Gly Thr Ser Pro Val Gly
720                 725                 730 gac cac ggc tcc ctg gtg cgc atc ccg ccg ccg cct gcc cac gag cgg     2377
Asp His Gly Ser Leu Val Arg Ile Pro Pro Pro Ala His Glu Arg
735                 740                 745                 750 tcg ctg tcc gcc tac ggc ggg ggc aac cgc gcc agc atg gag ttc ctg     2425
Ser Leu Ser Ala Tyr Gly Gly Gly Asn Arg Ala Ser Met Glu Phe Leu
                755                 760                 765 cgg cag gag gac acc ccg ggc tgc agg ccc ccc gag ggg aac ctg cgg     2473
Arg Gln Glu Asp Thr Pro Gly Cys Arg Pro Pro Glu Gly Asn Leu Arg
            770                 775                 780 gac agc gac acg tcc atc tcc atc ccg tcc gtg gac cac gag gag ctg     2521
Asp Ser Asp Thr Ser Ile Ser Ile Pro Ser Val Asp His Glu Glu Leu
785                 790                 795 gag cgt tcc ttc agc ggc ttc agc atc tcc cag tcc aag gag aac ctg     2569
Glu Arg Ser Phe Ser Gly Phe Ser Ile Ser Gln Ser Lys Glu Asn Leu
800                 805                 810 gat gct ctc aac agc tgc tac gcg gcc gtg gcg cct tgt gcc aaa gtc     2617
Asp Ala Leu Asn Ser Cys Tyr Ala Ala Val Ala Pro Cys Ala Lys Val
815                 820                 825                 830 agg ccc tac att gcg gag gga gag tca gac acc gac tcc gac ctc tgt     2665
Arg Pro Tyr Ile Ala Glu Gly Glu Ser Asp Thr Asp Ser Asp Leu Cys
                835                 840                 845 acc ccg tgc ggg ccc ccg cca cgc tcg gcc acc ggc gag ggt ccc ttt     2713
Thr Pro Cys Gly Pro Pro Pro Arg Ser Ala Thr Gly Glu Gly Pro Phe
            850                 855                 860 ggt gac gtg ggc tgg gcc ggg ccg ggc cca gga agt gag gcg gcg ctg     2761
Gly Asp Val Gly Trp Ala Gly Pro Gly Pro Gly Ser Glu Ala Ala Leu
865                 870                 875 ggc cag tgg acc cgc ccg cgg ccc tcc tca gca cgg tgc ctc cga ggt     2809
Gly Gln Trp Thr Arg Pro Arg Pro Ser Ser Ala Arg Cys Leu Arg Gly
880                 885                 890 ttt gag gcg gga acc ctc tgg ggc cct ttt ctt aca gta act gag tgt     2857
Phe Glu Ala Gly Thr Leu Trp Gly Pro Phe Leu Thr Val Thr Glu Cys
895                 900                 905                 910 ggc ggg aag ggt ggg ccc tgg agg ggc cca tgt ggg ctg aag gat ggg     2905
Gly Gly Lys Gly Gly Pro Trp Arg Gly Pro Cys Gly Leu Lys Asp Gly
                915                 920                 925
```

-continued

```
ggc tcc tgg cag tgacctttta caaaagttat tttccaacag gggctggagg      2957
Gly Ser Trp Gln
        930 gctgggcagg gcctgtggct ccaggagcag cgtgcaggag caaggctgcc ctgtccactc  3017 tgctcaaggc cgcggccgac atcagcccgg tgtgaagagg ggcggagtga tgacgggtgt  3077 tgcaacctgg caacaagcng ggggttgncc agccgancca agggaagcac anaaggaagc  3137 tgtncccctaa gacctnccccn aaaggcggcc tgtttggtaa gactgcgcct tggtccggtg  3197 ggttccggca gcaaaagcgg gttttgccgc ccctgtcgtg                         3237
```

<210> SEQ ID NO 96
<211> LENGTH: 930
<212> TYPE: PRT
<213> ORGANISM: Homo sapiens

<400> SEQUENCE: 96

```
Met Val Gln Lys Ser Arg Asn Gly Gly Val Tyr Pro Gly Pro Ser Gly
 1               5                  10                  15

Glu Lys Lys Leu Lys Val Gly Phe Val Gly Leu Asp Pro Gly Ala Pro
                20                  25                  30

Asp Ser Thr Arg Asp Gly Ala Leu Leu Ile Ala Gly Glu Ala Pro
            35                  40                  45

Lys Arg Gly Ser Ile Leu Ser Lys Pro Arg Ala Gly Ala Gly Ala
        50                  55                  60

Gly Lys Pro Pro Lys Arg Asn Ala Phe Tyr Arg Lys Leu Gln Asn Phe
 65                  70                  75                  80

Leu Tyr Asn Val Leu Glu Arg Pro Arg Gly Trp Ala Phe Ile Tyr His
                85                  90                  95

Ala Tyr Val Phe Leu Leu Val Phe Ser Cys Leu Val Leu Ser Val Phe
            100                 105                 110

Ser Thr Ile Lys Glu Tyr Glu Lys Ser Ser Glu Gly Ala Leu Tyr Ile
        115                 120                 125

Leu Glu Ile Val Thr Ile Val Val Phe Gly Val Glu Tyr Phe Val Arg
    130                 135                 140

Ile Trp Ala Ala Gly Cys Cys Cys Arg Tyr Arg Gly Trp Arg Gly Arg
145                 150                 155                 160

Leu Lys Phe Ala Arg Lys Pro Phe Cys Val Ile Asp Ile Met Val Leu
                165                 170                 175

Ile Ala Ser Ile Ala Val Leu Ala Ala Gly Ser Gln Gly Asn Val Phe
            180                 185                 190

Ala Thr Ser Ala Leu Arg Ser Leu Arg Phe Leu Gln Ile Leu Arg Met
        195                 200                 205

Ile Arg Met Asp Arg Arg Gly Gly Thr Trp Lys Leu Leu Gly Ser Val
    210                 215                 220

Val Tyr Ala His Ser Lys Glu Leu Val Thr Ala Trp Tyr Ile Gly Phe
225                 230                 235                 240

Leu Cys Leu Ile Leu Ala Ser Phe Leu Val Tyr Leu Ala Glu Lys Gly
                245                 250                 255

Glu Asn Asp His Phe Asp Thr Tyr Ala Asp Ala Leu Trp Trp Gly Leu
            260                 265                 270

Ile Thr Leu Thr Thr Ile Gly Tyr Gly Asp Lys Tyr Pro Gln Thr Trp
        275                 280                 285

Asn Gly Arg Leu Leu Ala Ala Thr Phe Thr Leu Ile Gly Val Ser Phe
    290                 295                 300
```

```
Phe Ala Leu Pro Ala Gly Ile Leu Gly Ser Gly Phe Ala Leu Lys Val
305                 310                 315                 320

Gln Glu Gln His Arg Gln Lys His Phe Glu Lys Arg Arg Asn Pro Ala
            325                 330                 335

Ala Gly Leu Ile Gln Ser Ala Trp Arg Phe Tyr Ala Thr Asn Leu Ser
            340                 345                 350

Arg Thr Asp Leu His Ser Thr Trp Gln Tyr Tyr Glu Arg Thr Val Thr
            355                 360                 365

Val Pro Met Tyr Ser Ser Gln Thr Gln Thr Tyr Gly Ala Ser Arg Leu
            370                 375                 380

Ile Pro Pro Leu Asn Gln Leu Glu Leu Leu Arg Asn Leu Lys Ser Lys
385                 390                 395                 400

Ser Gly Leu Ala Phe Arg Lys Asp Pro Pro Glu Pro Ser Pro Ser
            405                 410                 415

Lys Gly Ser Pro Cys Arg Gly Pro Leu Cys Gly Cys Pro Gly Arg
            420                 425                 430

Ser Ser Gln Lys Val Ser Leu Lys Asp Arg Val Phe Ser Ser Pro Arg
            435                 440                 445

Gly Val Ala Ala Lys Gly Lys Gly Ser Pro Gln Ala Gln Thr Val Arg
450                 455                 460

Arg Ser Pro Ser Ala Asp Gln Ser Leu Glu Asp Ser Pro Ser Lys Val
465                 470                 475                 480

Pro Lys Ser Trp Ser Phe Gly Asp Arg Ser Arg Ala Arg Gln Ala Phe
            485                 490                 495

Arg Ile Lys Gly Ala Ala Ser Arg Gln Asn Ser Glu Glu Ala Ser Leu
            500                 505                 510

Pro Gly Glu Asp Ile Val Asp Asp Lys Ser Cys Pro Cys Glu Phe Val
            515                 520                 525

Thr Glu Asp Leu Thr Pro Gly Leu Lys Val Ser Ile Arg Ala Val Cys
            530                 535                 540

Val Met Arg Phe Leu Val Ser Lys Arg Lys Phe Lys Glu Ser Leu Arg
545                 550                 555                 560

Pro Tyr Asp Val Met Asp Val Ile Glu Gln Tyr Ser Ala Gly His Leu
            565                 570                 575

Asp Met Leu Ser Arg Ile Lys Ser Leu Gln Ser Arg Val Asp Gln Ile
            580                 585                 590

Val Gly Arg Gly Pro Ala Ile Thr Asp Lys Asp Arg Thr Lys Gly Pro
            595                 600                 605

Ala Glu Ala Glu Leu Pro Glu Asp Pro Ser Met Met Gly Arg Leu Gly
610                 615                 620

Lys Val Glu Lys Gln Val Leu Ser Met Glu Lys Lys Leu Asp Phe Leu
625                 630                 635                 640

Val Asn Ile Tyr Met Gln Arg Met Gly Ile Pro Pro Thr Glu Thr Glu
            645                 650                 655

Ala Tyr Phe Gly Ala Lys Glu Pro Glu Pro Ala Pro Pro Tyr His Ser
            660                 665                 670

Pro Glu Asp Ser Arg Glu His Val Asp Arg His Gly Cys Ile Val Lys
            675                 680                 685

Ile Val Arg Ser Ser Ser Ser Thr Gly Gln Lys Asn Phe Ser Ala Pro
            690                 695                 700

Pro Ala Ala Pro Pro Val Gln Cys Pro Pro Ser Thr Ser Trp Gln Pro
705                 710                 715                 720

Gln Ser His Pro Arg Gln Gly His Gly Thr Ser Pro Val Gly Asp His
```

-continued

```
                725                 730                 735
Gly Ser Leu Val Arg Ile Pro Pro Pro Ala His Glu Arg Ser Leu
                740                 745                 750

Ser Ala Tyr Gly Gly Asn Arg Ala Ser Met Glu Phe Leu Arg Gln
                755                 760                 765

Glu Asp Thr Pro Gly Cys Arg Pro Pro Glu Gly Asn Leu Arg Asp Ser
770                 775                 780

Asp Thr Ser Ile Ser Ile Pro Ser Val Asp His Glu Glu Leu Glu Arg
785                 790                 795                 800

Ser Phe Ser Gly Phe Ser Ile Ser Gln Ser Lys Glu Asn Leu Asp Ala
                805                 810                 815

Leu Asn Ser Cys Tyr Ala Ala Val Ala Pro Cys Ala Lys Val Arg Pro
                820                 825                 830

Tyr Ile Ala Glu Gly Glu Ser Asp Thr Asp Ser Asp Leu Cys Thr Pro
                835                 840                 845

Cys Gly Pro Pro Pro Arg Ser Ala Thr Gly Glu Gly Pro Phe Gly Asp
850                 855                 860

Val Gly Trp Ala Gly Pro Gly Pro Gly Ser Glu Ala Ala Leu Gly Gln
865                 870                 875                 880

Trp Thr Arg Pro Arg Pro Ser Ser Ala Arg Cys Leu Arg Gly Phe Glu
                885                 890                 895

Ala Gly Thr Leu Trp Gly Pro Phe Leu Thr Val Thr Glu Cys Gly Gly
                900                 905                 910

Lys Gly Gly Pro Trp Arg Gly Pro Cys Gly Leu Lys Asp Gly Gly Ser
                915                 920                 925

Trp Gln
    930
```

<210> SEQ ID NO 97
<211> LENGTH: 23
<212> TYPE: DNA
<213> ORGANISM: Homo sapiens

<400> SEQUENCE: 97
acatcatggt gctcatcgcc tcc                                              23

<210> SEQ ID NO 98
<211> LENGTH: 22
<212> TYPE: DNA
<213> ORGANISM: Homo sapiens

<400> SEQUENCE: 98
gctgtgcaag cagagggagg tg                                               22

<210> SEQ ID NO 99
<211> LENGTH: 21
<212> TYPE: DNA
<213> ORGANISM: Homo sapiens

<400> SEQUENCE: 99
ccgtgcagca gccgtcagtc c                                                21

<210> SEQ ID NO 100
<211> LENGTH: 161
<212> TYPE: DNA
<213> ORGANISM: Homo sapiens

<400> SEQUENCE: 100

```
gttcctcctg gttttctcct gcctcgtgct gtctgtgttt tccaccatca aggagtatga    60
gaagagctcg gagggggccc tctacatcct ggtgagcccc gagggagggc gggggctgga   120
agtgcccagg aaggagctgg agctgcctgg gcgtctgtct t                        161

<210> SEQ ID NO 101
<211> LENGTH: 204
<212> TYPE: DNA
<213> ORGANISM: Homo sapiens

<400> SEQUENCE: 101
aggcctcaag gtggcctcag cttttcctcc ctgcaggaaa tcgtgactat cgtggtgttt    60
ggcgtggagt acttcgtgcg gatctgggcc gcaggctgct gctgccggta ccgtggctgg   120 aggggcggc tcaagtttgc ccggaaaccg ttctgtgtga ttggtgaggc ctggtggggg   180
tggtattgct agaatcaggg ccag                                           204

<210> SEQ ID NO 102
<211> LENGTH: 171
<212> TYPE: DNA
<213> ORGANISM: Homo sapiens

<400> SEQUENCE: 102
acatcatggt gctcatcgcc tccattgcgg tgctggccgc cggctcccag ggcaacgtct    60
ttgccacatc tgcgctccgg agcctgcgct tcctgcagat tctgcggatg atccgcatgg   120
accggcgggg aggcacctgg aagctgctgg gctctgtggt ctatgcccac a             171

<210> SEQ ID NO 103
<211> LENGTH: 215
<212> TYPE: DNA
<213> ORGANISM: Homo sapiens

<400> SEQUENCE: 103
tggtcactgc ctggtacatc ggcttccttt gtctcatcct ggcctcgttc ctggtgtact    60
tggcagagaa gggggagaac gaccactttg acacctacgc ggatgcactc tggtggggcc   120
tggtgagttg tggtcattgt ggttttccct ttccctgctg atacacccct gtccctgtgc   180
tgggaccagg ctctcactgg ctgagcctgc tccat                               215

<210> SEQ ID NO 104
<211> LENGTH: 241
<212> TYPE: DNA
<213> ORGANISM: Homo sapiens

<400> SEQUENCE: 104
gcaggccctt cgtgtgacta gagcctgcgg tcccacagat cacgctgacc accattggct    60
acggggacaa gtaccccag acctggaacg gcaggctcct tgcggcaacc ttcaccctca   120
tcggtgtctc cttcttcgcg ctgcctgcag taagtccagc tgccctgcc tgccttggag   180 ggggacgagg tcttgtaggc tcccgaggtg accacaggcc cctgggcaca gttccctagg   240
t                                                                    241

<210> SEQ ID NO 105
<211> LENGTH: 238
<212> TYPE: DNA
<213> ORGANISM: Homo sapiens

<400> SEQUENCE: 105
atggtctgac cctgatgaat tggggtgtgg ggggtccctg gggtgtgacc tgaccctgat    60
```

```
gaattgcagg gcatcttggg gtctgggttt gccctgaagg ttcaggagca gcacaggcag    120
aagcactttg agaagaggcg gaacccggca gcaggcctga tccaggtgag tccaggtgtc    180
ccccggggac cagcacagcc cttgtcctgg tcccaccttg ttgaggagtg gaggccgc      238
```

<210> SEQ ID NO 106
<211> LENGTH: 232
<212> TYPE: DNA
<213> ORGANISM: Homo sapiens

<400> SEQUENCE: 106

```
agctgtgcaa gcagagggag gtgtcccagg actcggagg gtgagacgct cactcccctc     60
tccttctctt gccccagact tatccccccg ctgaaccagc tggagctgct gaggaacctc   120
aagagtaaat ctggactcgc tttcaggtca gctggggagc tccaggtggg gcgggtgggc   180
gtctcagtcc tcctggggc cccagctgcc cacagaagac acgccaggac ag            232
```

<210> SEQ ID NO 107
<211> LENGTH: 128
<212> TYPE: DNA
<213> ORGANISM: Homo sapiens
<220> FEATURE:
<221> NAME/KEY: misc_feature
<222> LOCATION: (1)..(128)
<223> OTHER INFORMATION: n may be any nucleotide

<400> SEQUENCE: 107

```
cccaggacta actgtgctct cctcatttcc agtaaaggca gcccgtgcag agggcccctg    60
tgtggatgct gccccggacg ctctaggtac nrcggaacac rmsscacgga ctgacggctg   120
ctgcacgg                                                             128
```

<210> SEQ ID NO 108
<211> LENGTH: 318
<212> TYPE: DNA
<213> ORGANISM: Homo sapiens

<400> SEQUENCE: 108

```
gcagagtgac ttctctccct gtttttctgt ctgtctgtct gtctgtcggt tcccgtggga    60
gcagccagaa ggtcagtttg aaagatcgtg tcttctccag cccccgaggc gtggctgcca   120
aggggaaggg gtccccgcag gcccagactg tgaggcggtc acccagcgcc gaccagagcc   180
tcgaggacag ccccagcaag gtgcccaaga gctggagctt cggggaccgc agccgggcac   240
gccaggcttt ccgcatcaag ggtgccgcgt cacggcagaa ctcagaaggg gtgtggccgc   300
atcctctcct ggtccatc                                                  318
```

<210> SEQ ID NO 109
<211> LENGTH: 187
<212> TYPE: DNA
<213> ORGANISM: Homo sapiens

<400> SEQUENCE: 109

```
ccctcacggc atgtgtcctt cccccagaa gcaagcctcc ccggagagga cattgtggat     60
gacaagagct gccctgcga gtttgtgacc gaggacctga ccccgggcct caaagtcagc    120
atcagagccg tgtggtgagg cccctgccca gccgggagcc tgggggagtg aggaggggcc   180
tcccgct                                                              187
```

<210> SEQ ID NO 110

```
<211> LENGTH: 211
<212> TYPE: DNA
<213> ORGANISM: Homo sapiens

<400> SEQUENCE: 110
ggtctctggc ccagggctca cagccccacc cacccccctg cagtgtcatg cggttcctgg      60
tgtccaagcg gaagttcaag gagagcctgc ggccctacga cgtgatggac gtcatcgagc     120
agtactcagc cggccacctg gacatgctgt cccgaattaa gagcctgcag tccaggcaag     180
agccccgcct gcctgtccag caggggacaa g                                   211

<210> SEQ ID NO 111
<211> LENGTH: 287
<212> TYPE: DNA
<213> ORGANISM: Homo sapiens

<400> SEQUENCE: 111
cccagcccag cagccccttt tgcaggtctt gtccatggag aagaagctgg acttcctggt      60
gaatatctac atgcagcgga tgggcatccc ccgacagaga accgaggcct actttggggc     120
caaagagccg gagccggcgc cgccgtacca cagcccggaa gacagccggg agcatgtcga     180
caggcacggc tgcattgtca agatcgtgcg ctccagcagc tccacgggcc agaagaactt     240
ctcggcgccc ccggccgcgc cccctgtcca gtgtccgccc tccacct                  287

<210> SEQ ID NO 112
<211> LENGTH: 289
<212> TYPE: DNA
<213> ORGANISM: Homo sapiens

<400> SEQUENCE: 112
ctccacgggc cagaagaact tctcggcgcc ccggccgcg ccccctgtcc agtgtccgcc       60
ctccacctcc tggcagccac agagccaccc gcgccagggc cacggcacct cccccgtggg     120
ggaccacggc tccctggtgc gcatcccgcc gccgcctgcc cacgagcggt cgctgtccgc     180
ctacggcggg ggcaaccgcg ccagcatgga gttcctgcgg caggaggaca ccccgggctg     240 caggccccc gaggggaacc tgcgggacag cgacacgtcc atctccatc                 289

<210> SEQ ID NO 113
<211> LENGTH: 236
<212> TYPE: DNA
<213> ORGANISM: Homo sapiens

<400> SEQUENCE: 113
tggagttcct gcggcaggag gacaccccga gctgcaggcc ccccgagggg accctgcggg      60
acagcgacac gtccatctcc atcccgtccg tggaccacga ggagctggag cgttccttca     120
gcggcttcag catctcccag tccaaggaga acctggatgc tctcaacagc tgctacgcgg     180
ccgtggcgcc ttgtgccaaa gtcaggccct acattgcgga gggagagtca gacacc        236

<210> SEQ ID NO 114
<211> LENGTH: 636
<212> TYPE: DNA
<213> ORGANISM: Homo sapiens
<220> FEATURE:
<221> NAME/KEY: misc_feature
<222> LOCATION: (1)..(636)
<223> OTHER INFORMATION: n may be any nucleotide

<400> SEQUENCE: 114
gtggcgcctt gtgccaaagt caggccctac attgcggagg gagagtcaga caccgactcc      60
```

```
gacctctgta ccccgtgcgg gcccccgcca cgctcggcca ccggcgaggg tccctttggt      120
gacgtgggct gggccgggcc caggaagtga ggcggcgctg ggccagtgga cccgcccgcg      180
gccctcctca gcacggtgcc tccgaggttt tgaggcggga accctctggg gccttttct       240 tacagtaact gagtgtggcg ggaagggtgg gccctggagg ggcccatgtg ggctgaagga      300
tgggggctcc tggcagtgac cttttacaaa agttattttc aacaggggc tggagggctg       360 ggcagggcct gtggctccag gagcagcgtg caggagcaag gctgccctgt ccactctgct      420
caaggccgcg gccgacatca gcccggtgtg aagagggcg gagtgatgac gggtgttgca       480
acctggcaac aagcnggggg ttgnccagcc ganccaaggg aagcacanaa ggaagctgtn      540
ccctaagacc tncccnaaag gcggcctgtt tggtaagact gcgccttggt ccggtgggtt      600
ccggcagcaa aagcgggttt tgccgcccct gtcgtg                                636
```

<210> SEQ ID NO 115
<211> LENGTH: 245
<212> TYPE: DNA
<213> ORGANISM: Homo sapiens

<400> SEQUENCE: 115

```
ggcgacgtgg agcaagtcac cttggcgctc ggggccggag ccgacaaaga cgggaccctg       60
ctgctggagg gcggcggccg cgacgagggg cagcggagga ccccgcaggg catcgggctc      120
ctggccaaga ccccgctgag ccgcccagtc aagagaaaca acgccaagta ccggcgcatc      180
caaactttga tctacgacgc cctggagaga ccgcggggct gggcgctgct ttaccacgcg      240
ttggt                                                                  245
```

<210> SEQ ID NO 116
<211> LENGTH: 841
<212> TYPE: DNA
<213> ORGANISM: Homo sapiens

<400> SEQUENCE: 116

```
aacttctctc acattgtttt atttaactgg gatgattgtt tccgcctgcc ttgcaggttt       60
gtcgtgaaga ttgaatggga tagcatataa agcacatgtc aatgtccagc agaagttgca      120
gcttcatcct ggaagacacc tttccccatc ttagcctcaa agcaagccat gactcaaagg      180
ttccttagtc catttctttc ttcccctcta ggttcctgat tgtcctgggg tgcttgattc      240
tggctgtcct gaccacattc aaggagtatg agactgtctc gggagactgg cttctgttac      300
tggtaagatt gcattctggg gtaaatgctt ctggttgggc ttccagagtg atgaaaagga      360
ggttgccctt gggtgcactc ctccctgact ggttgcagct tcttgtagtc tccagtcaag      420
tccaggccca aggaaaagca aagcctccat tactyggtat ggcccgccat gggcacatgt      480
ggggtgaaga atggcattcc tggtaaagct ttgctattcc acattagaga aaggggaaa       540 taaagtcaaa gcaaaaacca atgcatgtta ttaaattata aaatacagct tcccaatcct      600
ctgaaaggta acacaaaggc atgtttcatt ctaaaacctg tctctgcttt tcttcctgg       660 gatcctacaa tctaaactcc aaggatctct cattctctcc aaggccaggt acagaattcc      720
atttatacac gaaacctcta aatctccct cctgggggcct gcatttgttt tcactctctg      780
tcctccatca ggtggtgtga tggaaacaga gcaggattag aattcctggg caagtcagct      840
a                                                                      841
```

<210> SEQ ID NO 117

```
<211> LENGTH: 859
<212> TYPE: DNA
<213> ORGANISM: Homo sapiens

<400> SEQUENCE: 117
agggctgcct ggcccaggag ccaggctttta taaccattag ccacaattag caatgccagg      60
gtacaggcac tgggtggaat ttacagattg tgtttcactc atatctctct tttcaaccca     120
actgcacttc ttgggggctt ttcattcatt aaagggactt ttaaagctga cctattggaa     180
caaaaacata gaaaaagaa cgagtaatca ctgtgccagg tttaacagca ttaaggacaa      240
ttagcacatc agaatgaaga tgggaggcct ccaaactgaa tggcggtgat ggacctgttc     300
tcccggttcc ccttccccac ccccatcccc agccatccct gccaaccaga caaccagcaa     360
cagcacaaaa tggagttctt cagaacttcc gaatagaaat caccagctcc cgacaagtgg     420
atctcggtta atcagtgcct ctccatatgc tcttccatgc aggagacatt tgctattttc     480
atctttggag ccgagtttgc tttgaggatc tgggctgctg gatgttgctg ccgatacaaa     540
ggctggcggg gccgactgaa gtttgccagg aagcccctgt gcatgttggg taagtcctga     600
ccctgagcct cccagcctcc tcagttccct tcttttgggg cattgtttct ctgagaaaag     660
tttaagcagc tattctggga aatcacgcgg cactgtggag gccagctcag cccctgacgc     720
tgcctcgatg agaagggaca tgtcaacctt ctgggtcctc aaattcctcc ttctgtgact     780
ggtccttata aggactgcac aggacaggga ttcttatttg gcagggtagg gtgtcactct     840
tggcaattgg gttgtggag                                                  859

<210> SEQ ID NO 118
<211> LENGTH: 649
<212> TYPE: DNA
<213> ORGANISM: Homo sapiens

<400> SEQUENCE: 118
gggggccttg gtaaattgct gctctggagc cagcattaaa gtgtggtagg cctatgctac      60
ttctggccag gtggccttgg aaagtcactc aggctcagag cttcagtttc ctcatcagtc     120
atgggagaat aatcccactt accatgtgtt gttggtggca agattcaaca gcagtgctca     180
gattgtccca ctgcttggca catgctgatc tgccagcaaa cagcacctat gatgacgcca     240
ttgctttcgc atgaccttcc tttccctctt ccctcccact ctgtctgtcc tctctcccag     300
acatctttgt gctgattgcc tctgtgccag tggttgctgt gggaaaccaa ggcaatgttc     360
tggccacctc cctgcgaagc ctgcgcttcc tgcagatcct cgcgcatgctg cggatggacc     420 ggagaggtgg cacctggaag cttctgggct cagccatctg tgcccacagc aaagtaagtg     480
tggtggagaa actgcaggac cacatgggct tcccacccac ctatgccctt ccatgacatc     540
ccttcctttg cagtgtcccc agaaggcagt cattctgcca cccttgatga taacgacaaa     600
gaggaagagg aggaggagaa acaggaagtg gcggggctgg ggtaggggc                  649

<210> SEQ ID NO 119
<211> LENGTH: 973
<212> TYPE: DNA
<213> ORGANISM: Homo sapiens

<400> SEQUENCE: 119
acgcaagtcc tggaatagac ccaaagtttc ctgagtcctg agccttgtat tagaagaagg      60
agccacttcc tcctgccttc ttgccttcct ctgaagcctt tgagctgtg atattgaagt     120 ggccctaagc tagaaatctt cctctcctcc tggagccata cactttttct ggtaaattaa     180
```

```
tgaatgaaat aactaccatg ttaatgatcc cattttacag tgatggaaga tgaagatcag    240
agaaggtgag tgatttgacc acagtcacag agctggtaaa cttggactct aactctggtg    300
tgtctggctc cagcatccac tcaacgactc cccagtgacc acttttcatg tccactgttc    360
attctttcag gaactcatca cggcctgtac atcggtttcc tgacactcat cctttcttca    420
tttcttgtct acctggttga gaaagacgtc ccagaggtgg atgcacaagg agaggagatg    480
aaagaggagt ttgagaccta tgcagatgcc ctgtggtggg gcctggtgag tcactacctt    540
ggaggccaat tctgtgagat tgactgtcaa gagtcagaga gaggtggagg gcatcacatg    600
agcatgttca gccaggcagc tgcattctgc agtcagaggt aagctctaga ccaatttcag    660
ctcagaacct gctgacagaa gaccctcctt caaggtgggc acttggaatt gacttttctc    720
tagcgtttat aagaagccag ggcttggaac agcctggttg catggtcgtt tatggactta    780
gccttattag tcataggcta ttttcagcca agccatgcat gtgcaaacaa acccagtgac    840
agatacacat gtgtgctcac acagaccctgt gtgtgcacaa ccctacaccc acaaggacac    900
acagtactaa agctggcatt cactgaaggc tttctttgct ccagagcatc tctctgggtg    960
ctttactttc act                                                       973

<210> SEQ ID NO 120
<211> LENGTH: 1117
<212> TYPE: DNA
<213> ORGANISM: Homo sapiens
<220> FEATURE:
<221> NAME/KEY: misc_feature
<222> LOCATION: (1)..(1117)
<223> OTHER INFORMATION: n may be any nucleotide

<400> SEQUENCE: 120
gaacagatac atgcacagac attagacata cacacatata tacacaatac atacaaatat     60
actcacaagc acacatatat tcacaaacat ggctataaat aaaatcacaa attcacaaat    120
atacacacac atgaatgctc gtgtacatac acatttgcaa ttgctgaaat atttgttgac    180
tgactaaggt aggaaaccct taacttatca acaagtctca aggcatccat ataagttagt    240
aggtacttgg tgtctttttct cctaagggaa ccttgttatg aatgggagca ttgcccaagc    300
tgatggagag gcttacaggt agagctcagt taacacgttc ctgatattcc tctccatgtg    360
gtactccatg tctgaactct tctctcttca gatcacactg gccaccattg gctatggaga    420
caagacaccc aaaacgtggg aaggccgtct gattgccgcc acctttcct taattggcgt     480 ctccttttt gcccttccag cggtaagtac ctttgatata tgcatcccc aatgtgacgt     540 gcaggacccc ttaccgcctg gtgccagctc aactttccag tgtcatcttc tatcctctta    600 tacccctacca actccctagc cattcccctta agcatgatga tcctgccttt ttgccacagg    660
ccctgctgct ttcctctgcc aaagatttct tcacacatca actcctcttt caatgctgcc    720
ttctttaggc tgagctagtc gctctgggca taactctggg aataattctg taaggagtt     780 tctgccccta tgctaggatt acacatttct agatctgcct tccccagagg actgtgaatt    840
ccttgggttc tgggattata ttttcattc atgcattccc agtgccttgc acggagcagg    900
tccttcattt atgtgagttc ccttctcttg tcctgttacn tactggctta tgtaaaaaat    960
acatgtctct caagaataag tctgacctat gatagagtaa ctncccccaac gcccagtgtc   1020 caggtacgta ataataatga aagcagattg catttggttg aactcactgt ggcctgaatc   1080
atgccaaaag gtttacccac atcatctcat ttaatct                            1117
```

<210> SEQ ID NO 121
<211> LENGTH: 1083
<212> TYPE: DNA
<213> ORGANISM: Homo sapiens
<220> FEATURE:
<221> NAME/KEY: misc_feature
<222> LOCATION: (1)..(1083)
<223> OTHER INFORMATION: n may be any nucleotide

<400> SEQUENCE: 121

```
gaaaatcaaa acagatccca attctgggaa gttccggcta tagtcaaagt atcacgtgac         60
agttcaagca gctaaaatat ttttaaaact cagttaacat tactgggcat ctattttgtg        120
cagtacccct tactggcagt ttataaaggt tatctcactt ttttctaatc atgcattagg        180
tattattatc ccacatccct atagaaaaaa ccaatatgca acagggctaa ggggcttgcc        240
caggccctca cacctggaaa gtggcagtgt cagaattgga acccaggtct tcctgacttc        300
aaggctcatt tcacttaacc aagctcccta ctctcttcaa gagaaggaag ggctcttttcc       360
cccttccctt cttagtacag tgttgtcact gcaaggactt gaagtgcaat tgagccctac        420
agtccccatt accctggcaa tggagcggga atgctgggac agtctagctg ggggctgact        480
gcctgcctgc ctctccctca gggcatcctg ggtccgggc tggccctcaa ggtgcaggag         540
caacaccgtc agaagcactt tgagaaaagg aggaagccag ctgctgagct cattcaggtc        600
tgtctgcctg ggaatgaact ggaatgggat taagatccat gcatatgtac atacgtgtgt        660
gtgtgtgtat gtgtgcatgt gtgcacatgt ggagggaca tactcatgaa ctgggacagg         720
accgattcca tgtgtgtctg tgtgtcttgt gtgtctgtgt gtgtgtgtgt gtgtgtatgt        780
gtgtgtgtgt gtgtattaat gtgcccaggc aggagcaggc ctgcttgcac atgcttactt        840
gtggatggct atggggagtt tccatgggta tctatttcac ctgttcttct gtgtactgaa        900
ggtgacaatc ctgtcactct ctcattcagt ttctaagcca agaaagaaat agacacagaa        960
ctcaaggacc aacctatcat cttttttttg atacggtggt tttttgaggt ttttttttgag      1020
actctcttgt ccaggctgga ttgtagggtg cgatcatact cactgcagcc tccatcnccc       1080
agg                                                                     1083
```

<210> SEQ ID NO 122
<211> LENGTH: 819
<212> TYPE: DNA
<213> ORGANISM: Homo sapiens

<400> SEQUENCE: 122

```
aactcttggc ctcaaagtga tcctcccacc ttggtctccc aaagtgctgg gattacaggc         60
gtgagccata gcaccggcct ttagtacttg ttcctttcag ggattttatg cctactactc        120
tcttctctcc ctccactcca gttcatctct ccattccccc actcaccaca acaccaatta        180
tagctccaag atggtcaagg aagttttttct tcccaaagca gcttcaaaaa gccaagaatc        240
tcggtttttc tgaatgttgg ctcaatgcac attcaaattc ttaggagtcc agggcttaaa        300
cattgttttg ttggtgtggg agtctgtgcg aaagtttcgg tggtgcccac tcattgttgc        360
ccctcttttc tgcccctcag gctgcctgga ggtattatgc taccaacccc aacaggattg        420
acctggtggc gacatgggat tttatgaatc agtcgtctct tttcctttct tcaggcaagt        480
ggggactcac ctgaatgctc agggcgtgac cagccatctc tcctgcggtc tgtattcgtg        540
tctggcctca cgggtccctg gagaacactc ttcagggcaa tgttcccaa tttgggctgc         600
accctagaat tatctggtag cttaaacagt tctggctggg cgcggtggct cacacccata        660
```

| | |
|---|---|
| atcccagcac tttgggaggc cgaggcgggt ggatcacctg aggtcaggag ttccatacca | 720 |
| gcctggccaa catggtgaaa tcccgttcct actaaaaatg caaaaattac ccgggcgtgg | 780 |
| tggtgtgtgc ctgtaatccc agctactcag gaggctgaa | 819 |

<210> SEQ ID NO 123
<211> LENGTH: 914
<212> TYPE: DNA
<213> ORGANISM: Homo sapiens

<400> SEQUENCE: 123

| | |
|---|---|
| gactgaatgg acttagtaca agttggtcat aagggtcccg aggggctaca ggaagatgct | 60 |
| ggggtaggag tgatggcaga ttatacgttc ttatatacaa gcagggatga gggaagctgt | 120 |
| taaaaatcag acattgcttt ttataaacag agcatgtgca ttgttttatt cctggtaggg | 180 |
| agagtggaat tatgtctggc ttttcatttt ctatagctgc accgttcaat atggtagcca | 240 |
| ctagcctcat gtggctagtg agaatttgac tgttagcact gcaattgagg aacagatttt | 300 |
| ttaatttaa agtaaataac cttctatgac taatgactac tctattggac agcacagctc | 360 |
| tggaattgtt agctatgaga actgaaatgg agataagaag acttcgccca cgatgtagaa | 420 |
| aatacttgac caagaacagg tagttcattg tgtaaccagg acttgttcct tttaacaggg | 480 |
| tcaagattat tggagtgctt agaaatggag aaagggact atatgcacta gtcatttcct | 540 |
| atggccaaat aacattggat ctgctttcat acatactatc ttatttaagc tttaggatgt | 600 |
| cctggaaggt aagtagaagg ggtaactcca ttttcataa ccccattttt ataggtaaag | 660 |
| aataagagag tcaatgagat taattagctt gcttaatatc gctcagctga taagtgatgg | 720 |
| aacaaagatt ggaactcagg tcttgtgcca aaacctatgt tttatttg cattgtatct | 780 |
| ctgggaagaa aacattattt agggagaaaa ctggataaaa gtaagatgac acaagggttg | 840 |
| tttggataat aagacccatt tttgaagatt gttgtttgga tggtcaaact gagtaaaatg | 900 |
| tgtgagagtg gttg | 914 |

<210> SEQ ID NO 124
<211> LENGTH: 1232
<212> TYPE: DNA
<213> ORGANISM: Homo sapiens

<400> SEQUENCE: 124

| | |
|---|---|
| tacaatgtga tccacgtaat aatgacagag taccattcca cttgtgaggg gatttgctca | 60 |
| gtgtagacct tgggcaattg aataagaacc cctaggaggg cccctccagg tgtacataaa | 120 |
| ggatgagtag gcctgttcca agcagggaaa agaggaaggg agttccaggc agaaggagag | 180 |
| cctgagaaaa ggcttggagt catgaatatg tgtaaagcac gggctggtgc acctcccagt | 240 |
| taggagtgag ggctccagag ccagatcacc tgggtttgga tcctgacttt gctgcctcct | 300 |
| aactgtgagc ccttgagcaa ttcatttaat ccctctgtgc ctcaattttc tcctcaggga | 360 |
| aatgggatga taatagtact tcataggggtt gttatgagga ttaattgagt taagacaatg | 420 |
| ttcgctatga tgacaatggt agtgacaaag ttatggggt gtgtgactgc tacattatga | 480 |
| cattcctggt ttcctggtct gtctccacca ccaaataaat ttcctgagct caacatgaga | 540 |
| gctggggcag agtaagtgct cagcaaccat tttctggatg aataaatgaa tgaatgagtg | 600 |
| gctgaaaaga gccctgaaaa cctcagagcc aacgggagta gcatgggctg gggtctggat | 660 |
| gggtaaaccc gcctccttca ttggttccct ccacactgac catcctgtcc tagagctcaa | 720 |

| | |
|---|---:|
| ctctgctcca tcatcttcag agagaagctt tgcagcaatc tttcgaggaa ggatacagct | 780 |
| gtttcacgta atttatgctt tattctttct ccctcttctc tttctaggaa agaacagctg | 840 |
| gaggcagcat ccaggtaagt ttctgattat gaattccctt cttcacatct ctgtgtcaag | 900 |
| acagagcatc ctgctccata tggtgtaggg ccccatggga ggtcatgctg gtcccaagat | 960 |
| agagtctttg gggtcacact gttgctgacc accatagtcc tctgcctggt ttccttctgg | 1020 |
| ttgatctgag ggaaacttaa taggaatcat ggcagcagcc tcttattgag ggtctgggtt | 1080 |
| ctgtgtcagg agttctgcat atgttatctc atttggtctt cacaaccaca atgtaacgat | 1140 |
| aggccctaat atcatccctt gtggatgagg agattgtggc tcagagaggt tgggttgaga | 1200 |
| ttgagtggca acaaccaaaa ttcatagtca gg | 1232 |

<210> SEQ ID NO 125
<211> LENGTH: 1172
<212> TYPE: DNA
<213> ORGANISM: Homo sapiens

<400> SEQUENCE: 125

| | |
|---|---:|
| aagaagtgtt gctttacgtc catttgtgtg gccagtttct tttcaaggag gaatcctttg | 60 |
| ataaggattt gtctgtgtaa atcactatct gggtaccatg ggatgataca caggaaaggc | 120 |
| aggaagttat tgatgcagga aatgggcatg ggaaagatga atctctgcag catactagga | 180 |
| tgagctaggc aatttatagc gggcacctca tgtaagctac atttaatcgt atgggaaaat | 240 |
| tgacattcag agaagtcttg cccagggtat aagagctagc aggctgtgga gctaggattt | 300 |
| gaaccacgcc ctgtccgatt ccaagctgct gagtcagatt cagcactgtg aaatgcacgg | 360 |
| tccccatttc tccttggagg agaatgtgtg agtctttatg gagggatggg aaattttaag | 420 |
| agcctgcact gaaggaggaa aattttcact tttgcttatt ttgagccaaa agctgggtct | 480 |
| cttggatcgg gttcgcctta atcctcgtgg tagcaatact aaaggaaagc tatttacccc | 540 |
| tctgaatgta gatgccatag aagaaagtcc ttctaaagaa ccaaagcctg ttggcttaaa | 600 |
| caataaagag cgtttccgca cggccttccg catgaaagcc tacgctttct ggcagagttc | 660 |
| tgaaggtaat gccttttat ctccctcc ct gtctcttcca cttcttcctc ccccaagtcc | 720 |
| acttccttcc tcacctctcc ctttgcccac ttaagaacct ttgactccac aaggtaactc | 780 |
| tctcccttcc ctcgacaagc caacttcttg cttccctaac tcctcctgtc ccttgggctg | 840 |
| aggcattgtg atgtattccc aggagtctag ggctgcaggc tcccaagtta ggagcctgga | 900 |
| aacctgtcac cttggtttct gagggtccgc cccgaccccc cgcccatga ttggattgtt | 960 |
| atggaggtca acttgaagga tggggcggtg ccaggtgcaa agcaatttag agaccagggc | 1020 |
| acgggaagag tggcagaaaa gcgccctctg gaggctgtag gagtcatggc tcatgtgcc | 1080 |
| tcttttactt atgcaaaggg aggacatgca gaaaagcctg tttcctcagt gtctgagccc | 1140 |
| acccaggccc tcaatcctca ttgtatcatt ca | 1172 |

<210> SEQ ID NO 126
<211> LENGTH: 1028
<212> TYPE: DNA
<213> ORGANISM: Homo sapiens
<220> FEATURE:
<221> NAME/KEY: misc_feature
<222> LOCATION: (1)..(1028)
<223> OTHER INFORMATION: n may be any nucleotide

<400> SEQUENCE: 126

| | |
|---|---:|
| kttctctcma aggcctctng atgtgtgsgg ctcagaaagt gacktctcca aggtcaccag | 60 |

```
gatagagact tgasagagca aawakcccag ctgaggsctg cacagtgkgt gktgkttgct    120
ggsttcwgtg tcstttgstg gctkytggct ctgggggcca ytctggaact gsggagctca    180
cttctcctcc ctgctagcct tttccctcac taccagtcat gagtgcgcac acttttgact    240
tggacttctg ggtaatagaa tgagggtgcc aagaaaggct gaacagcatc acagcttgag    300
aataccgtgg agtcttgcaa cgtggaaata aagactctgg ggattgacac atccagaggc    360
gtggaaggct ttgaccgaac agtggggtcc ccaagccttt tccaggtctg tggcctgccg    420
ttcatatgtg tgtctccctc ccagatgccg ggacaggtga ccccatggcg aagacaggg     480 gctatgggaa tgacttcccc atcgaagaca tgatccccac cctgaaggcc gccatccgag    540
ccgtcaggta atgccccac ggtcccacct gtgcctgtgt gcctccccg ctccagctca      600 actcccacag aagggggctt ataaaattat cttgcacttt gggaagggg aagagaagcc     660 cctccactaa ccctgagtta ggtccctgaa gtatgtaaat actgtatgct gccccagaaa    720
aaatgatcca gacgttagca agtcatgatg ggtgactcgt aggtgcctgc cttgttataa    780
acacgcccca cagccctcct gacagtattt ccacctgcta tgttctgctc tgtctgtaac    840
taccatgtat tttaaagggt gtcagagtgg agggttttct tcctgtagag gcttcttgct    900
caaaatggtt tttcttctgc ctaacttcat ccatatagtt tgttttaatt agttcgcatt    960
tttaacaaga taataaatta tagtattttt ttgtctgtat cagcagagac cataatccat    1020
tctaccta                                                             1028

<210> SEQ ID NO 127
<211> LENGTH: 1021
<212> TYPE: DNA
<213> ORGANISM: Homo sapiens

<400> SEQUENCE: 127
agcagtgtga cagtgattaa gagcaccagc cttgtcagca ccctgtctgg gtttgaggac     60
cagctcagcc cttattagct atatggccct gggatgatgc tgaaggttca aatccacaat    120
cacatcatct ataaatggat ctgttatcca ggattgttca taaagcatta attaagctca    180
tggtctggca tacagtgaat gctcaataaa tgttagctct tattaatact atgatttact    240
tattattcaa atgattgaag ggagtaatcc tgatggagat gtactaactc tgtgtgttcc    300 aagggggtaga accagaacca aacgttggaa gttcttccag caagctcttt tatctttggt    360
tcttttctcc ccctgccctg gagtttgcta gccttctgtt atagctcccc gcactctcca    420
catgggatgc acaaatgcct ctactttgcc ttgcagaatt ctacaattcc gtctctataa    480
aaaaaaattc aaggagactt tgaggcctta cgatgtgaag gatgtgattg agcagtattc    540
tgccgggcat ctcgacatgc tttccaggat aaagtacctt cagacgaggt gagacagtca    600
catctggagg gactgcgctc ccctcaaagc cctatgaacc ttagagttta aggtgagagg    660
tattcagaaa taattcaaaa tgcagggaga gattttaaga agacaaatat ccacgaagcc    720
ttgtggatgt ctaggccaac aaagcaccag atcggacaga ctgtgaaata gctgtatgac    780
attgccatgg ccaaggtcag caccctgatc aggcctgtca gagaggagaa agcacacatt    840
taaatggctt ctgactgtga tgctttcgat gttgccaaca aaacaggatc atccgaatta    900
aaccgaatcc agctgcctaa ttaattctca atacaattct ttaccatatt taaaatgtt    960 catcaggtat tacttataat agttgaaaga tatggaaata gcatcaatgc ctaactaata   1020
a                                                                    1021
```

<210> SEQ ID NO 128
<211> LENGTH: 1019
<212> TYPE: DNA
<213> ORGANISM: Homo sapiens
<220> FEATURE:
<221> NAME/KEY: misc_feature
<222> LOCATION: (1)..(1019)
<223> OTHER INFORMATION: n may be any nucleotide

<400> SEQUENCE: 128

```
ccaagatgca gccgtcacct ctctcagtgg tttgtctgcc tccctctctc ctgggataga      60
aagatgcttt cagtatcacc agatcaaaac aagcggaaga atataccgag gttataggtt     120
ctctctggct ctgtctttct ctctgtagct agtatgcact ctctctttcc tctcctctcc     180
tcccctctcc tctcctcact tctcctctcc tcccctctcc tctcctcact tctcctctcc     240
tctcctctcc tcttatatat tccaaaccct tatctcattc tagagagaat agaatgattt     300
gttttcctgt caaaacaaag ctctgtgtaa tttaatccct gctctgtttg tttctttcag     360
aatagatatg attttcaccc ctggacctcc ctccacgcca aaacacaaga agtctcagaa     420
agggtcagca ttcaccttcc catcccagca atctcccagg aatgaaccat atgtagccag     480
accatccaca tcagaaatcg aagaccaaag catgatgggg aagtttgtaa agttgaaag      540
acaggtaagt cttttcttcc tctcaccaaa aactggatct gtgacattta ttttcaaatg     600
ccatttcttt ttttctttc tttccttttt tttttaaga cgaaggttcn actctgttgc       660
ccaggctgga gtgcaatggc gcgatcttga ctcactgcaa cctctgcctc ccaggttcaa     720
gtgattctcc tgcctcagcc tcctnaggag ctgagattac aggcgcctgc catcatgccc     780
agctaatttt tgtatttnta gtagagatgg ggtttcacca tgttggccag gctggtctcg     840
aactcctgac ctcaggtgat ctgcccaact cggcctacca aagtgctggg attacagaca     900
tgagccactg tgcccagtcc ccaccattgt ttttcaaagg gagataagat acttgagtac     960
tactacctac cattcaaaaa agatatggna atcaaatcac tgatttagca tttactgag    1019
```

<210> SEQ ID NO 129
<211> LENGTH: 1341
<212> TYPE: DNA
<213> ORGANISM: Homo sapiens
<220> FEATURE:
<221> NAME/KEY: misc_feature
<222> LOCATION: (1)..(1341)
<223> OTHER INFORMATION: n may be any nucleotide

<400> SEQUENCE: 129

```
cgggtgcctg taatcccagc tacttgggag gctgaggcat agcactgcnt gaacccggga      60
ggcggaagta gcaatgagcc cagatcgcgc cactgcactc cagcctgggt gacagaactg     120
agcttcgtct caaaaaaaaa aaaaaaaaa aaaaaagaa tatttcctcc caaccaatag      180
caacgatccc caccctcaga gaaagtggta attcacagct cctttgattt tccaggttca     240
ggacatccgg aagaagctgg acttcctcgt ggatatgcac atgcaacaca tggaacggtt     300
gcaggtgcag gtcacggagt attacccaac caagggcacc tcctcgccag ctgaagcaga     360
gaagaaggag gacaacaggt attccgattt gaaaaccatc atctgcaact attctgagac     420
aggcccccg gaaccaccct acagcttcca ccaggtgacc attgacaaag tcagccccta     480
tgggttttt gcacatgacc ctgtgaacct gccccgaggg ggacccagtt ctggaaaggt     540
tcaggcaact cctccttcct cagcaacaac gtatgtggag aggcccacgg tcctgcctat     600
cttgactctt ctcgactccc gagtgagctg ccactcccag gctgacctgc agggccccta     660
```

```
ctcggaccga atctcccccc ggcagagacg tagcatcacg cgagacagtg acacacctct    720
gtccctgatg tcggtcaacc acgaggagct ggagaggtct caagtggctt cagcatctcc    780
caggacagag atgattatgt gttcggcccc aatgggggt cgagctggat gagggagaag    840
cggtacctcg ccgagggtga gacggacaca gacacggacc ccttcacgcc cagcggctcc    900
atgcctctgt cgtccacagg ggatgggatt tctgattcag tatggacccc ttccaataag    960
cccatttaaa agaggtcact ggctgacccc tccttgtaat gtagacagac tttgtatagt   1020
tcacttactc ttacacccga cgcttaccag cggggacacc aatggctgca tcaaatgcat   1080
gcgtgtgcgt ggtggcccca cccaggcagg ggcttcccac agcctcttcc tccccatgtc   1140
accacaacaa agtgcttcct tttcagcatg gnttgcatga ctttacacta tataaatggt   1200
tccgctaatc tcttctagga tacacattta tctgctgttc ttacttttaa tcacgattgg   1260
accagtacag ggagaaatta ctgatgagcc atgctatttg tctgtttggt tggctggtat   1320
gggttttggt ttggtaagca a                                             1341
```